(12) United States Patent
Dillon et al.

(10) Patent No.: US 9,546,173 B2
(45) Date of Patent: Jan. 17, 2017

(54) SUBSTITUTED PYRROLO[3,4-D]PYRIMIDINES AS KINASE INHIBITORS

(71) Applicants: Michael Patrick Dillon, Boston, MA (US); Mika Lindvall, Oakland, CA (US); Daniel Poon, Piedmont, CA (US); Savithri Ramurthy, Arlington, MA (US); Vivek Rauniyar, Cambridge, MA (US); Cynthia Shafer, El Sobrante, CA (US); Sharadha Subramanian, San Ramon, CA (US); Huw Rowland Tanner, San Francisco, CA (US)

(72) Inventors: Michael Patrick Dillon, Boston, MA (US); Mika Lindvall, Oakland, CA (US); Daniel Poon, Piedmont, CA (US); Savithri Ramurthy, Arlington, MA (US); Vivek Rauniyar, Cambridge, MA (US); Cynthia Shafer, El Sobrante, CA (US); Sharadha Subramanian, San Ramon, CA (US); Huw Rowland Tanner, San Francisco, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/428,546

(22) PCT Filed: Sep. 17, 2013

(86) PCT No.: PCT/US2013/060032
§ 371 (c)(1),
(2) Date: Mar. 16, 2015

(87) PCT Pub. No.: WO2014/047020
PCT Pub. Date: Mar. 27, 2014

(65) Prior Publication Data
US 2015/0274733 A1 Oct. 1, 2015

Related U.S. Application Data

(60) Provisional application No. 61/702,981, filed on Sep. 19, 2012.

(51) Int. Cl.
| | | |
|---|---|---|
| A61K 31/519 | (2006.01) | |
| C07D 239/70 | (2006.01) | |
| C07D 487/04 | (2006.01) | |
| C07D 207/36 | (2006.01) | |
| A61K 31/527 | (2006.01) | |
| A61K 45/06 | (2006.01) | |
| C07D 487/10 | (2006.01) | |

(52) U.S. Cl.
CPC .......... *C07D 487/04* (2013.01); *A61K 31/519* (2013.01); *A61K 31/527* (2013.01); *A61K 45/06* (2013.01); *C07D 207/36* (2013.01); *C07D 487/10* (2013.01)

(58) Field of Classification Search
CPC .... A61K 31/519; C07D 239/70; C07D 487/04
USPC .............. 514/265.1; 544/280, 386; 546/244, 546/268.1; 548/235, 335.1, 373.1, 557, 548/953; 549/28, 68, 424, 480
See application file for complete search history.

(56) References Cited

FOREIGN PATENT DOCUMENTS

| | | | |
|---|---|---|---|
| CA | 2882410 | * | 3/2014 |
| WO | 2012/118850 A1 | | 9/2012 |
| WO | 2013/127267 A1 | | 9/2013 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Hackam, et al. JAMA, 296(14), 2006, 1731-1732.*
Biftu et al., Novel tetrahydropyran analogs as dipeptidyl peptidase IV inhibitors: Profile of clinical candidate (2S,3S,5R)-2-(2,5-difluorophenyl)-5-(4,6-dihydropyrrolo[3,4-c]pyrazol-5-(1H)-yl)tetrahydro-2H-pyran-3-amine (23) [corrected]. Bioorg Med Chem Lett. Oct. 1, 2013;23(19):5361-6. Epub Aug. 5, 2013. Erratum in: Bioorg Med Chem Lett. Jun. 1, 2014;24(11):2590.

* cited by examiner

*Primary Examiner* — Douglas M Willis
(74) *Attorney, Agent, or Firm* — Shawn D. Britt

(57) ABSTRACT

The present invention provides compounds of Formula (I) and pharmaceutically acceptable salts thereof; as further described herein. The present invention further provides pharmaceutical compositions comprising these compounds, and combinations comprising these compounds combined with or used with a therapeutic co-agent, as well as therapeutic uses of these compounds and compositions. These are useful in the treatment of diseases such as cancer that are associated with activation of ERK1 and/or ERK2, and especially for MAPK pathway dependent cancers showing resistance to Raf and/or MEK inhibitory cancer therapeutics.

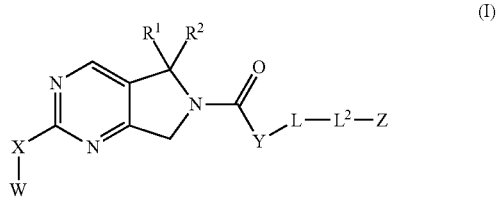

17 Claims, No Drawings

SUBSTITUTED PYRROLO[3,4-D]PYRIMIDINES AS KINASE INHIBITORS

This application is a U.S. National Phase filing of International Application No. PCT/US2013/060032 filed 17 Sep. 2013, which claims priority to U.S. Application No. 61/702,981 filed 19 Sep. 2012, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Mar. 31, 2015, is named PAT055194-US-PCT_SL.txt and is 970 bytes in size.

BACKGROUND

Protein Kinases are involved in very complex signaling cascades that regulate most cellular functions, including survival and proliferation. These signaling pathways have been heavily studied, particularly in the context of disorders caused by dysregulated cellular function, such as cancer. The extracellular signal-regulated kinases (ERKs) are one class of signaling kinases that are involved in conveying extracellular signals into cells and subcellular organelles. ERK1 and ERK2 (ERK1/2) are kinases in the mitogen activated protein kinase (MAPK) pathway, and are also referred to as p42 and p44, respectively. ERK1 and ERK2 are present in relatively large quantities in cells (~$10^7$ molecules per cell), and are involved in regulating a wide range of activities. Indeed, dysregulation of the ERK1/2 cascade is known to cause a variety of pathologies including neurodegenerative diseases, developmental diseases, diabetes and cancer. Wortzel and Seger, *Genes & Cancer*, 2:195-209 (2011), published online 9 May 2011.

The role of ERK1/2 in cancer is of special interest because activating mutations upstream of ERK1/2 in its signaling cascade are said to be responsible for more than half of all cancers. Id. Moreover, excessive ERK1/2 activity was also found in cancers where the upstream components were not mutated, suggesting that ERK1/2 signaling plays a role in carcinogenesis even in cancers without mutational activations. The ERK pathway has also been shown to control tumor cell migration and invasion, and thus may be associated with metastasis. See A. von Thun, et al., *ERK2 drives tumour cell migration in 3D microenvironments by suppressing expression of Rab 17 and Liprin-β2, J. Cell Sciences*, online publication date 10 Feb. 2012. In addition, it has been reported that silencing either ERK1 or ERK2 using shRNA killed melanoma cells in culture, and also made melanoma cells more sensitive to inhibitors of BRAF. J. Qin, et al., *J. Translational Med.* 10:15 (2012). Indazole derivatives acting as ERK inhibitors have been reported as therapeutics for treating cancers. WO2012/118850; WO2012/030685; WO2007/070398; WO2008/153858. Certain bicyclic systems having pyrazole fused to a pyrrolidine ring are known in the art also—see e.g., WO2006/072831, WO2012/065935—and have been reported to inhibit other kinases. However, there remains a need for new therapeutic agents that inhibit ERK1 and/or ERK2 to treat disorders associated with undesired levels of ERK1/2 activity, particularly in cancers where mutations elsewhere in the MAPK pathway promote resistance to inhibitors of other pathway enzymes including Raf and MEK. The current invention provides novel fused pyrrolidine compounds that inhibit ERK1, ERK2, or preferably both (dual inhibitors), for use to treat diseases such as cancer that are associated with activation of ERK1 and/or ERK2, and especially for MAPK pathway dependent cancers showing resistance to Raf and/or MEK inhibitory cancer therapeutics.

SUMMARY OF THE INVENTION

In one aspect, the invention provides a compound of the formula (I):

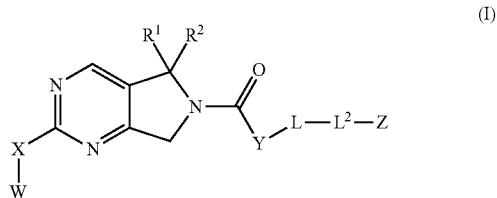

or a pharmaceutically acceptable salt thereof, wherein:
$R^1$ is H, COOR', or an optionally substituted $C_{1-4}$ alkyl, $C_{2-4}$ alkenyl, or $C_{2-4}$ alkynyl, where each R' is independently H or $C_{1-4}$ alkyl;
$R^2$ is H or an optionally substituted $C_{1-4}$ alkyl;
or $R^1$ and $R^2$ taken together can optionally form a 3-6 membered cycloalkyl ring, or a 3-6 membered heterocyclic ring containing N, O or S as a ring member, each of which is optionally substituted;
each $R^3$ and $R^4$ is independently H or $C_{1-4}$ alkyl optionally substituted with up to three groups, or $R^3$ and $R^4$ taken together can form a $C_{3-5}$ cycloalkyl optionally substituted with up to three groups;
X is a bond or $NR^5$;
$R^5$ is H or an optionally substituted group selected from $C_{1-4}$ alkyl, 5-6 membered heterocyclic, and 5-6 membered heteroaryl;
W is an optionally substituted group selected from $C_{1-6}$ alkyl, $C_{3-7}$ cycloalkyl, 4-7 membered heterocyclic, aryl, and 5-10 membered heteroaryl;
Y is $NR^6$, where $R^6$ is H or optionally substituted $C_{1-4}$ alkyl;
L is a bond or an optionally substituted $C_{3-7}$ cycloalkyl or $C_{4-7}$ heterocyclic ring;
$L^2$ is a divalent linker selected from a bond, $-(CR^3R^4)_{1-2}-$, $-SO_2-$, and $-SO_2-CR^3R^4-$;
Z is optionally substituted $C_{1-6}$ alkyl, or an optionally substituted 5-10 membered aryl, aryl-($C_{1-4}$)alkyl, heteroaryl, cycloalkyl, or heterocyclic ring;
wherein the optional substituents for each optionally substituted alkyl, alkenyl, alkynyl, cycloalkyl, and heterocyclyl, are selected from halo, oxo, CN, hydroxy, amino, $C_{1-4}$ alkoxy, $C_{1-4}$ haloalkyl, $C_{1-4}$ haloalkoxy, ($C_{1-4}$)alkylamino, di($C_{1-4}$)alkylamino, $C_{1-4}$ acylamino, $C_{3-6}$ cycloalkyl, 4-7 membered heterocyclyl, 5-6 membered heteroaryl, $C_{1-4}$ haloalkyl, $-S(O)_q(C_{1-4})$alkyl, $-S(O)_q(C_{1-4})$haloalkyl, $-S(O)_q(C_{3-6})$cycloalkyl, $-S(O)_q$Ar, $-$OAr,
and two of these substituents on the same atom or on adjacent directly connected atoms can cyclize to form a 3-6 membered cycloalkyl ring, a phenyl ring, or a 5-6 membered heterocyclic ring containing one heteroatom selected from N, O and S,
wherein the cycloalkyl, phenyl or heterocyclic ring can be substituted by up to three groups selected from halo, CN, hydroxy, oxo (except not on phenyl), $C_{1-4}$ alkyl, $C_{1-4}$ haloalkyl, —O-G, —COOG, and —C(O)-G, where each G is independently $C_{1-4}$ alkyl;

and the optional substituents for each aryl and heteroaryl ring are independently selected from $C_{1-4}$ alkyl and —(CH$_2$)$_m$-T, where each T is selected from amino, halo, CN, hydroxy, amino, $C_{1-4}$ alkoxy, $C_{1-4}$ haloalkyl, $C_{1-4}$ haloalkoxy, $(C_{1-4})$alkylamino, di$(C_{1-4})$alkylamino, $C_{1-4}$ acylamino, $C_{3-6}$ cycloalkyl, 4-7 membered heterocyclyl, 5-6 membered heteroaryl, —S(O)$_p$(C$_{1-4}$)alkyl, —S(O)$_p$(C$_{1-4}$)haloalkyl, Ar, —S(O)$_p$Ar, —OAr, COOR", CONR"$_2$, —NR"C(O)R", and —NR"C(O)OR", where each R" is independently H or $C_{1-4}$ alkyl, wherein m is independently at each occurrence 0, 1 or 2;

and two of these substituents on the same atom or on adjacent directly connected atoms can cyclize to form a 3-6 membered cycloalkyl ring, a phenyl ring, or a 5-6 membered heterocyclic ring containing one heteroatom selected from N, O and S, wherein the cycloalkyl, phenyl or heterocyclic ring can be substituted by up to three groups selected from halo, CN, hydroxy, oxo (except not on phenyl), $C_{1-4}$ alkyl, $C_{1-4}$ haloalkyl, —O-G, —COOG, and —C(O)-G, where each G is independently $C_{1-4}$ alkyl;

each p is independently 0, 1 or 2;
each q is independently 0, 1 or 2; and
each Ar is independently phenyl optionally substituted with up to three groups selected from halo, $C_{1-4}$ alkyl, $C_{1-4}$ haloalkyl, and $C_{1-4}$ alkoxy;

including the pharmaceutically acceptable salts of these compounds. These compounds are inhibitors of ERK1 and/or ERK2, preferably dual inhibitors, and are thus useful to treat conditions associated with excessive or undesired levels of ERK1/2 activity. Some of the compounds of Formula (I) and (IA) also inhibit kinases in the RSK (90 kD ribosomal S6 kinase) family, e.g., RSK1 and RSK2 and RSK3, which are downstream effectors of the ERK/MAPK signaling cascade. Inhibition of these downstream effectors may contribute to usefulness of these compounds for treatment of cancers associated with excessive or undesired levels of MAPK pathway activity. The compounds are particularly useful for treating MAPK pathway dependent cancers that exhibit resistance to Raf and/or MEK inhibitors having anticancer activity.

In another aspect, the invention provides pharmaceutical compositions comprising a compound of Formula (I) or (IA) admixed with at least one pharmaceutically acceptable carrier or excipient, optionally admixed with two or more pharmaceutically acceptable carriers or excipients.

In another aspect, the invention provides a method to treat a condition characterized by excessive or undesired levels of activity of one or both of ERK1 and ERK2, which comprises administering to a subject in need of such treatment an effective amount of a compound of Formula (I) and (IA) or any subgenus thereof as described herein, or a pharmaceutical composition comprising such compound. The subject can be a mammal, and is preferably a human. Conditions treatable by the compounds and methods described herein include various forms of cancer, such as solid tumors, melanoma, breast cancer, lung cancer, ovarian cancer, colorectal cancer, thyroid cancer, and pancreatic cancer and other conditions mentioned herein. In some embodiments, the subject has a cancer that has exhibited resistance to anticancer compounds that act by inhibition of Raf and/or MEK, or a cancer having one or more mutations associated with resistance to Raf and/or MEK inhibitors.

The pharmaceutical compositions and methods described herein can also be used with or formulated with a co-therapeutic agent; for example, compounds of Formula I and IA can be used with or formulated with inhibitors of B-RAF and other therapeutic agents as further described herein.

In another aspect, the invention provides methods of making the compounds of Formula I as well as key intermediate compounds useful for making the compounds of the invention.

In one aspect, the invention provides compounds of formula (I) and the subgenera of Formula (I) described herein, as well as pharmaceutically acceptable salts of these compounds, and all stereoisomers (including diastereoisomers and enantiomers), tautomers and isotopically enriched versions thereof (including deuterium substitutions).

Compounds of the present invention also comprise polymorphs of compounds of formula I or IA (or subformulae thereof) and salts thereof. References to compounds of Formula I or IA as used above include the subgenera and species of those compounds that are described herein unless the context indicates otherwise.

DETAILED DESCRIPTION

The following definitions apply unless otherwise expressly provided or clearly indicated by context:

As used herein, the term "halogen" (or halo) refers to fluorine, bromine, chlorine or iodine, in particular fluorine or chlorine when on a non-aromatic carbon atom, and fluoro, chloro and bromo when on an aromatic carbon. Halogen-substituted groups and moieties, such as alkyl substituted by halogen (haloalkyl) can be mono-, poly- or per-halogenated.

As used herein, the term "hetero atoms" refers to nitrogen (N), oxygen (O) or sulfur (S) atoms, in particular nitrogen or oxygen.

As used herein, the term "alkyl" refers to a fully saturated branched or unbranched hydrocarbon moiety having up to 20 carbon atoms. Unless otherwise provided, alkyl refers to hydrocarbon moieties having 1 to 10 carbon atoms, 1 to 6 carbon atoms, or 1 to 4 carbon atoms. Typically, alkyl groups have 1-6 carbon atoms. "Lower alkyl" refers to groups having 1-4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

A substituted alkyl is an alkyl group containing one or more substituents in place of hydrogen, such as one, two or three substituents, up to the number of Hydrogens on the unsubstituted alkyl group. In typical embodiments, substituted alkyl has up to three substituents in place of hydrogen atoms unless otherwise specified. Suitable substituents for alkyl groups, if not otherwise specified, may be selected from halo, CN, oxo (=O), hydroxy, amino, —OR, —NR$_2$, —SR, —SOR, —SO$_2$R, —SO$_2$NR$_2$, —COOR, —CONR$_2$, —NRC(O)R, —C(O)R, —NRSO$_2$R, —OC(O)NR$_2$, —NRC(O)NR$_2$, where each R is independently selected from H, C1-C4 haloalkyl, and C1-C4 alkyl that is optionally substituted with up to three groups selected from oxo, —CN, —OH, —OMe, —OEt, —NH$_2$, —NHMe, and —NMe$_2$, and where two R groups on the same or adjacent covalently linked atoms can optionally cyclize together to form a 3-6 membered heterocyclic ring containing up to two heteroatoms selected from N, O and S as ring members; such heterocyclic ring can have the same substituents as the two combined R groups. Preferred substituents for alkyl groups include F, Cl, CN, oxo, hydroxy, amino, and $C_{1-4}$ alkoxy groups.

As used herein, the term "alkylene" refers to a divalent alkyl group having 1 to 10 carbon atoms, and two open valences to attach other structures. Unless otherwise provided, alkylene refers to moieties having 1 to 6 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like. A substituted alkylene is an alkylene group containing one or more, such as one, two or three substituents; unless otherwise specified, suitable and preferred substituents are selected from the suitable and preferred substituents described above for alkyl groups.

As used herein 'acyl' refers to a group of general formula R—C(=O)—, where R is a hydrocarbyl group (consisting of carbon and hydrogen only, unless described as substituted) that can be substituted with the suitable and preferred substituents described for alkyl groups above, typically an optionally substituted phenyl, $C_{1-6}$ alkyl or $C_{3-6}$ cycloalkyl group, unless otherwise described. 'Acylamino' refers to a corresponding group of general formula R—C(=O)—NH—.

As used herein, the term "haloalkyl" refers to an alkyl as defined herein, which is substituted by one or more halo groups as defined herein. The haloalkyl can be monohaloalkyl, dihaloalkyl, trihaloalkyl, or polyhaloalkyl including perhaloalkyl. A monohaloalkyl can have one iodo, bromo, chloro or fluoro on the alkyl group. Chloro and fluoro are preferred on alkyl or cycloalkyl groups. Dihaloalkyl and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, chloroethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms, e.g, trifluoromethyl.

As used herein, the term "alkoxy" refers to alkyl-O—, wherein alkyl is as defined above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have 11-10, or 1-6 carbons, and preferably 1-4 carbon atoms unless otherwise specified.

A substituted alkoxy is an alkoxy group containing one or more, such as one, two or three substituents on the alkyl portion of the alkoxy. Unless otherwise specified, suitable substituents are selected from the substituents described above for alkyl groups.

Similarly, each alkyl part of other groups like "alkylaminocarbonyl", "alkoxyalkyl", "alkoxycarbonyl", "alkoxycarbonylalkyl", "alkylsulfonyl", "alkylsulfoxyl", "alkylamino", "haloalkyl" shall have the same meaning as described in the above-mentioned definition of "alkyl". When used in this way, unless otherwise indicated, the alkyl group is often a 1-4 carbon alkyl and is not further substituted by groups other than the component named. When such alkyl groups are substituted or optionally substituted, suitable substituents are those suitable and preferred substituents named above for alkyl groups.

As used herein, the term "haloalkoxy" refers to haloalkyl-O—, wherein haloalkyl is defined above. Representative examples of haloalkoxy include, but are not limited to, fluoromethoxy, difluoromethoxy, trifluoromethoxy, trichloromethoxy, 2-chloroethoxy, 2,2,2-trifluoroethoxy, 1,1,1,3,3,3-hexafluoro-2-propoxy, and the like.

As used herein, the term "cycloalkyl" refers to saturated or unsaturated non-aromatic monocyclic, bicyclic, tricyclic or spirocyclic hydrocarbon groups of 3-12 carbon atoms: the cycloalkyl group may be unsaturated, and may be fused to another ring that can be saturated, unsaturated or aromatic, heterocyclic or heteroaromatic, provided the ring atom of the cycloalkyl group that is connected to the molecular formula of interest is in a non-aromatic carbocyclic ring. Unless otherwise provided, cycloalkyl refers to cyclic hydrocarbon groups having between 3 and 7 ring carbon atoms. Preferably, cycloalkyl groups are saturated monocyclic rings having 3-7 ring atoms unless otherwise specified.

A substituted cycloalkyl is a cycloalkyl group substituted by one, or two, or three, or more substituents, up to the number of hydrogens on the unsubstituted group. Typically, a substituted cycloalkyl will have 1-4 or 1-2 substituents. Suitable substituents, unless otherwise specified, are independently selected from the group consisting of C1-C4-alkyl, C2-C4-alkenyl, C2-C4-alkynyl, C1-C4-alkoxy, C1-C4-thioalkyl, C2-C4-alkenyloxy, C2-C4-alkynyloxy, C1-C4-alkylcarbonyl, carboxy, C1-C4-alkoxycarbonyl, amino, C1-C4-alkylamino, di-C1-C4-alkylamino, C1-C4-alkylaminocarbonyl, di-C1-C4-alkylaminocarbonyl, C1-C4-alkylcarbonylamino, C1-C4-alkylcarbonyl(C1-C4-alkyl)amino, C1-C4-alkylsulfonyl, C1-C4-alkylsulfamoyl, and C1-C4-alkylaminosulfonyl, where each of the aforementioned hydrocarbon groups (e.g., alkyl, alkenyl, alkynyl, alkoxy residues) may be further substituted by one or more groups independently selected at each occurrence from the list of substituents for 'alkyl' groups herein. Preferred substituents include C1-C4 alkyl and the suitable and preferred substituent groups described above for alkyl groups.

Exemplary monocyclic 'cycloalkyl' groups include, but are not limited to, cyclopropyl, cyclobutyl, cyclopentyl, cyclopentenyl, cyclohexyl and cyclohexenyl and the like. Exemplary polycyclic 'cycloalkyl' groups include bornyl, indyl, hexahydroindyl, tetrahydronaphthyl, decahydronapthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl, adamantyl and the like.

Similarly, each cycloalkyl part of other groups like "cycloalkyloxy", "cycloalkoxyalkyl", "cycloalkoxycarbonyl", "cycloalkoxy-carbonylalkyl", "cycloalkylsulfonyl", "halocycloalkyl" shall have the same meaning as described in the above-mentioned definition of "cycloalkyl". When used in these terms, the cycloalkyl is typically a monocyclic 3-7 carbon ring, that is unsubstituted or is substituted with 1-2 groups. When substituted, the substituents are typically selected from C1-C4 alkyl and those set forth above as suitable and preferred for cycloalkyl groups.

As used herein, the term "aryl" refers to an aromatic hydrocarbon group having 6-20 carbon atoms in the ring portion. Typically, aryl is monocyclic, bicyclic or tricyclic aryl having 6-20 carbon atoms, often 6-10 carbon atoms, e.g., phenyl or naphthyl, preferably phenyl. Furthermore, the term "aryl" as used herein, refers to an aromatic group that can be a single aromatic ring, or multiple aromatic rings that are fused together. Non-limiting examples include phenyl, naphthyl and tetrahydronaphthyl, provided the tetrahydronaphthyl is connected to the formula of interest through a carbon of the aromatic ring of the tetrahydronaphthyl group.

A substituted aryl is an aryl group substituted by 1-5 (such as one, or two, or three) substituents independently selected from the group consisting of hydroxyl, halogen, thiol, cyano, nitro, C1-C4-alkyl, C2-C4-alkenyl, C2-C4-alkynyl, C1-C4-alkoxy, C1-C4-haloalkyl, C1-C4-alkoxy, C1-C4-haloalkoxy, C1-C4-thioalkyl, C2-C4-alkenyloxy, C2-C4-alkynyloxy, C1-C4-alkylcarbonyl, carboxy, C1-C4-alkoxycarbonyl, amino, C1-C4-alkylamino, di-(C1-C4)-alkylamino, C1-C4-alkylaminocarbonyl, di-(C1-C4)-alkylaminocarbonyl, C1-C4-alkylcarbonylamino, C1-C4-alkylcarbonyl(C1-C4-alkyl)amino, C1-C4-alkylsulfonyl, sulfamoyl, C1-C4-alkylsulfamoyl, and C1-C4-alkylaminosulfonyl, where each of the afore-mentioned hydrocarbon groups (e.g., alkyl, alkenyl, alkynyl, alkoxy residues) may be further substituted by one or more groups independently selected at each occurrence from the groups listed above as suitable and preferred substituents for alkyl groups.

Similarly, each aryl part of other groups like "aryloxy", "aryloxyalkyl", "aryloxycarbonyl", "aryloxy-carbonylalkyl" shall have the same meaning as described in the above-mentioned definition of "aryl".

As used herein, the term "heterocyclyl" or "heterocyclic" refers to a cyclic radical that is saturated or partially saturated but not aromatic, and is a monocyclic or a polycyclic ring (in case of a polycyclic ring, particularly a bicyclic, tricyclic or a spirocyclic ring); and has 3 to 16, more preferably 5 to 10 and most preferably a monocyclic ring having 5 to 7 ring atoms; wherein one or more, preferably one to four, especially one or two ring atoms are heteroatoms independently selected from O, S and N (the remaining ring atoms therefore being carbon). Preferably, a heterocyclyl group has one or two heteroatoms as ring atoms, and preferably the heteroatoms are not directly connected to each other. The bonding ring of a bicyclic or polycyclic heterocycle (i.e. the ring connecting to the Formula of interest) typically has 4 to 12, especially 5 to 7 ring atoms. The heterocyclic group can be fused to an aromatic ring or other ring, provided it is attached to the Formula of interest at an atom of the heterocyclic ring that is not aromatic. The heterocyclic group can be attached to the Formula of interest via a heteroatom (typically nitrogen) or a carbon atom of the heterocyclic group. The heterocyclyl can include fused or bridged rings as well as spirocyclic rings, and only one ring of a polycyclic heterocyclic group needs to contain a heteroatom as a ring member. Unless otherwise specified, preferred heterocyclic groups are monocyclic and have 5-7 ring atoms, 1 or 2 of which are heteroatoms selected from N, O and S. Examples of heterocycles include oxetane, tetrahydrofuran (THF), dihydrofuran, 1,4-dioxane, morpholine, 1,4-dithiane, piperazine, homopiperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

A substituted heterocyclyl is a heterocyclic group substituted by 1-5 (such as one, or two, or three) substituents independently selected from the substituents described above for a cycloalkyl group. In particular, S when present as a ring atom in these groups can be substituted with one or two 'oxo' groups.

Similarly, each heterocyclyl part of other groups like "heterocyclyloxy", "heterocyclyloxyalkyl", "heterocyclyloxycarbonyl" shall have the same meaning as described in the above-mentioned definition of "heterocyclyl".

As used herein, the term "heteroaryl" refers to a 5-14 membered monocyclic- or bicyclic- or tricyclic-aromatic ring system, having 1 to 8 heteroatoms as ring members; the heteroatoms are selected from N, O and S. Typically, the heteroaryl is a 5-10 membered ring system (e.g., 5-6 membered monocyclic or an 8-10 membered bicyclic group) or a 5-6 membered monocyclic ring containing up to four heteroatoms, not more than one of which is oxygen or sulfur. Typical heteroaryl groups include 2- or 3-thienyl, 2- or 3-furyl, 1, 2- or 3-pyrrolyl, 1, 2-, 4-, or 5-imidazolyl, 1-, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, 1- or 2-tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl, tetrazolyl, and triazinyl. The skilled person has sufficient knowledge to select an appropriate combination of carbon atoms and heteroatoms to provide stable heteroaryl and heterocyclic groups; these generic terms are not intended to embrace combinations other than those known to be suitable for use in pharmaceutical compounds.

The term "heteroaryl" also includes a group in which a heteroaromatic ring is fused to one or more aryl, cycloalkyl, or heterocyclyl rings, where the radical or point of attachment to the Formula of interest is on a heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1 H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A substituted heteroaryl is a heteroaryl group containing one or more substituents, typically 1-3 or 1-2 substituents selected from the substituent groups described above as suitable for an aryl group. Suitable and preferred substituents include those described as suitable or preferred for aryl groups.

Similarly, each heteroaryl part of other groups like "heteroaryloxy", "heteroaryloxyalkyl", "heteroaryloxycarbonyl" shall have the same meaning as described in the above-mentioned definition of "heteroaryl".

Various enumerated embodiments of the invention are described herein. It will be recognized that features specified in each embodiment may be combined with other specified features to provide further embodiments of the present invention. Specific compounds of Formula I described herein are each preferred embodiments of the invention.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog 'R—S' system. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and synthesis procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques.

If the compound contains a double bond, the substituents on the double bond may be in an E or Z configuration unless specified. If the compound contains a disubstituted cycloalkyl or heterocyclic group, two groups on the ring may have a cis- or trans-configuration, and all such relative configurations are included unless otherwise specified. All atropisomeric and tautomeric forms are also intended to be included.

In many cases, the compounds of the present invention are capable of forming acid and/or base salts by virtue of the presence of amino and/or carboxyl groups or groups similar thereto. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

Pharmaceutically acceptable acid addition salts can be formed with inorganic acids and organic acids, e.g., acetate, adipate, aluminum, ascorbate, aspartate, benzoate, besylate, bromide/hydrobromide, bicarbonate/carbonate, bisulfate/sulfate, camphorsulfonate, caproate, chloride/hydrochloride, chloroprocaine, chlortheophyllonate, citrate, edetate, calcium edetate, ethandisulfonate, ethylsulfonate, ethylene diamine, fumarate, galactarate (mucate), gluceptate, gluconate, glucuronate, glutamate, glutarate, glycolate, hexyl resorcinate, hippurate, hydroiodide/iodide, hydroxynapthoate (xinafoate), isethionate, lactate, lactobionate, laurylsulfate, lithium, malate, maleate, malonate, mandelate, mesylate, methylsulphate, naphthoate, napsylate, nicotinate, nitrate, octadecanoate, oleate, oxalate, palmitate, pamoate, pantothenate, phosphate/hydrogen phosphate/dihydrogen phosphate, polygalacturonate, procaine, propionate, salicylate, sebacate, stearate, subacetate, succinate, sulfate, sulfosalicylate, tannate, tartrate, bitartrate, tosylate, triphenylacetate, and trifluoroacetate salts. Lists of additional suitable salts can be found, e.g., in REMINGTON'S PHARMACEUTICAL SCIENCES, 20th ed., Mack Publishing Company, Easton, Pa., (1985); and in HANDBOOK OF PHARMACEUTICAL SALTS: PROPERTIES, SELECTION, AND USE, by Stahl and Wermuth (Wiley-VCH, Weinheim, Germany, 2002).

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic or organic bases and can have inorganic or organic counterions.

Inorganic counterions for such base salts include, for example, ammonium salts and metals from columns I to XII of the periodic table. In certain embodiments, the counterion is selected from sodium, potassium, ammonium, alkylammonium having one to four C1-C8 alkyl groups, calcium, lithium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Suitable organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, tetrahydrofuran, toluene, chloroform, dichloromethane, methanol, ethanol, isopropanol, or acetonitrile is desirable, where practicable.

Any formula given herein can represent unlabeled forms (i.e., compounds wherein all atoms are present at natural isotopic abundances, and not isotopically enriched), or it can also include isotopically enriched or labeled forms of the compounds. Isotopically enriched or labeled compounds have structures depicted by the formulas given herein except that at least one atom of the compound is replaced by an atom having an atomic mass or mass number different from the atomic mass or the atomic mass distribution that occurs naturally. Examples of isotopes that can be incorporated into enriched or labeled compounds of the invention include isotopes of hydrogen, carbon, nitrogen, oxygen, phosphorous, sulfur, fluorine, chlorine and iodine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. The invention includes various isotopically labeled compounds as defined herein, for example those in which radioactive isotopes, such as $^3$H and $^{14}$C, or those in which non-radioactive isotopes, such as $^2$H and $^{13}$C, are present at levels significantly above the natural abundance for these isotopes. These isotopically labeled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO, as well as solvates with non-enriched solvents.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable excipients" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like that are used in pharmaceutical compositions along with active ingredients, as would be known to those skilled in the art (see, for example, REMINGTON'S PHARMACEUTICAL SCIENCES, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by a kinase such as ERK1/2 or (ii) associated with activity of a kinase such as ERK1/2, or (2) reduce or inhibit the activity of a kinase such as ERK1/2 or (3) reduce or inhibit the expression of a kinase such as ERK1/2.

The term "a therapeutically effective amount" refers to the amount of the compound of the present invention that, when administered to a cell, or a tissue, or a non-cellular biological material, or a medium, is effective to at least partially reduce or inhibit the activity of a kinase such as ERK1/2, or at least partially reduce or inhibit the expression of a kinase such as ERK1/2.

As used herein, the term "subject" refers to an animal. Typically the animal is a mammal. A subject also refers to, for example, primates (e.g., humans, male or female), cows, sheep, goats, horses, dogs, cats, rabbits, rats, mice, fish, birds and the like. In certain embodiments, the subject is a primate. In specific embodiments, the subject is a human. In preferred embodiments, the subject is one diagnosed as being in need of a treatment for a condition described herein.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration; i.e., for optically active compounds, it is often preferred to use one enantiomer to the substantial exclusion of the other enantiomer. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, or tautomers or as a mixture thereof, for example, as substantially pure geometric (cis or trans) isomers, diastereomers, optical isomers (antipodes), racemates or mixtures thereof. 'Substantially pure' or 'substantially free of other isomers' as used herein means the product contains less than 5%, and preferably less than 2%, of other isomers relative to the amount of the preferred isomer, by weight.

A mixture of isomers can be separated on the basis of the physicochemical differences of the constituents, into the pure or substantially pure geometric or optical isomers, diastereomers, racemates, for example, by chromatography and/or fractional crystallization.

A resulting racemate of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral stationary phase.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

The following enumerated embodiments represent selected aspects of the invention.

Embodiment 1

A compound of formula (I):

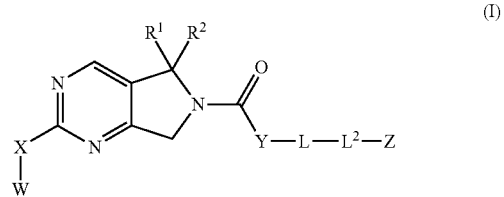

or a pharmaceutically acceptable salt thereof, wherein:
$R^1$ is H, COOR', or an optionally substituted $C_{1-4}$ alkyl, $C_{2-4}$ alkenyl, or $C_{2-4}$ alkynyl, where each R' is independently H or $C_{1-4}$ alkyl;
$R^2$ is H or an optionally substituted $C_{1-4}$ alkyl;
or $R^1$ and $R^2$ taken together can optionally form a 3-6 membered cycloalkyl ring, or a 3-6 membered heterocyclic ring containing N, O or S as a ring member, each of which is optionally substituted;
each $R^3$ and $R^4$ is independently H or $C_{1-4}$ alkyl optionally substituted with up to three groups, or $R^3$ and $R^4$ taken together can form a C3-5 cycloalkyl optionally substituted with up to three groups;
X is a bond or $NR^5$;
$R^5$ is H or an optionally substituted group selected from $C_{1-4}$ alkyl, 5-6 membered heterocyclic, and 5-6 membered heteroaryl;
W is an optionally substituted group selected from $C_{1-6}$ alkyl, $C_{3-7}$ cycloalkyl, 4-7 membered heterocyclic, aryl, and 5-10 membered heteroaryl;
Y is $NR^6$, where $R^6$ is H or optionally substituted $C_{1-4}$ alkyl;
L is a bond or an optionally substituted $C_{3-7}$ cycloalkyl or $C_{4-7}$ heterocyclic ring;
$L^2$ is a divalent linker selected from a bond, $-(CR^3R^4)_{1-2}-$, $-SO_2-$, and $-SO_2-CR^3R^4-$;
Z is optionally substituted $C_{1-6}$ alkyl, or an optionally substituted 5-10 membered aryl, aryl-($C_{1-4}$)alkyl, heteroaryl, cycloalkyl, or heterocyclic ring;
wherein the optional substituents for each optionally substituted alkyl, alkenyl, alkynyl, cycloalkyl, and heterocyclyl, are selected from halo, oxo, CN, hydroxy, amino, $C_{1-4}$ alkyl, $C_{1-4}$ alkoxy, $C_{1-4}$ haloalkyl, $C_{1-4}$ haloalkoxy, ($C_{1-4}$)alkylamino, di($C_{1-4}$)alkylamino, $C_{1-4}$ acylamino, $C_{3-6}$ cycloalkyl, 4-7 membered heterocyclyl, 5-6 membered heteroaryl, $C_{1-4}$ haloalkyl, —S(O)$_q$(C$_{1-4}$)alkyl, —S(O)$_q$(C$_{1-4}$)haloalkyl, —S(O)$_q$(C$_{3-6}$)cycloalkyl, —S(O)$_q$Ar, and —OAr, and two of these substituents on the same atom or on adjacent directly connected atoms can cyclize to form a 3-6 membered cycloalkyl ring, a phenyl ring, or a 5-6 membered heterocyclic ring containing one heteroatom selected from N, O and S, wherein the cycloalkyl, phenyl or heterocyclic ring can be substituted by up to three groups selected from halo, CN, hydroxy, oxo (except not on phenyl), $C_{1-4}$ alkyl, $C_{1-4}$ haloalkyl, —O-G, —COOG, and —C(O)-G, where each G is independently $C_{1-4}$ alkyl;

and the optional substituents for each aryl and heteroaryl ring are independently selected from $C_{1-4}$ alkyl and —(CH$_2$)$_m$-T, where each T is selected from amino, halo, CN, hydroxy, amino, $C_{1-4}$ alkoxy, $C_{1-4}$ haloalkyl, $C_{1-4}$ haloalkoxy, (C$_{1-4}$)alkylamino, di(C$_{1-4}$)alkylamino, $C_{1-4}$ acylamino, $C_{3-6}$ cycloalkyl, 4-7 membered heterocyclyl, 5-6 membered heteroaryl, —S(O)$_p$(C$_{1-4}$)alkyl, —S(O)$_p$(C$_{1-4}$)haloalkyl, Ar, —S(O)$_p$Ar, —OAr, COOR", CONR"$_2$, —NR"C(O)R", and —NR"C(O)OR", where each R" is independently H or $C_{1-4}$ alkyl, wherein m is independently at each occurrence 0, 1 or 2;

and two of these substituents on the same atom or on adjacent directly connected atoms can cyclize to form a 3-6 membered cycloalkyl ring, a phenyl ring, or a 5-6 membered heterocyclic ring containing one heteroatom selected from N, O and S, wherein the cycloalkyl, phenyl or heterocyclic ring can be substituted by up to three groups selected from halo, CN, hydroxy, oxo (except not on phenyl), $C_{1-4}$ alkyl, $C_{1-4}$ haloalkyl, —O-G, —COOG, and —C(O)-G, where each G is independently $C_{1-4}$ alkyl;

each p is independently 0, 1 or 2;
each q is independently 0, 1 or 2; and
each Ar is independently phenyl optionally substituted with up to three groups selected from halo, CN, $C_{1-4}$ alkyl, $C_{1-4}$ haloalkyl, and $C_{1-4}$ alkoxy.

Embodiment I also includes compounds of Formula (I) wherein $R^1$ and $R^2$ are not both H.

In certain implementations of the invention, compounds of Embodiment 1 encompass compounds of formula (IA):

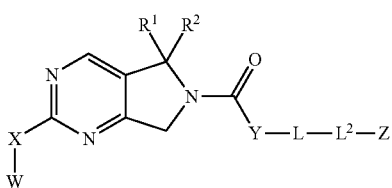

(IA)

or a pharmaceutically acceptable salt thereof, wherein:
$R^1$ is H, COOR', or an optionally substituted $C_{1-4}$ alkyl, $C_{2-4}$ alkenyl, $C_{2-4}$ alkynyl, or $C_{3-6}$ cycloalkyl, where each R' is independently H or $C_{1-4}$ alkyl;
$R^2$ is H or an optionally substituted $C_{1-4}$ alkyl, provided $R^1$ and $R^2$ are not both H;
    or $R^1$ and $R^2$ taken together can optionally form a 3-6 membered cycloalkyl ring, or a 3-6 membered heterocyclic ring containing N, O or S as a ring member, each of which is optionally substituted;
Y is NR$^6$, where R$^6$ is H or optionally substituted $C_{1-4}$ alkyl; or R$^6$ and L taken together with the N to which they are attached form a 5-7 membered heterocyclic group that optionally contains an additional heteroatom selected from N, O and S as a ring member and is substituted with -L$^2$-Z and up to two groups selected from $C_{1-4}$ alkyl, hydroxy, $C_{1-4}$ alkoxy, amino, $C_{1-4}$ alkylamino and di-(C$_{1-4}$ alkyl)amino;
L is a bond or an optionally substituted $C_{3-7}$ cycloalkyl, $C_{5-6}$ heteroaryl, or $C_{4-7}$ heterocyclic ring;
L$^2$ is a divalent linker selected from a bond, —(CR$^3$R$^4$)$_{1-2}$—, —SO$_2$—, and —SO$_2$—CR$^3$R$^4$—;
each R$^3$ and R$^4$ is independently H or $C_{1-4}$ alkyl optionally substituted with up to three groups, or R$^3$ and R$^4$ taken together can form a $C_{3-5}$ cycloalkyl optionally substituted with up to three groups, wherein the up to three groups substituting R$^3$, R$^4$, or R$^3$ and R$^4$ taken together to form a $C_{3-5}$ cycloalkyl, are selected from Me, Et, CF$_3$, F, Cl, hydroxy, methoxy, oxo, amino, methylamino and dimethylamino;
Z is optionally substituted $C_{1-6}$ alkyl, or an optionally substituted 5-10 membered aryl, aryl-(C$_{1-4}$)alkyl, heteroaryl, cycloalkyl, or heterocyclic ring; or when Y is NR$^6$, Z is optionally taken together with R$^6$ to form a 5-6 membered heterocyclic ring that can be substituted with up to two groups selected from Me, Et, CF$_3$, F, Cl, hydroxy, methoxy, oxo, amino, methylamino and dimethylamino;
X is a bond or NR$^5$;
R$^5$ is H or an optionally substituted group selected from $C_{1-4}$ alkyl, 5-6 membered heterocyclic, and 5-6 membered heteroaryl;
W is an optionally substituted group selected from $C_{1-6}$ alkyl, $C_{3-7}$ cycloalkyl, 4-7 membered heterocyclic, aryl, and 5-10 membered heteroaryl;
wherein the optional substituents for each optionally substituted alkyl, alkenyl, alkynyl, cycloalkyl, and heterocyclyl, are selected from halo, oxo, CN, hydroxy, amino, $C_{1-4}$ alkyl, $C_{1-4}$ alkoxy, $C_{1-4}$ haloalkyl, $C_{1-4}$ haloalkoxy, (C$_{1-4}$)alkylamino, di(C$_{1-4}$)alkylamino, $C_{1-4}$ acylamino, COOR$^\#$ or CONR$^\#_2$ where each R$^\#$ is independently H or $C_{1-4}$ alkyl, $C_{3-6}$ cycloalkyl, 4-7 membered heterocyclyl, 5-6 membered heteroaryl, $C_{1-4}$ haloalkyl, —S(O)$_q$(C$_{1-4}$)alkyl, —S(O)$_q$(C$_{1-4}$)haloalkyl, —S(O)$_q$(C$_{3-6}$)cycloalkyl, —S(O)$_q$Ar, and —OAr, and two of these substituents on the same atom or on adjacent directly connected atoms can cyclize to form a 3-6 membered cycloalkyl ring, a phenyl ring, or a 5-6 membered heterocyclic ring containing one heteroatom selected from N, O and S, wherein the cycloalkyl, phenyl or heterocyclic ring can be substituted by up to three groups selected from halo, CN, hydroxy, oxo (except not on phenyl), $C_{1-4}$ alkyl, $C_{1-4}$ haloalkyl, —O-G, —COOG, and —C(O)-G, where each G is independently $C_{1-4}$ alkyl;

and the optional substituents for each optionally substituted aryl and heteroaryl ring are independently selected from $C_{1-4}$ alkyl and —(CH$_2$)$_m$-T, where each T is selected from amino, F, Cl, Br, I, CN, hydroxy, amino, $C_{1-4}$ alkoxy, $C_{1-4}$ haloalkyl, $C_{1-4}$ haloalkoxy, (C$_{1-4}$)alkylamino, di(C$_{1-4}$)alkylamino, $C_{1-4}$ acylamino, $C_{3-6}$ cycloalkyl, 4-7 membered heterocyclyl, 5-6 membered heteroaryl, 4-7 membered heterocyclyl substituted with 1-2 groups selected from $C_{1-4}$ alkyl and oxo, 5-6 membered heteroaryl substituted with 1-2 groups selected from $C_{1-4}$ alkyl and halo, —S(O)$_p$(C$_{1-4}$)alkyl, —S(O)$_p$(C$_{1-4}$)haloalkyl, —S(O)$_p$(C$_{3-7}$)cycloalkyl, Ar, —S(O)$_p$Ar, —OAr, COOR", CONR"$_2$, —NR"C(O)R", and —NR"C(O)OR", where each R" is independently H or $C_{1-4}$ alkyl,
wherein m is independently at each occurrence 0, 1 or 2;

and two of these substituents on the same atom or on adjacent directly connected atoms can cyclize to form a 3-6 membered cycloalkyl ring, a phenyl ring, or a 5-6 membered heterocyclic ring containing one heteroatom selected from N, O and S, wherein the cycloalkyl, phenyl or heterocyclic ring can be substituted by up to three groups selected from halo, CN, hydroxy, oxo (except not on phenyl), $C_{1-4}$ alkyl, $C_{1-4}$ haloalkyl, —O-G, —COOG, and —C(O)-G, where each G is independently $C_{1-4}$ alkyl;

each p is independently 0, 1 or 2;
each q is independently 0, 1 or 2; and
each Ar is independently phenyl optionally substituted with up to three groups selected from halo, CN, $C_{1-4}$ alkyl, $C_{1-4}$ haloalkyl, and $C_{1-4}$ alkoxy.

Subsequent numbered embodiments below suitably refer to each of Formulas (I) and (IA).

2. The compound of embodiment 1 or pharmaceutically acceptable salt thereof, wherein $R^1$ and $R^2$ are each Methyl. In alternative embodiments, $R^1$ is Me and $R^2$ is Et, or $R^1$ and $R^2$ taken together form a cyclopropyl or cyclobutyl ring.

3. The compound of embodiment 1 or embodiment 2, wherein X is NH, or a pharmaceutically acceptable salt thereof. In these embodiments, W is sometimes phenyl, cyclohexyl, or tetrahydropyranyl (e.g., 4-tetrahydrpyranyl), and can be substituted with 1-2 groups selected from $C_{1-4}$ alkyl, halo, hydroxy, $C_{1-4}$ alkoxy, and $C_{1-4}$ haloalkyl.

4. The compound of any of embodiments 1-3, wherein Y is NH, or a pharmaceutically acceptable salt thereof.

5. The compound of any one of embodiments 1 to 4 or a pharmaceutically acceptable salt thereof, $L^2$ is —$(CR^3R^4)_{1,2}$— or —$SO_2$—. In preferred embodiments, $L^2$ is $CHR^3$, $CH_2$ or $SO_2$, particularly when L is a cycloalkyl or heterocyclic ring.

When L is a bond, $L^2$ is often $CR^3R^4$.

6. The compound of any one of embodiments 1 to 5 or a pharmaceutically acceptable salt thereof, wherein $L^2$ is $CR^3R^4$, wherein $R^4$ is H. In such embodiments, $R^3$ is often methyl, hydroxymethyl, aminomethyl, or dimethylaminomethyl.

7. The compound of any one of embodiments 1-5, wherein L is an optionally substituted $C_{3-7}$ cycloalkyl or $C_{4-7}$ heterocyclic ring. In these embodiments, $L^2$ is often $SO_2$ or $CH_2$. Also in these embodiments, Y and $L^2$ are often attached to the same carbon atom of the ring represented by L.

8. The compound of any one of embodiments 1-7, wherein L is a cyclopropane ring or a piperidine ring. When L is a piperidine ring, it is often linked to Y at the 3-position of the piperidine ring, and L is often attached at N of the piperidine ring.

9. The compound of any of embodiments 1-8, wherein Z is an optionally substituted phenyl, cyclohexyl, or pyridinyl ring.

10. The compound of any of embodiments 1-8, wherein Z is an optionally substituted piperidine or tetrahydropyran ring.

11. The compound of any of embodiments 1-10, wherein W is optionally substituted with up to three groups selected from the group consisting of halo, R, CN, —$(CH_2)_{0-2}NR'_2$, —OR', —$SO_2R$, —$SO_2Ph$, and also including oxo (═O) when W is not aromatic; wherein each R is independently $C_{1-4}$ alkyl, $C_{3-6}$ cycloalkyl, or $C_{1-4}$ haloalkyl; each R' is independently H or $C_{1-4}$ alkyl, and two R' attached to the same atom can optionally cyclize to form a 5-6 membered heterocyclic group; and Ph represents phenyl optionally substituted with up to two groups selected from halo, $C_{1-4}$ alkyl, CN, $C_{1-4}$ haloalkyl, $C_{1-4}$ alkoxy, and $C_{1-4}$ alkylsulfonyl. In these embodiments, W is often phenyl, tetrahydropyranyl, or cyclohexyl.

12. The compound of any of embodiments 1-11, wherein optional substituents for Z are selected from the group consisting of halo, R, CN, —$(CH_2)_{0-2}NR'_2$, —OR', —$SO_2R$, and —$SO_2Ph$, and can be oxo (═O) when Z is not aromatic;
wherein each R is independently C—$(CH_2)_{0-2}NR'_2$, alkyl, $C_{3-6}$ cycloalkyl, or C—$(CH_2)_{0-2}NR'_2$, haloalkyl; each R' is independently H or $C_{1-4}$ alkyl, and two R' attached to the same atom can optionally cyclize to form a 5-6 membered heterocyclic group; and Ph represents phenyl optionally substituted with up to two groups selected from halo, $C_{1-4}$ alkyl, CN, $C_{1-4}$ haloalkyl, $C_{1-4}$ alkoxy, and $C_{1-4}$ alkylsulfonyl.

13. The compound of any one of embodiments 1 to 9 or a pharmaceutically acceptable salt thereof, having the Formula II:

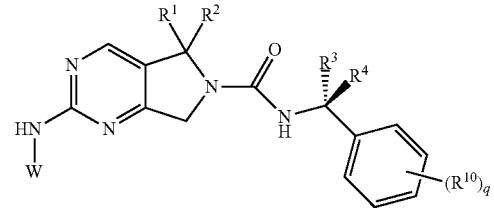

wherein $R^3$ is Me, Et, —$CH_2NH_2$, —$CH_2NHMe$, —$CH_2NMe_2$, or —$CH_2OH$;
$R^4$ is H or Me,
or $R^3$ and $R^4$ taken together form a cyclopropane ring;
q is 0, 1 or 2; and
each $R^{10}$ is individually selected from halo, $C_{1-4}$ alkyl, $C_{1-4}$ haloalkyl, CN, $C_{1-4}$ alkoxy, hydroxy, amino, $C_{1-4}$ alkylsulfonyl, $C_{1-4}$ acylamino, $CONH_2$, and $CONH(C_{1-4})$alkyl.

14. The compound of any one of embodiments 1 to 13 or a pharmaceutically acceptable salt thereof, wherein W is an optionally substituted 5-6 membered heteroaryl or heterocyclic ring.

15. The compound of embodiment 14, wherein W is tetrahydropyranyl or pyridinyl. 4-tetrahydropyranyl is sometimes preferred.

16. The compound of any one of embodiments 1 to 11 or a pharmaceutically acceptable salt thereof, wherein W is an optionally substituted phenyl or 5-6 membered cycloalkyl ring.

17. The compound of any one of embodiments 1-12, which is of the formula:

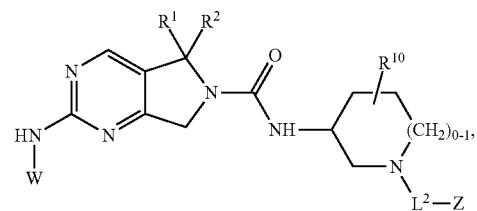

wherein $R^{10}$ represents one or two optional substituents selected from halo, oxy, COOR, $CONR_2$, hydroxy, amino, $C_{1-4}$ alkyl, $C_{1-4}$ haloalkyl, $C_{1-4}$ alkyl-$SO_2$—, $C_{1-4}$ alkoxy, and $C_{1-4}$ alkyl substituted with up to three halo, hydroxy, methoxy, and/or methylsulfonyl groups, where each R is independently H or $C_{1-4}$ alkyl.

18. The compound of embodiment 17, wherein $L^2$ is —$SO_2$— or $CH_2$. In these embodiments, Z is sometimes phenyl substituted with up to three groups selected from halo, methyl, methoxy, and methylsulfonyl.

19. A compound selected from the compounds in Table 1 and the pharmaceutically acceptable salts thereof. Preferred are the compounds in Table 1 having an ERK2 $IC_{50}$ less than 1 micromolar, and particularly those having an ERK2 $IC_{50}$ less than 100 nanomolar.

20. A pharmaceutical composition comprising a compound of any of embodiments 1-19 and at least one pharmaceutically acceptable excipient. In some embodiments, the composition contains at least two pharmaceutically acceptable excipients.

21. A method to treat cancer, comprising administering to a subject in need thereof an effective amount of a compound of any of embodiments 1-19; or a pharmaceutical composition of embodiment 20. In some embodiments, the method is for treatment of a condition selected from adenoma, bladder cancer, brain cancer, breast cancer, colon cancer, epidermal carcinoma, follicular carcinoma, genitourinary cancers, glioblastoma, Hodgkin's disease, non-Hodgkin's lymphoma, hepatoma, head and neck cancers, kidney cancer, lung cancers such as small cell or non-small cell lung cancer, leukemias such as AML or CML, multiple myeloma, lymphoid disorders, skin cancers including melanoma, neuroblastoma, ovarian cancer, pancreatic cancer, prostate cancer, rectal cancer, sarcoma, testicular cancer, and thyroid cancer.

22. The method of embodiment 21, further comprising administering a second therapeutic agent to the subject. Suitable co-therapeutic agents are described herein, and include anticancer compounds, analgesics, and anti-inflammatory compounds.

23. A compound according to any one of embodiments 1 to 19 or a pharmaceutically acceptable salt thereof, for use as a medicament, or for use in the manufacture of a medicament.

24. The compound of embodiment 23 or a pharmaceutically acceptable salt thereof for use as a medicament for (or for use in the manufacture of a medicament for) the treatment of a disorder or disease selected from melanoma, breast cancer, lung cancer, ovarian cancer, colorectal cancer, thyroid cancer, and pancreatic cancer.

25. Use of a compound according to any one of embodiments 1 to 19 or a pharmaceutically acceptable salt thereof in the manufacture of a medicament for the treatment of a disorder or disease selected from adenoma, bladder cancer, brain cancer, breast cancer, colon cancer, epidermal carcinoma, follicular carcinoma, genitourinary cancers, glioblastoma, Hodgkin's disease, non-Hodgkin's lymphoma, hepatoma, head and neck cancers, kidney cancer, lung cancers such as small cell or non-small cell lung cancer, leukemias such as AML or CML, multiple myeloma, lymphoid disorders, skin cancers including melanoma, neuroblastoma, ovarian cancer, pancreatic cancer, prostate cancer, rectal cancer, sarcoma, testicular cancer, and thyroid cancer.

26. The pharmaceutical composition of embodiment 20, further comprising a co-therapeutic agent. Some suitable co-therapeutic agents are named hereinbelow.

27. The pharmaceutical composition of embodiment 26, wherein the co-therapeutic agent is selected from anticancer agents, analgesics, and anti-inflammatory agents.

28. A method to treat cancer, comprising administering to a subject in need of such treatment a therapeutically effective amount of a compound according to any of embodiments 1-19 or a pharmaceutical composition of any of embodiments 20 or 26-27.

29. A compound according to any one of embodiments 1-19 for use in the manufacture of a medicament, which can be a medicament for treating a condition such as adenoma, bladder cancer, brain cancer, breast cancer, colon cancer, epidermal carcinoma, follicular carcinoma, genitourinary cancers, glioblastoma, Hodgkin's disease, non-Hodgkin's lymphoma, hepatoma, head and neck cancers, kidney cancer, lung cancers such as small cell or non-small cell lung cancer, leukemias such as AML or CML, multiple myeloma, lymphoid disorders, skin cancers including melanoma, neuroblastoma, ovarian cancer, pancreatic cancer, prostate cancer, rectal cancer, sarcoma, testicular cancer, or thyroid cancer.

30. A method to prepare a compound of Formula I as described in embodiment 1, which comprises providing a compound of this formula:

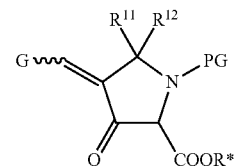

wherein G is —$OR^{14}$ or —$NR^{14}R^{15}$, wherein $R^{14}$ and $R^{15}$ are each independently $C_{1-4}$ alkyl, or $R^{14}$ and $R^{15}$ taken together with N in $NR^{14}R^{15}$ can form a 5-6 membered heterocyclic ring selected from pyrrolidine, piperidine, morpholine, piperazine, and thiomorpholine; where $R^{11}$ and $R^{12}$ are each H or $C_{1-4}$ alkyl, or $R^{11}$ and $R^{12}$ taken together form a cyclopropyl or cyclobutyl ring;

and contacting this compound with a guanidine derivative of the formula Q-C(=NH)—$NH_2$ or a salt thereof, to form a compound of this formula:

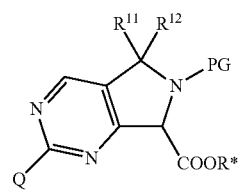

wherein Q is $R^{16}$—S— or $R^{17}$—NH—,
where $R^{16}$ is $C_{1-4}$ alkyl, and $R^{17}$ is an optionally substituted phenyl, heteroaryl, or heterocyclic ring; and R is H or $C_{1-4}$ alkyl. PG represents a nitrogen protecting group, and can be $C_{1-6}$ acyl, $C_{1-6}$ alkoxycarbonyl, or benzyloxycarbonyl.

31. The process of embodiment 30, which further comprises providing a compound of the formula:

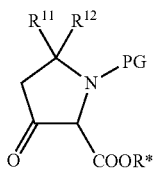

where $R^{11}$, $R^{12}$ and $R^*$ are as defined in embodiment 30, and PG is a nitrogen protecting group;
contacting this compound with a formylating reagent to form a compound of the formula

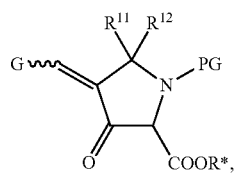

wherein G is $C_{1-4}$ alkoxy or $di(C_{1-4})$alkylamino.

32. A process for preparing a compound of Formula I as described in embodiment 1, which comprises providing a compound of the formula:

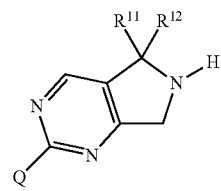

wherein Q is $R^{16}$—S—, wherein $R^{11}$, $R^{12}$ and $R^{16}$ are each independently $C_{1-4}$ alkyl, or $R^{11}$ and $R^{12}$ taken together form a cyclopropyl or cyclobutyl ring;
and acylating the cyclic amine to form a compound of the formula:

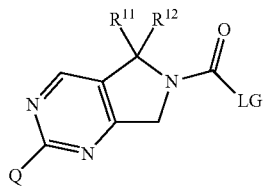

wherein LG is a leaving group such as halo;
or a compound of the formula:

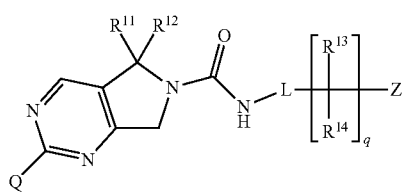

wherein $R^{13}$ and $R^{14}$ are each independently H or an optionally substituted $C_{1-4}$ alkyl;
q is 0, 1 or 2;
L is a bond or an optionally substituted $C_{3-7}$ cycloalkyl or $C_{3-4}$ heterocyclic ring;
and
Z is optionally substituted $C_{1-4}$ alkyl, or an optionally substituted 5-6 membered aryl, aryl-$(C_{1-4})$alkyl, heteroaryl, cycloalkyl, or heterocyclic ring.

33. The process of embodiment 32, further comprising the step of oxidizing the group —$SR^{16}$ to form —$SO_2R^{16}$.

34. A compound of the formula:

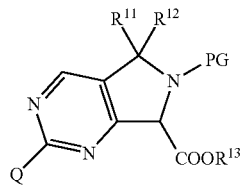

where $R^{11}$, $R^{12}$ and $R^{13}$ are each independently $C_{1-4}$ alkyl, PG is a nitrogen protecting group;
Q is $R^{16}$—$S(O)_{0-2}$— or W—X—, wherein $R^{16}$ is $C_{1-4}$ alkyl;
X is a bond or $NR^5$, where $R^5$ is H or $C_{1-4}$ alkyl; and
W is a group selected from $C_{1-6}$ alkyl, $C_{3-7}$ cycloalkyl, 4-7 membered heterocyclic, and 5-6 membered heteroaryl, optionally substituted with up to two groups selected from halo, $C_{1-4}$ alkyl, CN, $C_{1-4}$ haloalkyl, $C_{1-4}$ alkoxy, and $C_{1-4}$ alkylsulfonyl.

35. A compound of the formula:

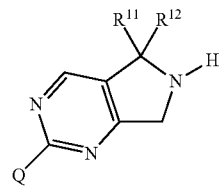

wherein $R^{11}$ and $R^{12}$ are each independently C14 alkyl;
Q is $R^{16}$—S— or W—X—, wherein $R^{16}$ is $C_{1-4}$ alkyl;
X is a bond or $NR^5$, where $R^5$ is H or $C_{1-4}$ alkyl; and
W is a group selected from $C_{1-6}$ alkyl, $C_{3-7}$ cycloalkyl, 4-7 membered heterocyclic, and 5-6 membered heteroaryl, optionally substituted with up to two groups selected from halo, $C_{1-4}$ alkyl, CN, $C_{1-4}$ haloalkyl, $C_{1-4}$ alkoxy, and $C_{1-4}$ alkylsulfonyl.

36. A compound of the formula:

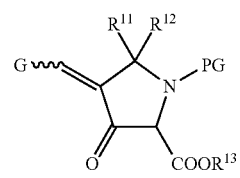

wherein G is —$OR^{14}$ or —$NR^{14}R^{15}$,
$R^{11}$, $R^{12}$, $R^{13}$, $R^{14}$ and $R^{15}$ are each independently $C_{1-4}$ alkyl,
or $R^{14}$ and $R^{15}$ taken together with N in $NR^{14}R^{15}$ can form a 5-6 membered heterocyclic ring selected from pyrrolidine, piperidine, morpholine, piperazine, and thiomorpholine;

and PG is a nitrogen protecting group selected from $C_{1-6}$ acyl, $C_{1-6}$ alkoxycarbonyl, and benzyloxycarbonyl.

Typically, the compounds of formula (I) can be prepared according to the Schemes provided infra. The compounds shown in embodiments 30-36 are all useful for preparing preferred compounds within the scope of Formula (I) and embodiment 1 described above. Related methods are known in the art, see e.g., WO2005/121130, and can be used for guidance for reaction conditions for certain of these steps even though the methods in the reference would not provide the compounds of the present invention without further modification as suggested herein or understood by a practitioner of ordinary skill.

Scheme 1 illustrates a process that can be used to make a wide variety of compounds of Formula I starting with a dialkyl ketone:

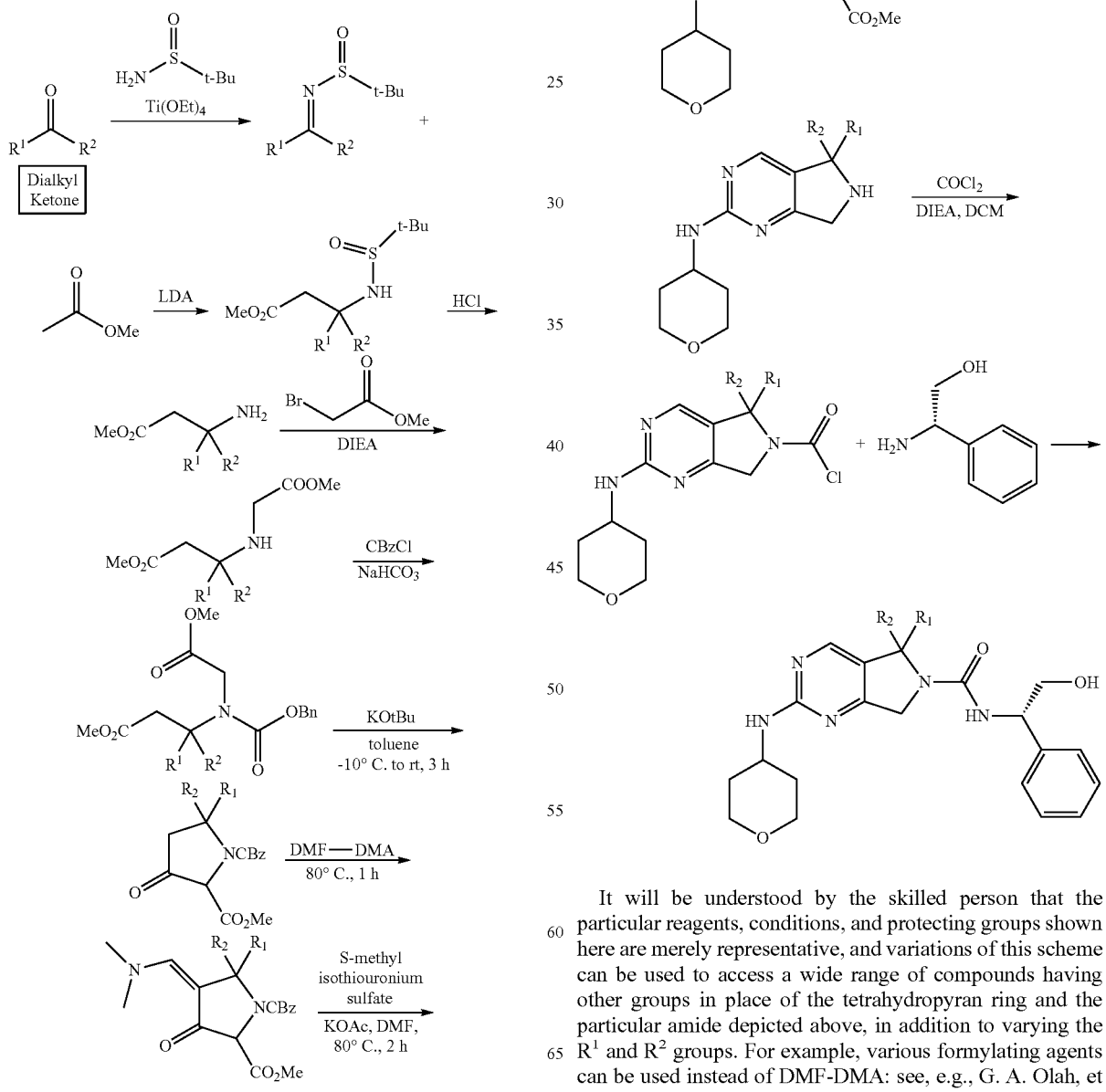

It will be understood by the skilled person that the particular reagents, conditions, and protecting groups shown here are merely representative, and variations of this scheme can be used to access a wide range of compounds having other groups in place of the tetrahydropyran ring and the particular amide depicted above, in addition to varying the $R^1$ and $R^2$ groups. For example, various formylating agents can be used instead of DMF-DMA: see, e.g., G. A. Olah, et al., *Chem. Reviews*, 87(4), 671-686 (1987).

This scheme illustrates the synthesis and subsequent reactions of a highly versatile intermediate:

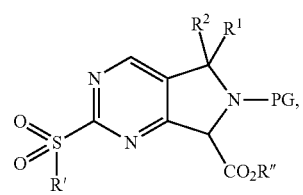

(INT-1)

where R' and R" are C1-C4 alkyl, and PG represents a suitable nitrogen protecting group such as —COOR*, where R* is C1-C6 alkyl (especially Me, Et, iPr, tBu), aryl, or arylalkyl such as benzyl. Accordingly, this intermediate is another aspect of the invention, which is useful for preparation of compounds of Formula I as demonstrated herein. In these compounds of Formula INT-1, $R^1$ is H, CN, COOR', CONR'$_2$, or an optionally substituted $C_{1-4}$ alkyl, $C_{2-4}$ alkenyl, or $C_{2-4}$ alkynyl, where each R' is independently H or $C_{1-4}$ alkyl; $R^2$ is H, CN, or an optionally substituted $C_{1-4}$ alkyl; or $R^1$ and $R^2$ taken together can optionally form a 3-6 membered cycloalkyl ring, or a 3-6 membered heterocyclic ring containing N, O or S as a ring member, each of which is optionally substituted as described for compounds of Formula (I).

A wide variety of W—X— groups can be introduced using $S_NAr$ chemistry to replace the activated alkylsulfonyl group ($R'$—$SO_2$—) of (INT-1), providing access to various compounds of Formula I where X is NH or NMe, for example, and to heterocyclic groups attached via a ring nitrogen atom, such as piperidine, pyrrolidine, morpholine, and the like. Similarly, by removing the PG group and making the carbamyl chloride as illustrated above, a wide variety of N, O and S nucleophiles can be used to introduce a wide variety of —YL-$L^2$-Z or —Y-L-$(CR^3R^4)_n$—Z substituents wherein Y is NH or NMe, for example.

Scheme 2 illustrates the synthesis of compounds of Formula I wherein $R^1$ or $R^2$ is CN; such compounds can be further used to make compounds of the invention wherein $R^1$ or $R^2$ is an ester, carboxylate, amide, or methyl group substituted with $NH_2$ or alkoxy groups, as well as formyl and alkenyl and alkynyl groups. Various formylating agents can be used in the second step; see, e.g., G. A. Olah, et al., *Chem. Reviews*, 87(4), 671-686 (1987).

Scheme 2.

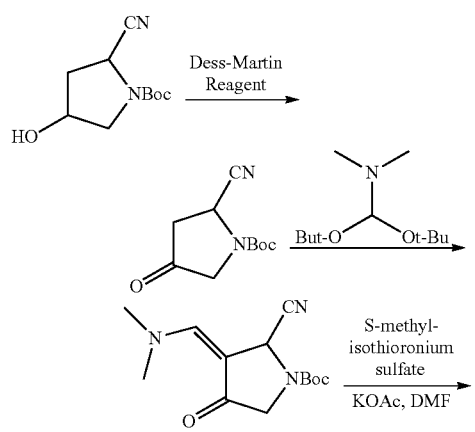

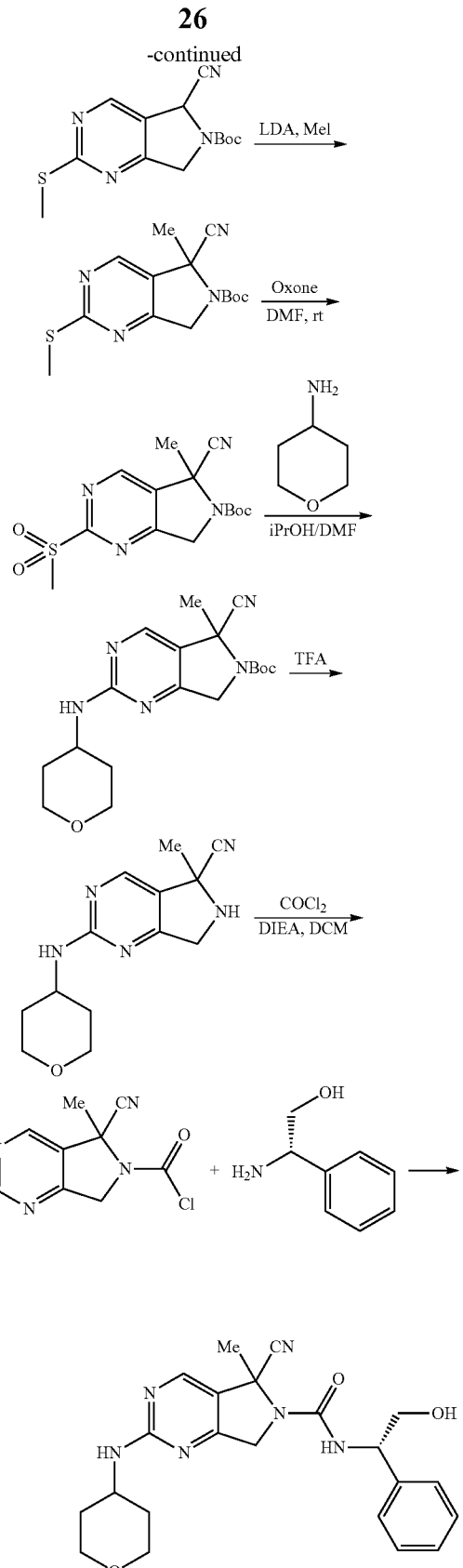

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

In another aspect, the invention provides intermediates and processes especially well-suited for making the compounds of Formula I and IA. The compounds of Formula I and IA can be prepared from a versatile pyrimidino-pyrrolidine intermediate by the following general route:

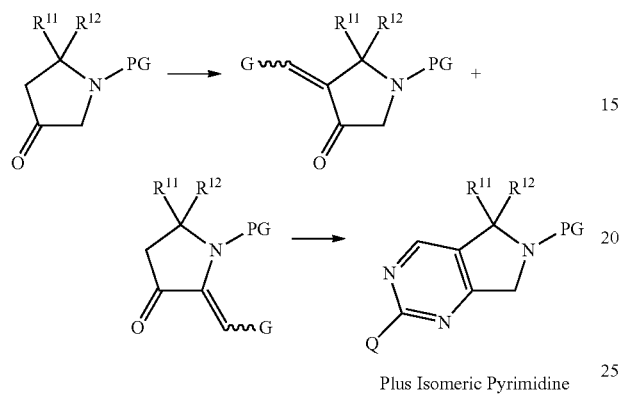

Plus Isomeric Pyrimidine

The starting material is readily prepared by Claisen condensation as shown herein, followed by hydrolysis and decarboxylation. The methylenation of the keto-pyrrolidine typically involves treatment with a formylation reagent such as dimethylformamide or an acetal of a dialkyl formamide as illustrated above with the di-t-butoxy acetal of DMF. The reaction can be accomplished thermally and it may be catalyzed by a Lewis acid or dehydrating agent such as $POCl_3$ under Vilsmeier reaction conditions (G=—$NMe_2$). Once the formylation reaction is performed, the enaminone can be reacted with an amidine or guanidine species to provide a compound with a desired Q group. In the examples herein, alkyl isothiouronium is used to produce intermediates where Q is an alkylthio group, and a heteroaryl guanidinium is used to produce intermediates where Q is Het-NH— (Het represents a desired heteroaryl group).

Any suitable N-protecting group (PG) can be used, so deprotection conditions can be selected to be compatible with various substitutions of Q; selection of such protecting groups is well within the level of ordinary skill in the art. Activated amides (trichloroacetamide, trifluoroacetamide) and carbamates such as t-butyl or benzyl carbamate are particularly useful as protecting groups in this process.

An alternative method for making the versatile pyrimidinyl intermediate for this synthesis avoids formation of the isomeric pyrimidine ring, by retaining the ester group during the formylation step:

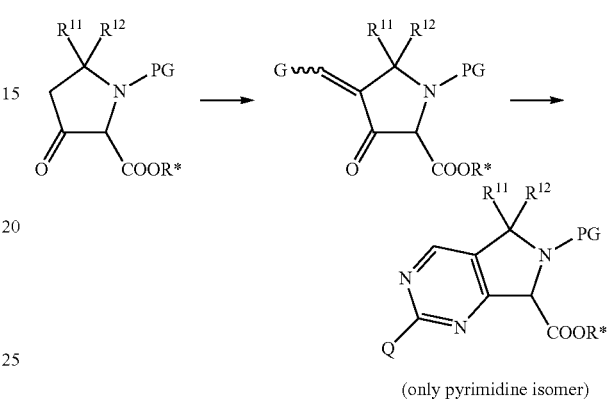

(only pyrimidine isomer)

The starting material for this can be made by a Claisen condensation, without decarboxylation. By retaining the ester, the regiochemistry of the formylation was completely controlled, eliminating formation of the isomeric pyrimidine: otherwise the sequence is the same as above. The ester can readily be hydrolyzed and removed by decarboxyation after cyclization to form the pyrimidine ring, before, after or concurrently with deprotection, depending largely upon the selection of the protecting group PG.

Using this versatile intermediate, compounds of Formula I can be prepared by deprotection of the amine and decarboxylation followed by N-acylation to install the Z— containing group before installing the W—X— group. Alternatively, the W—X— group can be attached first by replacing Q using $S_NAr$ chemistry, and the deprotection, decarboxylation and N-acylation can be done later.

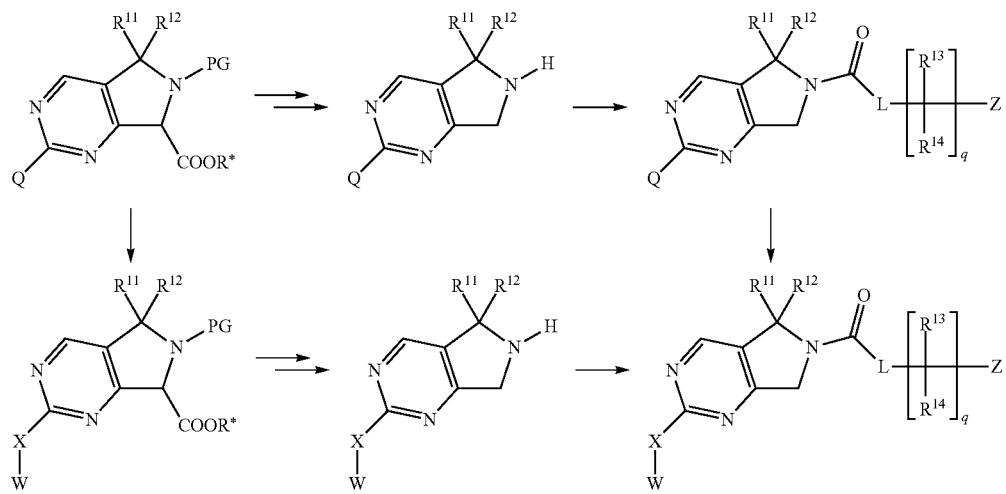

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and at least one pharmaceutically acceptable carrier. The pharmaceutical composition can be formulated for particular routes of administration such as oral administration, parenteral administration, and rectal administration, and the like. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with one or more carriers or one or more of the following excipients:
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Selection of suitable capsules for encapsulation and of suitable excipients for formulating the compound of Formula I to make oral dosage forms is within the ordinary level of skill. Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives. As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in salt form, exhibit valuable pharmacological properties, e.g. they modulate or inhibit activity of ERK1 and/or ERK2, as indicated by test data provided in the following sections, and are therefore indicated for therapy as described herein, or for use as research chemicals, e.g. as tool compounds to further the understanding of the effects of EKR1/2 inhibition or inhibition of a biochemical pathway (MAPK).

Thus, as a further embodiment, the present invention provides the use of a compound of formula (I) or any of the embodiments within the scope of Formula (I) as described herein, in therapy, or for the manufacture of a medicament. In a further embodiment, the therapy or medicament is for a disease which may be treated by inhibition of ERK1 and/or ERK2. In another embodiment, the compounds of the invention are useful to treat cancers, including but not limited to those mentioned herein.

In some embodiments, the compounds are used in combination with one or more co-therapeutic agents. Suitable co-therapeutic agents include anticancer agents, analgesics, anti-inflammatory agents, and the like. In some embodiments, the compositions include a co-therapeutic agent that acts on the RAF pathway, such as a B-RAF inhibitor or a C-Raf inhibitor.

In another embodiment, the invention provides a method of treating a disease which is treatable by inhibition of ERK1 and/or ERK2, comprising administration of a therapeutically effective amount of a compound of formula (I) or (IA) or any of the embodiments of the invention as described herein. In a further embodiment, the disease is selected from the afore-mentioned lists of suitable conditions. The method typically comprises administering an effective amount of a compound as described herein or a pharmaceutical composition comprising such compound to a subject in need of such treatment. The compound may be administered by any suitable method such as those described herein, and the administration may be repeated at intervals selected by a treating physician. The invention thus provides a compound of Formula I and IA or any subgenus thereof as described herein for use to treat a condition mediated by or associated with excessive or undesired levels of ERK1/2 activity, including those mentioned above.

Thus, as a further embodiment, the present invention provides the use of a compound of formula (I), or any of the embodiments of such compounds described herein, for the manufacture of a medicament. In a further embodiment, the medicament is for treatment of a disease which may be treated by inhibition of ERK1 and/or ERK2. In another embodiment, the disease is a cancer, e.g., a cancer selected from the aforementioned list, suitably.

The pharmaceutical composition or combination of the present invention can be in unit dosage of about 0.1-1000 mg of active ingredient(s) for a subject of about 50-70 kg, or about 10-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range, depending on the route of administration, between about 0.1-500 mg/kg, or between about 0.1-50 mg/kg.

The activity of a compound according to the present invention can be assessed by the in vitro and in vivo methods described herein and by conventional methods known in the art.

The compound of the present invention may be administered either simultaneously with, or before or after, one or more co-therapeutic agent(s). The compound of the present invention may be administered separately, by the same or different route of administration, or together in the same pharmaceutical composition as the co-agent(s).

In one embodiment, the invention provides a product comprising a compound of formula (I) and at least one other therapeutic co-agent as a combined preparation for simultaneous, separate or sequential use in therapy. In one embodiment, the therapy is the treatment of a disease or condition mediated by ERK1 and/or ERK2, such as cancer. Products provided as a combined preparation include a composition comprising the compound of formula (I) and one or more co-therapeutic agent(s) together in the same pharmaceutical composition, or the compound of formula (I) and the other co-therapeutic agent(s) in separate form, e.g. in the form of a kit.

In one embodiment, the invention provides a pharmaceutical composition comprising a compound of formula (I) and at least one co-therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic co-agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by ERK1 and/or ERK2, wherein the medicament is prepared for administration with another therapeutic agent. The invention also provides the use of another co-therapeutic agent for treating a disease or condition, wherein the co-agent is administered with a compound of formula (I).

The invention also provides a compound of formula (I) for use in a method of treating a disease or condition mediated by ERK1 and/or ERK2, wherein the compound of formula (I) is prepared for administration with another therapeutic agent. The invention also provides another therapeutic co-agent for use in a method of treating a disease or condition mediated by ERK1 and/or ERK2, wherein the other therapeutic co-agent is prepared for administration with a compound of formula (I). The invention also provides a compound of formula (I) for use in a method of treating a disease or condition mediated by ERK1 and/or ERK2, wherein the compound of formula (I) is administered with another therapeutic co-agent. The invention also provides another co-therapeutic agent for use in a method of treating a disease or condition mediated by ERK1 and/or ERK2, wherein the other therapeutic co-agent is administered with a compound of formula (I).

The invention also provides the use of a compound of formula (I) for treating a disease or condition mediated by ERK1 and/or ERK2, wherein the patient is one treated previously or subsequently (e.g. within 24 hours) with another therapeutic agent. The invention also provides the use of a co-therapeutic agent for treating a disease or condition mediated by ERK1 and/or ERK2, wherein the patient has previously (e.g. within 24 hours) been treated with a compound of formula (I).

In one embodiment, the other therapeutic agent (co-therapeutic agent) is a compound useful for treating a cancer, and is typically an FDA approved drug approved for treating at least one type of cancer. Suitable co-therapeutic agents include erlotinib, bortezomib, fulvestrant, sunitib imatinib mesylate, letrozole, finasunate, platins such as oxaliplatin, carboplatin, and cisplatin, finasunate, fluorouracil, rapamycin, leucovorin, lapatinib, lonafamib, sorafenib, gefitinib, capmtothecin, topotecan, bryostatin, adezelesin, anthracyclin, carzelesin, bizelesin, dolastatin, auristatins, duocarmycin, eleutherobin, taxols such as paclitaxel or docetaxel, cyclophasphamide, doxorubicin, vincristine, prednisone or prednisolone, other alkylating agents such as mechlorethamine, chlorambucil, and ifosfamide, antimetabolites such as azathioprine or mercaptopurine, other microtubule inhibitors (vinca alkaloids like vincristine, vinblastine, vinorelbine and vindesine, as well as taxanes), podophyllotoxins (etoposide, teniposide, etoposide phosphate, and epipodophyllotoxins), topoisomerase inhibitors, other cytotoxins such as actinomycin, daunorubicin, valrubicin, idarubicin, edrecolomab, epirubicin, bleomycin, plicamycin, mitomycin, as well as other anticancer antibodies (cetuximab, bevacizumab, ibritumomab, abagovomab, adecatumumab, afutuzumab, alacizumab, alemtuzumab, anatumomab, apolizumab, bavituximab, belimumab, bivatuzumab mertansine, blinatumomab, brentuximab vedotin, cantuzumab mertansine, catumazomab, cetuximab, citatuzumab bogatox, cixutumumab, clivatuzumab tetraxetan, conatumumab, dacetuzumab, daclizumab, detumomab, ecromeximab, edrecolomab, elotuzumab, epratuzumab, ertumaxomab, etaracizumab, farletuzumab, figitumumab, fresolimumab, galiximab, gembatumumab vedotin, gemtuzumab, ibritumomab tiuxetan, inotuzumab ozogamicin, intetumumab, ipilimumab, iratumumab, labetuzumab, lexatumumab, lintuzumab, lucatumumab, lumilisimab, mapatumumab, matuzumab, milatuzumab, mitumomab, nacolomab tafenatox, naptumomab estafenatox, necitumumab, nimotuzumab, ofatumumab, olaratumab, oportuzumab monatox, oregovomab, panitumumab, pemtumomab, pertuzumab, pintumomab, pritumumab, ramucirumab, rilotumumab, robatumumab, rituximab, sibrotuzumab, tacatuzumab tetraxetan, taplitumomab paptox, tenatumomab, ticilimumab, tigatuzumab, tositumomab or $^{131}$I-tositumomab, trastuzumab, tremelimumab, tuocotuzumab celmoleukin, veltuzumab, visilizumab, volocixumab, votumumab, zalutumumab, zanolimumab, IGN-101, MDX-010, ABX-EGR, EMD72000, ior-t1, MDX-220, MRA, H-11 scFv, huJ591, TriGem, TriAb, R$^3$, MT-201, G-250, ACA-125, Onyvax-105, CD:-960, Cea-Vac, Breva-Rex AR54, IMC-1C11, GlioMab-H, ING-1, anti-LCG MAbs, MT-103, KSB-303, Therex, KW2871, anti-HMI.24, Anti-PTHrP, 2C4 antibody, SGN-30, TRAIL-RI MAb, Prostate Cancer antibody, H22xKi-r, ABX-Mai, Imuteran, Monopharm-C), and antibody-drug conjugates comprising any of the above agents (especially auristatins MMAE and MMAF, maytansinoids like DM-1, calicheamycins, or various cytotoxins).

Compounds of Formula I can be prepared by methods described below. The Schemes provide general methods for preparing the compounds of Formula I, and the Examples provide specific guidance from which a person of ordinary skill may make other compounds of Formula I.

The following Examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (20-133 mbar). If not specified otherwise, chromatographic separations use commercially available grades of silica gel. The structures of final products, intermediates and starting materials were confirmed by standard analytical methods, including mass spectral properties, HPLC retention times, and in some cases via microanalysis and spectroscopic characteristics, e.g., MS, IR, NMR.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4th Ed. 1952, METHODS OF ORGANIC SYNTHESIS, THIEME, Volume 21). Further, the compounds of the present invention can be produced by organic synthesis methods known to one of ordinary skill in the art in view of the following examples.

The compounds and/or intermediates were characterized by high performance liquid chromatography (HPLC) using a Waters Millennium chromatography system with a 2695 Separation Module (Milford, Mass.). The analytical columns were reversed phase Phenomenex Luna C18 –5µ, 4.6×50 mm, from Alltech (Deerfield, Ill.). A gradient elution was used (flow 2.5 mL/min), typically starting with 5% acetonitrile/95% water and progressing to 100% acetonitrile over a period of 10 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.).

Mass spectrometric analysis was performed on a Waters System (Waters Acquity UPLC and a Waters SQD mass spectrometer detector; Column: Phenomenex Kinetex 2.6 um C18, column size 4.6×50 mm; column temperature 50° C. gradient: 2-98% acetonitrile in water with 0.1% TFA over a 1.5 min period; flow rate 1.2 mL/min (or Polar gradient 1-0% over 1.3 min, NonPolar gradient 55-30% over 1.3 min); Mass Spectrometer molecular weight scan range 150-850; or 150-1900. cone Voltage 20 V. All masses were reported as those of the protonated parent ions. Nuclear magnetic resonance (NMR) analysis was performed on selected compounds, using a Varian 400 MHz NMR (Palo Alto, Calif.). The spectral reference was either TMS or the known chemical shift of the solvent.

Abbreviations used herein have their ordinary meaning in the art unless otherwise indicated or defined in the following list:
ACN acetonitrile
ATP adenosine 5'-triphosphate
BINAP racemic 2,2'-bis(diphenylphosphino)-1,1'-binaphthyl
BOC tertiary butyl carboxy
br broad
BSA bovine serum albumin
d doublet
dd doublet of doublets
DCM dichloromethane
DIEA diethylisopropylamine
DMA N,N-dimethylacetamide
DME 1,4-dimethoxyethane
DMF N,N-dimethylformamide
DMSO dimethylsulfoxide
DTT dithiothreitol
EDTA ethylenediamine tetraacetic acid
ESI electrospray ionization
EtOAc ethyl acetate
FCC flash column chromatography
h hour(s)
HBTU 1-[bis(dimethylamino)methylene]-1H-benzotriazolium hexafluorophosphate(1-) 3-oxide
HOBt 1-hydroxy-7-azabenzotriazole
HPLC high pressure liquid chromatography
LCMS liquid chromatography and mass spectrometry
MeOH methanol
MS mass spectrometry
MTBE Methyl t-butyl ether
MW microwave
m multiplet
mL milliliter(s)
m/z mass to charge ratio
NMP N-methyl pyrrolidinone
ppm parts per million
PyBOP benzotriazol-1-yloxytripyrrolidinophosphonium hexafluorophosphate
rac racemic
rt room temperature
s singlet
t triplet
TFA trifluoroacetic acid
THF tetrahydrofuran
Tris.HCl aminotris(hydroxymethyl)methane hydrochloride
Method 1.

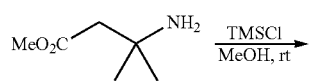

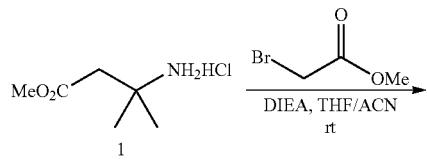

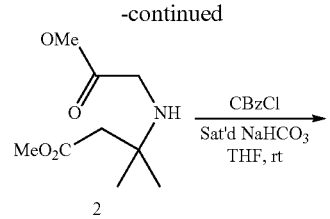

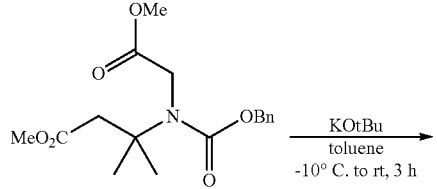

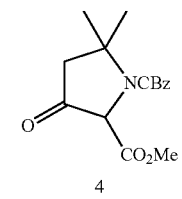

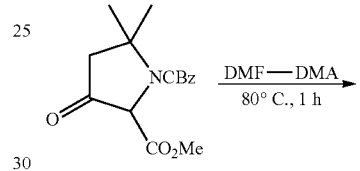

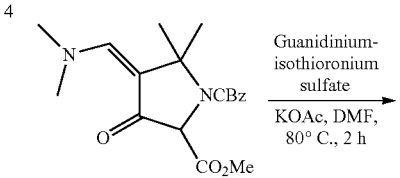

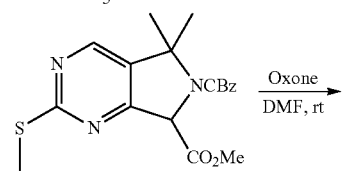

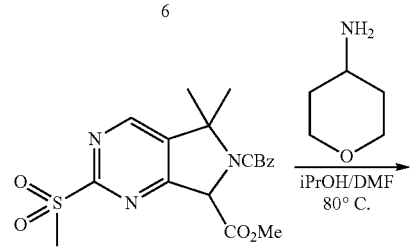

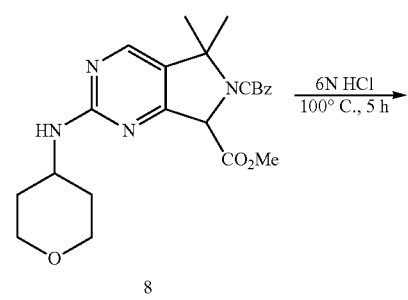

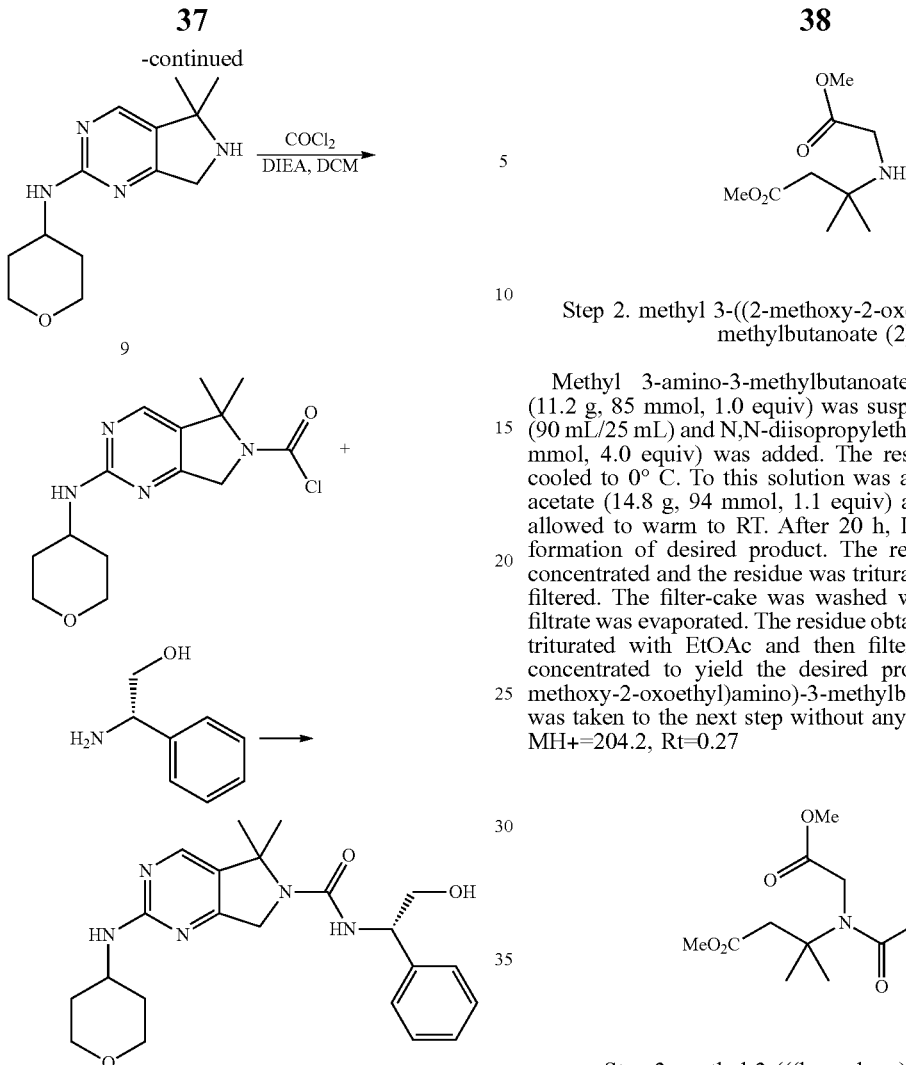

Example 1

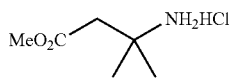

Step 1. Methyl 3-amino-3-methylbutanoate hydrochloride (1)

3-Amino-3-Methyl-butyric acid (10.0 g, 85 mmol, 1.0 equiv) was charged into a RB-flask. At RT, TMSCI (18.6 g, 171 mmol, 2.0 equiv) was then added slowly. This was followed by slow addition of MeOH (85 mL) and the mixture was let to stir overnight. The next morning, LCMS indicated the formation of desired methylester adduct. The reaction mixture was concentrated in vacuo and the residue placed under high vacuum for 2 h upon which it solidified. The product 1 (methyl 3-amino-3-methylbutanoate hydrochloride) was taken to the next step without any further purification. MH+=132.4, Rt=0.24

Step 2. methyl 3-((2-methoxy-2-oxoethyl)amino)-3-methylbutanoate (2)

Methyl 3-amino-3-methylbutanoate hydrochloride, 1 (11.2 g, 85 mmol, 1.0 equiv) was suspended in ACN/THF (90 mL/25 mL) and N,N-diisopropylethylamine (43.5 g, 340 mmol, 4.0 equiv) was added. The resulting solution was cooled to 0° C. To this solution was added methylbromoacetate (14.8 g, 94 mmol, 1.1 equiv) and the mixture was allowed to warm to RT. After 20 h, LCMS indicated the formation of desired product. The reaction mixture was concentrated and the residue was triturated with EtOAc and filtered. The filter-cake was washed with EtOAc and the filtrate was evaporated. The residue obtained was once again triturated with EtOAc and then filtered and the filtrate concentrated to yield the desired product methyl 3-((2-methoxy-2-oxoethyl)amino)-3-methylbutanoate 2 which was taken to the next step without any further purification. MH+=204.2, Rt=0.27

Step 3. methyl 3-(((benzyloxy)carbonyl)(2-methoxy-2-oxoethyl)amino)-3-methylbutanoate (3)

Methyl 3-((methoxycarbonyl)amino)-3-methylbutanoate 2, (17.2 g, 85 mmol, 1.0 equiv) was suspended in a mixture of THF (95 mL) and Saturated NaHCO3 (95 mL) and the resulting slurry was cooled to 0° C. Benzylchloroformate (21.8 g, 128 mmol, 1.5 equivalent) was added dropwise and the reaction was let to warm to room temperature and stir overnight. The next morning, LCMS indicated the formation of desired product MH+=338, Rt=0.92. The reaction mixture was concentrated in vacuo and the residue partitioned between EtOAc and water. The aqueous layer was separated and extracted with EtOAc and the combined organic extracts were dried over anhydrous MgSO4, filtered and concentrated in vacuo, and the residue was purified by flash chromatography (0-20% EtOAc/heptanes) to give 17.4 g of the desired product methyl 3-(((benzyloxy)carbonyl)(2-methoxy-2-oxoethyl)amino)-3-methylbutanoate 3. MH+=338, Rt=0.92

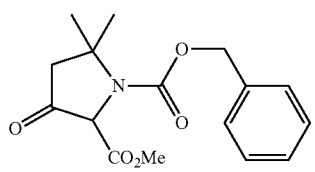 [SMILES: COC(=O)C1C(=O)CC(C)(C)N1C(=O)OCc1ccccc1]

Step 4. 1-Benzyl 2-methyl 5,5-dimethyl-3-oxopyrrolidine-1,2-dicarboxylate (4)

To a suspension of KOtBu (3.98 g, 35.5 mmol, 1.35 equiv) in toluene (74 mL) at −10° C. was added Methyl 3-((benzyloxycarbonyl)(methoxycarbonyl)amino)-3-methylbutanoate 3 in toluene (80 mL) and the reaction was warmed to RT and stirred for 3 h. LCMS showed consumption of starting material and formation of the desired product. The reaction mixture was neutralized to pH 7 and the organic layer was separated. The organic layer was dried over anhydrous MgSO4 and concentrated in vacuo. The residue was purified by flash chromatography (0-20% EtOAc/heptanes) to give 3.67 g of the desired product, Benzyl 2-methyl 5,5-dimethyl-3-oxopyrrolidine-1,2-dicarboxylate 4. MH+=306.2, Rt=0.88

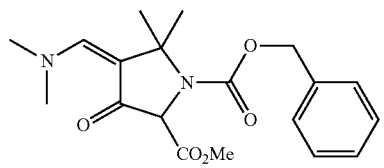 [SMILES: COC(=O)C1C(=O)/C(=C\N(C)C)C(C)(C)N1C(=O)OCc1ccccc1]

Step 5. (Z)-1-benzyl 2-methyl 4-((dimethylamino)methylene)-5,5-dimethyl-3-oxopyrrolidine-1,2-dicarboxylate (5)

1-Benzyl 2-methyl 5,5-dimethyl-3-oxopyrrolidine-1,2-dicarboxylate (6.2 g, 20.3 mmol, 1.0 equiv) was dissolved in DMF-DMA (44.5 g, 373 mmol, 18.3 equiv) and the mixture was heated to 80° C. for 1 h upon which LCMS indicated formation of the desired enaminone. The mixture was concentrated and the residue (Z)-1-benzyl 2-methyl 4-((dimethylamino)methylene)-5,5-dimethyl-3-oxopyrrolidine-1,2-dicarboxylate 5 taken as such to the next step. MH+=361.6, Rt=0.81

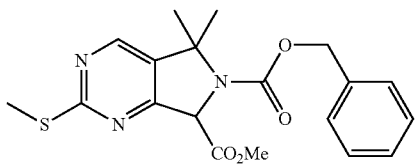 [SMILES: COC(=O)C1c2nc(SC)ncc2C(C)(C)N1C(=O)OCc1ccccc1]

Step 6. 6-benzyl 7-methyl 5,5-dimethyl-2-(methylthio)-5H-pyrrolo[3,4-d]pyrimidine-6,7(7H)-dicarboxylate (6)

The residue from Step 5 (20.3 mmol, 100% theoretical yield) was dissolved in DMF (45 mL) and to the solution was added KOAc (5.99 g, 61.1 mmol, 3.0 equiv) and then S-Methyl-isothiouronium sulfate (7.34 g, 20.36 mmol, 1.5 equiv) and the mixture was heated at 90° C. for 2 h. LCMS indicated the formation of desired product. The reaction mixture was cooled to room temperature and diluted with water and extracted with EtOAc. The combined organic extract was washed with water and dried over anhydrous MgSO4, filtered and concentrated in vacuo. The residue was purified by flash chromatography (0-20% EtOAc/heptanes) to provide 4.6 g of the desired product 6-benzyl 7-methyl 5,5-dimethyl-2-(methylthio)-5H-pyrrolo[3,4-d]pyrimidine-6,7(7H)-dicarboxylate 6 as yellow syrup. MH+=388.1, Rt=1.03

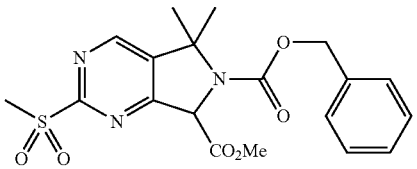 [SMILES: COC(=O)C1c2nc(S(C)(=O)=O)ncc2C(C)(C)N1C(=O)OCc1ccccc1]

Step 7. 6-benzyl 7-methyl 5,5-dimethyl-2-(methylsulfonyl)-5H-pyrrolo[3,4-d]pyrimidine-6,7(7H)-dicarboxylate (7)

6-benzyl 7-methyl 5,5-dimethyl-2-(methylthio)-5H-pyrrolo[3,4-d]pyrimidine-6,7(7H)-dicarboxylate (4.56 g, 11.6 mmol, 1.0 equiv) was dissolved in DMF (31 mL) and to the solution at RT was added Oxone (18.1 g, 29.4 mmol, 2.5 equiv). The heterogeneous mixture was stirred for 3 h upon which LCMS indicated complete consumption of the starting material and formation of the desired product. The mixture was diluted with water and extracted with EtOAc and the combined organic extract was washed with water and dried over anhydrous MgSO4, filtered and concentrated in vacuo to yield colorless syrup. The residue was purified by flash chromatography (0-60% EtOAc/heptanes) to yield 4.8 g of the desired product 6-benzyl 7-methyl 5,5-dimethyl-2-(methylsulfonyl)-5H-pyrrolo[3,4-d]pyrimidine-6,7(7H)-dicarboxylate 7 as a gummy colorless syrup which solidified upon standing. MH+=420.2, Rt=0.85

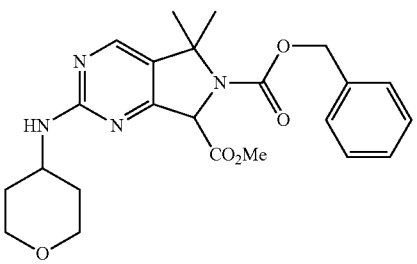 [SMILES: COC(=O)C1c2nc(NC3CCOCC3)ncc2C(C)(C)N1C(=O)OCc1ccccc1]

Step 8. 6-benzyl 7-methyl 5,5-dimethyl-2-((tetrahydro-2H-pyran-4-yl)amino)-5H-pyrrolo[3,4-d]pyrimidine-6,7(7H)-dicarboxylate (8)

6-benzyl 7-methyl 5,5-dimethyl-2-(methylsulfonyl)-5H-pyrrolo[3,4-d]pyrimidine-6,7(7H)-dicarboxylate (3.31 g, 7.81 mmol, 1.0 equiv) was dissolved in iPrOH/DMF (30 mL/5 mL) and 4-aminotetrahydropyran (3.99 g, 39.4 mmol, 5.0 equiv) was added in one portion. The resulting mixture was heated to 80° C. overnight. The next morning, LCMS of the reaction mixture indicated formation of the desired product. The reaction mixture was cooled to room temperature and diluted with EtOAc and washed with water. The organic layer was dried over anhydrous MgSO4, filtered and concentrated in vacuo to yield syrup. The residue was purified by flash chromatography (0-60% EtOAc/heptanes) to yield 2.3 g of the desired product 6-benzyl 7-methyl 5,5-dimethyl-2-((tetrahydro-2H-pyran-4-yl)amino)-5H-pyrrolo[3,4-d]pyrimidine-6,7(7H)-dicarboxylate 8 as a gummy colorless syrup.

MH+=441.3, Rt=0.89.

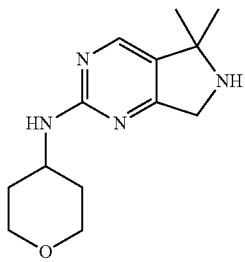 [SMILES: CC1(C)NCc2nc(NC3CCOCC3)ncc21]

Step 9. 5,5-dimethyl-N-(tetrahydro-2H-pyran-4-yl)-6,7-dihydro-5H-pyrrolo[3,4-d]pyrimidin-2-amine (9)

6-benzyl 7-methyl 5,5-dimethyl-2-((tetrahydro-2H-pyran-4-yl)amino)-5H-pyrrolo[3,4-d]pyrimidine-6,7(7H)-dicarboxylate (2.3 g, 5.22 mmol) was suspended in 6 N HCl (100 mL) and the mixture was heated at 100° C. for 5 h. LCMS at this stage indicated complete deprotection of the CBz group as well as decarboxylation of the methylester. The reaction mixture was cooled to room temperature and washed with Ether and the aqueous layer was basified to pH 8 with solid $Na_2CO_3$ and the product was extracted with EtOAc and was dried over anhydrous $MgSO_4$, filtered and concentrated in vacuo to yield 1.28 g of the desired product 5,5-dimethyl-N-(tetrahydro-2H-pyran-4-yl)-6,7-dihydro-5H-pyrrolo[3,4-d]pyrimidin-2-amine 9 as a yellow solid. MH+=249.2, Rt=0.55

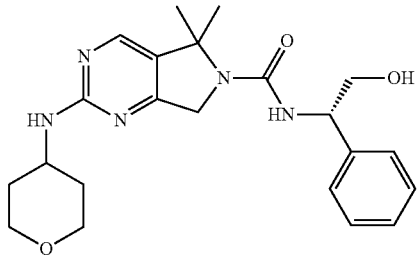 [SMILES: CC1(C)c2cnc(NC3CCOCC3)nc2CN1C(=O)N[C@H](CO)c1ccccc1]

Step 10. (S)—N-(2-hydroxy-1-phenylethyl)-5,5-dimethyl-2-((tetrahydro-2H-pyran-4-yl)amino)-5H-pyrrolo[3,4-d]pyrimidine-6(7H)-carboxamide (10)

To a flame-dried flask was charged phosgene (0.048 mL [15 wt % in toluene], 0.092 mmol, 1.1 equiv) and DCM (0.5 mL) and the solution was cooled to 0° C. DIEA (0.029 mL, 0.167 mmol, 2.0 equiv) was added next. This was followed by addition of 5,5-dimethyl-N-(tetrahydro-2H-pyran-4-yl)-6,7-dihydro-5H-pyrrolo[3,4-d]pyrimidin-2-amine (20.7 mg, 0.083 mmol, 1.0 equiv) in DCM (0.5 mL). After 5 minute, phosgene (0.048 mL [15 wt % in toluene], 0.092 mmol, 1.1 equiv) was added again and then after 3 minutes, LCMS indicated the formation of desired carbamoyl chloride intermediate MH+=311.2, Rt=0.68. The reaction mixture was quenched by addition of water and the product extracted with DCM, and the combined organic extract was dried over anhydrous MgSO4, filtered and concentrated in vacuo to yield the crude intermediate, which was dissolved in DCM (1.0 mL). To this solution at room temperature was added DIEA (0.044 mL, 0.250 mmol, 3.0 equiv) and then (S)-2-amino-2-phenylethanol (17.2 mg, 0.125 mmol, 1.5 equiv). The reaction mixture was stirred overnight. The next morning LCMS indicated formation of desired product. The reaction mixture was concentrated in vacuo, and the residue purified by reverse phase preparatory LC to provide 15.8 mg of the desired product (S)—N-(2-hydroxy-1-phenylethyl)-5,5-dimethyl-2-((tetrahydro-2H-pyran-4-yl)amino)-5H-pyrrolo[3,4-d]pyrimidine-6(7H)-carboxamide 10 as the TFA adduct. MH+=412.2, Rt=0.58. 1 H-NMR δ (ppm) 8.11 (s, 1H), 7.20-7.35 (m, 4H), 7.14 (d, J=7.04 Hz, 1H), 4.81-4.91 (m, 1H), 4.56 (d, J=1.96 Hz, 2H), 3.84-4.04 (m, 3H), 3.60-3.78 (m, 2H), 3.35-3.54 (m, 2H), 1.88 (d, J=10.17 Hz, 2H), 1.46-1.70 (m, 8H).

Method 2.

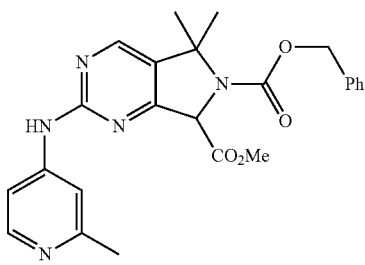 [SMILES: COC(=O)C1c2nc(Nc3ccnc(C)c3)ncc2C(C)(C)N1C(=O)OCc1ccccc1]

Example 2

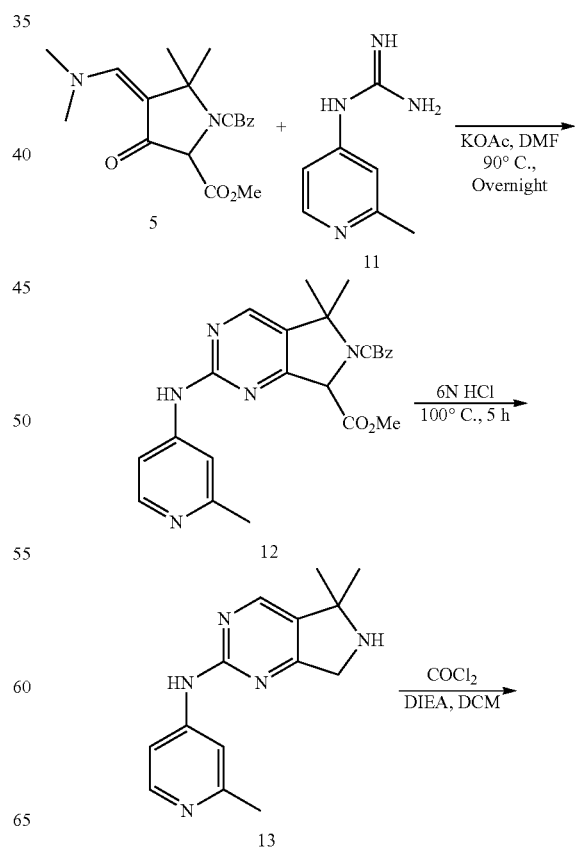

-continued

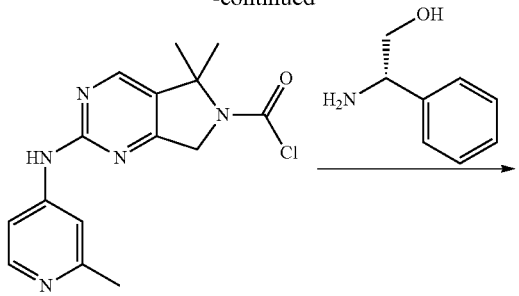

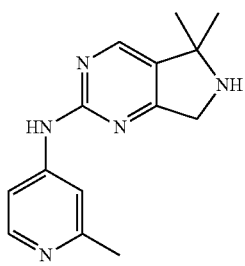 [SMILES: Cc1cc(Nc2ncc3c(n2)CNC3(C)C)ccn1]

6-benzyl 7-methyl 5,5-dimethyl-2-((2-methylpyridin-4-yl)amino)-5H-pyrrolo[3,4-d]pyrimidine-6,7(7H)-dicarboxylate (12)

Into a RB flask equipped with a magnetic stir bar and a reflux condenser was charged (Z)-1-benzyl 2-methyl 4-((dimethylamino)methylene)-5,5-dimethyl-3-oxopyrrolidine-1,2-dicarboxylate 5 (1.36 g, 3.78 mmol, 1.0 equiv), 1-(2-methylpyridin-4-yl)guanidine trifluoroacetate 11 (2.85 g, 10.78 mmol, 2.85 equiv), potassium acetate (1.85 g, 18.8 mmol, 5.0 equiv) and DMF (10 mL). The heterogeneous reaction mixture was heated at 90° C. overnight. The next morning, LCMS indicated desired product formation and complete consumption of 5. Reaction mixture was diluted with water and extracted with EtOAc. The combined organic extract was washed with water and dried over anhydrous MgSO$_4$, filtered and concentrated in vacuo and the residue purified by silica gel chromatography (0-20% EtOAc) to afford 431 mg of the desired product 6-benzyl 7-methyl 5,5-dimethyl-2-((2-methylpyridin-4-yl)amino)-5H-pyrrolo[3,4-d]pyrimidine-6,7(7H)-dicarboxylate (12). LCMS MH+=448.3, Rt=0.773.

5,5-dimethyl-N-(2-methylpyridin-4-yl)-6,7-dihydro-5H-pyrrolo[3,4-d]pyrimidin-2-amine (13).

6-benzyl 7-methyl 5,5-dimethyl-2-((2-methylpyridin-4-yl)amino)-5H-pyrrolo[3,4-d]pyrimidine-6,7(7H)-dicarboxylate (12) (431 mg, 0.98 mmol) was suspended in 6 N HCl and the mixture heated at 100° C. for 3 h upon which complete deprotection of the CBz group and decarboxylation was observed. The reaction mixture was cooled to room temperature and washed with Ether and the aqueous layer basified with solid Na$_2$CO$_3$ to pH 10 and back extracted with EtOAc. The combined organic extract was dried over anhydrous MgSO$_4$, filtered and concentrated in vacuo to afford 103 mg of the desired product 5,5-dimethyl-N-(2-methylpyridin-4-yl)-6,7-dihydro-5H-pyrrolo[3,4-d]pyrimidin-2-amine 13 as a brown syrup. LCMS MH+=256.1, Rt=0.293.

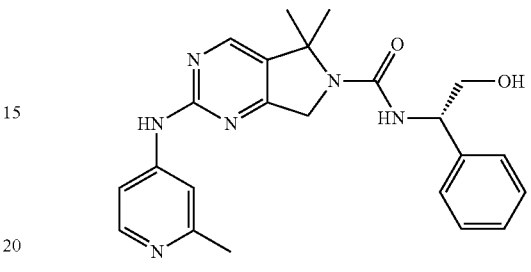

(S)—N-(2-hydroxy-1-phenylethyl)-5,5-dimethyl-2-((2-methylpyridin-4-yl)amino)-5H-pyrrolo[3,4-d]pyrimidine-6(7H)-carboxamide (14)

To a flame-dried flask was charged phosgene (0.130 mL [15 wt % in toluene], 0.168 mmol, 1.1 equiv) and DCM (0.5 mL) and the solution was cooled to 0° C. DIEA (0.059 mL, 0.336 mmol, 2.0 equiv) was added next. This was followed by addition of 5,5-dimethyl-N-(2-methylpyridin-4-yl)-6,7-dihydro-5H-pyrrolo[3,4-d]pyrimidin-2-amine (42.9 mg, 0.168 mmol, 1.0 equiv) in DCM (0.5 mL). After 5 minutes, phosgene (0.130 mL [15 wt % in toluene], 0.168 mmol, 1.1 equiv) was added again and then after 3 minutes, LCMS indicated the formation of desired carbamoyl chloride intermediate. The reaction mixture was quenched by addition of water and the product extracted with DCM, and the combined organic extract was dried over anhydrous MgSO$_4$, filtered and concentrated in vacuo to yield the crude intermediate, which was dissolved in DCM (1.0 mL). To this solution at room temperature was added DIEA (0.088 mL, 0.504 mmol, 3.0 equiv) and then (S)-2-amino-2-phenylethanol (46.1 mg, 0.336 mmol, 2.0 equiv). The reaction mixture was stirred overnight. The next morning LCMS indicated formation of desired product. The reaction mixture was concentrated in vacuo, and the residue purified by reverse phase preparatory LC to provide 15.8 mg of the desired product (S)—N-(2-hydroxy-1-phenylethyl)-5,5-dimethyl-2-((2-methyl pyridin-4-yl)amino)-5H-pyrrolo[3,4-d]pyrimidine-6(7H)-carboxamide 14 as the TFA adduct. MH+=419.3, Rt=0.577.

Method 3. Late Stage S$_N$Ar

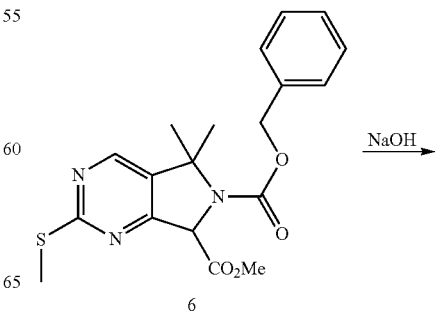

-continued

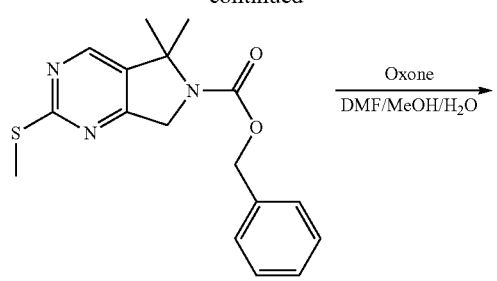

15

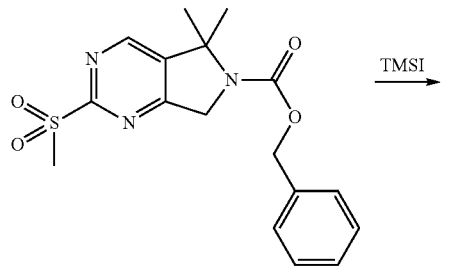

16

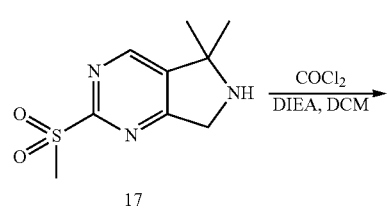

17

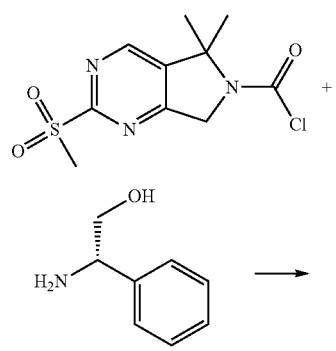

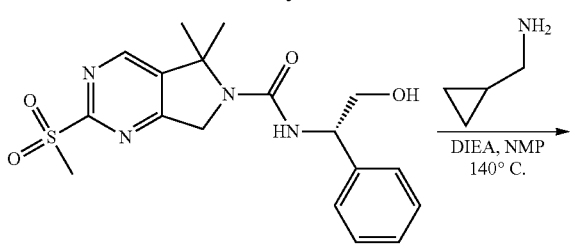

18

19

Example 3

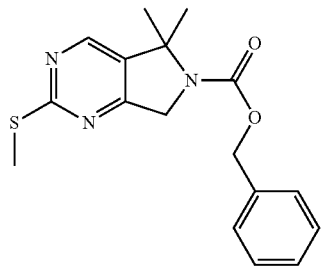 [SMILES: CSc1ncc2c(n1)CN(C(=O)OCc1ccccc1)C2(C)C]

Benzyl 5,5-dimethyl-2-(methylthio)-5H-pyrrolo[3,4-d]pyrimidine-6(7H)-carboxylate (15)

6-benzyl 7-methyl 5,5-dimethyl-2-(methylthio)-5H-pyrrolo[3,4-d]pyrimidine-6,7(7H)-dicarboxylate 7 (5.106 g, 13.18 mmol, 1.0 equiv) was suspended in dioxane (13.2 mL) and NaOH (5.0 M) (52.7 mL, 264 mmol, 20.0 equiv) was added. The mixture was heated at 110° C. for 3 h. At this stage saturated NH₄Cl was added and the product extracted with MTBE. The organic extract is dried (MgSO4) and filtered and concentrated to afford 3.396 g of benzyl 5,5-dimethyl-2-(methylthio)-5H-pyrrolo[3,4-d]pyrimidine-6(7H)-carboxylate 15 which was taken to the next step without any further purification. MH+=330.2, Rt=0.87.

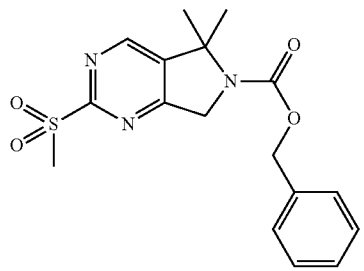 [SMILES: CC1(C)c2cnc(S(C)(=O)=O)nc2CN1C(=O)OCc1ccccc1]

Benzyl 5,5-dimethyl-2-(methylsulfonyl)-5H-pyrrolo[3,4-d]pyrimidine-6(7H)-carboxylate (16)

Benzyl 5,5-dimethyl-2-(methylthio)-5H-pyrrolo[3,4-d]pyrimidine-6(7H)-carboxylate 15 (3.39 g, 10.31 mmol, 1.0 equiv) was dissolved in DMF (28 mL) and to the solution was added oxone (15.84 g, 25.8 mmol, 2.5 equiv) and the heterogeneous mixture was stirred at room temperature overnight. The next morning, LCMS indicated formation of the desired product. The reaction mixture was diluted with water and the product extracted with EtOAc. The combined organic extract was dried over MgSO₄, filtered and concentrated in vacuo to give the crude product which was purified by flash chromatography (0-60% EtOAc/heptanes) to give 3.47 g of the desired product benzyl 5,5-dimethyl-2-(methylsulfonyl)-5H-pyrrolo[3,4-d]pyrimidine-6(7H)-carboxylate 16 as a gummy syrup. MH+=362.2, Rt=0.87.

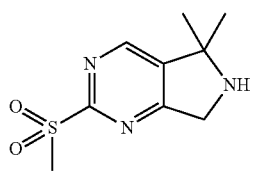

5,5-dimethyl-2-(methylsulfonyl)-6,7-dihydro-5H-pyrrolo[3,4-d]pyrimidine (17)

Benzyl 5,5-dimethyl-2-(methylsulfonyl)-5H-pyrrolo[3,4-d]pyrimidine-6(7H)-carboxylate 16 (1.20 g, 3.32 mmol, 1.0 equiv) was dissolved in anhydrous acetonitrile (16.6 mL) and cooled to 0° C. TMSI (2.66 g, 13.3 mmol, 4.0 equiv) was added in one portion and after 1 h, reaction was deemed complete by LCMS. The reaction was quenched by addition of methanol and evacuated under vacuum. The brown oil was suspended in 3N HCl and washed with ether and then basified with solid NaHCO$_3$ to pH 7 and then with solid Na$_2$CO$_3$ to pH 10. To this aq. solution was added NaHCO$_3$ to saturation and the aqueous layer was then extracted with EtOAC four times. The organic extracts were combined and dried over MgSO$_4$, filtered and concentrated in vacuo to give 562.3 mg of the desired product 5,5-dimethyl-2-(methylsulfonyl)-6,7-dihydro-5H-pyrrolo[3,4-d]pyrimidine 17 as a white solid. MH+=228.1, Rt=0.20.

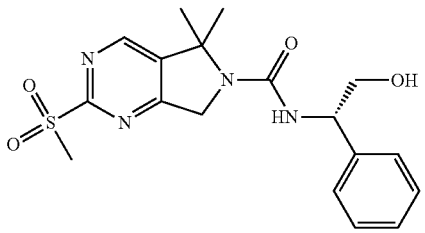 [SMILES: CC1(C)c2cnc(S(C)(=O)=O)nc2CN1C(=O)N[C@H](CO)c1ccccc1]

(S)—N-(2-hydroxy-1-phenylethyl)-5,5-dimethyl-2-(methylsulfonyl)-5H-pyrrolo[3,4-d]pyrimidine-6(7H)-carboxamide (18)

Phosgene in toluene (15%) (1.908 ml, 2.72 mmol, 1.1 equiv.) was charged into a 100 mL RBF. To this was added dichloromethane (2.0 mL) and the solution was cooled to 0° C. To this solution was added DIEA (1.296 ml, 7.42 mmol, 2.5 equiv) and then a solution of 5,5-dimethyl-2-(methylsulfonyl)-6,7-dihydro-5H-pyrrolo[3,4-d]pyrimidine 17 (562 mg, 2.473 mmol, 1.0 equiv) in 3 mL dichloromethane was added. After 5 minutes, Phosgene in toluene (15%) (1.908 ml, 2.72 mmol, 1.1 equiv) was added and at this point, LCMS indicated clean formation of the carbamoyl chloride. The mixture was quenched with water and extracted with dichloromethane and the combined organic extract was dried over anhydrous Na$_2$SO$_4$ and filtered and concentrated in vacuo. To this crude carbamoyl chloride was added dichloromethane (5.0 mL) and then DIEA (1.29 mL, 7.42 mmol, 3.0 equiv) and then a (S)-2-amino-2-phenylethanol (678 mg, 4.95 mmol, 2.0 equiv) and the mixture was let to stir overnight at room temperature. The next morning, LCMS indicated formation of desired product. Water and Sat'd NaHCO$_3$ were added sequentially and the product extracted with dichloromethane. The organic layer was separated, dried over anhydrous MgSO$_4$, filtered, concentrated and the residue purified by flash chromatography (0-7% DCM/MeOH) to provide 955 mg of the desired product (S)—N-(2-hydroxy-1-phenylethyl)-5,5-dimethyl-2-(methylsulfonyl)-5H-pyrrolo[3,4-d]pyrimidine-6(7H)-carboxamide 18 as an off-white solid. A 30 mg sample was re-purified by Prep LC for analytical sample as a TFA salt. 1H NMR (400 MHz, CD$_3$OD) δ 8.82 (s, 1H), 7.27-7.32 (m, 2H), 7.23 (t, J=7.63 Hz, 2H), 7.11-7.18 (m, 1H), 4.84 (s, 3H), 3.62-3.77 (m, 2H), 3.29 (s, 3H), 1.75 (s, 3H), 1.66-1.71 (m, 3H).

MH+=391.2, Rt=0.59.

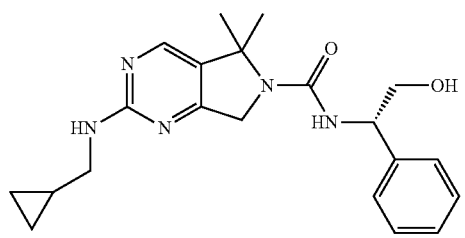 [SMILES: CC1(C)c2cnc(NCC3CC3)nc2CN1C(=O)N[C@H](CO)c1ccccc1]

(S)-2-((cyclopropylmethyl)amino)-N-(2-hydroxy-1-phenylethyl)-5,5-dimethyl-5H-pyrrolo[3,4-d]pyrimidine-6(7H)-carboxamide (19)

In a microwave vial was charged (S)—N-(2-hydroxy-1-phenylethyl)-5,5-dimethyl-2-(methylsulfonyl)-5H-pyrrolo[3,4-d]pyrimidine-6(7H)-carboxamide 18 (30 mg, 0.077 mmol, 1.0 equiv) and then DMF (0.4 mL). To the obtained solution was added methylcyclopropylamine (32 mg, 0.450 mmol, 6.0 equiv) followed by DIEA (107 µl, 0.615 mmol, 8.0 equiv) and the mixture was irridated at 130° C. for 40 min under high absorption conditions. LCMS indicated complete consumption of the starting material. The reaction mixture was diluted with DMSO and the product purified by prep-LC, which provided the desired product (S)-2-((cyclopropylmethyl)amino)-N-(2-hydroxy-1-phenylethyl)-5,5-dimethyl-5H-pyrrolo[3,4-d]pyrimidine-6(7H)-carboxamide 19 as the TFA adduct. 1H NMR (400 MHz, CD$_3$OD) δ 8.10 (s, 1H), 7.26-7.31 (m, 2H), 7.19-7.26 (m, 2H), 7.10-7.17 (m, 1H), 4.83 (dd, J=5.28, 7.63 Hz, 1H), 4.58 (d, J=1.96 Hz, 2H), 3.59-3.79 (m, 2H), 1.64 (s, 3H), 1.58 (s, 3H), 0.97-1.14 (m, 1H), 0.37-0.54 (m, 2H), 0.12-0.29 (m, 2H). MH+=391.2, Rt=0.59. MH+=382.3 Rt=0.62.

Method 4. Variation of the Gem-Dimethyl Substituent

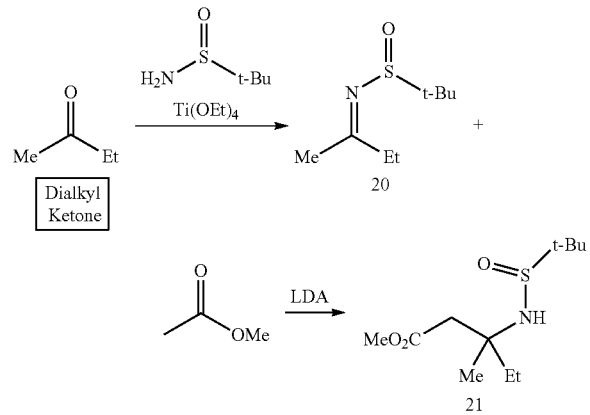

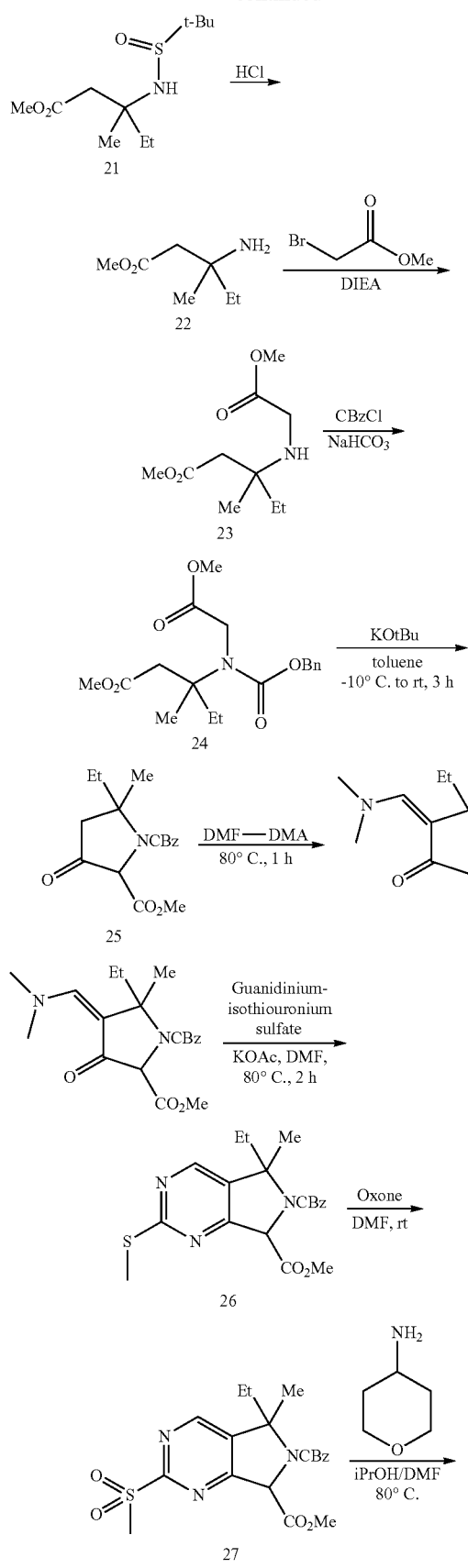
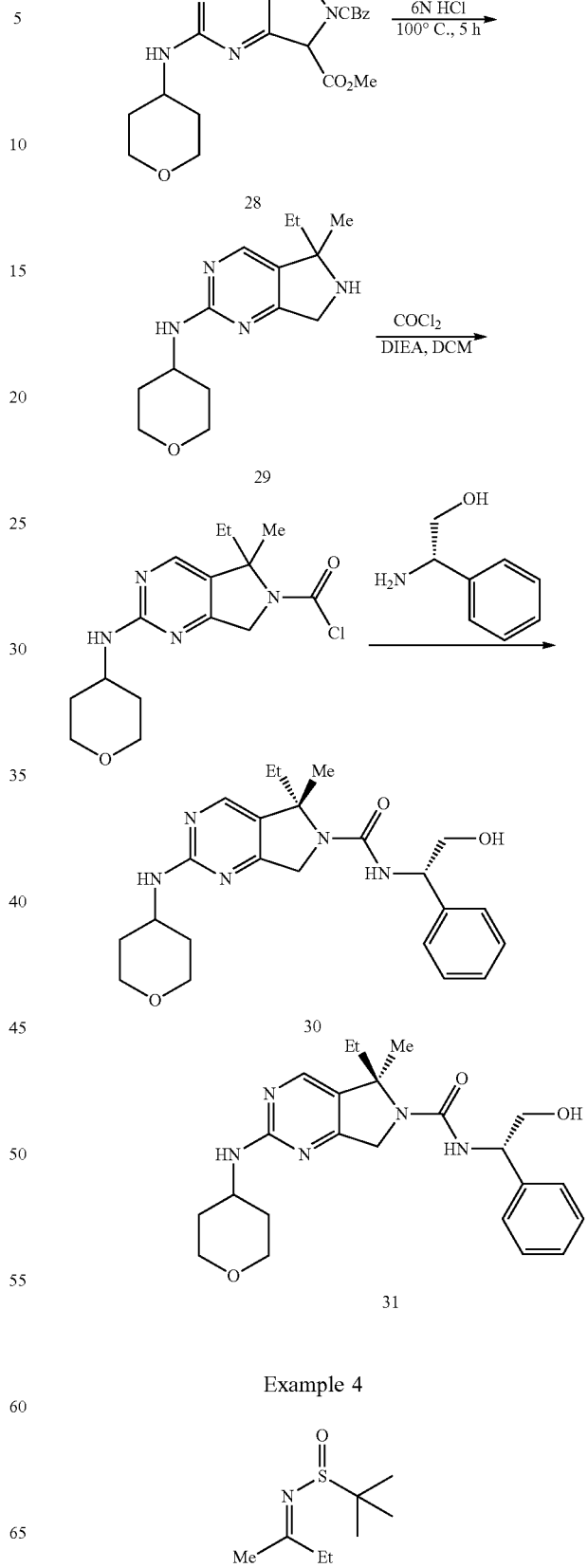
Example 4

(Z)—N-(butan-2-ylidene)-2-methylpropane-2-sulfinamide (20)

Into a flame dried round bottom flask equipped with a stirring bar and a reflux condenser was charged racemic-t-butylsulfinamide (8.40 g, 69.3 mmol, 1.0 equiv), methylethylketone (7.45 mL, 83 mmol, 1.2 equiv) and then THF (50 mL) followed by Ti(OEt)$_4$, and the mixture was heated at 70° C. overnight. The next morning the reaction mixture was poured over brine (100 mL) and the slurry was diluted with EtOAc (300 mL). The slurry was filtered and washed with EtOAc (200 mL) and the filtrate was charged into a separatory funnel and the organic layer was separated. The organic layer was dried over MgSO$_4$ and filtered and concentrated in vacuo and the crude product purified by silica gel chromatography (0-20% EtOAc/heptanes) to give 6.9 g of the title compound (Z)—N-(butan-2-ylidene)-2-methylpropane-2-sulfinamide 20

MH+=176.6, Rt=0.60.

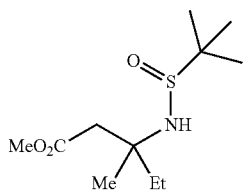 [SMILES: CCC(C)(CC(=O)OC)NS(=O)C(C)(C)C]

Methyl 3-(1,1-dimethylethylsulfinamido)-3-methylpentanoate (21)

Into a round bottom flask was charged N,N-diisopropylamine (15.22 ml, 87 mmol, 2.2 equiv) and THF (198 ml) and the solution was cooled to 0° C. Butyllithium (52.0 ml, 83 mmol, 2.1 equiv) was added slowly and the mixture stirred at 0° C. for 30 min and cooled to −78° C. Methyl acetate (6.31 ml, 79 mmol, 2.0 equiv) in THF (20 mL) was added and the mixture was stirred for 30 min. After 30 min, (Z)—N-(butan-2-ylidene)-2-methylpropane-2-sulfinamide (6.95 g, 39.6 mmol, 1.0 equiv) in THF (15 mL) was added and the mixture was stirred for 2.5 h at −78° C. LCMS indicated consumption of starting material and desired product formation. Sat'd NH4Cl was added and the reaction was allowed to warm to room temp and stir for 20 min. Water was added and then EtOAc. The biphasic layer was separated and the aq. layer was extracted with EtOAc. The combined organic layer was dried (MgSO$_4$), filtered and concentrated in vacuo to yield the crude product which was purified by silica gel chromatography (0-100% EtOAc/heptanes) to afford 7.28 g of the desired product methyl 3-(1,1-dimethylethylsulfinamido)-3-methylpentanoate 21 as an oil. MH+=250.3, Rt=0.72.

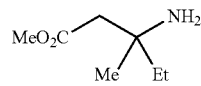

Methyl 3-amino-3-methylpentanoate hydrochloride (22)

Methyl 3-(1,1-dimethylethylsulfinamido)-3-methylpentanoate (7.28 g, 29.2 mmol) was dissolved in dioxane (29.2 ml) and then hydrochloric acid 4.0 M in dioxane (17 ml, 68.0 mmol) was added dropwise. After 1 h, reaction was deemed complete. At this stage, dioxane was evaporated and the residue dissolved in 3N HCl and washed twice with ether. The aq. layer was basified with Na$_2$CO$_3$ and saturated with NaCl and then extracted with DCM. The DCM layer was separated and then 4 N HCl in dioxane (15 mL) was added and the solvent evaporated to give Methyl 3-amino-3-methylpentanoate hydrochloride. The residue was taken to the next step without any further purification. MH+=146.2, Rt=0.43.

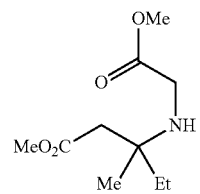

Methyl 3-((2-methoxy-2-oxoethyl)amino)-3-methylpentanoate (23)

Methyl 3-amino-3-methylpentanoate hydrochloride (4.67 g, 25.7 mmol, 1.0 equiv) was suspended in ACN/THF (36 mL/3.6 mL) and N,N-diisopropylethylamine (22.45 mL, 129 mmol, 5.0 equiv) was added. The resulting solution was cooled to 0° C. To this solution was added methylbromoacetate (4.33 g, 28.3 mmol, 1.0 equiv) and the mixture was allowed to warm to RT and stirred. After 20 h, the reaction mixture was concentrated and the residue triturated with EtOAc and filtered. The filtrate was concentrated in vacuo and the residue methyl 3-((2-methoxy-2-oxoethyl)amino)-3-methylpentanoate 23 was taken to the next step as such. MH+=218.2, Rt=0.51.

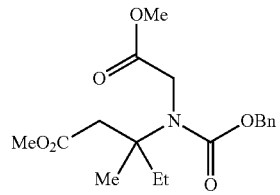 [SMILES: CCC(C)(CC(=O)OC)N(CC(=O)OC)C(=O)OCc1ccccc1]

Methyl 3-(((benzyloxy)carbonyl)(2-methoxy-2-oxoethyl)amino)-3-methylpentanoate (24)

methyl 3-((2-methoxy-2-oxoethyl)amino)-3-methylpentanoate (5.58 g, 25.7 mmol, 1.0 equiv) was dissolved in THF (Volume: 30 mL, Ratio: 1.000) and NaHCO$_3$ (sat'd) (Volume: 30.0 mL, Ratio: 1.000) and cooled to 0° C. Benzyl chloroformate (5.79 mL, 38.6 mmol, 1.5 equiv) was added and the mixture was allowed to warm to room temperature and stir overnight. The next morning, LCMS indicated formation of the desired product. The reaction mixture was concentrated and extracted with EtOAc and the organic layer was dried (MgSO$_4$) and then filtered and concentrated in vacuo and the crude product was purified by silica gel chromatography (0-20% EtOAc/heptanes) to give 3.8 g of the desired product methyl 3-(((benzyloxy)carbonyl)(2-methoxy-2-oxoethyl)amino)-3-methylpentanoate 24. MNa+=374.2, Rt=0.92.

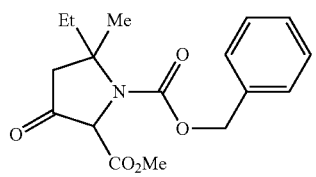 [SMILES: CCC1(C)CC(=O)C(C(=O)OC)N1C(=O)OCc1ccccc1]

1-benzyl 2-methyl 5-ethyl-5-methyl-3-oxopyrrolidine-1,2-dicarboxylate (25)

To a suspension of potassium tert-butoxide (1.638 g, 14.60 mmol, 1.3 equiv) in toluene (50 mL) at −10° C. was added a solution of methyl 3-(((benzyloxy)carbonyl)(2-methoxy-2-oxoethyl)amino)-3-methylpentanoate (3.8 g, 10.81 mmol, 1.0 equiv) in toluene (30 mL). The mixture was stirred at −10° C. for 1 h and then at room temperature for 3 h. LCMS indicated desired product formation. The reaction mixture was poured over ice-water and neutralized to pH=4 using AcOH. The aq. layer was extracted with EtOAc and the combined organic layer was dried (MgSO$_4$), filtered and concentrated in vacuo to give the residue which was purified by silica gel chromatography (0-20% EtOAc/heptanes) to afford 2.044 g of the desired product 1-benzyl 2-methyl 5-ethyl-5-methyl-3-oxopyrrolidine-1,2-dicarboxylate 25.

MH+=320.2, Rt=0.94.

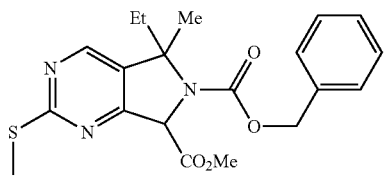 [SMILES: CCC1(C)c2cnc(SC)nc2C(C(=O)OC)N1C(=O)OCc1ccccc1]

6-benzyl 7-methyl 5-ethyl-5-methyl-2-(methylthio)-5H-pyrrolo[3,4-d]pyrimidine-6,7(7H)-dicarboxylate (26)

1-benzyl 2-methyl 5-ethyl-5-methyl-3-oxopyrrolidine-1, 2-dicarboxylate (2.094 g, 6.56 mmol) was dissolved in DMF-DMA (23.44 g, 197 mmol) and the mixture was heated to 85° C. for 3 h. The mixture was then concentrated and the residue was dissolved in DMF (Volume: 18.73 ml) and potassium acetate (1.931 g, 19.67 mmol, 3.0 equiv) was added followed by S-Methylisothiouronium sulfate (2.74 g, 9.84 mmol, 1.5 equiv). The mixture was heated to 90° C. for 2 h. LCMS after 2 h indicated complete conversion of the starting material. Reaction mixture was then cooled to RT and then diluted with EtOAc. Water was added and the aq. layer extracted with EtOAc. The combined organic extract was washed twice with water and then dried (MgSO$_4$), filtered and concentrated in vacuo and the residue purified by silica gel chromatography (0-20% EtOAc/heptanes) to provide 1.270 g of the desired product 6-benzyl 7-methyl 5-ethyl-5-methyl-2-(methylthio)-5H-pyrrolo[3,4-d]pyrimidine-6,7(7H)-dicarboxylate 26 as a gummy syrup. MH+=402.2, Rt=1.08.

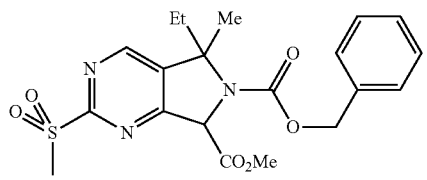 [SMILES: CCC1(C)c2cnc(S(C)(=O)=O)nc2C(C(=O)OC)N1C(=O)OCc1ccccc1]

6-benzyl 7-methyl 5-ethyl-5-methyl-2-(methylsulfonyl)-5H-pyrrolo[3,4-d]pyrimidine-6,7(7H)-dicarboxylate (27)

6-benzyl 7-methyl 5-ethyl-5-methyl-2-(methylthio)-5H-pyrrolo[3,4-d]pyrimidine-6,7(7H)-dicarboxylate (1.270 g, 3.16 mmol, 1.0 equiv) was dissolved in DMF (10.54 ml) and at room temperature was added oxone (4.86 g, 7.91 mmol, 2.5 equiv) in one portion. The reaction mixture was stirred overnight. The next morning, LCMS indicated desired product formation. The reaction mixture was diluted with EtOAc and filtered through celite and the filtrate was washed with water. The aq. wash was extracted with EtOAc and the combined organic extract was washed with water twice. The organic layer was separated and dried (MgSO$_4$), filtered and concentrated in vacuo to give the residue which was purified by silica gel chromatography (0-80% EtOAc/heptane) to give 842 mg of 6-benzyl 7-methyl 5-ethyl-5-methyl-2-(methylsulfonyl)-5H-pyrrolo[3,4-d]pyrimidine-6,7(7H)-dicarboxylate 27 as the desired product.

MH+=434.2, Rt=0.90.

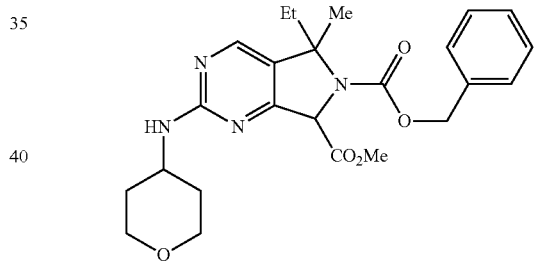

6-benzyl 7-methyl 5-ethyl-5-methyl-2-((tetrahydro-2H-pyran-4-yl)amino)-5H-pyrrolo[3,4-d]pyrimidine-6,7(7H)-dicarboxylate (28)

6-benzyl 7-methyl 5-ethyl-5-methyl-2-(methylsulfonyl)-5H-pyrrolo[3,4-d]pyrimidine-6,7(7H)-dicarboxylate (521.3 mg, 1.203 mmol, 1.0 equiv) was dissolved in a mixture of DMF (4 ml) and 2-Propanol (0.500 ml). Tetrahydro-2H-pyran-4-amine (608 mg, 6.01 mmol, 5.0 equiv) was added next and the mixture heated to 95° C. After 3 h, LCMS indicated complete conversion to the desired product. The reaction mixture was cooled to room temperature and diluted with EtOAc and the organic layer washed with water three times. The organic layer was separated and dried (MgSO$_4$), filtered and concentrated to give quantitative yield of the crude desired product 6-benzyl 7-methyl 5-ethyl-5-methyl-2-((tetrahydro-2H-pyran-4-yl)amino)-5H-pyrrolo[3, 4-d]pyrimidine-6,7(7H)-dicarboxylate 28 as a colorless syrup which was taken to the next step without any further purification. MH+=454.5, Rt=0.93.

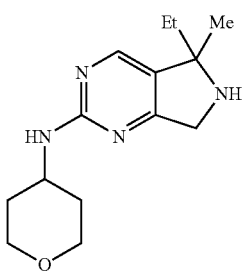 [SMILES: CCC1(C)NCc2nc(NC3CCOCC3)ncc21]

5-ethyl-5-methyl-N-(tetrahydro-2H-pyran-4-yl)-6,7-dihydro-5H-pyrrolo[3,4-d]pyrimidin-2-amine (29)

6-Benzyl 7-methyl 5-ethyl-5-methyl-2-((tetrahydro-2H-pyran-4-yl)amino)-5H-pyrrolo[3,4-d]pyrimidine-6,7(7H)-dicarboxylate (547 mg, 1.203 mmol) was suspended in 6 N HCl (40 mL) and heated to 100° C. After 3 h, complete deprotection and decarboxylation was observed. The reaction mixture was cooled to room temperature and extracted with ether and then the acidic aq. layer was basicified to pH10 ($Na_2CO_3$) and then extracted with DCM. The organic extracts were combined and dried ($MgSO_4$), filtered and concentrated in vacuo to give 266 mg the desired product 5-ethyl-5-methyl-N-(tetrahydro-2H-pyran-4-yl)-6,7-dihydro-5H-pyrrolo[3,4-d]pyrimidin-2-amine 29 as a yellowish-brown solid. MH+=263.3, Rt=0.38.

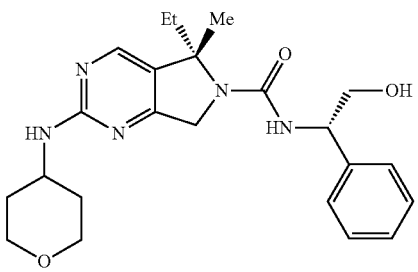 [SMILES: CC[C@@]1(C)c2cnc(NC3CCOCC3)nc2CN1C(=O)N[C@H](CO)c1ccccc1]

(S)-5-ethyl-N—((S)-2-hydroxy-1-phenylethyl)-5-methyl-2-((tetrahydro-2H-pyran-4-yl)amino)-5H-pyrrolo[3,4-d]pyrimidine-6(7H)-carboxamide (30)

Phosgene (15% in toluene) (32.7 μl, 0.311 mmol, 1.1 equiv) was added to DCM (Volume: 3 mL) and the flask was cooled to 0° C. To the mixture was added N,N-diisopropylethylamine (91 μl, 0.518 mmol, 2.0 equiv) and then after 5 minutes, a solution of 5-ethyl-5-methyl-N-(tetrahydro-2H-pyran-4-yl)-6,7-dihydro-5H-pyrrolo[3,4-d]pyrimidin-2-amine (68 mg, 0.259 mmol) in DCM (3 mL). After 5 minutes, Phosgene (15% in toluene) (32.7 μl, 0.311 mmol) was added and then after 5 min, the reaction was deemed complete. Water was added and the carbamoyl chloride intermediate was extracted with DCM. The combined organic extract was dried ($Na_2SO_4$), filtered and concentrated in vacuo to give the crude product which was dissolved in DCM (Volume: 5.00 mL) and N,N-diisopropylethylamine (136 μl, 0.778 mmol, 3.0 equiv) was added followed by (S)-2-amino-2-phenylethanol (71.1 mg, 0.518 mmol, 2.0 equiv). The reaction mixture was stirred overnight and the next morning, the LCMS indicated complete consumption of starting material. The solvent was evaporated and the residue dissolved in DMSO (3 mL) and the product purified by reverse phase HPLC to afford separable diastereomers of which the non polar is represented by (S)-5-ethyl-N—((S)-2-hydroxy-1-phenylethyl)-5-methyl-2-((tetrahydro-2H-pyran-4-yl)amino)-5H-pyrrolo[3,4-d]pyrimidine-6(7H)-carboxamide 30 obtained in 19.6 mg quantity after lyophillization as the TFA adduct MH+=426.4, Rt=0.60.

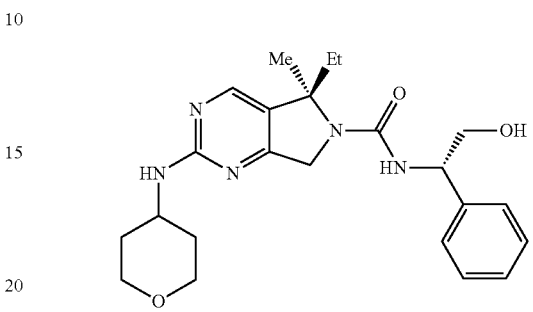

(R)-5-ethyl-N—((S)-2-hydroxy-1-phenylethyl)-5-methyl-2-((tetrahydro-2H-pyran-4-yl)amino)-5H-pyrrolo[3,4-d]pyrimidine-6(7H)-carboxamide (31)

The polar fraction from the above separation yielded (R)-5-ethyl-N—((S)-2-hydroxy-1-phenylethyl)-5-methyl-2-((tetrahydro-2H-pyran-4-yl)amino)-5H-pyrrolo[3,4-d]pyrimidine-6(7H)-carboxamide (8.1 mg) as the TFA salt after lyophillization.

MH+=426.4, Rt=0.62.

Method 5.

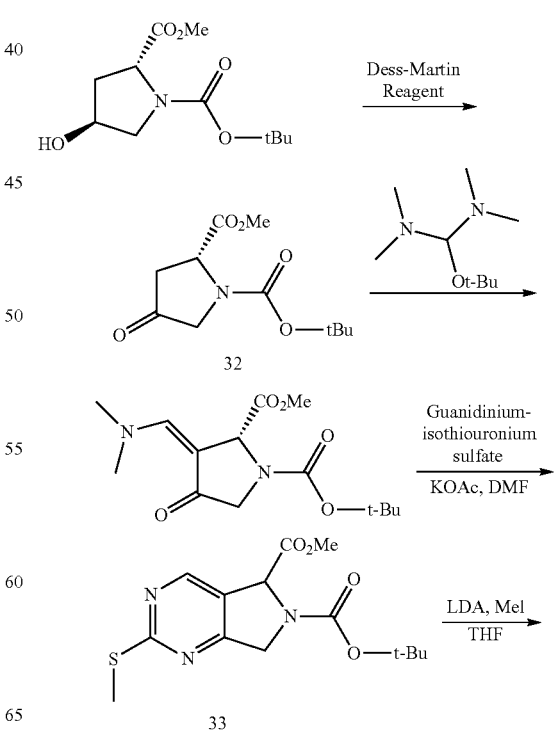

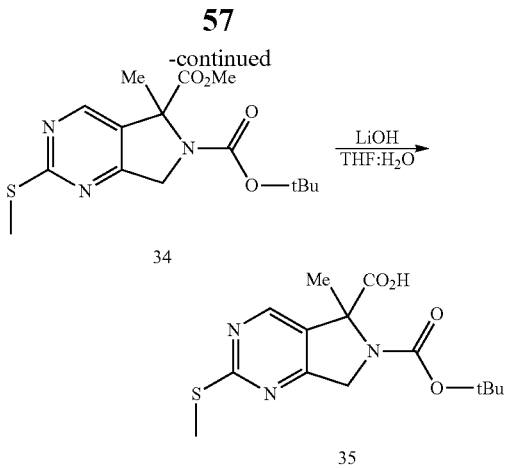

34

35

Example 5

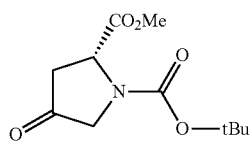 [SMILES: COC(=O)[C@H]1CC(=O)CN1C(=O)OC(C)(C)C]

(R)-1-tert-butyl 2-methyl 4-oxopyrrolidine-1,2-dicarboxylate (32)

(2S,4R)-1-tert-butyl 2-methyl 4-hydroxypyrrolidine-1,2-dicarboxylate (10 g, 40.8 mmol, 1.0 equiv) was suspended in DCM (Volume: 408 ml) and Dess-Martin periodinane (20.75 g, 48.9 mmol) was added in one portion. The reaction mixture was stirred at room temperature overnight and then diluted with water and DCM and filtered. The organic layer was separated and washed with water twice and dried (MgSO$_4$), filtered and concentrated in vacuo to afford the crude product which was purified by silica gel chromatography (0-20% EtOAc/heptanes) to afford 9.92 g of the desired product (R)-1-tert-butyl 2-methyl 4-oxopyrrolidine-1,2-dicarboxylate 32 which solidified upon standing. [M-C4H9+]=188.1, Rt=0.65.

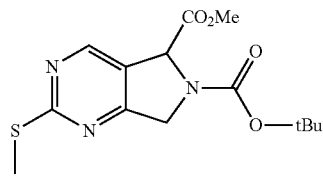 [SMILES: COC(=O)C1c2cnc(SC)nc2CN1C(=O)OC(C)(C)C]

6-tert-butyl 5-methyl 2-(methylthio)-5H-pyrrolo[3,4-d]pyrimidine-5,6(7H)-dicarboxylate (33)

(S)-1-tert-butyl 2-methyl 4-oxopyrrolidine-1,2-dicarboxylate (9.37 g, 38.5 mmol, 1.0 equiv) was dissolved in DME (Volume: 300 ml) and 1-tert-butoxy-N,N,N',N'-tetramethylmethanediamine (13.43 g, 77 mmol, 2.0 equiv) was added. The mixture was heated to 80° C. for 3 h. The solvent was evaporated and the residue suspended in DMF (60 ml) and Potassium acetate (11.34 g, 116 mmol, 3.0 equiv) was added followed by S-methyl isothiouronium sulfate (16.03 g, 57.8 mmol, 1.5 equiv). The reaction mixture was stirred overnight at 90° C. and then cooled to room temperature and diluted with EtOAc and water (1:1). The aq. layer was extracted with EtOAc twice and then organic extracts were combined and washed with water twice. The organic layer was separated and then dried (MgSO$_4$), filtered and concentrated in vacuo to give the crude product which was purified by silica gel chromatography (0-20% EtOAc/heptanes) to give the product which was recrystallized from ether/heptane to give 9.04 g of the desired product 6-tert-butyl 5-methyl 2-(methylthio)-5H-pyrrolo[3,4-d]pyrimidine-5,6(7H)-dicarboxylate 33 as a white amorphous solid. MH+=326.2, Rt=0.88.

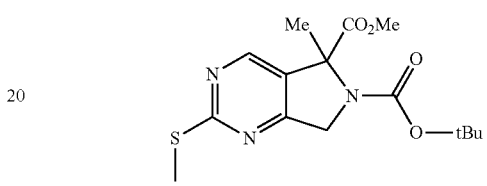

6-tert-butyl 5-methyl 5-methyl-2-(methylthio)-5H-pyrrolo[3,4-d]pyrimidine-5,6(7H)-dicarboxylate (34)

N,N-diisopropylamine (6.04 ml, 34.6 mmol, 1.25 equiv) was dissolved in THF (100 mL) and cooled to 0° C. n-Butyllithium (19.89 ml, 31.8 mmol, 1.1) was added next and the mixture stirred for 30 min. At this stage, the reaction mixture was cooled to −78° C. and 6-tert-butyl 5-methyl 2-(methylthio)-5H-pyrrolo[3,4-d]pyrimidine-5,6(7H)-dicarboxylate (9.004 g, 27.7 mmol, 1.0 equiv) dissolved in THF (30 mL) was added. The mixture was stirred for 30 min and then methyl iodide (5.19 ml, 83 mmol, 3.0 equiv) was added dropwise. The reaction mixture was then gradually brought to 0° C. and stirred for 4 h and then quenched with Sat'd NH$_4$Cl and extracted with EtOAc. The combined organic extract was dried (MgSO$_4$), filtered and concentrated in vacuo to afford the crude product which was purified by silica gel chromatography (0-20% EtOAc/heptanes) to afford the desired product 6-tert-butyl 5-methyl 5-methyl-2-(methylthio)-5H-pyrrolo[3,4-d]pyrimidine-5,6(7H)-dicarboxylate 34. MH+=341.3, Rt=0.93.

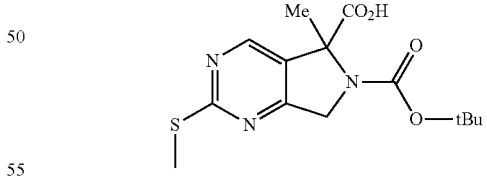

6-(tert-butoxycarbonyl)-5-methyl-2-(methylthio)-6,7-dihydro-5H-pyrrolo[3,4-d]pyrimidine-5-carboxylic acid (35)

6-tert-butyl 5-methyl 5-methyl-2-(methylthio)-5H-pyrrolo[3,4-d]pyrimidine-5,6(7H)-dicarboxylate (1.499 g, 4.42 mmol, 1.0 equiv) was dissolved in THF (20 mL) and water (10 mL) and then Lithium Hydroxide (1.058 g, 44.2 mmol, 10.0 equiv) was added next and the mixture was heated to 80° C. for 2 h and then overnight at 40° C. After the elapsed time, the reaction mixture showed complete conversion to the desired product. The solvent was evaporated and the aq. layer neutralized with NH₄Cl (Sat'd) and extracted with EtOAc twice. The combined organic layer was dried (MgSO₄), filtered and concentrated in vacuo to give the crude product 6-(tert-butoxycarbonyl)-5-methyl-2-(methylthio)-6,7-dihydro-5H-pyrrolo[3,4-d]pyrimidine-5-carboxylic acid 35 which was taken to the next step without any further purification. MH+=326.2, Rt=0.79.

Method 6.

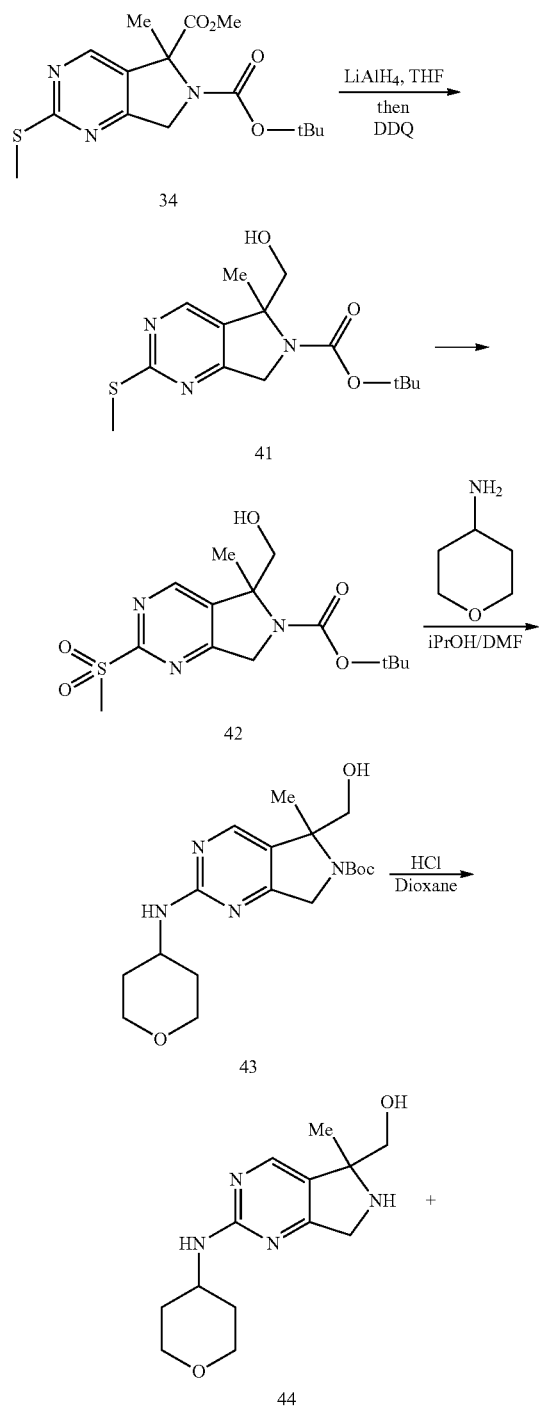

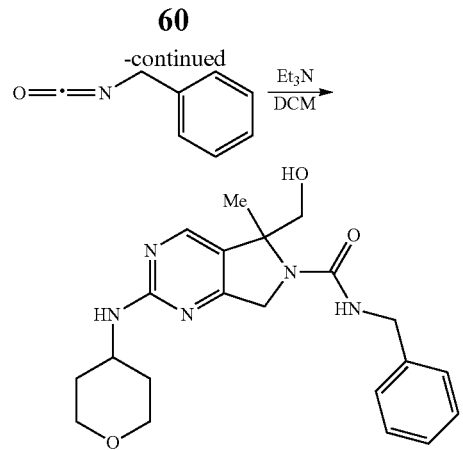

Example 6 tert-butyl 5-(hydroxymethyl)-5-methyl-2-(methylthio)-5H-pyrrolo[3,4-d]pyrimidine-6(7H)-carboxylate (41)

To a suspension of lithium aluminum hydride (0.345 g, 9.09 mmol, 2.3 equiv) in THF (20 mL) at 0° C. was added a solution of tert-butyl 5-(hydroxymethyl)-5-methyl-2-(methylthio)-5H-pyrrolo[3,4-d]pyrimidine-6(7H)-carboxylate (1.341 g, 3.95 mmol, 1.0 equiv) in THF (10 mL). The mixture was stirred at 0° C. for 90 min upon which LCMS indicated ester reduction and pyrimidine reduction. DDQ (1.076 g, 4.74 mmol, 2.3 equiv) was added in one portion and then after 5 min, LCMS indicated desired product formation. The reaction mixture was quenched with Sat'd Na₂CO₃ and diluted with water and DCM. The organic layer was separated and washed three times with Sat'd Na₂CO₃, dried (MgSO₄), filtered and concentrated in vacuo to provide a yellowish orange residue which was then purified by silica gel chromatography (0-50% EtOAc/heptane) to provide 1.15 g of the desired product tert-butyl 5-(hydroxymethyl)-5-methyl-2-(methylthio)-5H-pyrrolo[3,4-d]pyrimidine-6(7H)-carboxylate 41 as a white solid. MH+=312.3, Rt=0.78.

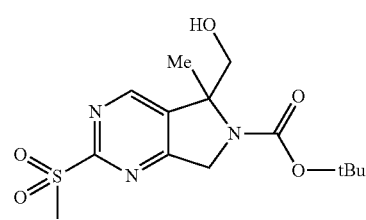 [SMILES: CC(C)(C)OC(=O)N1Cc2nc(S(C)(=O)=O)ncc2C1(C)CO]

tert-butyl 5-(hydroxymethyl)-5-methyl-2-(methylsulfonyl)-5H-pyrrolo[3,4-d]pyrimidine-6(7H)-carboxylate (42)

tert-butyl 5-(hydroxymethyl)-5-methyl-2-(methylthio)-5H-pyrrolo[3,4-d]pyrimidine-6(7H)-carboxylate (1.1512 g, 3.70 mmol, 1.0 equiv) was dissolved in DMF (20 mL) and then oxone (5.68 g, 9.24 mmol, 2.5 equiv) was added in one portion. The reaction mixture was let to stir overnight. Reaction mixture was filtered and the filtrate diluted with EtOAc, washed with water twice and dried (MgSO₄), then concentrated in vacuo to give 1.083 g of the desired product tert-butyl 5-(hydroxymethyl)-5-methyl-2-(methylsulfonyl)-5H-pyrrolo[3,4-d]pyrimidine-6(7H)-carboxylate 42 which was used as such without any further purification. MH+=344.3, Rt=0.62.

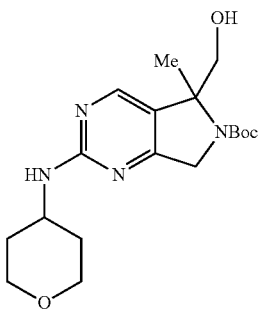 [SMILES: CC(C)(C)OC(=O)N1Cc2nc(NC3CCOCC3)ncc2C1(C)CO]

tert-butyl 5-(hydroxymethyl)-5-methyl-2-((tetrahydro-2H-pyran-4-yl)amino)-5H-pyrrolo[3,4-d]pyrimidine-6(7H)-carboxylate (43)

Tert-butyl 5-(hydroxymethyl)-5-methyl-2-(methylsulfonyl)-5H-pyrrolo[3,4-d]pyrimidine-6(7H)-carboxylate (496 mg, 1.444 mmol, 1.0 equiv) was dissolved in DMF/iPrOH (3 mL/3 mL) and to the mixture was added tetrahydro-2H-pyran-4-amine (877 mg, 8.67 mmol, 6.0 equiv) and the mixture was heated to 80° C. for 5 h and then in microwave at 100° C. for 1 h and then N-methylpiperazine (0.5 mL) was added. The reaction mixture was stirred overnight at 60° C. and then LCMS indicated consumption of starting material. Reaction mixture was diluted with EtOAc and washed with water. The aq. layer was extracted with EtOAc and the combined organic layer was washed twice with water and then dried (MgSO₄), filtered and concentrated in vacuo to yield a colorless residue which was purified by silica gel chromatography (0-5% MeOH/DCM) to yield 190.5 mg of the desired product tert-butyl 5-(hydroxymethyl)-5-methyl-2-((tetrahydro-2H-pyran-4-yl)amino)-5H-pyrrolo[3,4-d]pyrimidine-6(7H)-carboxylate 43. MH+=365.3, Rt=0.63.

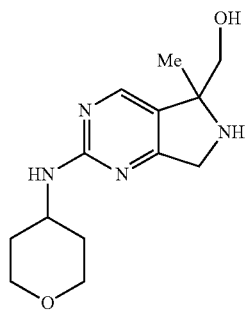 [SMILES: CC1(CO)NCc2nc(NC3CCOCC3)ncc21]

(5-methyl-2-((tetrahydro-2H-pyran-4-yl)amino)-6,7-dihydro-5H-pyrrolo[3,4-d]pyrimidin-5-yl)methanol (44)

Tert-butyl 5-(hydroxymethyl)-5-methyl-2-((tetrahydro-2H-pyran-4-yl)amino)-5H-pyrrolo[3,4-d]pyrimidine-6(7H)-carboxylate (190.5 mg, 0.523 mmol) was dissolved in dioxane (3 mL) and 4 N HCl (in dioxane) was added next. The reaction mixture was heated to 60° C. for 1 h and then concentrated in vacuo to afford the desired product (5-methyl-2-((tetrahydro-2H-pyran-4-yl)amino)-6,7-dihydro-5H-pyrrolo[3,4-d]pyrimidin-5-yl)methanol 44 as the hydrochloride salt which was used as such without any further purification. MH+=265.3, Rt=0.30.

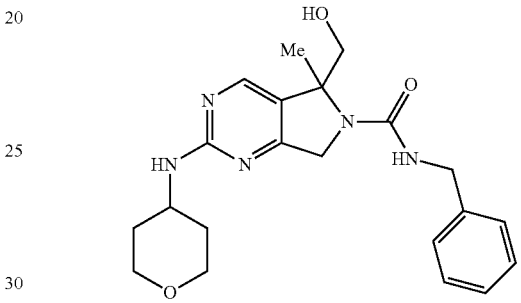

N-benzyl-5-(hydroxymethyl)-5-methyl-2-((tetrahydro-2H-pyran-4-yl)amino)-5H-pyrrolo[3,4-d]pyrimidine-6(7H)-carboxamide (45)

(5-methyl-2-((tetrahydro-2H-pyran-4-yl)amino)-6,7-dihydro-5H-pyrrolo[3,4-d]pyrimidin-5-yl)methano (45.2 mg, 0.171 mmol, 1.0 equiv) was dissolved in DCM (1.0 mL) and N,N-diisopropylethylamine (119 μl, 0.684 mmol, 4.0 equiv) was added. Then Benzylisocyanate (27.3 mg, 0.205 mmol, 1.2 equiv) was added. After 5 min, the reaction was deemed complete. The solvent was evaporated and the crude mixture was purified by reverse phase HPLC to afford the desired product N-benzyl-5-(hydroxymethyl)-5-methyl-2-((tetrahydro-2H-pyran-4-yl)amino)-5H-pyrrolo[3,4-d]pyrimidine-6(7H)-carboxamide 45 as the TFA adduct. MH+=398.7, Rt=0.57. 1H NMR (400 MHz, CD₃OD) δ 8.13 (s, 1H), 7.18-7.28 (m, 4H), 7.13 (d, J=6.65 Hz, 1H), 4.42-4.59 (m, 2H), 4.23-4.37 (m, 2H), 4.08 (d, J=11.35 Hz, 1H), 3.81-4.04 (m, 3H), 3.69 (d, J=11.35 Hz, 1H), 3.42 (dt, J=1.76, 11.64 Hz, 2H), 1.87 (d, J=13.30 Hz, 2H), 1.47-1.63 (m, 5H).

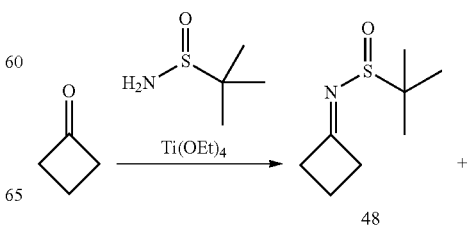

48

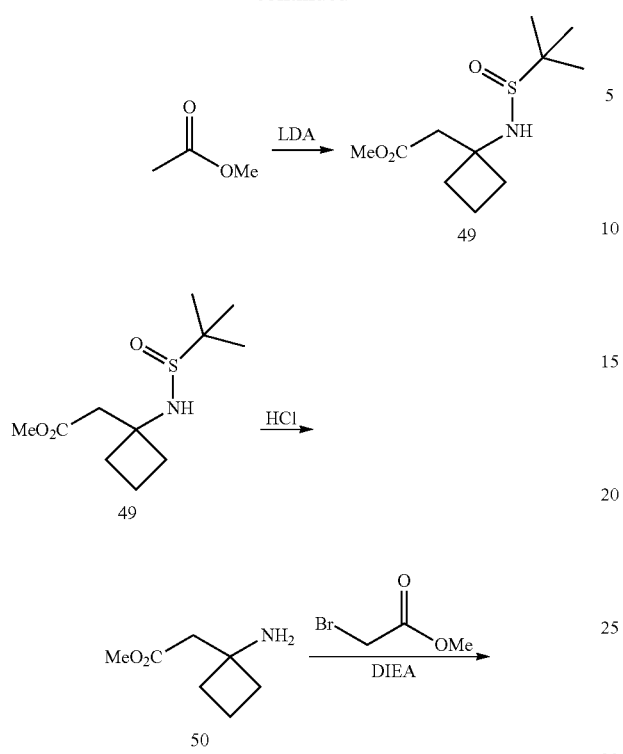
Example 7
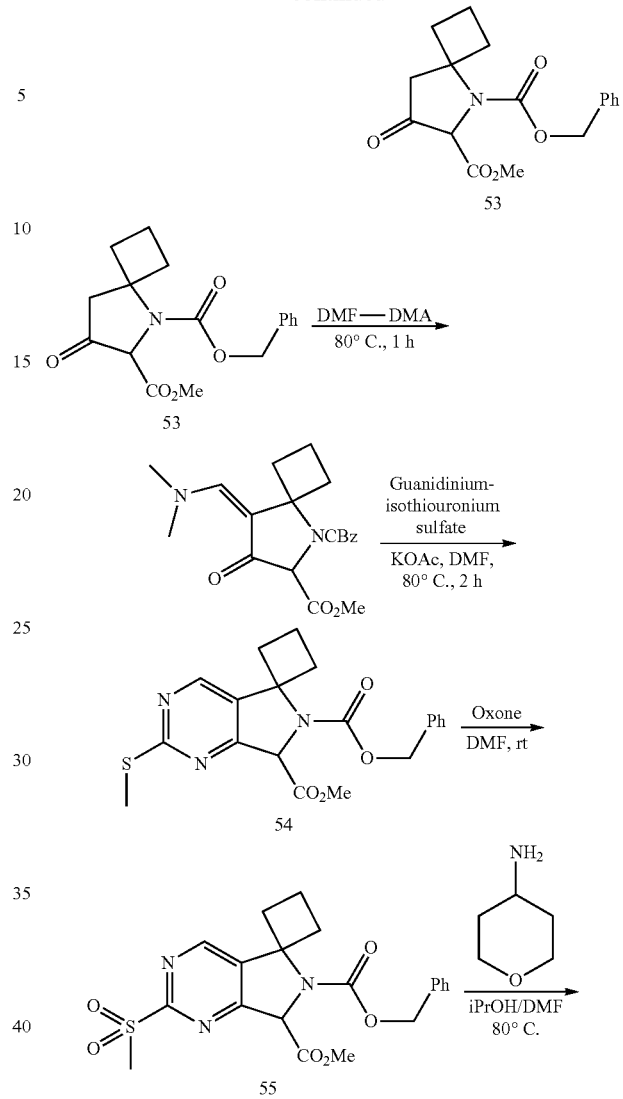
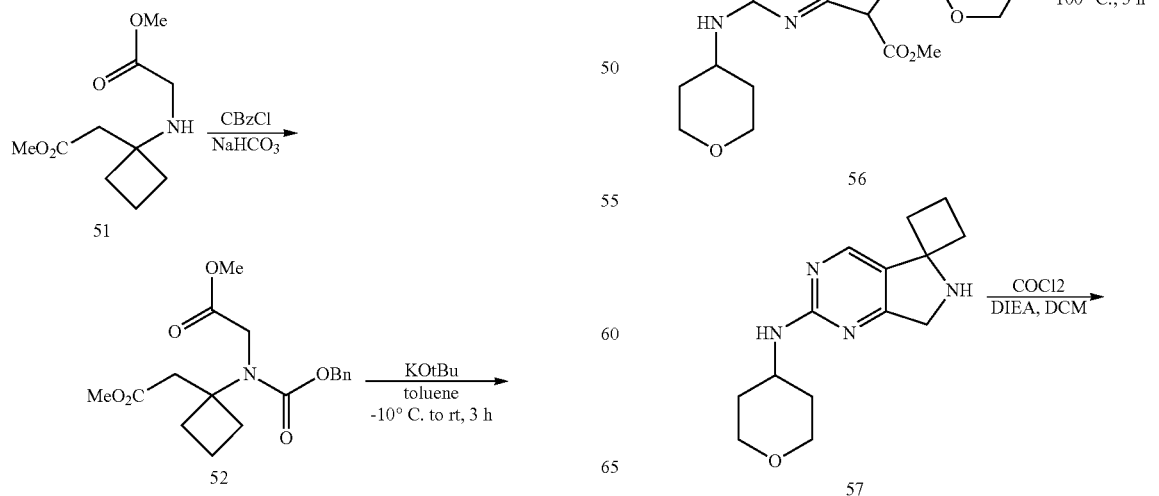

-continued

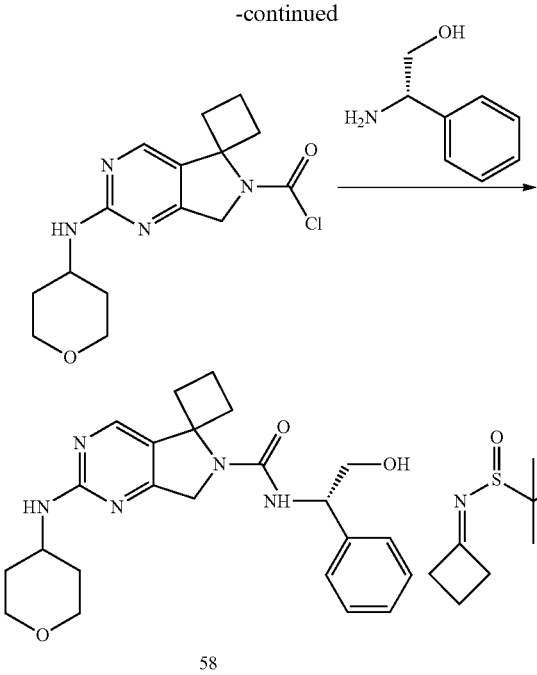

58

N-cyclobutylidene-2-methylpropane-2-sulfinamide (48)

Into a flame dried flask equipped with a stir bar and a reflux condenser were charged racemic-t-butylsulfinamide (8.65 g, 71.3 mmol, 1.0 equiv), cyclobutanone (6.40 mL, 86 mmol, 1.2 equiv) and THF (50 mL), and then titanium(IV) ethoxide (45.3 mL, 143 mmol, 2.0 equiv) was added and the mixture was heated at 70° C. overnight. The next morning the reaction mixture was poured over brine (100 mL) and the slurry was diluted with EtOAc (300 mL). The slurry was filtered and washed with EtOAc (200 mL) and the filtrate was charged into a separatory funnel and the organic layer was separated. The organic layer was dried over MgSO₄ and filtered and concentrated in vacuo and the crude product purified by silica gel chromatography (0-20% EtOAc/heptanes) to give N-cyclobutylidene-2-methylpropane-2-sulfinamide 48 as a colorless oil. MH+=174.2, Rt=0.55.

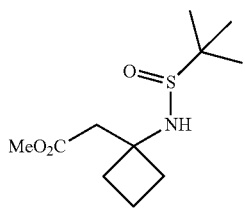

Methyl 2-(1-(1,1-dimethylethylsulfinamido)cyclobutyl)acetate (49)

Into a flame-dried flask was charged N,N-diisopropylamine (20.84 ml, 119 mmol, 2.2 equiv) and THF (Volume: 180 ml) and the solution was cooled to 0° C. Butyllithium (71.2 ml, 114 mmol, 2.1 equiv) was added slowly and the mixture stirred at 0° C. for 30 min and cooled to −78° C. Methyl acetate (8.64 ml, 108 mmol, 2.0 equiv) in THF (20 mL) added and the mixture stirred for 30 min. After 30 min, N-cyclobutylidene-2-methylpropane-2-sulfinamide 48 (9.4 g, 54.2 mmol, 1.0 equiv) in THF (15 mL) was added and the mixture was stirred for 2.5 h at −78° C. LCMS indicated consumption of SM and desired product formation. Sat'd NH₄Cl was added and the reaction was allowed to warm to room temp and stir for 20 min. Water was added and then EtOAc. The biphasic layer was separated and the aq. layer was extracted with EtOAc. The combined organic layer was dried (MgSO₄), filtered and concentrated in vacuo to yield the desired product methyl 2-(1-(1,1-dimethylethylsulfinamido)cyclobutyl)acetate 49 which was taken to the next step without any further purification. MH+=248.2, Rt=0.68.

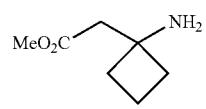

Methyl 2-(1-aminocyclobutyl)acetate (50)

Methyl 2-(1-(1,1-dimethylethylsulfinamido)cyclobutyl)acetate 49 (13.41 g, 54.2 mmol) was suspended in dioxane (30 mL) and 4 N HCl (27.1 ml, 108 mmol, 2.0 equiv) was added. The reaction mixture was stirred at room temperature. After 1 h, reaction complete. At this stage, dioxane was evaporated and the residue was dissolved in 3N HCl and washed with ether twice. The aq. acidic layer was basified with Na₂CO₃ and saturated with solid NaCl and then extracted with DCM. The DCM layer was separated and then 4 N HCl in dioxane (20 mL) was added and the solvent evaporated to give the desired product methyl 2-(1-aminocyclobutyl)acetate 50 as the HCl salt, which was taken to the next step without any further purification. MH+=144, Rt=0.38.

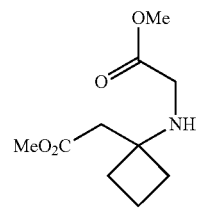 [SMILES: COC(=O)CNC1(CC(=O)OC)CCC1]

Methyl 2-(1-((2-methoxy-2-oxoethyl)amino)cyclobutyl)acetate (51)

Methyl 2-(1-aminocyclobutyl)acetate (8.66 g, 60.5 mmol, 1.0 equiv) was suspended in ACN (36 mL)/THF (3.6 mL) and N,N-diisopropylethylamine (42.3 mL, 242 mmol, 4.0 equiv) was added. The resulting solution was cooled to 0° C. To this solution was added methylbromoacetate (6.3 mL, 63.5 mmol, 1.1 equiv) and the mixture was allowed to warm to RT and stirred for 20 h, after which the reaction mixture was concentrated and the residue was triturated with EtOAc and filtered. The filtrate was evaporated and the residue was triturated with EtOAc again. The solution was filtered and concentrated in vacuo to give the desired product methyl 2-(1-((2-methoxy-2-oxoethyl)amino)cyclobutyl)acetate 51 which was taken to the next step as such. MH+=216.2, Rt=0.47.

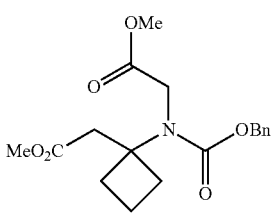 [SMILES: COC(=O)CN(C(=O)OCc1ccccc1)C1(CC(=O)OC)CCC1]

Methyl 2-(((benzyloxy)carbonyl)(1-(2-methoxy-2-oxoethyl)cyclobutyl)amino)acetate (52)

Methyl 2-(1-((2-methoxy-2-oxoethyl)amino)cyclobutyl)acetate 51 (13.02 g, 60.5 mmol, 1.0 equiv) was dissolved in THF (60 mL) and NaHCO$_3$ (sat'd) (60.0 mL) and cooled to 0° C. Benzyl chloroformate (13.64 mL, 91 mmol, 1.5 equiv) was added and the mixture was allowed to warm to room temperature and stir for 5 h. LCMS indicated desired product formation. The layers were separated and the aq. layer was extracted with EtOAc and the combined organic layer dried (MgSO$_4$), filtered and concentrated in vacuo and the residue purified by silica gel chromatography (0-20% EtOAc/heptanes) to give 4.544 g of methyl 2-(((benzyloxy)carbonyl)(1-(2-methoxy-2oxoethyl)cyclobutyl)amino)acetate 52 as the desired product. MH+=350.3, Rt=0.93.

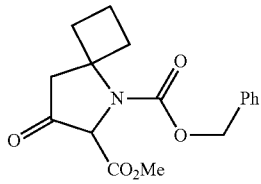

5-benzyl 6-methyl 7-oxo-5-azaspiro[3.4]octane-5,6-dicarboxylate (53)

To a suspension of potassium tert-butoxide (1.970 g, 17.56 mmol, 1.3 equiv) in toluene (50 mL) at −10° C. was added a solution of methyl 2-(((benzyloxy)carbonyl)(1-(2-methoxy-2-oxoethyl)cyclobutyl)amino)acetate 52 (4.544 g, 13.01 mmol, 1.0 equiv) in toluene (30 mL). The mixture was stirred at −10° C. for 1 h and then at room temperature for 3 h. LCMS indicated desired product formation. The reaction mixture was poured over ice-water and neutralized to pH=4 using AcOH. The aq. layer was extracted with EtOAc and the combined organic layer was dried (MgSO4), filtered and concentrated in vacuo to give the residue which was purified by silica gel chromatography (0-20% EtOAc/heptanes) to afford 2.55 g of the desired product 5-benzyl 6-methyl 7-oxo-5-azaspiro[3.4]octane-5,6-dicarboxylate 53 as the major product. MH+=318.2, Rt=0.93.

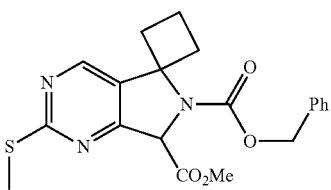 [SMILES: COC(=O)C1c2nc(SC)ncc2C2(CCC2)N1C(=O)OCc1ccccc1]

6'-benzyl 7'-methyl 2'-(methylthio)spiro[cyclobutane-1,5'-pyrrolo[3,4-d]pyrimidine]-6',7'(7'H)-dicarboxylate (54)

5-benzyl 6-methyl 7-oxo-5-azaspiro[3.4]octane-5,6-dicarboxylate 53 (2.55 g, 8.04 mmol) was dissolved in DMF-DMA (28.7 g, 241 mmol, 30 equiv) and the mixture was heated to 85° C. for 1 h. The reaction mixture was concentrated and then diluted with DMF (Volume: 20.09 ml) followed by addition of potassium acetate (2.366 g, 24.11 mmol, 3.0 equiv) and then S-Methylisothiouronium sulfate (3.36 g, 12.05 mmol, 1.50 equiv). This mixture was heated at 100° C. LCMS after 1 h indicated complete conversion of the starting material. Reaction mixture was cooled to room temperature and then diluted with EtOAc. Water was added and the aq. layer was extracted with EtOAc. The combined organic extract was washed with water twice and then dried (MgSO$_4$), filtered and concentrated in vacuo and the residue purified by silica gel chromatography (0-20% EtOAc/heptane) to provide 1.81 g of the desired product 6'-benzyl 7'-methyl 2'-(methylthio)spiro[cyclobutane-1,5'-pyrrolo[3,4-d]pyrimidine]-6',7'(7'H)-dicarboxylate 54 as a gummy syrup. MH+=400.3, Rt=1.08.

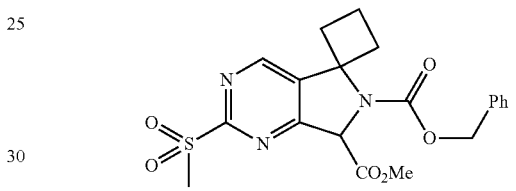

6'-benzyl 7'-methyl 2'-(methylsulfonyl)spiro[cyclobutane-1,5'-pyrrolo[3,4-d]pyrimidine]-6',7'(7'H)-dicarboxylate (55)

6'-benzyl 7'-methyl 2'-(methylthio)spiro[cyclobutane-1,5'-pyrrolo[3,4-d]pyrimidine]-6',7'(7'H)-dicarboxylate 54 (1.8105 g, 4.53 mmol, 1.0 equiv) was dissolved in DMF (15.11 ml) and at room temperature was added oxone (6.97 g, 11.33 mmol, 2.5 equiv) in one portion. The reaction mixture was stirred overnight. The next morning, LCMS indicated desired product formation. The reaction mixture was diluted with EtOAc and filtered through celite and the filtrate was washed with water. The aq. wash was extracted with EtOAc and the combined organic extract was washed with water twice. The organic layer was separated and dried (MgSO$_4$), filtered and concentrated in vacuo to give the residue which was purified by silica gel chromatography (0-20% EtOAc and then 20-80% EtOAc) to give 1.66 g of 6'-benzyl 7'-methyl 2'-(methylsulfonyl)spiro[cyclobutane-1, 5'-pyrrolo[3,4-d]pyrimidine]-6',7'(7'H)-dicarboxylate 55 as the desired product. MH+=432.2, Rt=0.89.

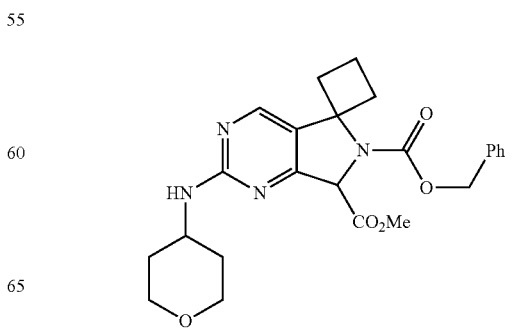

6'-benzyl 7'-methyl 2'-((tetrahydro-2H-pyran-4-yl)amino)spiro[cyclobutane-1,5'-pyrrolo[3,4-d]pyrimidine]-6',7'(7'H)-dicarboxylate (56)

6'-benzyl 7'-methyl 2'-(methylsulfonyl)spiro[cyclobutane-1,5'-pyrrolo[3,4-d]pyrimidine]-6',7'(7'H)-dicarboxylate 55 (682.8 mg, 1.583 mmol) was dissolved in DMF (Volume: 4 ml) and 2-Propanol (Volume: 0.500 ml). Tetrahydro-2H-pyran-4-amine (800 mg, 7.91 mmol, 4.0 equiv) was added next and the mixture was heated to 95° C. After 3 h, LCMS indicated complete conversion to the desired product. The reaction mixture was cooled to room temperature and diluted with EtOAc and the organic layer washed with water three times. The organic layer was separated and dried (MgSO₄), filtered and concentrated to give the desired product 6'-benzyl 7'-methyl 2'-((tetrahydro-2H-pyran-4-yl)amino)spiro[cyclobutane-1,5'-pyrrolo[3,4-d]pyrimidine]-6',7'(7'H)-dicarboxylate 56 as a colorless syrup which was taken to the next step without any further purification. MH+=453.3, Rt=0.93.

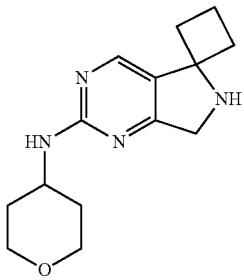 [SMILES: c1nc(NC2CCOCC2)nc2c1C1(CCC1)NC2]

N-(tetrahydro-2H-pyran-4-yl)-6',7'-dihydrospiro[cyclobutane-1,5'-pyrrolo[3,4-d]pyrimidin]-2'-amine (57)

6'-benzyl 7'-methyl 2'-((tetrahydro-2H-pyran-4-yl)amino)spiro[cyclobutane-1,5'-pyrrolo[3,4-d]pyrimidine]-6',7'(7'H)-dicarboxylate 56 (716 mg, 1.583 mmol) was suspended in 6 N HCl (40 mL) and heated to 100° C. After 3 h, complete deprotection and decarboxylation was observed. The reaction mixture was cooled to room temperature and extracted with ether and then the acidic aq. layer was basicified to pH=10 using solid Na₂CO₃ and then extracted with DCM. The organic extracts were combined and dried (MgSO₄), filtered and concentrated in vacuo to give 412 mg of the desired product N-(tetrahydro-2H-pyran-4-yl)-6',7'-dihydrospiro[cyclobutane-1,5'-pyrrolo[3,4-d]pyrimidin]-2'-amine 57 as a yellowish-brown solid. MH+=261.3, Rt=0.37.

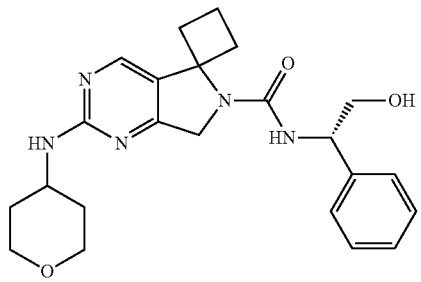 [SMILES: O=C(N[C@H](CO)c1ccccc1)N1Cc2nc(NC3CCOCC3)ncc2C12CCC2]

(S)—N-(2-hydroxy-1-phenylethyl)-2'-((tetrahydro-2H-pyran-4-yl)amino)spiro[cyclobutane-1,5'-pyrrolo[3,4-d]pyrimidine]-6'(7'H)-carboxamide (58)

Into a flask was charged phosgene (15% in toluene) (32.9 μl, 0.313 mmol, 1.1 equiv) and DCM (Volume: 3 mL, Ratio: 1.000) and the flask was cooled to 0° C. To the mixture was added N,N-diisopropylethylamine (91 μl, 0.521 mmol, 2.0 equiv) and then after 5 minutes, a solution of N-(tetrahydro-2H-pyran-4-yl)-6',7'-dihydrospiro[cyclobutane-1,5'-pyrrolo[3,4-d]pyrimidin]-2'-amine 57 (67.8 mg, 0.260 mmol, 1.0 equiv) in DCM (3 mL) was added. After 5 minutes, Phosgene (15% in toluene) (32.9 μl, 0.313 mmol, 1.1 equiv) was added and then after 5 min, formation of the carbamoyl chloride intermediate was deemed complete by LCMS. Water was added and the carbamoyl chloride intermediate was extracted with DCM. The combined organic extract was dried (Na₂SO₄), filtered and concentrated in vacuo to give the crude product which was dissolved in DCM (2 ml) and N,N-diisopropylethylamine (136 μl, 0.781 mmol, 3.0 equiv) was added followed by (S)-2-amino-2-phenylethanol (71.5 mg, 0.521 mmol, 2.0 equiv). The reaction mixture was stirred overnight and the next morning, the LCMS indicated complete consumption of SM. The solvent was evaporated and the residue dissolved in DMSO (3 mL) and divided into 3 vials and purified by reverse phase HPLC to afford the desired product (S)—N-(2-hydroxy-1-phenylethyl)-2'-((tetrahydro-2H-pyran-4-yl)amino)spiro[cyclobutane-1,5'-pyrrolo[3,4-d]pyrimidine]-6'(7'H)-carboxamide 58 as a yellowish white amorphous solid in the form of TFA adduct. MH+=424.3, Rt=0.62. $^1$H NMR (400 MHz, CD₃OD) δ 8.40 (s, 1H), 7.20-7.34 (m, 4H), 7.09-7.18 (m, 1H), 4.88 (dd, J=5.09, 7.43 Hz, 1H), 4.33-4.64 (m, 2H), 3.85-4.17 (m, 3H), 3.59-3.79 (m, 2H), 3.25-3.53 (m, 4H), 1.78-2.26 (m, 6H), 1.41-1.65 (m, 2H).

Example 8

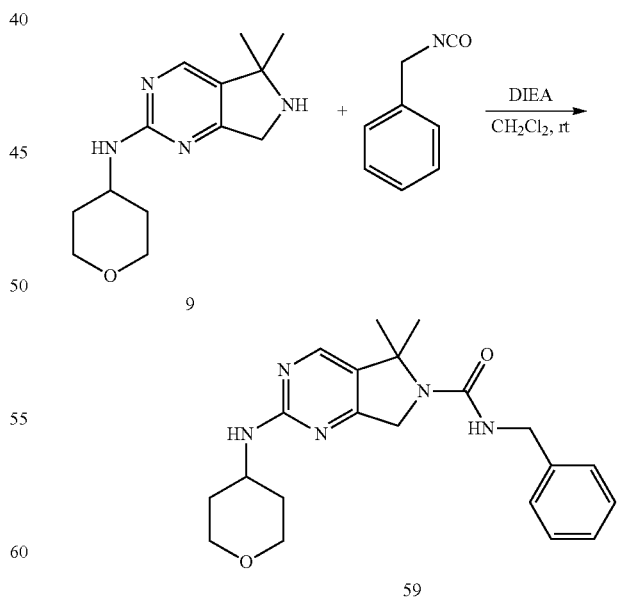

Into a vial equipped with a stir bar was charged 9 (30.0 mg, 0.121 mmol, 1.0 equiv) and dichloromethane (1.0 mL). To the solution was added triethylamine (0.025 mL, 0.180 mmol, 1.5 equiv) followed by benzylisocyanate (0.015 mL, 0.121 mmol, 1.0 equiv) and the reaction mixture was let to stir at room temperature for 30 min and then concentrated in vacuo to afford the crude product which was directly purified by reverse phase HPLC to afford the desired product as the TFA adduct. MH+=382.3, $R_f$=0.65.
Example 9
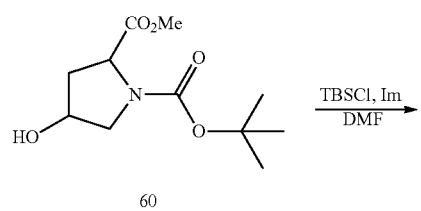
60
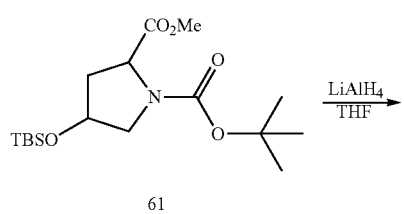
61
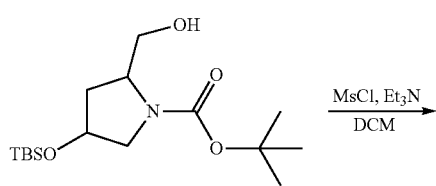
62
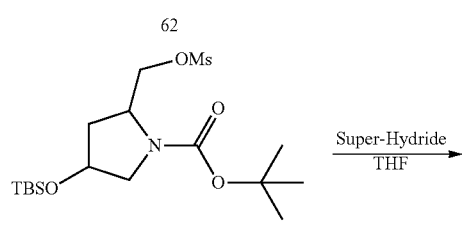
63
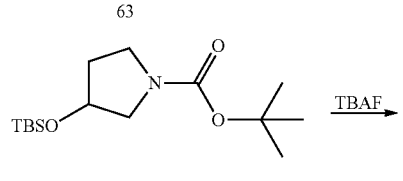
64
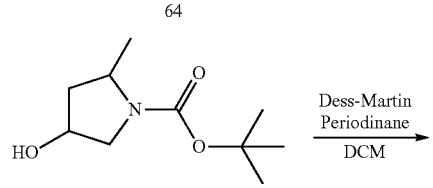
65
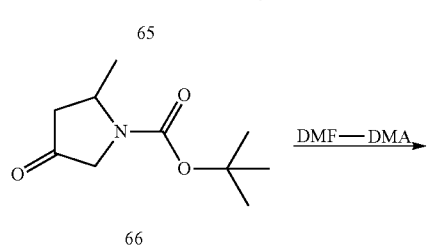
66
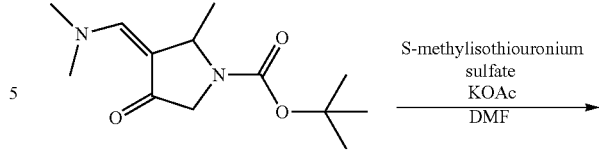
67
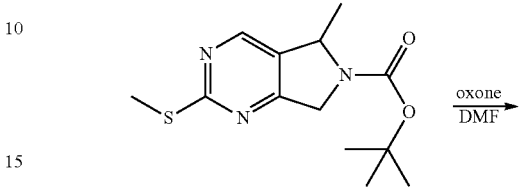
68
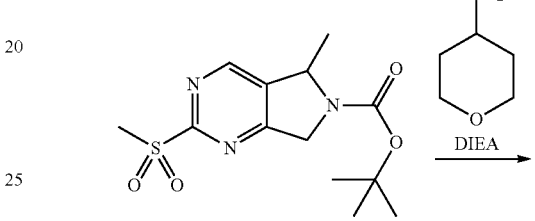
69
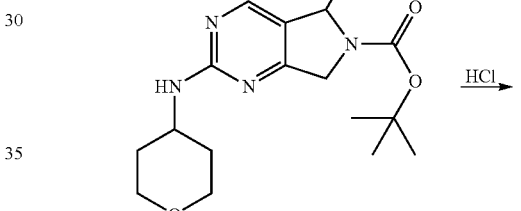
70
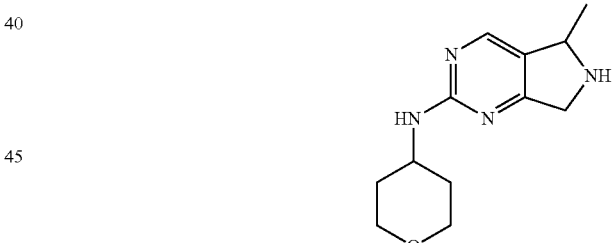
71
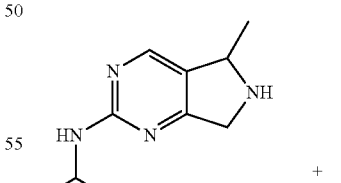
71
+
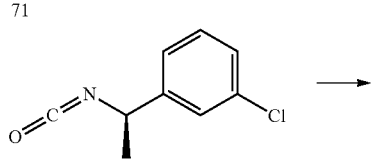

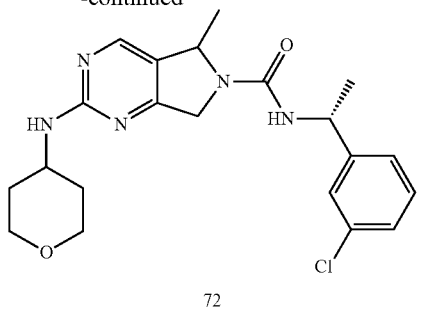

72

1-tert-butyl 2-methyl 4-((tert-butyldimethylsilyl)oxy)pyrrolidine-1,2-dicarboxylate (61)

1-tert-butyl 2-methyl 4-hydroxypyrrolidine-1,2-dicarboxylate (60) (8.00 g, 32.6 mmol) was dissolved in DMF (17 mL) and then ImH (imidazole, 4.44 g, 65.2 mmol) followed by TBSCl (7.37 g, 48.9 mmol) were added in this order. After 1 h at room temperature, the reaction mixture was diluted with ether and the organic layer was washed with water twice and the organic layer was dried (MgSO$_4$), filtered and concentrated in vacuo and the residue taken to the next step without any further purification. Assume quantitative yield. MH-100+=260.2, Rt=0.47 and 0.49.

Tert-butyl 4-((tert-butyldimethylsilyl)oxy)-2-(hydroxymethyl)pyrrolidine-1-carboxylate (62). 1-Tert-butyl 2-methyl 4-((tert-butyldimethylsilyl)oxy)pyrrolidine-1,2-dicarboxylate (11.72 g, 32.6 mmol) was dissolved in THF (82 mL) and cooled to 0° C. To the solution was added LiBH4 (22.82 ml, 45.6 mmol) dropwise and the mixture was allowed to warm to room temperature overnight. The next morning, the reaction mixture was quenched with dropwise addition of water and the product extracted with EtOAc and the combined organic layer was dried (MgSO$_4$), filtered and concentrated in vacuo to afford the crude product which was purified by flash chromatography (0-40% EtOAc/heptanes) to afford the desired product in quantitative yield. MH-56+=276.5, Rt=1.11.

Tert-butyl 4-((tert-butyldimethylsilyl)oxy)-2-(((methylsulfonyl)oxy)methyl)pyrrolidine-1-carboxylate (63)

Tert-butyl 4-((tert-butyldimethylsilyl)oxy)-2-(hydroxymethyl)pyrrolidine-1-carboxylate (10.81 g, 32.6 mmol) was dissolved in DCM (66 mL) and cooled to −10° C. Then triethylamine (9.09 ml, 65.2 mmol) was added and finally, MsCl (3.30 ml, 42.4 mmol) was added and the mixture was allowed to gradually warm to room temperature overnight. The next morning, the reaction mixture was quenched with water and extracted with DCM and the organic layer was washed with 1 N HCl and then Sat'd NaHCO$_3$ and then dried (MgSO$_4$), filtered and concentrated in vacuo to give 13.1 g of product which was used as such for the next reaction. MH-56+=354.2, Rt=1.15.

Tert-butyl 3-((tert-butyldimethylsilyl)oxy)pyrrolidine-1-carboxylate (64)

Tert-butyl 4-((tert-butyldimethylsilyl)oxy)-2-(((methylsulfonyl)oxy)methyl)pyrrolidine-1-carboxylate (11.28 g, 27.5 mmol) was dissolved in THF (100 mL) and then Super-hydride (82.5 mL, 82.5 mmol) was added and the mixture was stirred at room temperature for 2 h and quenched with water and extracted with EtOAc and washed with Sat'd NaHCO$_3$, and the organic layer was separated and dried (MgSO$_4$), filtered and concentrated in vacuo to give the crude product residue in quantitative yield and this residue was used as such for the next reaction. MH-56+=260.7, Rt=1.32, 1.33.

Tert-butyl 4-hydroxy-2-methylpyrrolidine-1-carboxylate (65)

Tert-butyl 3-((tert-butyldimethylsilyl)oxy)pyrrolidine-1-carboxylate from above was dissolved in THF (80 mL) and treated with TBAF (65.2 ml, 65.2 mmol) and the mixture was stirred at room temperature for 3 h and quenched with water and the product extracted with EtOAc twice and the organic layer was washed with water and dried (MgSO$_4$), filtered and concentrated in vacuo and the residue was purified by flash chromatography (0-60% EtOAC/heptanes) to provide 4.35 g of the desired product as a colorless syrup. MH+=202.2, Rt=0.62.

Tert-butyl 2-methyl-4-oxopyrrolidine-1-carboxylate (66)

Tert-butyl 4-hydroxy-2-methylpyrrolidine-1-carboxylate (4.35 g, 21.61 mmol) was dissolved in DCM (108 mL) and NaHCO$_3$ (8.17 g, 97 mmol) followed by Dess-Martin Periodinane (13.75 g, 32.4 mmol) were added and the mixture was agitated at room temperature. Additional DMP (10.0 g) was added after 5 h and the mixture stirred overnight. The next morning, the reaction mixture quenched with Sat'd Na$_2$S$_2$O$_3$ and then with aq. NaHCO$_3$ and after the effervescence had subsided, the reaction mixture was extracted with DCM and the organic layer was dried (MgSO$_4$), filtered and concentrated in vacuo and the residue purified by flash chromatography (0-50% EtOAc/heptane) to afford the desired product. $^1$H NMR (400 MHz, CDCl$_3$) δ ppm 4.45 (br. s., 1H) 3.91 (d, J=19.56 Hz, 1H) 3.65 (d, J=19.56 Hz, 1H) 2.82 (dd, J=18.39, 9.00 Hz, 1H) 2.21 (d, J=18.39 Hz, 1H) 1.42-1.55 (m, 9H), 1.25 (d, J=6.26 Hz, 3H).

(Z)-Tert-butyl 3-((dimethylamino)methylene)-2-methyl-4-oxopyrrolidine-1-carboxylate (67)

Tert-butyl 2-methyl-4-oxopyrrolidine-1-carboxylate (2.987 g, 14.99 mmol) was dissolved in DMF-DMA (20.07 ml, 150 mmol) and the mixture was heated at 110° C. for 1 h after which the mixture was concentrated in vacuo to afford the crude enaminone which was dissolved in EtOAc and washed with aq. NaHCO$_3$ and then with water and then brine and finally the organic layer was dried (MgSO$_4$), filtered and concentrated in vacuo to afford the crude product which was taken to the next step without any further purification. MH+=255.1, Rt=0.67.

Tert-butyl 5-methyl-2-(methylthio)-5H-pyrrolo[3,4-d]pyrimidine-6(7H)-carboxylate (68)

(Z)-Tert-butyl 3-((dimethylamino)methylene)-2-methyl-4-oxopyrrolidine-1-carboxylate (14.99 mmol) was dissolved in DMF (30 mL) and potassium acetate (4.41 g, 45.0 mmol) followed by S-methylisothiouronium sulfate (6.26 g, 22.49 mmol) were added, and the mixture was heated at 100° C. for 4 h and then cooled to room temperature. Water was added and the product was extracted with EtOAc. The organic layer was combined and washed with water thrice and then dried (MgSO$_4$), filtered and concentrated in vacuo and the residue purified by flash chromatography (0-30% EtOAc/heptanes) to afford the desired product. MH+=282.0, Rt=0.94.

Tert-butyl 5-methyl-2-(methylsulfonyl)-5H-pyrrolo [3,4-d]pyrimidine-6(7H)-carboxylate (69)

Tert-butyl 5-methyl-2-(methylthio)-5H-pyrrolo[3,4-d]pyrimidine-6(7H)-carboxylate (2.528 g, 8.98 mmol) was dissolved in DMF (29.9 mL) and oxone (13.81, 22.46 mmol) was added in one portion. The reaction mixture was agitated overnight and the next morning, the mixture was diluted with EtOAc/water and the aq. layer extracted with EtOAc. The combined organic layer was washed with water thrice and then dried (MgSO$_4$), filtered and concentrated in vacuo to afford the desired product which was taken to the next step without any further purification. MH+=314.0, Rt=0.71.

Tert-butyl 5-methyl-2-((tetrahydro-2H-pyran-4-yl) amino)-5H-pyrrolo[3,4-d]pyrimidine-6(7H)-carboxylate (70)

Tert-butyl 5-methyl-2-(methylsulfonyl)-5H-pyrrolo[3,4-d]pyrimidine-6(7H)-carboxylate (1.03 g, 3.29 mmol) was dissolved in NMP (6.0 mL) and then N,N-diisopropylethylamine (2.87 ml, 16.43 mmol) was added and this was followed by addition of tetrahydro-2H-pyran-4-amine (1.164 g, 11.50 mmol). The reaction mixture was sealed in a microwave vial and heated at 150° C. for 60 min and then diluted with water and extracted with EtOAc and the combined organic extract was washed with water thrice, and dried (MgSO$_4$), filtered and concentrated in vacuo to afford the crude product which was taken to the next step without any further purification. MH+=335.2, Rt=0.70.

5-methyl-N-(tetrahydro-2H-pyran-4-yl)-6,7-dihydro-5H-pyrrolo[3,4-d]pyrimidin-2-amine (71)

Tert-butyl 5-methyl-2-((tetrahydro-2H-pyran-4-yl) amino)-5H-pyrrolo[3,4-d]pyrimidine-6(7H)-carboxylate from above was dissolved in MeOH (8 mL) and then 4 N HCl in dioxane (8 mL) was added and the mixture was stirred at room temperature for 2 h and then concentrated in vacuo to afford the desired product which was dissolved in DCM and washed with Sat'd Na$_2$CO$_3$ and then dried (MgSO$_4$), filtered and concentrated in vacuo to afford the free base adduct which was used without any further purification. MH+=235.1, Rt=0.27.

N—((R)-1-(3-chlorophenyl)ethyl)-5-methyl-2-((tetrahydro-2H-pyran-4-yl)amino)-5H-pyrrolo[3,4-d] pyrimidine-6(7H)-carboxamide (72)

5-methyl-N-(tetrahydro-2H-pyran-4-yl)-6,7-dihydro-5H-pyrrolo[3,4-d]pyrimidin-2-amine (125 mg, 0.534 mmol) was dissolved in DCM (1 mL) and then N,N-diisopropylethylamine (280 µl, 1.601 mmol) followed by (R)-1-chloro-3-(1-isocyanatoethyl)benzene (116 mg, 0.640 mmol) were added. The reaction mixture was let to stay at room temperature for 30 min and loaded onto silica and the product purified by flash chromatography (0-10% MeOH/DCM) to afford the desired product (103.2 mg). MH+=416.2, Rt=0.73. 1H NMR (400 MHz, CDCl3) δ ppm 8.20 (s, 1H) 7.39 (s, 1H) 7.29 (d, J=5.09 Hz, 2H) 7.17-7.25 (m, 1H) 5.13 (q, J=6.26 Hz, 1H) 4.94 (q, J=7.04 Hz, 1H) 4.47-4.58 (m, 2H) 3.91-4.11 (m, 3H) 3.52 (td, J=11.64, 1.76 Hz, 2H) 3.30 (dt, J=3.13, 1.57 Hz, 2H) 1.96 (d, J=13.30 Hz, 2H) 1.54-1.67 (m, 2H) 1.49 (d, J=7.04 Hz, 3H) 1.43 (d, J=6.26 Hz, 3H).

Example 10

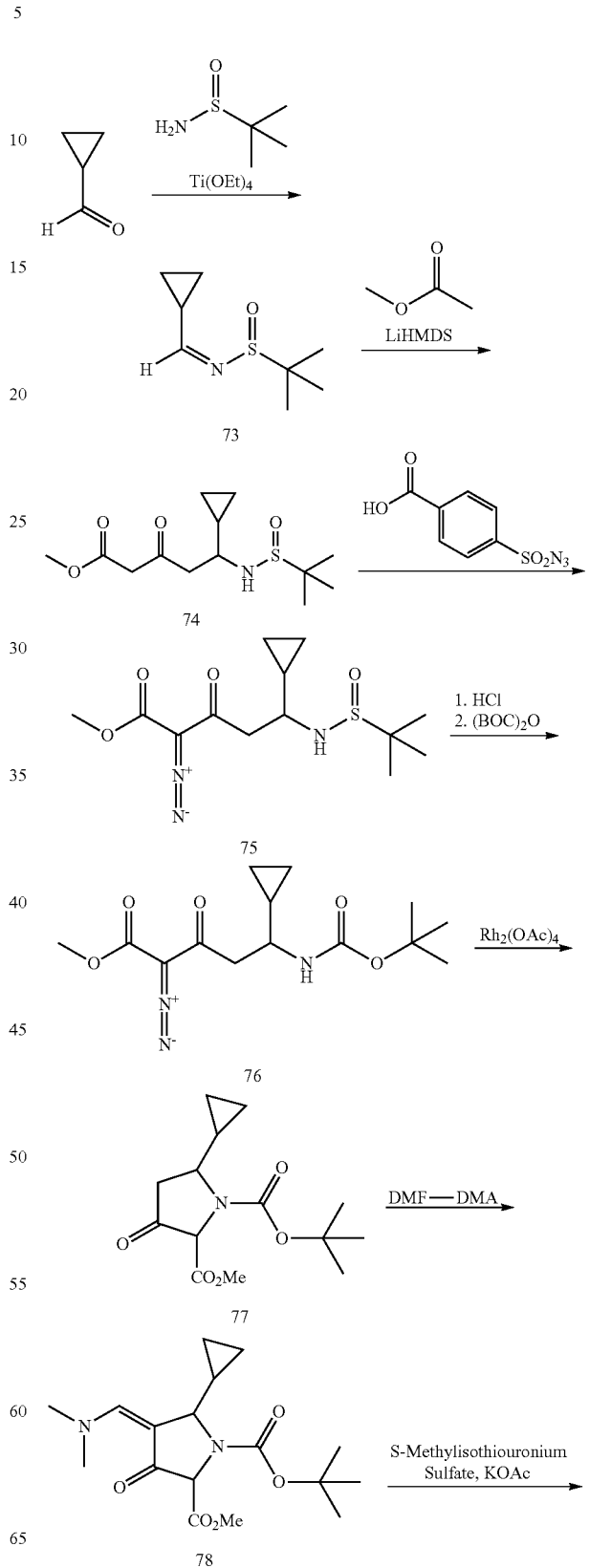

-continued

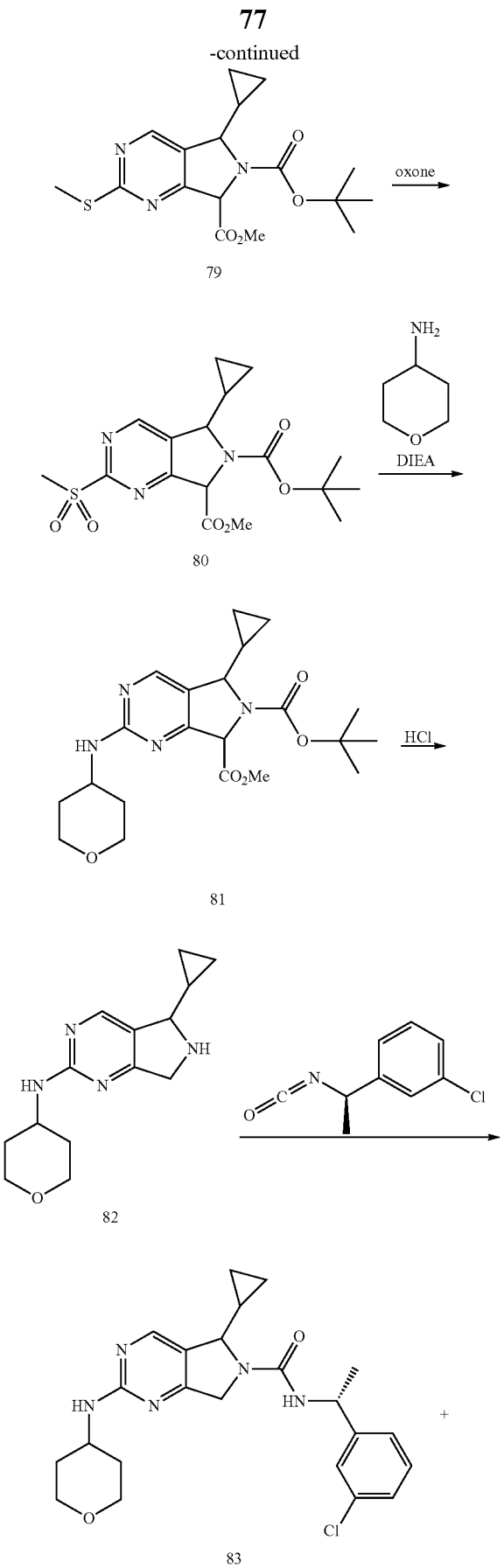

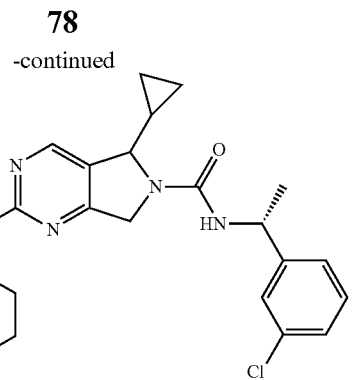

(Z)—N-(cyclopropylmethylene)-2-methylpropane-2-sulfinamide (73)

Into a flame dried flask equipped with a stir bar and a reflux condenser was charged racemic-t-butylsulfinamide (5.01 g, 41.4 mmol), cyclopropanecarbaldehyde (2.9 g, 41.4 mmol) and then THF (83 ml) and the mixture was stirred at 40° C. The next morning the reaction mixture was poured over brine (100 mL) and the slurry was diluted with EtOAc (300 mL). The slurry was filtered and washed with EtOAc (200 mL) and the filtrate was charged into a separatory funnel and the organic layer was separated. The organic layer was dried over MgSO$_4$ and filtered and concentrated in vacuo and the crude product was taken to the next step without any further purification. MH+=174, Rt=0.64.

Methyl 5-cyclopropyl-5-(1,1-dimethylethylsulfinamido)-3-oxopentanoate (74)

NaHMDS (102 mL, 102 mmol) was cooled to −78° C. and then methyl acetate (8.09 mL, 102 mmol) was added dropwise and the solution was stirred for 1 h at −78 C. Then, (Z)—N-(cyclopropylmethylene)-2-methylpropane-2-sulfinamide (3.52 g, 20.31 mmol) dissolved in THF (20 mL) was added and the mixture stirred at −20° C. for 3 h upon which LCMS indicated formation of desired product as a mixture of diastereomers LCMS MH+=290, 0.65 as major and 0.60 as minor. The reaction was diluted with Sat'd NH$_4$Cl and extracted with EtOAc and the organic extracts washed with Sat'd NaHCO$_3$ and then brine and dried (MgSO$_4$), filtered and concentrated in vacuo to afford the residue which was purified by flash chromatography (0-100% EtOAc/heptanes) to provide 2.45 g of the desired product. MH+=290.1, Rt=0.60, 0.65.

Methyl 5-cyclopropyl-2-diazo-5-(1,1-dimethylethylsulfinamido)-3-oxopentanoate (75)

Methyl 5-cyclopropyl-5-(1,1-dimethylethylsulfinamido)-3-oxopentanoate (2.451 g, 8.47 mmol) was dissolved in ACN (acetonitrile, 42 mL) and then triethylamine (3.54 ml, 25.4 mmol) followed by 4-(azidosulfonyl)benzoic acid (2.117 g, 9.32 mmol) were added. The reaction mixture was agitated at room temperature for 5 h and then quenched with sat'd NaCl and extracted with EtOAc. The combined organic layer was dried (MgSO$_4$), filtered and concentrated in vacuo to afford the crude diazo compound which was used in the next step as such. MH+=360.7, Rt=0.74.

Using these methods, compounds of the invention were prepared, including the ones in the following Table. Each compound in the Table is a preferred embodiment of the invention. The compound numbers in the Table do not correspond to the numbering used in the examples above, but the synthesis method used for most of the compounds is shown in the Table.

TABLE 1

| Cmpd No. | Structure | M + H Obs. | Ret'n-time (min) | Synth. Meth. |
|---|---|---|---|---|
| 1 | 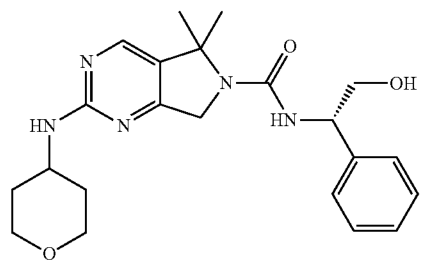 [SMILES: CC1(C)c2cnc(NC3CCOCC3)nc2CN1C(=O)N[C@H](CO)c1ccccc1] | 412.2 | 0.58 | 1 |
| 2 | 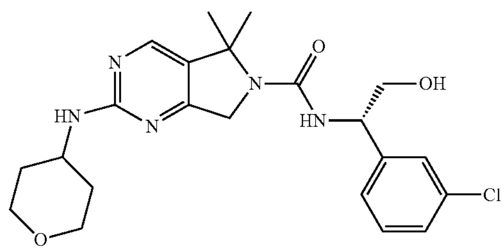 [SMILES: CC1(C)c2cnc(NC3CCOCC3)nc2CN1C(=O)N[C@H](CO)c1cccc(Cl)c1] | 446.2 | 0.67 | 1 |
| 3 | 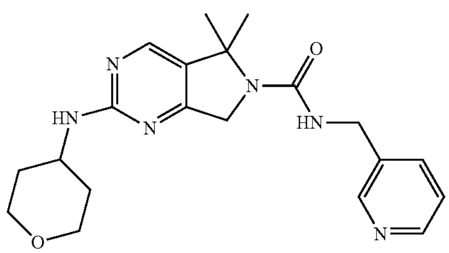 [SMILES: CC1(C)c2cnc(NC3CCOCC3)nc2CN1C(=O)NCc1cccnc1] | 383.3 | 0.42 | 1 |
| 4 | 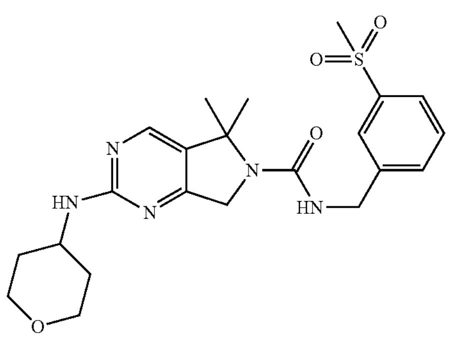 [SMILES: CC1(C)c2cnc(NC3CCOCC3)nc2CN1C(=O)NCc1cccc(S(C)(=O)=O)c1] | 460.2 | 0.56 | 1 |
| 5 | 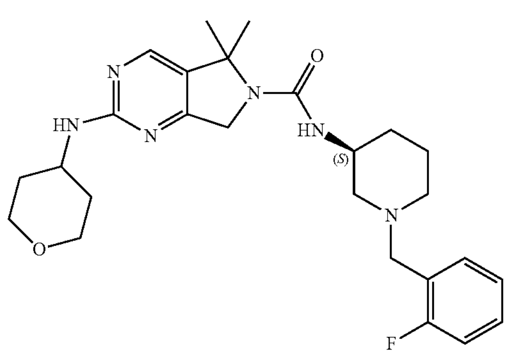 | 483.3 | 0.55 | 1 |

TABLE 1-continued

| Cmpd No. | Structure | M + H Obs. | Ret'n time (min) | Synth. Meth. |
|---|---|---|---|---|
| 6 | 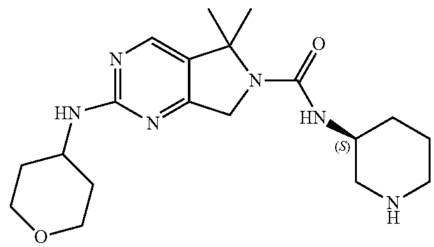 | 375.3 | 0.45 | 1 |
| 7 | 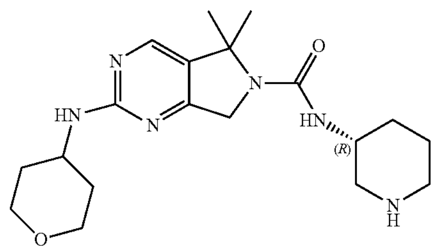 | 375.4 | 0.44 | 1 |
| 8 | 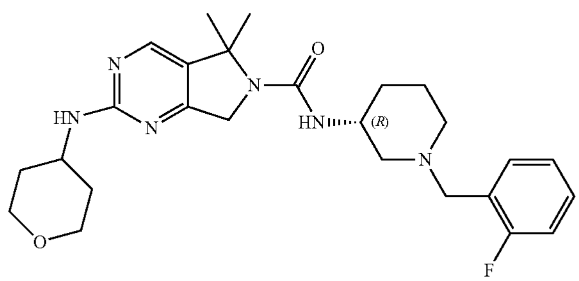 | 483.3 | 0.50 | 1 |
| 9 | 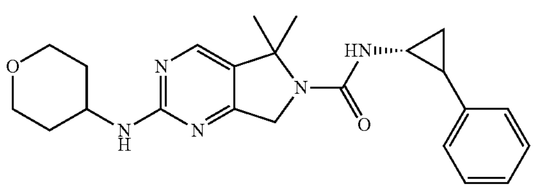 [SMILES: CC1(C)c2cnc(NC3CCOCC3)nc2CN1C(=O)N[C@@H]1CC1c1ccccc1] | 408.3 | 0.74 | 1 |
| 10 | 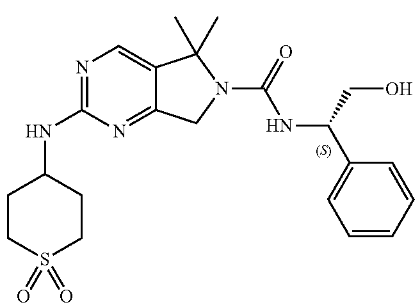 | 460.2 | 0.56 | 1 |
| 11 | 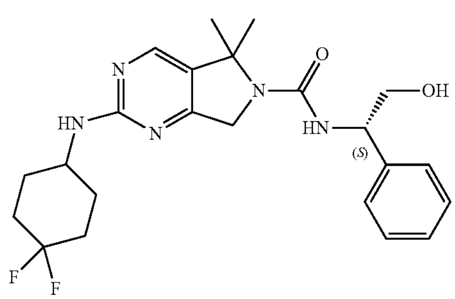 | 446.3 | 0.47 | 1 |

TABLE 1-continued

| Cmpd No. | Structure | M + H Obs. | Ret'n time (min) | Synth. Meth. |
|---|---|---|---|---|
| 12 | 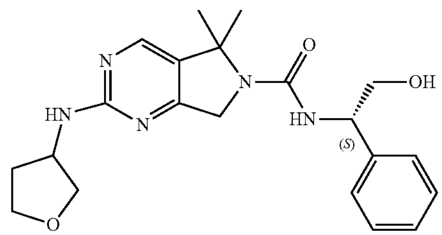 | 398.3 | 0.57 | 1 |
| 13 | 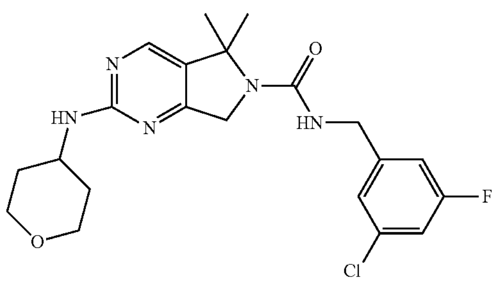 [SMILES: CC1(C)c2cnc(NC3CCOCC3)nc2CN1C(=O)NCc1cc(F)cc(Cl)c1] | 434.2 | 0.77 | 1 |
| 14 | 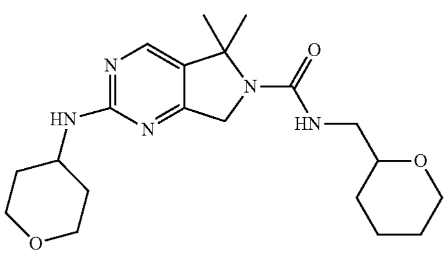 [SMILES: CC1(C)c2cnc(NC3CCOCC3)nc2CN1C(=O)NCC1CCCCO1] | 390.3 | 0.58 | 1 |
| 15 | 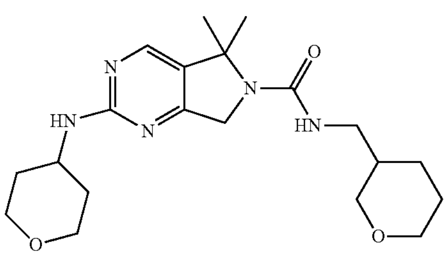 [SMILES: CC1(C)c2cnc(NC3CCOCC3)nc2CN1C(=O)NCC1CCCOC1] | 390.3 | 0.54 | 1 |
| 16 | 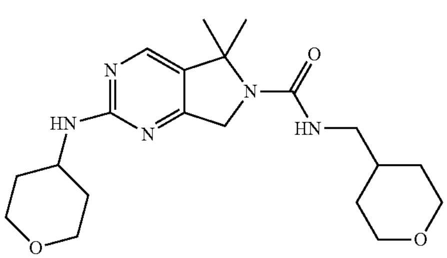 [SMILES: CC1(C)c2cnc(NC3CCOCC3)nc2CN1C(=O)NCC1CCOCC1] | 390.3 | 0.51 | 1 |
| 17 | 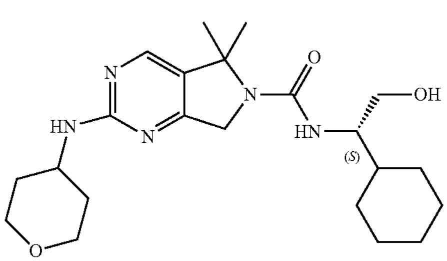 | 418.3 | 0.67 | 1 |

TABLE 1-continued

| Cmpd No. | Structure | M + H Obs. | Ret'n time (min) | Synth. Meth. |
|---|---|---|---|---|
| 18 | 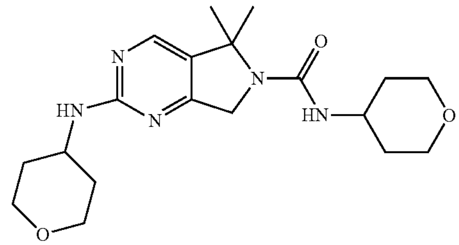 [SMILES: CC1(C)c2cnc(NC3CCOCC3)nc2CN1C(=O)NC1CCOCC1] | 376.4 | 0.49 | 1 |
| 19 | 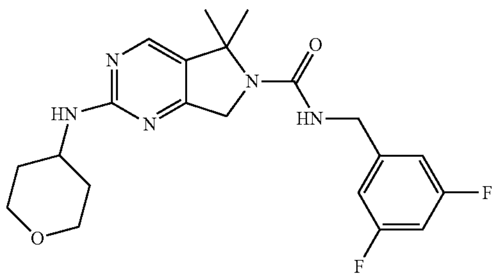 [SMILES: CC1(C)c2cnc(NC3CCOCC3)nc2CN1C(=O)NCc1cc(F)cc(F)c1] | 418.3 | 0.67 | 1 |
| 20 | 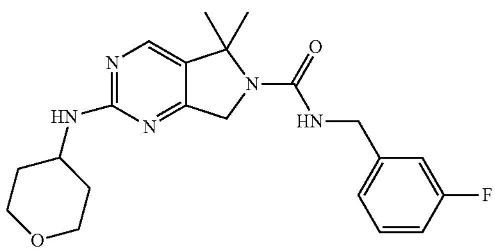 [SMILES: CC1(C)c2cnc(NC3CCOCC3)nc2CN1C(=O)NCc1cccc(F)c1] | 400.2 | 0.67 | 1 |
| 21 | 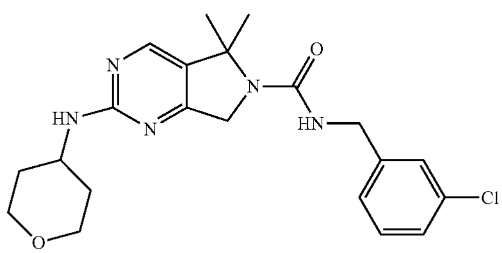 [SMILES: CC1(C)c2cnc(NC3CCOCC3)nc2CN1C(=O)NCc1cccc(Cl)c1] | 416.2 | 0.73 | 1 |
| 22 | 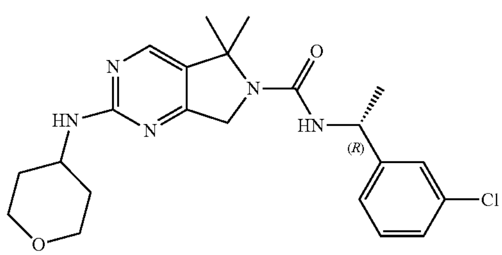 | 430.2 | 0.78 | 1 |
| 23 | 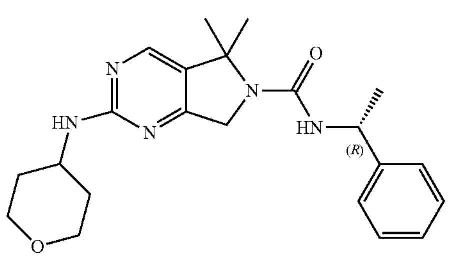 | 393.3 | 0.69 | 1 |

TABLE 1-continued

| Cmpd No. | Structure | M + H Obs. | Ret'n time (min) | Synth. Meth. |
|---|---|---|---|---|
| 24 | 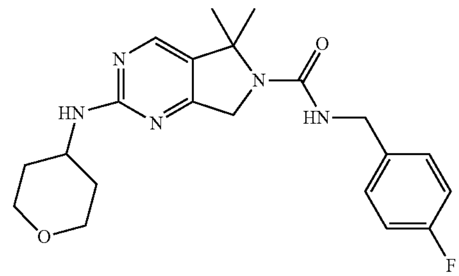 [SMILES: CC1(C)c2cnc(NC3CCOCC3)nc2CN1C(=O)NCc1ccc(F)cc1] | 400.2 | 0.67 | 1 |
| 25 | 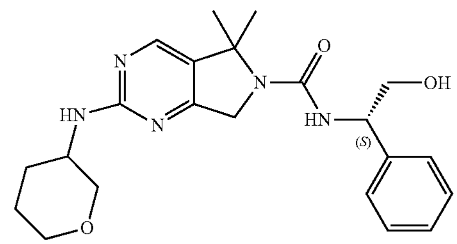 | 412.3 | 0.62 | 1 |
| 26 | 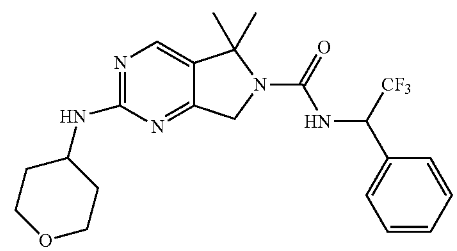 [SMILES: CC1(C)c2cnc(NC3CCOCC3)nc2CN1C(=O)NC(c1ccccc1)C(F)(F)F] | 450.2 | 0.81 | 1 |
| 27 | 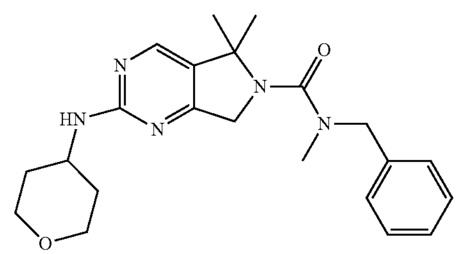 [SMILES: CN(Cc1ccccc1)C(=O)N1Cc2nc(NC3CCOCC3)ncc2C1(C)C] | 396.3 | 0.75 | 1 |
| 28 | 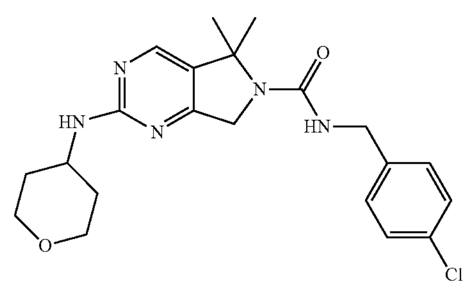 [SMILES: CC1(C)c2cnc(NC3CCOCC3)nc2CN1C(=O)NCc1ccc(Cl)cc1] | 416.2 | 0.75 | 1 |
| 29 | 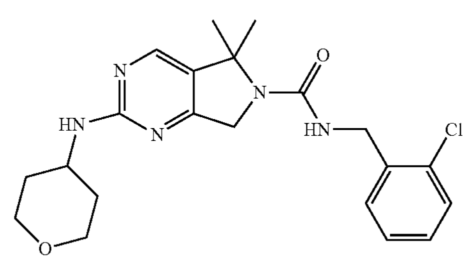 [SMILES: CC1(C)c2cnc(NC3CCOCC3)nc2CN1C(=O)NCc1ccccc1Cl] | 416.2 | 0.74 | 1 |

TABLE 1-continued
| Cmpd No. | Structure | M + H Obs. | Ret'n time (min) | Synth. Meth. |
|---|---|---|---|---|
| 30 | 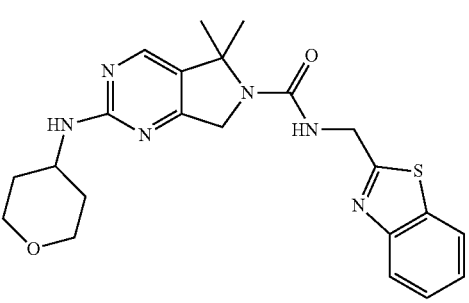 [SMILES: CC1(C)c2cnc(NC3CCOCC3)nc2CN1C(=O)NCc1nc2ccccc2s1] | 439.2 | 0.62 | 1 |
| 31 | 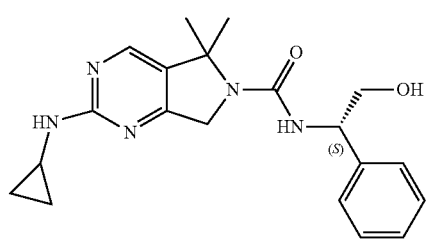 | 368.3 | 0.56 | 1 |
| 32 | 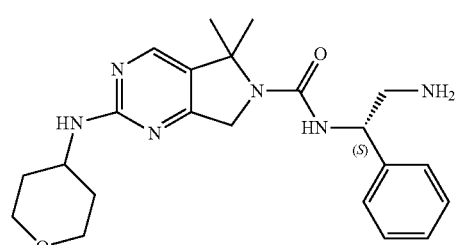 | 411.3 | 0.55 | 1 |
| 33 | 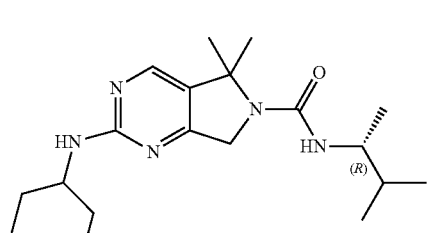 | 362.3 | 0.68 | 1 |
| 34 | 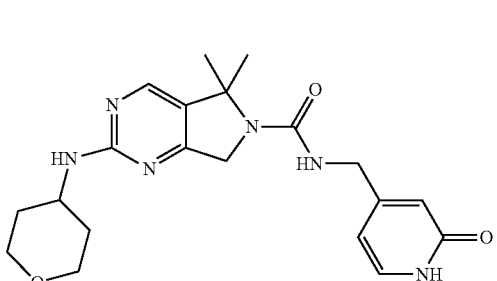 | 399.3 | 0.45 | 1 |

TABLE 1-continued

| Cmpd No. | Structure | M + H Obs. | Ret'n time (min) | Synth. Meth. |
|---|---|---|---|---|
| 35 | 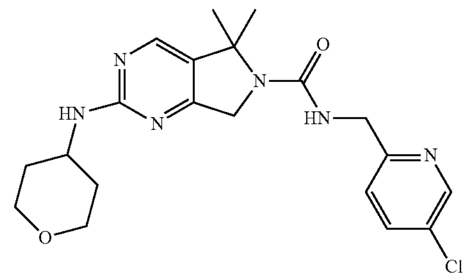 [SMILES: CC1(C)c2cnc(NC3CCOCC3)nc2CN1C(=O)NCc1ccc(Cl)cn1] | 417.2 | 0.60 | 1 |
| 36 | 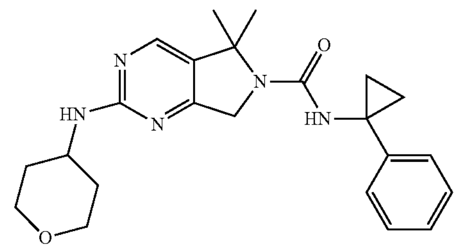 [SMILES: CC1(C)c2cnc(NC3CCOCC3)nc2CN1C(=O)NC1(c2ccccc2)CC1] | 408.3 | 0.73 | 1 |
| 37 | 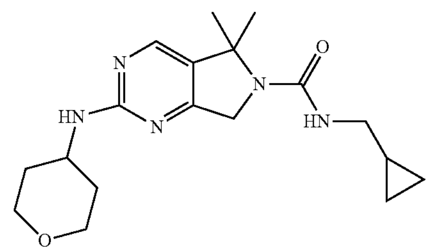 [SMILES: CC1(C)c2cnc(NC3CCOCC3)nc2CN1C(=O)NCC1CC1] | 346.3 | 0.61 | 1 |
| 38 | 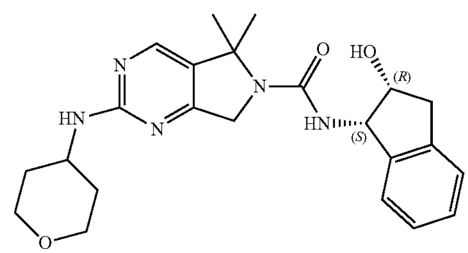 | 424.3 | 0.66 | 1 |
| 39 | 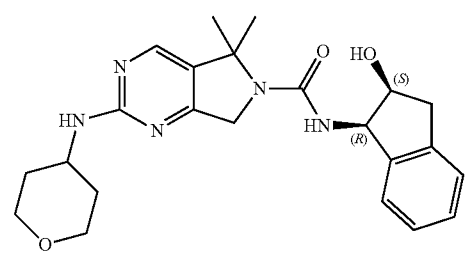 | 424.3 | 0.66 | 1 |
| 40 | 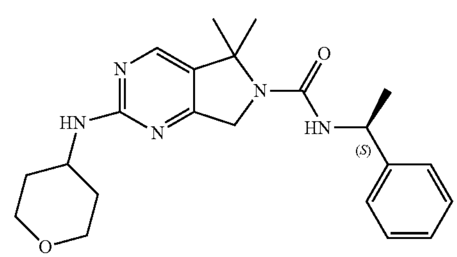 | 396.3 | 0.74 | 1 |

TABLE 1-continued
| Cmpd No. | Structure | M + H Obs. | Ret'n time (min) | Synth. Meth. |
|---|---|---|---|---|
| 41 | 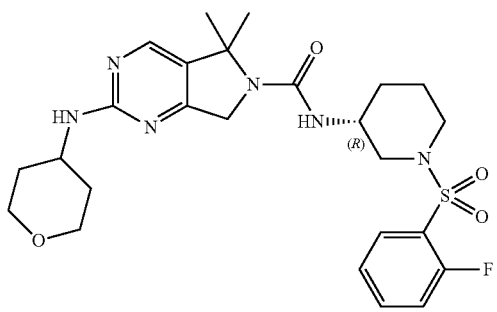 | 533.3 | 0.74 | 1 |
| 42 | 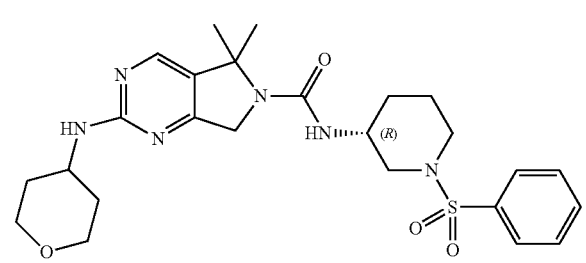 | 515.3 | 0.74 | 1 |
| 44 | 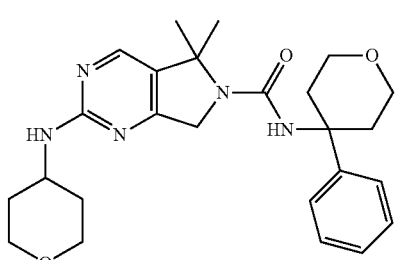 | 452.3 | 0.67 | 1 |
| 45 | 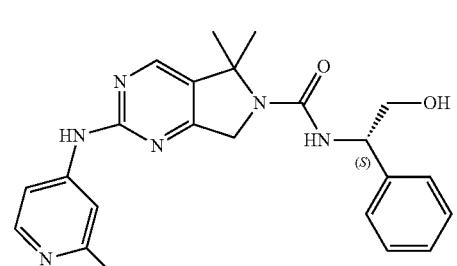 | 419.3 | 0.57 | 2 |
| 46 | 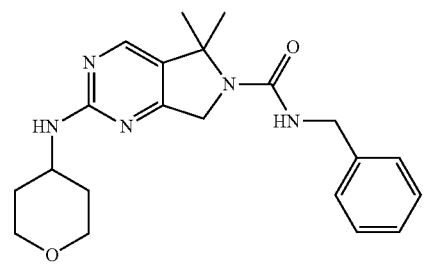 [SMILES: CC1(C)c2cnc(NC3CCOCC3)nc2CN1C(=O)NCc1ccccc1] | 382.3 | 0.65 | 8 |

TABLE 1-continued

| Cmpd No. | Structure | M + H Obs. | Ret'n time (min) | Synth. Meth. |
|---|---|---|---|---|
| 47 | 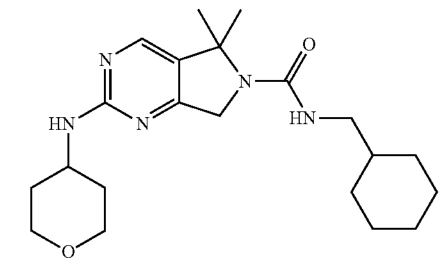 [SMILES: CC1(C)c2cnc(NC3CCOCC3)nc2CN1C(=O)NCC1CCCCC1] | 388.3 | 0.78 | 8 |
| 49 | 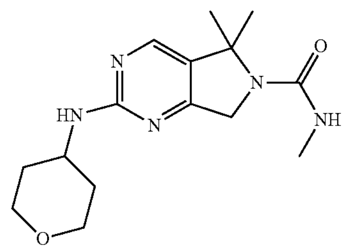 [SMILES: CNC(=O)N1Cc2nc(NC3CCOCC3)ncc2C1(C)C] | 306.2 | 0.43 | 8 |
| 50 | 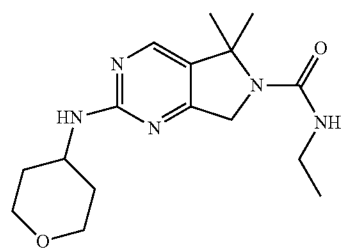 [SMILES: CCNC(=O)N1Cc2nc(NC3CCOCC3)ncc2C1(C)C] | 320.2 | 0.49 | 8 |
| 51 | 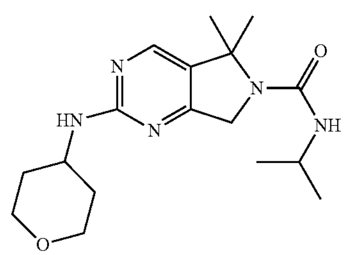 [SMILES: CC(C)NC(=O)N1Cc2nc(NC3CCOCC3)ncc2C1(C)C] | 334.3 | 0.43 | 8 |
| 52 | 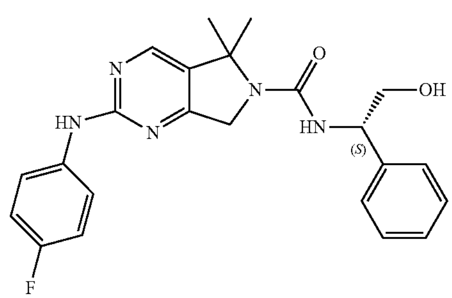 | 422.3 | 0.83 | 2 |
| 53 | 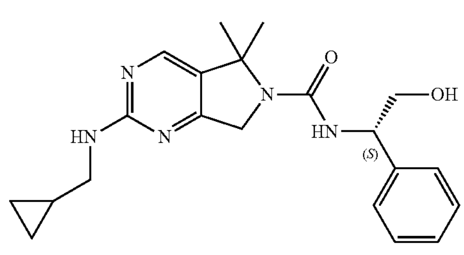 | 382.3 | 0.63 | 3 |

TABLE 1-continued

| Cmpd No. | Structure | M + H Obs. | Ret'n time (min) | Synth. Meth. |
|---|---|---|---|---|
| 54 | 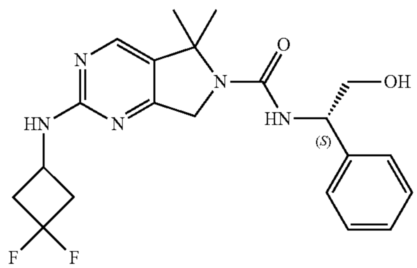 | 418.3 | 0.79 | 3 |
| 55 | 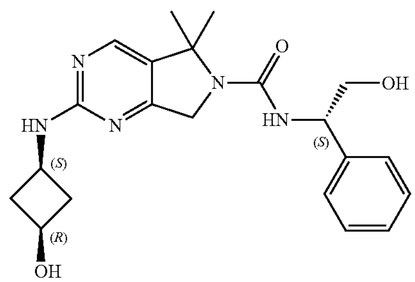 | 398.3 | 0.52 | 3 |
| 56 | 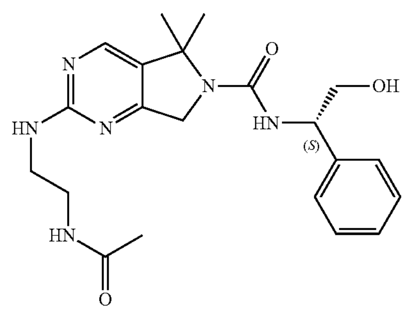 | 413.3 | 0.51 | 3 |
| 57 | 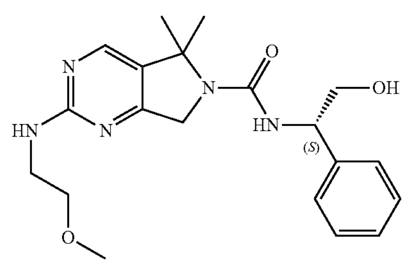 | 386.4 | 0.56 | 3 |
| 58 | 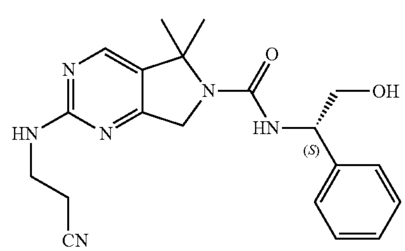 | 381.3 | 0.58 | 3 |

TABLE 1-continued

| Cmpd No. | Structure | M + H Obs. | Ret'n time (min) | Synth. Meth. |
|---|---|---|---|---|
| 59 | 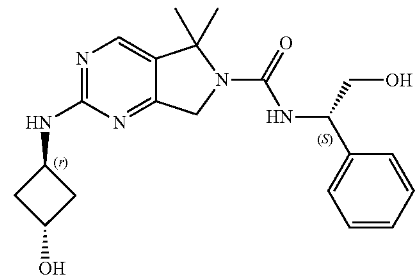 | 398.3 | 0.51 | 3 |
| 60 | 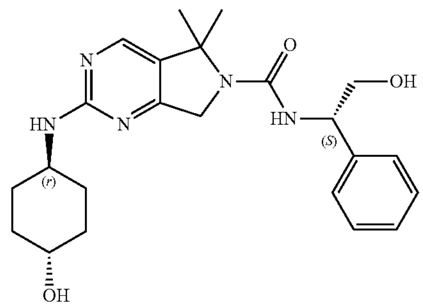 | 426.3 | 0.54 | 3 |
| 61 | 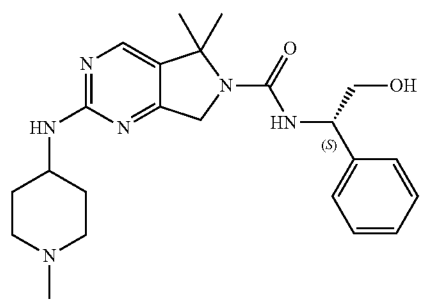 | 425.3 | 0.50 | 3 |
| 62 | 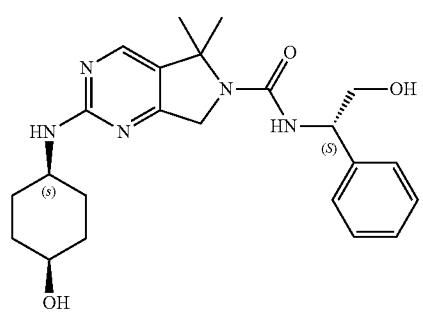 | 426.3 | 0.56 | 3 |
| 63 | 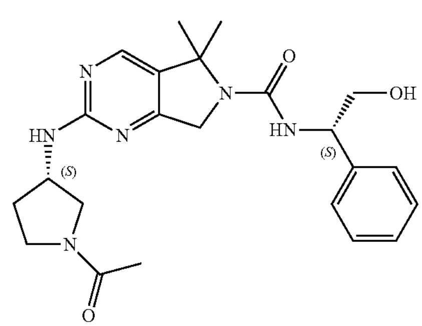 | 439.3 | 0.57 | 3 |

TABLE 1-continued

| Cmpd No. | Structure | M + H Obs. | Ret'n time (min) | Synth. Meth. |
|---|---|---|---|---|
| 64 | 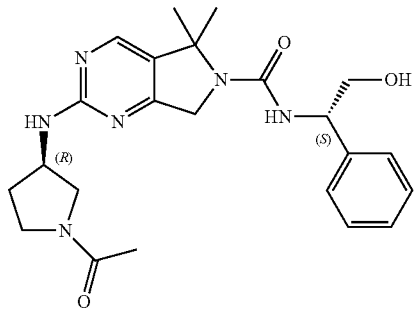 | 439.3 | 0.57 | 3 |
| 65 | 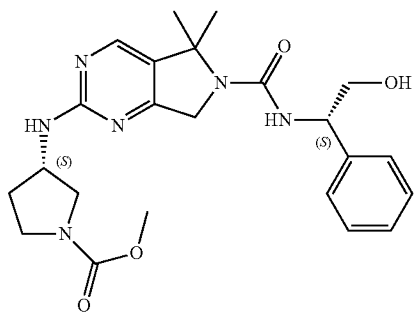 | 455.3 | 0.64 | 3 |
| 66 | 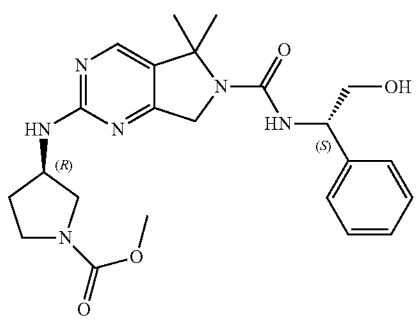 | 455.3 | 0.63 | 3 |
| 67 | 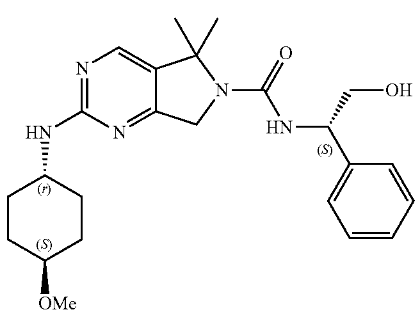 | 440.3 | 0.64 | 3 |

TABLE 1-continued
| Cmpd No. | Structure | M + H Obs. | Ret'n time (min) | Synth. Meth. |
|---|---|---|---|---|
| 68 | 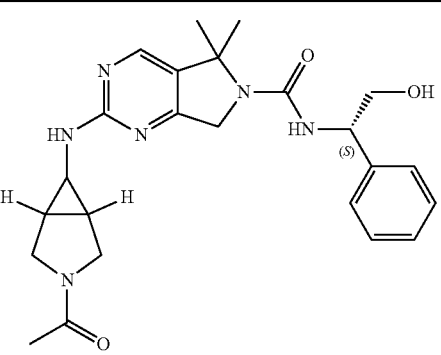 | 451.3 | 0.56 | 3 |
| 69 | 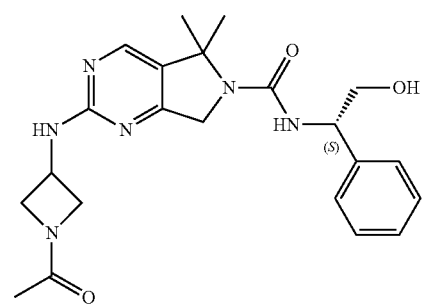 | 425.3 | 0.55 | 3 |
| 70 | 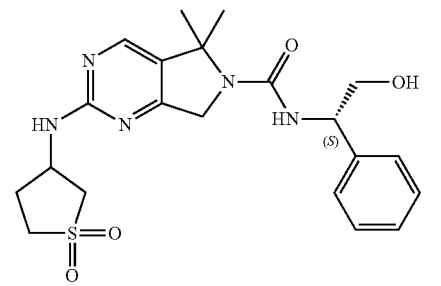 | 446.2 | 0.58 | 3 |
| 71 | 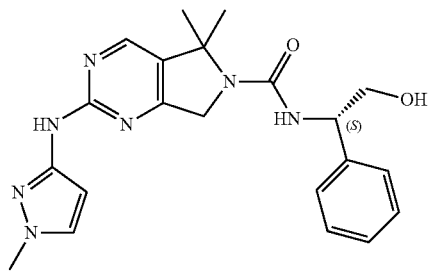 | 408.3 | 0.60 | 3 |
| 72 | 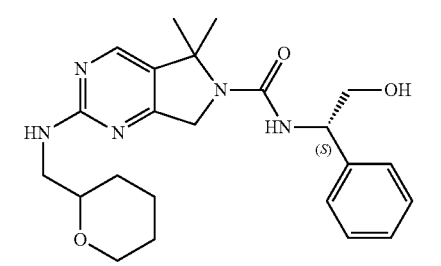 | 426.3 | 0.66 | 3 |

TABLE 1-continued

| Cmpd No. | Structure | M + H Obs. | Ret'n time (min) | Synth. Meth. |
|---|---|---|---|---|
| 73 | 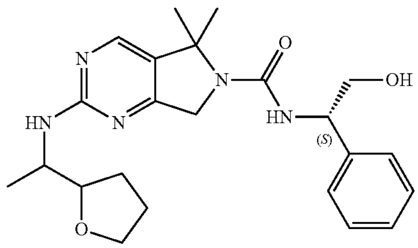 | 426.3 | 0.63 | 3 |
| 74 | 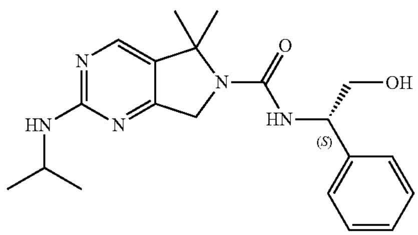 | 370.3 | 0.60 | 3 |
| 75 | 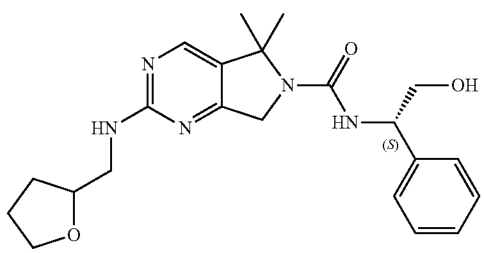 | 412.3 | 0.60 | 3 |
| 76 | 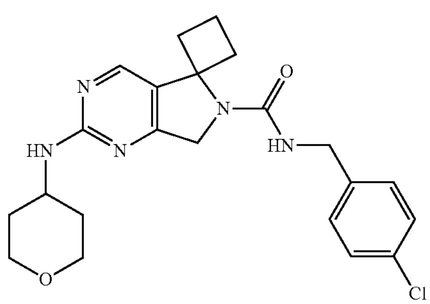 [SMILES: O=C(NCc1ccc(Cl)cc1)N1Cc2nc(NC3CCOCC3)ncc2C12CCC2] | 428.3 | 0.79 | 7 |
| 77 | 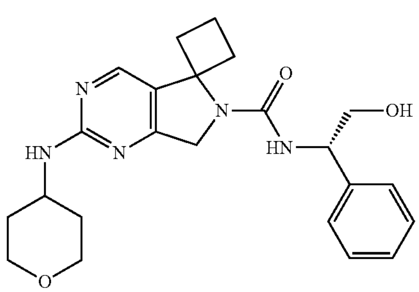 [SMILES: O=C(N[C@H](CO)c1ccccc1)N1Cc2nc(NC3CCOCC3)ncc2C12CCC2] | 424.3 | 0.62 | 7 |

TABLE 1-continued

| Cmpd No. | Structure | M + H Obs. | Ret'n time (min) | Synth. Meth. |
|---|---|---|---|---|
| 78 | 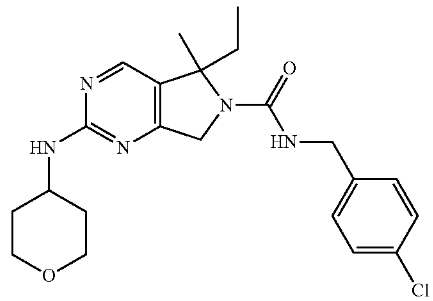 [SMILES: CCC1(C)c2cnc(NC3CCOCC3)nc2CN1C(=O)NCc1ccc(Cl)cc1] | 430.3 | 0.76 | 4 |
| 79 | 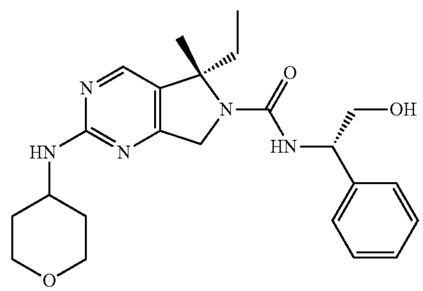 [SMILES: CC[C@@]1(C)c2cnc(NC3CCOCC3)nc2CN1C(=O)N[C@H](CO)c1ccccc1] | 426.4 | 0.60 | 4 |
| 80 | 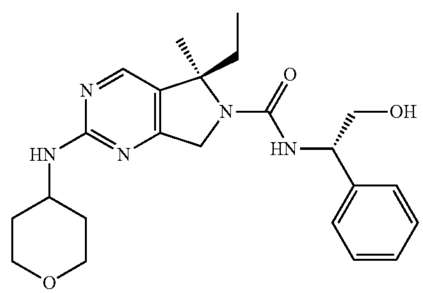 [SMILES: CC[C@]1(C)c2cnc(NC3CCOCC3)nc2CN1C(=O)N[C@H](CO)c1ccccc1] | 426.3 | 0.62 | 4 |
| 81 | 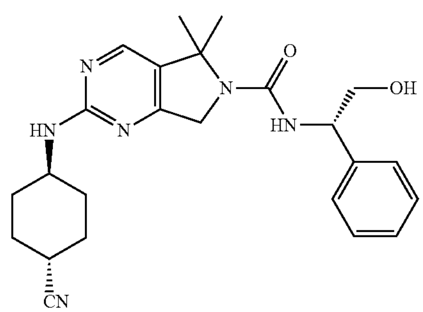 [SMILES: CC1(C)c2cnc(N[C@H]3CC[C@H](C#N)CC3)nc2CN1C(=O)N[C@H](CO)c1ccccc1] | 435.3 | 0.65 | 3 |
| 82 | 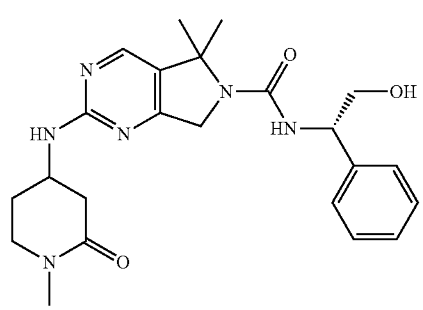 [SMILES: CN1CCC(Nc2ncc3c(n2)CN(C(=O)N[C@H](CO)c2ccccc2)C3(C)C)CC1=O] | 439.3 | 0.55 | 3 |

TABLE 1-continued

| Cmpd No. | Structure | M + H Obs. | Ret'n time (min) | Synth. Meth. |
|---|---|---|---|---|
| 83 | 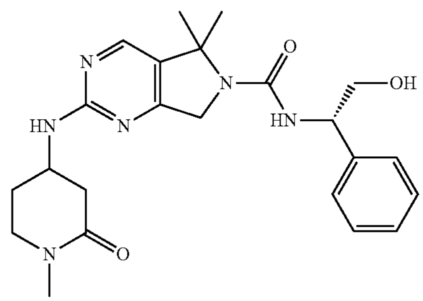 [SMILES: CN1CCC(Nc2ncc3c(n2)CN(C(=O)N[C@H](CO)c2ccccc2)C3(C)C)CC1=O] | 439.3 | 0.56 | 3 |
| 84 | 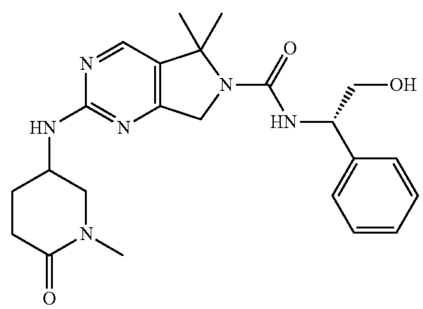 [SMILES: CN1CC(Nc2ncc3c(n2)CN(C(=O)N[C@H](CO)c2ccccc2)C3(C)C)CCC1=O] | 439.4 | 0.56 | 3 |
| 85 | 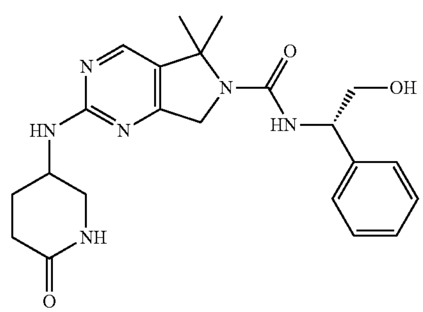 [SMILES: CC1(C)c2cnc(NC3CCC(=O)NC3)nc2CN1C(=O)N[C@H](CO)c1ccccc1] | 425.3 | 0.52 | 3 |
| 86 | 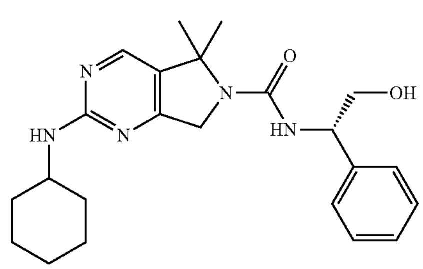 [SMILES: CC1(C)c2cnc(NC3CCCCC3)nc2CN1C(=O)N[C@H](CO)c1ccccc1] | 410.4 | 0.73 | 3 |
| 87 | 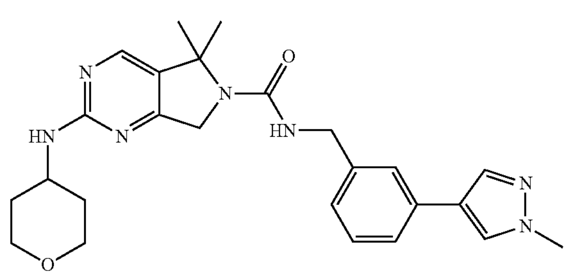 [SMILES: Cn1cc(-c2cccc(CNC(=O)N3Cc4nc(NC5CCOCC5)ncc4C3(C)C)c2)cn1] | 462.3 | 0.65 | 1 |

TABLE 1-continued

| Cmpd No. | Structure | M + H Obs. | Ret'n time (min) | Synth. Meth. |
|---|---|---|---|---|
| 88 | 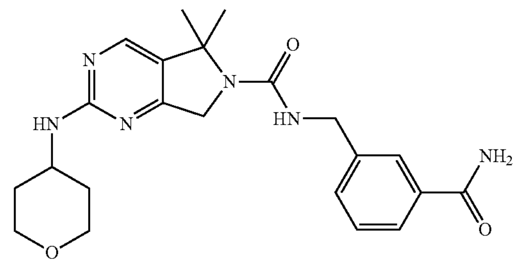 [SMILES: CC1(C)c2cnc(NC3CCOCC3)nc2CN1C(=O)NCc1cccc(C(N)=O)c1] | 425.3 | 0.50 | 1 |
| 89 | 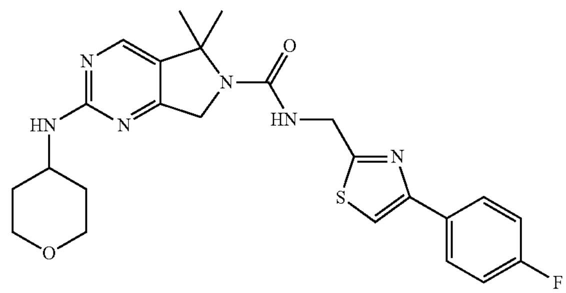 [SMILES: CC1(C)c2cnc(NC3CCOCC3)nc2CN1C(=O)NCc1nc(-c2ccc(F)cc2)cs1] | 483.3 | 0.77 | 1 |
| 90 | 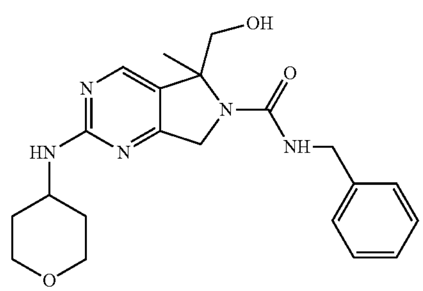 [SMILES: CC1(CO)c2cnc(NC3CCOCC3)nc2CN1C(=O)NCc1ccccc1] | 398.7 | 0.57 | 6 |
| 91 | 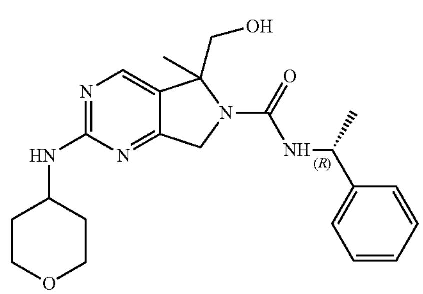 | 412.7 | 0.61 | 6 |
| 92 | 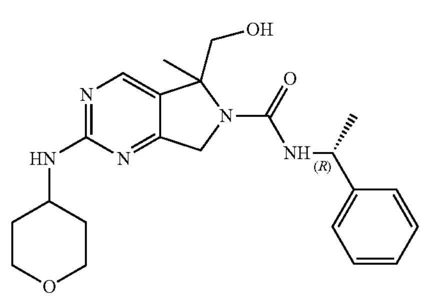 | 412.7 | 0.62 | 6 |

TABLE 1-continued
| Cmpd No. | Structure | M + H Obs. | Ret'n time (min) | Synth. Meth. |
|---|---|---|---|---|
| 96 | 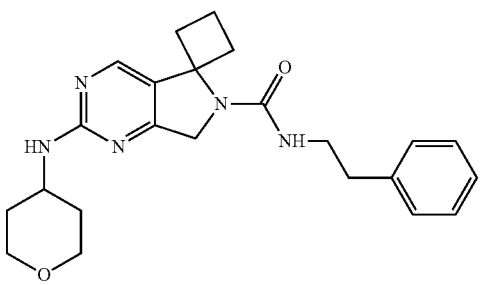 [SMILES: O=C(NCCc1ccccc1)N1Cc2nc(NC3CCOCC3)ncc2C12CCC2] | 408.3 | 0.75 | 7 |
| 99 | 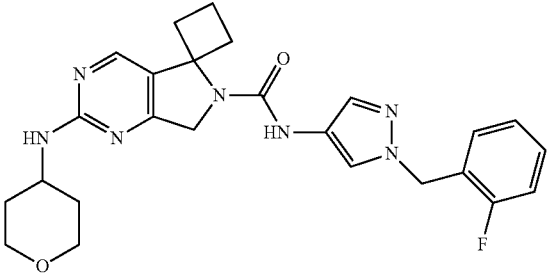 [SMILES: O=C(Nc1cnn(Cc2ccccc2F)c1)N1Cc2nc(NC3CCOCC3)ncc2C12CCC2] | 478.3 | 0.75 | 7 |
| 100 | 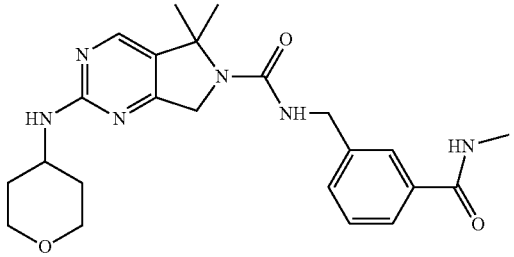 [SMILES: CNC(=O)c1cccc(CNC(=O)N2Cc3nc(NC4CCOCC4)ncc3C2(C)C)c1] | 439.3 | 0.53 | 1 |
| 101 | 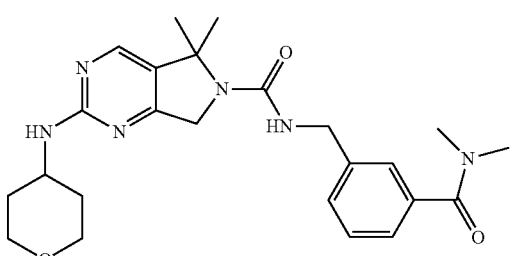 | 453.4 | 0.56 | 1 |
| 102 | 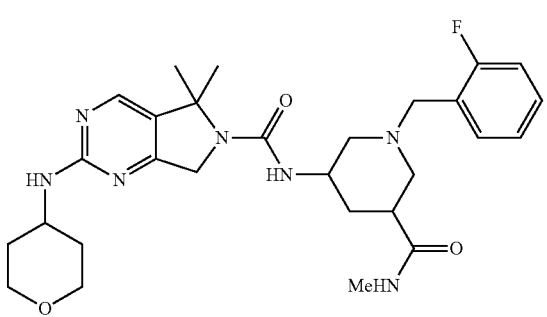 [SMILES: CNC(=O)C1CC(NC(=O)N2Cc3nc(NC4CCOCC4)ncc3C2(C)C)CN(Cc2ccccc2F)C1] | 540.4 | 0.53 | 1 |

TABLE 1-continued

| Cmpd No. | Structure | M + H Obs. | Ret'n time (min) | Synth. Meth. |
|---|---|---|---|---|
| 103 | 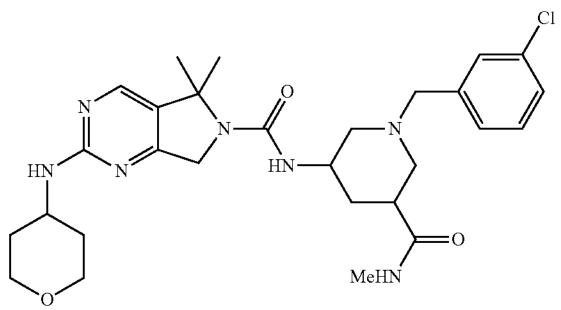 [SMILES: CNC(=O)C1CC(NC(=O)N2Cc3nc(NC4CCOCC4)ncc3C2(C)C)CN(Cc2cccc(Cl)c2)C1] | 556.4 | 0.59 | 1 |
| 104 | 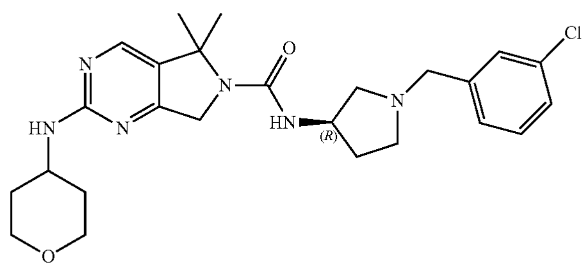 | 485.3 | 0.62 | 1 |
| 105 | 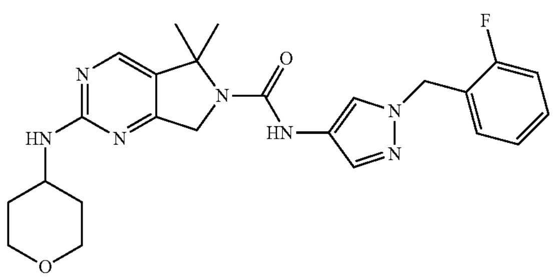 [SMILES: CC1(C)c2cnc(NC3CCOCC3)nc2CN1C(=O)Nc1cnn(Cc2ccccc2F)c1] | 466.4 | 0.68 | 1 |
| 106 | 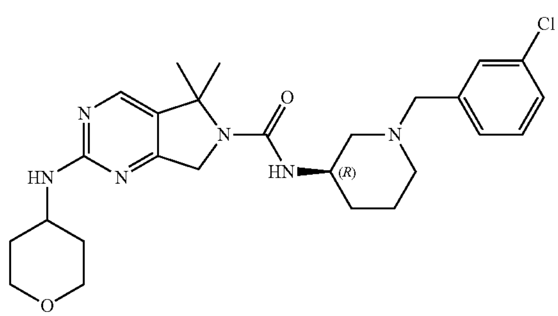 | 499.2 | 0.65 | 1 |
| 107 | 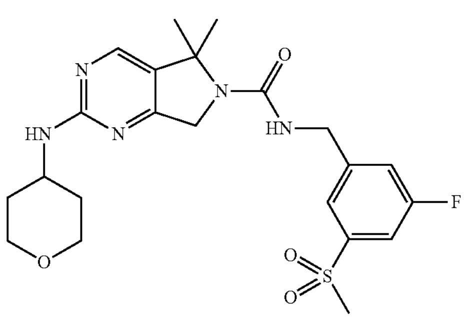 [SMILES: CC1(C)c2cnc(NC3CCOCC3)nc2CN1C(=O)NCc1cc(F)cc(S(C)(=O)=O)c1] | 478.3 | 0.60 | 1 |

TABLE 1-continued

| Cmpd No. | Structure | M + H Obs. | Ret'n – time (min) | Synth. Meth. |
|---|---|---|---|---|
| 108 | 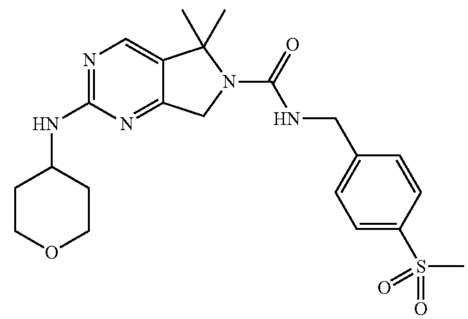 [SMILES: CC1(C)c2cnc(NC3CCOCC3)nc2CN1C(=O)NCc1ccc(S(C)(=O)=O)cc1] | 460.3 | 0.55 | 1 |
| 109 | 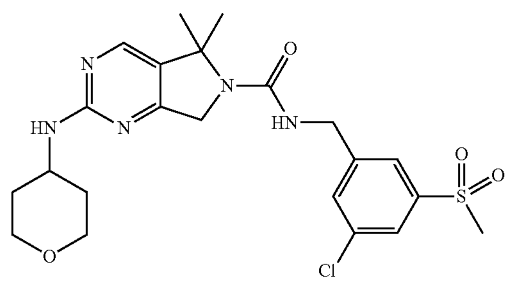 [SMILES: CC1(C)c2cnc(NC3CCOCC3)nc2CN1C(=O)NCc1cc(Cl)cc(S(C)(=O)=O)c1] | 494.2 | 0.65 | 1 |
| 110 | 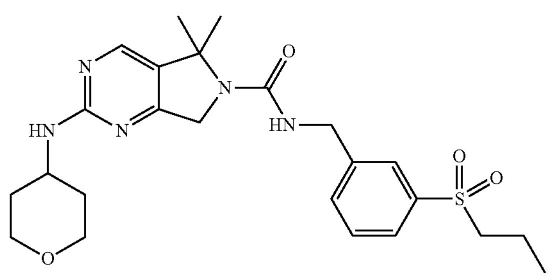 [SMILES: CCCS(=O)(=O)c1cccc(CNC(=O)N2Cc3nc(NC4CCOCC4)ncc3C2(C)C)c1] | 488.3 | 0.66 | 1 |
| 111 | 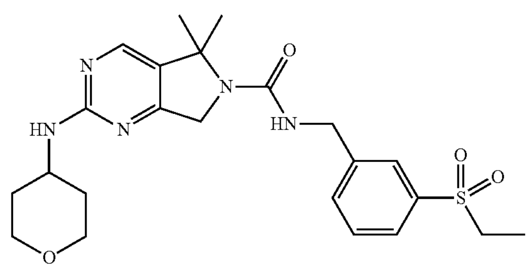 [SMILES: CCS(=O)(=O)c1cccc(CNC(=O)N2Cc3nc(NC4CCOCC4)ncc3C2(C)C)c1] | 474.3 | 0.60 | 1 |
| 112 | 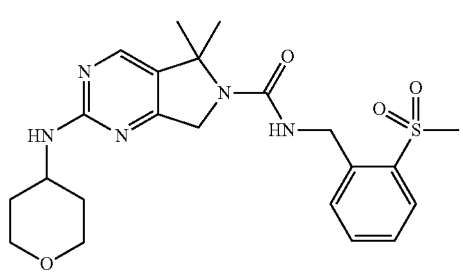 [SMILES: CC1(C)c2cnc(NC3CCOCC3)nc2CN1C(=O)NCc1ccccc1S(C)(=O)=O] | 460.3 | 0.59 | 1 |

TABLE 1-continued

| Cmpd No. | Structure | M + H Obs. | Ret'n time (min) | Synth. Meth. |
|---|---|---|---|---|
| 113 | 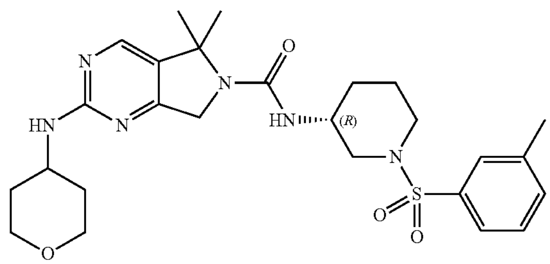 | 529.3 | 0.78 | 1 |
| 114 | 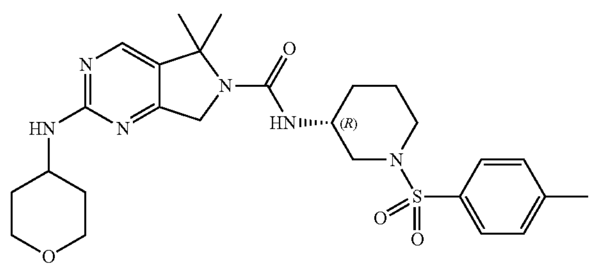 | 529.3 | 0.78 | 1 |
| 115 | 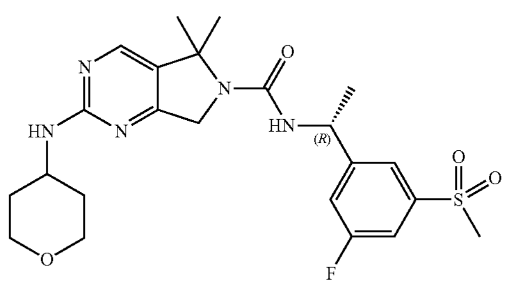 | 492.3 | 0.65 | 1 |
| 116 | 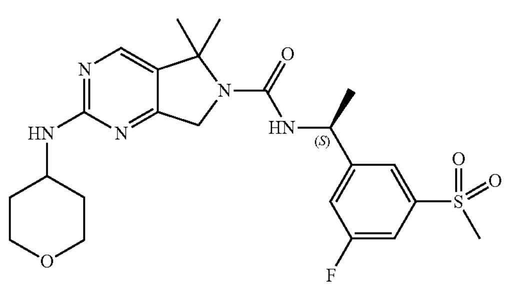 | 492.3 | 0.63 | 1 |
| 117 | 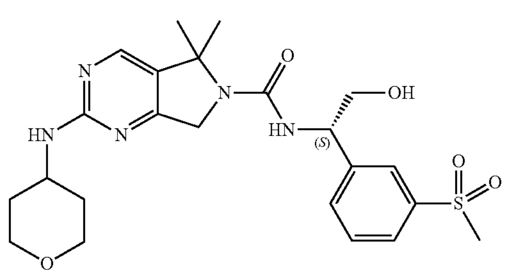 | 490.3 | 0.51 | 1 |

TABLE 1-continued

| Cmpd No. | Structure | M + H Obs. | Ret'n time (min) | Synth. Meth. |
|---|---|---|---|---|
| 118 | 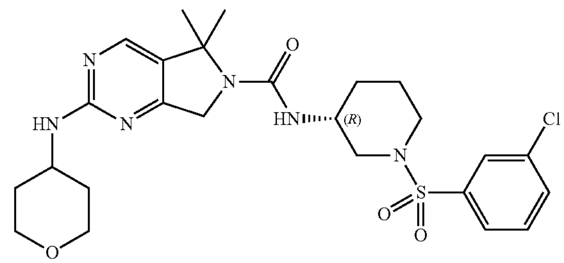 | 549.3 | 0.83 | 1 |
| 119 | 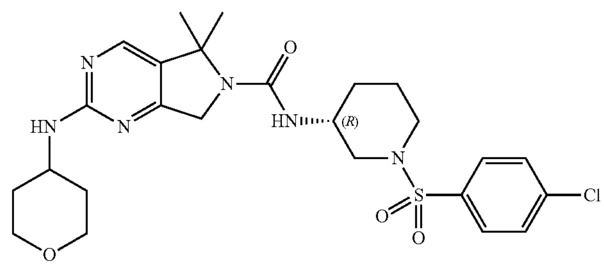 | 549.3 | 0.83 | 1 |
| 120 | 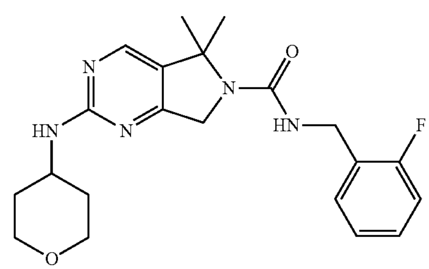 [SMILES: CC1(C)c2cnc(NC3CCOCC3)nc2CN1C(=O)NCc1ccccc1F] | 400.3 | 0.69 | 1 |
| 121 | 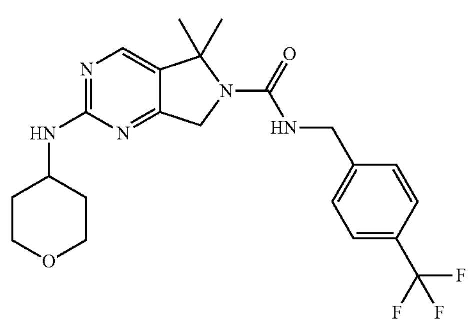 [SMILES: CC1(C)c2cnc(NC3CCOCC3)nc2CN1C(=O)NCc1ccc(C(F)(F)F)cc1] | 450.3 | 0.82 | 1 |
| 122 | 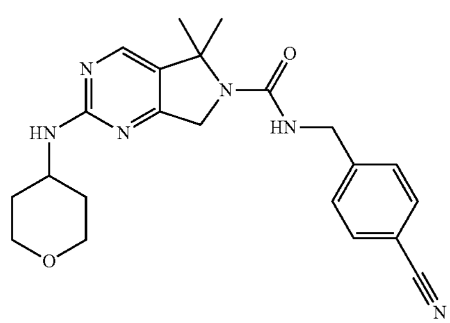 [SMILES: CC1(C)c2cnc(NC3CCOCC3)nc2CN1C(=O)NCc1ccc(C#N)cc1] | 407.3 | 0.64 | 1 |

TABLE 1-continued

| Cmpd No. | Structure | M + H Obs. | Ret'n time (min) | Synth. Meth. |
|---|---|---|---|---|
| 123 | 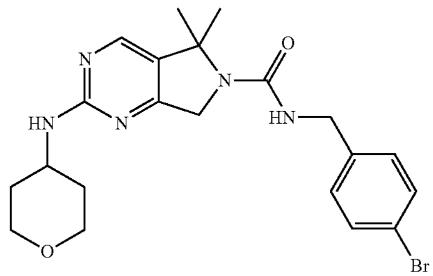 [SMILES: CC1(C)c2cnc(NC3CCOCC3)nc2CN1C(=O)NCc1ccc(Br)cc1] | 462.2 | 0.79 | 1 |
| 124 | 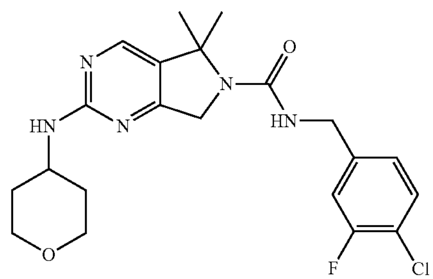 [SMILES: CC1(C)c2cnc(NC3CCOCC3)nc2CN1C(=O)NCc1ccc(Cl)c(F)c1] | 434.3 | 0.78 | 1 |
| 125 | 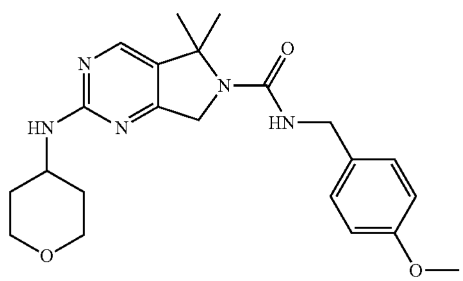 [SMILES: COc1ccc(CNC(=O)N2Cc3nc(NC4CCOCC4)ncc3C2(C)C)cc1] | 412.3 | 0.67 | 1 |
| 126 | 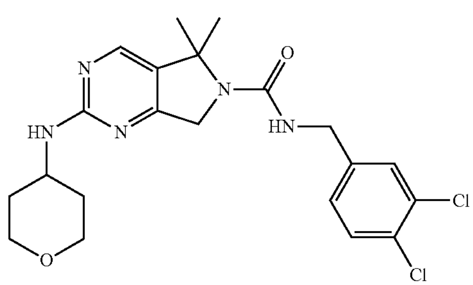 [SMILES: CC1(C)c2cnc(NC3CCOCC3)nc2CN1C(=O)NCc1ccc(Cl)c(Cl)c1] | 450.2 | 0.84 | 1 |
| 127 | 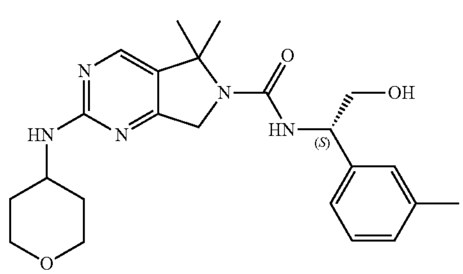 | 426.4 | 0.65 | 1 |

TABLE 1-continued

| Cmpd No. | Structure | M + H Obs. | Ret'n time (min) | Synth. Meth. |
|---|---|---|---|---|
| 128 | 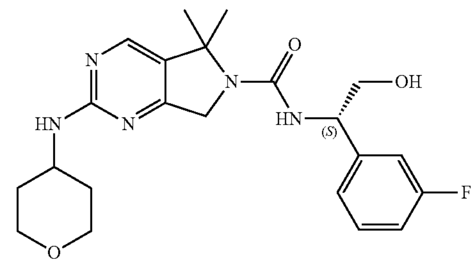 | 430.3 | 0.60 | 1 |
| 129 | 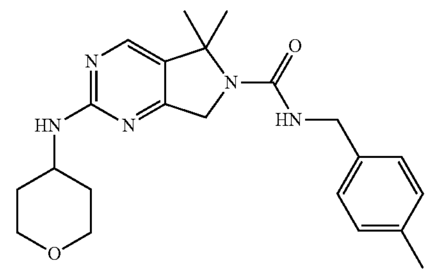 [SMILES: Cc1ccc(CNC(=O)N2Cc3nc(NC4CCOCC4)ncc3C2(C)C)cc1] | 396.4 | 0.74 | 1 |
| 130 | 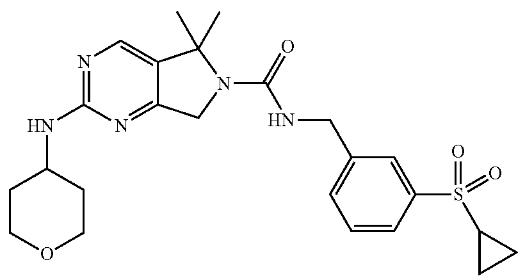 [SMILES: CC1(C)c2cnc(NC3CCOCC3)nc2CN1C(=O)NCc1cccc(S(=O)(=O)C2CC2)c1] | 486.3 | 0.62 | 1 |
| 131 | 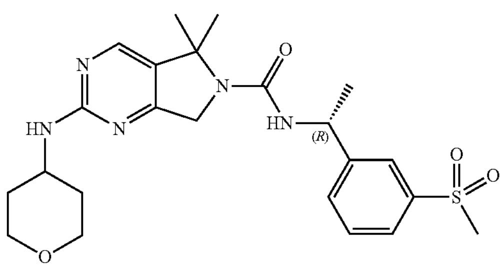 | 474.3 | 0.59 | 1 |
| 132 | 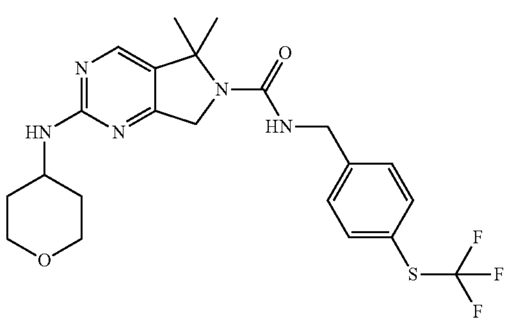 [SMILES: CC1(C)c2cnc(NC3CCOCC3)nc2CN1C(=O)NCc1ccc(SC(F)(F)F)cc1] | 482.2 | 0.86 | 1 |

TABLE 1-continued

| Cmpd No. | Structure | M + H Obs. | Ret'n time (min) | Synth. Meth. |
|---|---|---|---|---|
| 133 | 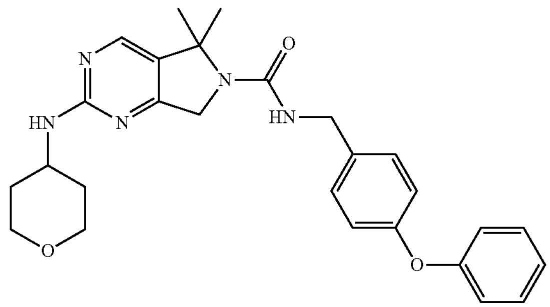 [SMILES: CC1(C)c2cnc(NC3CCOCC3)nc2CN1C(=O)NCc1ccc(Oc2ccccc2)cc1] | 474.3 | 0.59 | 1 |
| 134 | 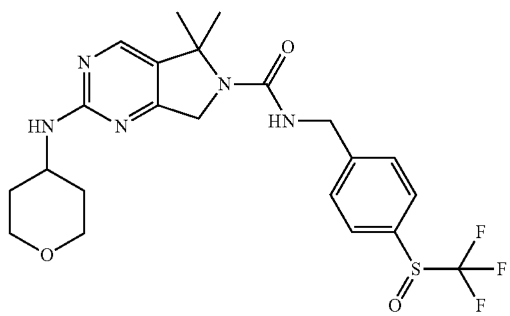 [SMILES: CC1(C)c2cnc(NC3CCOCC3)nc2CN1C(=O)NCc1ccc(S(=O)C(F)(F)F)cc1] | 498.2 | 0.68 | 1 |
| 135 | 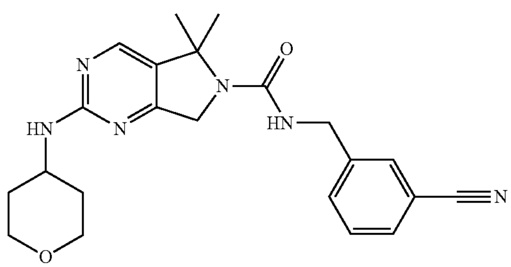 [SMILES: CC1(C)c2cnc(NC3CCOCC3)nc2CN1C(=O)NCc1cccc(C#N)c1] | 407.3 | 0.63 | 1 |
| 136 | 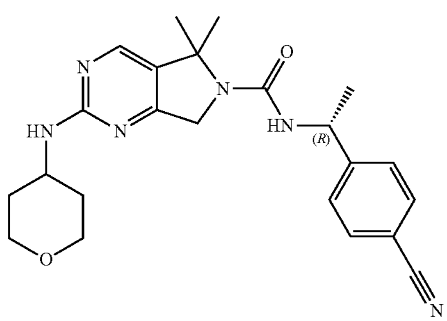 | 421.4 | 0.67 | 1 |
| 137 | 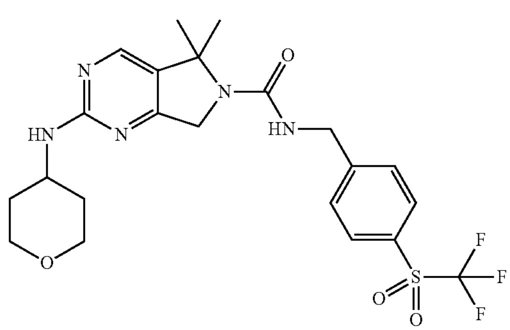 [SMILES: CC1(C)c2cnc(NC3CCOCC3)nc2CN1C(=O)NCc1ccc(S(=O)(=O)C(F)(F)F)cc1] | 514.3 | 0.78 | 1 |

TABLE 1-continued

| Cmpd No. | Structure | M + H Obs. | Ret'n time (min) | Synth. Meth. |
|---|---|---|---|---|
| 138 | 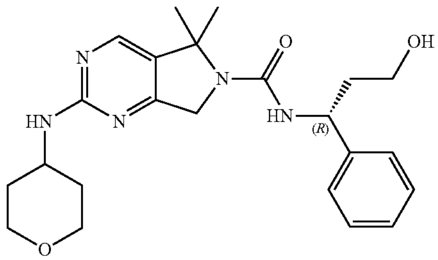 | 426.3 | 0.62 | 1 |
| 139 | 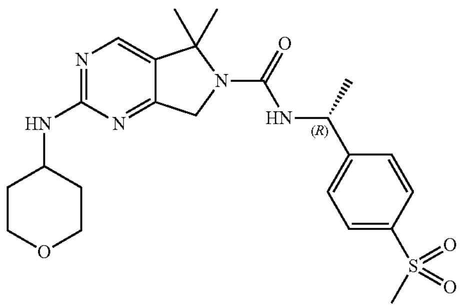 | 474.3 | 0.58 | 1 |
| 146 | 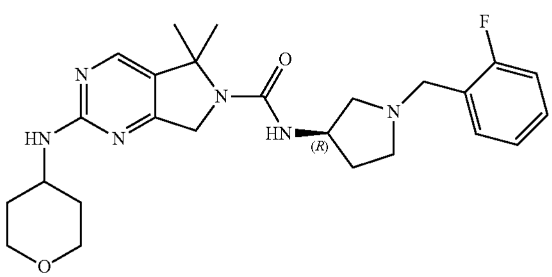 | 469.4 | 0.56 | 1 |
| 147 | 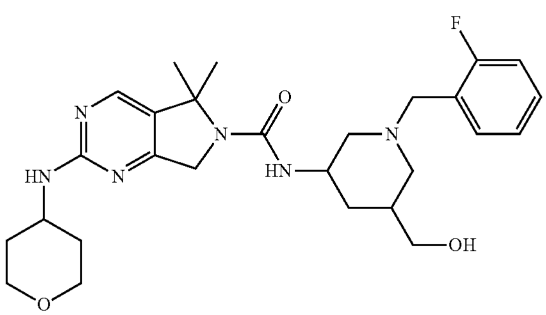 [SMILES: CC1(C)c2cnc(NC3CCOCC3)nc2CN1C(=O)NC1CC(CO)CN(Cc2ccccc2F)C1] | 513.4 | 0.52 | 1 |
| 148 | 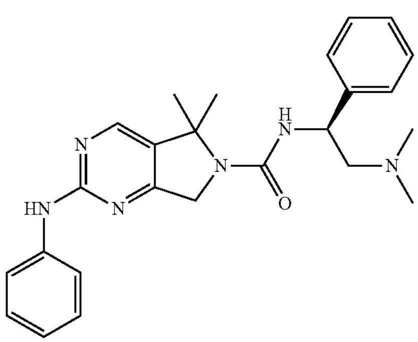 [SMILES: CN(C)C[C@@H](NC(=O)N1Cc2nc(Nc3ccccc3)ncc2C1(C)C)c1ccccc1] | | | |

TABLE 1-continued

| Cmpd No. | Structure | M + H Obs. | Ret'n time (min) | Synth. Meth. |
|---|---|---|---|---|
| 149 | 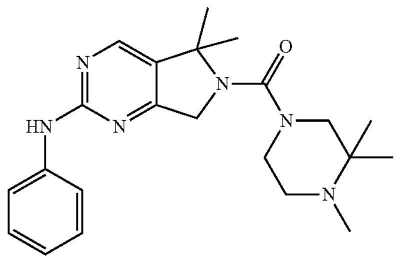 [SMILES: CN1CCN(C(=O)N2Cc3nc(Nc4ccccc4)ncc3C2(C)C)CC1(C)C] | | | |
| 150 | 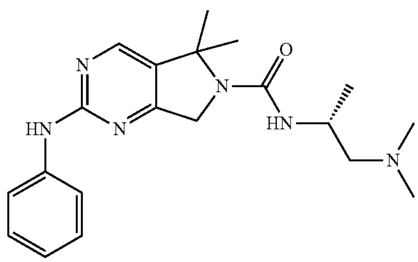 [SMILES: C[C@H](CN(C)C)NC(=O)N1Cc2nc(Nc3ccccc3)ncc2C1(C)C] | | | |
| 151 | 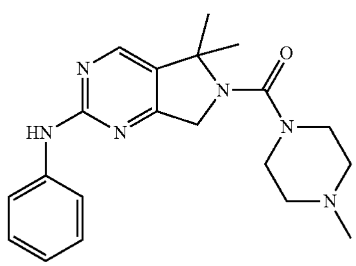 [SMILES: CN1CCN(C(=O)N2Cc3nc(Nc4ccccc4)ncc3C2(C)C)CC1] | | | |
| 152 | 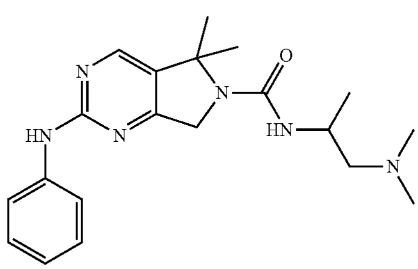 [SMILES: CC(CN(C)C)NC(=O)N1Cc2nc(Nc3ccccc3)ncc2C1(C)C] | | | |
| 153 | 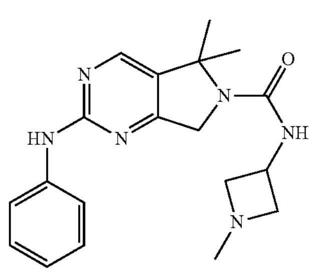 [SMILES: CN1CC(NC(=O)N2Cc3nc(Nc4ccccc4)ncc3C2(C)C)C1] | | | |

TABLE 1-continued

| Cmpd No. | Structure | M + H Obs. | Ret'n time (min) | Synth. Meth. |
|---|---|---|---|---|
| 154 | 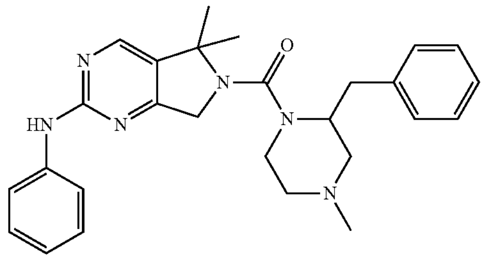 [SMILES: CN1CCN(C(=O)N2Cc3nc(Nc4ccccc4)ncc3C2(C)C)C(Cc2ccccc2)C1] | | | |
| 155 | 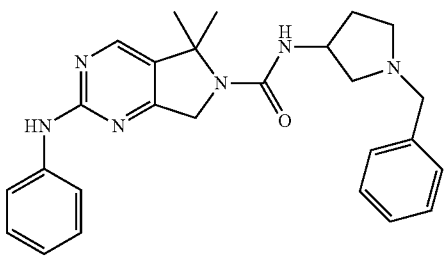 [SMILES: CC1(C)c2cnc(Nc3ccccc3)nc2CN1C(=O)NC1CCN(Cc2ccccc2)C1] | | | |
| 156 | 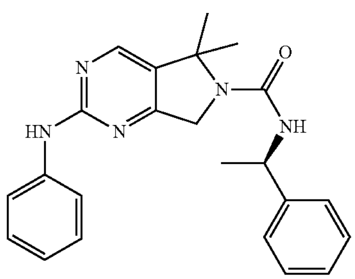 [SMILES: C[C@@H](NC(=O)N1Cc2nc(Nc3ccccc3)ncc2C1(C)C)c1ccccc1] | | | |
| 157 | 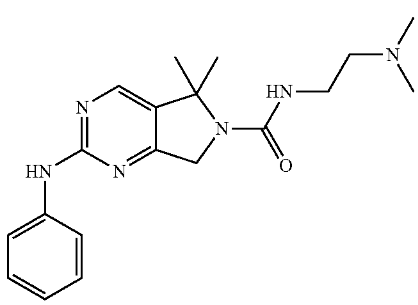 [SMILES: CN(C)CCNC(=O)N1Cc2nc(Nc3ccccc3)ncc2C1(C)C] | | | |
| 158 | 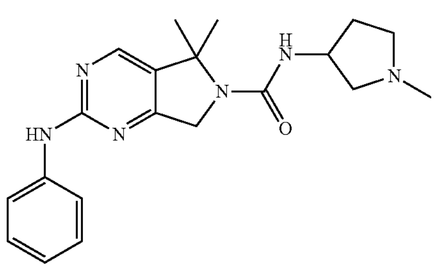 [SMILES: CN1CCC(NC(=O)N2Cc3nc(Nc4ccccc4)ncc3C2(C)C)C1] | | | |

TABLE 1-continued

| Cmpd No. | Structure | M + H Obs. | Ret'n time (min) | Synth. Meth. |
|---|---|---|---|---|
| 159 | 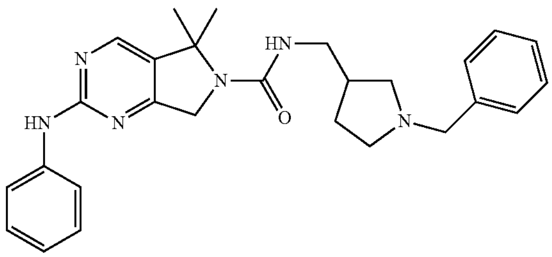 [SMILES: CC1(C)c2cnc(Nc3ccccc3)nc2CN1C(=O)NCC1CCN(Cc2ccccc2)C1] | | | |
| 160 | 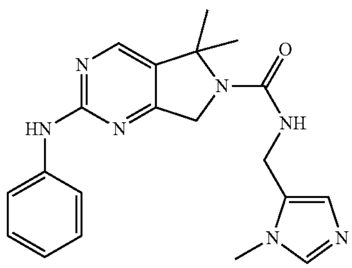 [SMILES: Cn1cncc1CNC(=O)N1Cc2nc(Nc3ccccc3)ncc2C1(C)C] | | | |
| 161 | 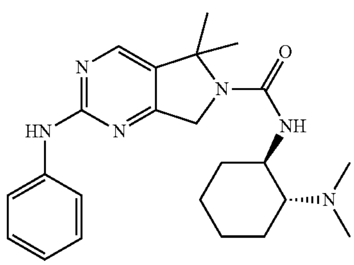 [SMILES: CN(C)[C@@H]1CCCC[C@H]1NC(=O)N1Cc2nc(Nc3ccccc3)ncc2C1(C)C] | | | |
| 152 | 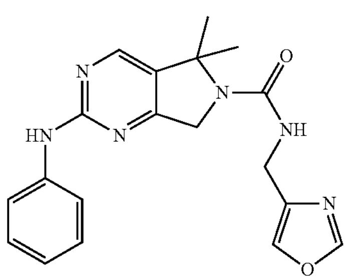 [SMILES: CC1(C)c2cnc(Nc3ccccc3)nc2CN1C(=O)NCc1cocn1] | | | |
| 163 | 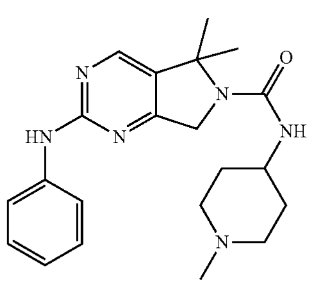 [SMILES: CN1CCC(NC(=O)N2Cc3nc(Nc4ccccc4)ncc3C2(C)C)CC1] | | | |

TABLE 1-continued
| Cmpd No. | Structure | M + H Obs. | Ret'n time (min) | Synth. Meth. |
|---|---|---|---|---|
| 164 | 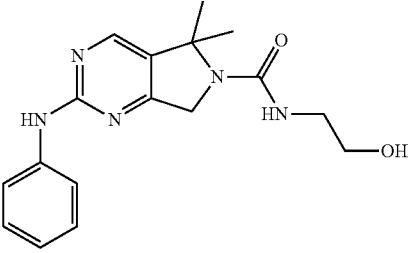 [SMILES: CC1(C)c2cnc(Nc3ccccc3)nc2CN1C(=O)NCCO] | | | |
| 165 | 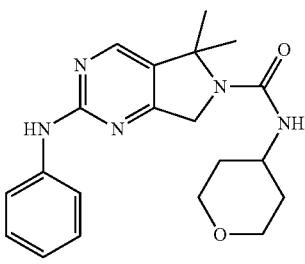 [SMILES: CC1(C)c2cnc(Nc3ccccc3)nc2CN1C(=O)NC1CCOCC1] | | | |
| 166 | 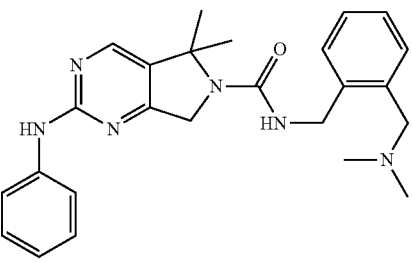 [SMILES: CN(C)Cc1ccccc1CNC(=O)N1Cc2nc(Nc3ccccc3)ncc2C1(C)C] | | | |
| 167 | 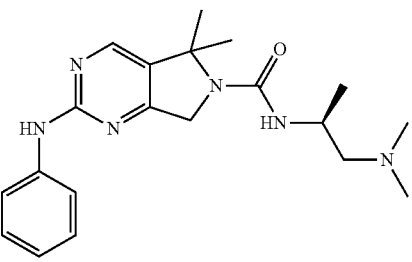 [SMILES: C[C@@H](CN(C)C)NC(=O)N1Cc2nc(Nc3ccccc3)ncc2C1(C)C] | | | |
| 168 | 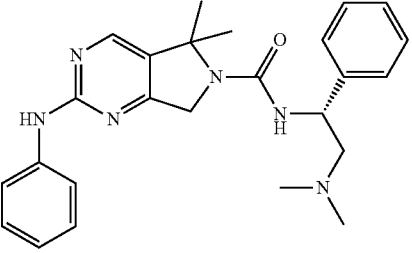 [SMILES: CN(C)C[C@H](NC(=O)N1Cc2nc(Nc3ccccc3)ncc2C1(C)C)c1ccccc1] | | | |

TABLE 1-continued

| Cmpd No. | Structure | M + H Obs. | Ret'n time (min) | Synth. Meth. |
|---|---|---|---|---|
| 169 | 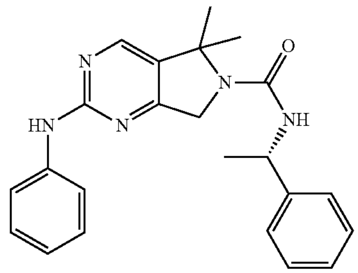 [SMILES: C[C@H](NC(=O)N1Cc2nc(Nc3ccccc3)ncc2C1(C)C)c1ccccc1] | | | |
| 170 | 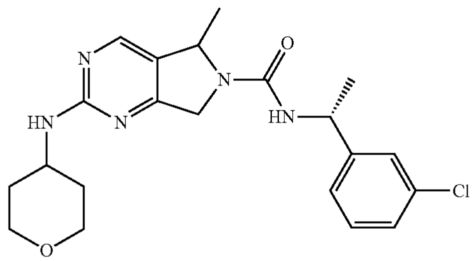 [SMILES: CC1c2cnc(NC3CCOCC3)nc2CN1C(=O)N[C@H](C)c1cccc(Cl)c1] | 416.2 | 0.73 | 9 |
| 171 | 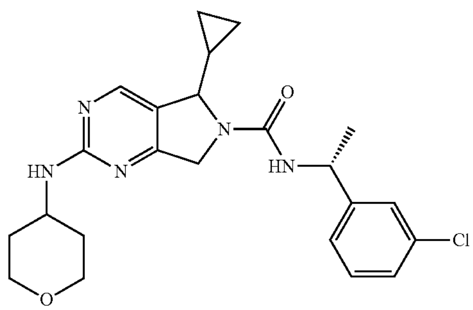 [SMILES: C[C@@H](NC(=O)N1Cc2nc(NC3CCOCC3)ncc2C1C1CC1)c1cccc(Cl)c1] | 442.2 | 0.78 | 10 |
| 172 | 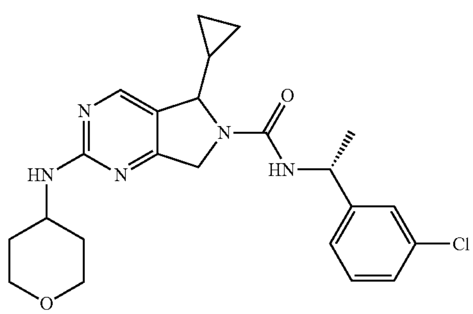 [SMILES: C[C@@H](NC(=O)N1Cc2nc(NC3CCOCC3)ncc2C1C1CC1)c1cccc(Cl)c1] | 442.2 | 0.79 | 10 |

Example 12

Biological Test Methods

Production of Activated ERK2 Protein:

Activated ERK2 protein was generated in insect cells by co-expression with a constitutively active form of MEK1. The ERK2 protein was expressed and purified as a nHis-PreScission-ERK tagged protein and then proteolytically processed to the full-length wild-type protein. The resulting ERK2 protein was a mixture of phosphorylation states. Double-phosphorylated ERK2 protein was purified from the mixture by mono-Q column separation.

Activated ERK2 Kinase Assay:

Compound potency against activated ERK2 was determined using a kinase assay that measures ERK2-catalyzed phosphorylation of biotinylated ERKtide peptide substrate ([Biotin]-AHA-K-R-E-L-V-E-P-L-T-P-S-G-E-A-P-N-Q-A-L-L-R- [$NH_2$], the peptide sequence derived from EGF receptor: SEQ ID NO:1). The assay was carried out in 50 mM HEPES [pH 7.5], 5 mM $MgCl_2$, 1 mM DTT, 0.01% Tween-20, 0.05% BSA using 0.25 nM ERK2, 200 nM ERKtide peptide and 35 μM ATP (all concentrations are final in the reaction) in a total volume of 10.25 μL. A 16-point, half-log dilution series of compounds at 41× final concentration was used for generating $IC_{50}$ curves. Compound dilution series were prepared in 100% DMSO. ERK2 was preincubated with compounds for 30 minutes at ambient temperature. Reaction was initiated by addition of a substrate cocktail of ERKtide peptide and ATP and was allowed to proceed for 2-3 hours at ambient temperature. Reaction was terminated by addition of 10 μL of a 2× stop buffer consisting of 100 mM Tris-Cl [pH 7.5], 25 mM EDTA, 0.01% Tween 20, 10 μg/mL of AlphaScreen Protein A Acceptor Beads, 10 μg/mL of Streptavidin Donor Beads (PerkinElmer, Waltham, Mass.), and 1.4 μg/mL phospho-EGF Receptor (Thr669) antibody (Cat #3056, Cell Signaling Technology, Danvers, Mass.). Terminated reactions were read, after overnight incubation in the dark, on an EnVision Multilabel Plate Reader (PerkinElmer, Waltham, Mass.), with excitation and emission wavelengths set to 680 nm and 570 nm, respectively. IC50 values were determined using a four-parameter fit. Table 2 provides biological test data for the compounds of Table 1 produced using this assay method.

Table 2 provides biological test data for the compounds of Table 1 produced using the above test methods.

TABLE 2

| Cmpd No. | Name | ERK2 IC$_{50}$ (μM) |
|---|---|---|
| 1 | (S)-N-(2-hydroxy-1-phenylethyl)-5,5-dimethyl-2-((tetrahydro-2H-pyran-4-yl)amino)-5H-pyrrolo[3,4-d]pyrimidine-6(7H)-carboxamide | 0.014 |
| 2 | (S)-N-(1-(3-chlorophenyl)-2-hydroxyethyl)-5,5-dimethyl-2-((tetrahydro-2H-pyran-4-yl)amino)-5H-pyrrolo[3,4-d]pyrimidine-6(7H)-carboxamide | 0.004 |
| 3 | 5,5-dimethyl-N-(pyridin-3-ylmethyl)-2-((tetrahydro-2H-pyran-4-yl)amino)-5H-pyrrolo[3,4-d]pyrimidine-6(7H)-carboxamide | 0.894 |
| 4 | 5,5-dimethyl-N-(3-(methylsulfonyl)benzyl)-2-((tetrahydro-2H-pyran-4-yl)amino)-5H-pyrrolo[3,4-d]pyrimidine-6(7H)-carboxamide | 0.018 |
| 5 | (S)-N-(1-(2-fluorobenzyl)piperidin-3-yl)-5,5-dimethyl-2-((tetrahydro-2H-pyran-4-yl)amino)-5H-pyrrolo[3,4-d]pyrimidine-6(7H)-carboxamide | 15.497 |
| 6 | (S)-5,5-dimethyl-N-(piperidin-3-yl)-2-((tetrahydro-2H-pyran-4-yl)amino)-5H-pyrrolo[3,4-d]pyrimidine-6(7H)-carboxamide | 2.338 |
| 7 | (R)-5,5-dimethyl-N-(piperidin-3-yl)-2-((tetrahydro-2H-pyran-4-yl)amino)-5H-pyrrolo[3,4-d]pyrimidine-6(7H)-carboxamide | 15.347 |
| 8 | (R)-N-(1-(2-fluorobenzyl)piperidin-3-yl)-5,5-dimethyl-2-((tetrahydro-2H-pyran-4-yl)amino)-5H-pyrrolo[3,4-d]pyrimidine-6(7H)-carboxamide | 0.082 |
| 9 | 5,5-dimethyl-N-((1R)-2-phenylcyclopropyl)-2-((tetrahydro-2H-pyran-4-yl)amino)-5H-pyrrolo[3,4-d]pyrimidine-6(7H)-carboxamide | 0.023 |
| 10 | (S)-2-((1,1-dioxidotetrahydro-2H-thiopyran-4-yl)amino)-N-(2-hydroxy-1-phenylethyl)-5,5-dimethyl-5H-pyrrolo[3,4-d]pyrimidine-6(7H)-carboxamide | 0.722 |
| 11 | (S)-2-((4,4-difluorocyclohexyl)amino)-N-(2-hydroxy-1-phenylethyl)-5,5-dimethyl-5H-pyrrolo[3,4-d]pyrimidine-6(7H)-carboxamide | 0.146 |
| 12 | N-((S)-2-hydroxy-1-phenylethyl)-5,5-dimethyl-2-((tetrahydrofuran-3-yl)amino)-5H-pyrrolo[3,4-d]pyrimidine-6(7H)-carboxamide | 0.375 |
| 13 | N-(3-chloro-5-fluorobenzyl)-5,5-dimethyl-2-((tetrahydro-2H-pyran-4-yl)amino)-5H-pyrrolo[3,4-d]pyrimidine-6(7H)-carboxamide | 0.008 |
| 14 | 5,5-dimethyl-N-((tetrahydro-2H-pyran-2-yl)methyl)-2-((tetrahydro-2H-pyran-4-yl)amino)-5H-pyrrolo[3,4-d]pyrimidine-6(7H)-carboxamide | 0.328 |
| 15 | 5,5-dimethyl-N-((tetrahydro-2H-pyran-3-yl)methyl)-2-((tetrahydro-2H-pyran-4-yl)amino)-5H-pyrrolo[3,4-d]pyrimidine-6(7H)-carboxamide | 0.842 |
| 16 | 5,5-dimethyl-2-((tetrahydro-2H-pyran-4-yl)amino)-N-((tetrahydro-2H-pyran-4-yl)methyl)-5H-pyrrolo[3,4-d]pyrimidine-6(7H)-carboxamide | 0.362 |
| 17 | (S)-N-(1-cyclohexyl-2-hydroxyethyl)-5,5-dimethyl-2-((tetrahydro-2H-pyran-4-yl)amino)-5H-pyrrolo[3,4-d]pyrimidine-6(7H)-carboxamide | 0.067 |

TABLE 2-continued

| Cmpd No. | Name | ERK2 IC$_{50}$ (μM) |
|---|---|---|
| 18 | 5,5-dimethyl-N-(tetrahydro-2H-pyran-4-yl)-2-((tetrahydro-2H-pyran-4-yl)amino)-5H-pyrrolo[3,4-d]pyrimidine-6(7H)-carboxamide | 2.386 |
| 19 | N-(3,5-difluorobenzyl)-5,5-dimethyl-2-((tetrahydro-2H-pyran-4-yl)amino)-5H-pyrrolo[3,4-d]pyrimidine-6(7H)-carboxamide | 0.021 |
| 20 | N-(3-fluorobenzyl)-5,5-dimethyl-2-((tetrahydro-2H-pyran-4-yl)amino)-5H-pyrrolo[3,4-d]pyrimidine-6(7H)-carboxamide | 0.016 |
| 21 | N-(3-chlorobenzyl)-5,5-dimethyl-2-((tetrahydro-2H-pyran-4-yl)amino)-5H-pyrrolo[3,4-d]pyrimidine-6(7H)-carboxamide | 0.006 |
| 22 | (R)-N-(1-(3-chlorophenyl)ethyl)-5,5-dimethyl-2-((tetrahydro-2H-pyran-4-yl)amino)-5H-pyrrolo[3,4-d]pyrimidine-6(7H)-carboxamide | 0.002 |
| 23 | (R)-5,5-dimethyl-N-(1-phenylethyl)-2-((tetrahydro-2H-pyran-4-yl)amino)-5H-pyrrolo[3,4-d]pyrimidine-6(7H)-carboxamide | 0.014 |
| 24 | N-(4-fluorobenzyl)-5,5-dimethyl-2-((tetrahydro-2H-pyran-4-yl)amino)-5H-pyrrolo[3,4-d]pyrimidine-6(7H)-carboxamide | 0.022 |
| 25 | N-((S)-2-hydroxy-1-phenylethyl)-5,5-dimethyl-2-((tetrahydro-2H-pyran-3-yl)amino)-5H-pyrrolo[3,4-d]pyrimidine-6(7H)-carboxamide | 0.193 |
| 26 | 5,5-dimethyl-2-((tetrahydro-2H-pyran-4-yl)amino)-N-(2,2,2-trifluoro-1-phenylethyl)-5H-pyrrolo[3,4-d]pyrimidine-6(7H)-carboxamide | 0.125 |
| 27 | N-benzyl-N,5,5-trimethyl-2-((tetrahydro-2H-pyran-4-yl)amino)-5H-pyrrolo[3,4-d]pyrimidine-6(7H)-carboxamide | 0.202 |
| 28 | N-(4-chlorobenzyl)-5,5-dimethyl-2-((tetrahydro-2H-pyran-4-yl)amino)-5H-pyrrolo[3,4-d]pyrimidine-6(7H)-carboxamide | 0.010 |
| 29 | N-(2-chlorobenzyl)-5,5-dimethyl-2-((tetrahydro-2H-pyran-4-yl)amino)-5H-pyrrolo[3,4-d]pyrimidine-6(7H)-carboxamide | 0.159 |
| 30 | N-(benzo[d]thiazol-2-ylmethyl)-5,5-dimethyl-2-((tetrahydro-2H-pyran-4-yl)amino)-5H-pyrrolo[3,4-d]pyrimidine-6(7H)-carboxamide | 0.049 |
| 31 | (S)-2-(cyclopropylamino)-N-(2-hydroxy-1-phenylethyl)-5,5-dimethyl-5H-pyrrolo[3,4-d]pyrimidine-6(7H)-carboxamide | 0.317 |
| 32 | (S)-N-(2-amino-1-phenylethyl)-5,5-dimethyl-2-((tetrahydro-2H-pyran-4-yl)amino)-5H-pyrrolo[3,4-d]pyrimidine-6(7H)-carboxamide | 0.014 |
| 33 | (R)-5,5-dimethyl-N-(3-methylbutan-2-yl)-2-((tetrahydro-2H-pyran-4-yl)amino)-5H-pyrrolo[3,4-d]pyrimidine-6(7H)-carboxamide | 0.596 |
| 34 | 5,5-dimethyl-N-((2-oxo-1,2-dihydropyridin-4-yl)methyl)-2-((tetrahydro-2H-pyran-4-yl)amino)-5H-pyrrolo[3,4-d]pyrimidine-6(7H)-carboxamide | 5.440 |
| 35 | N-((5-chloropyridin-2-yl)methyl)-5,5-dimethyl-2-((tetrahydro-2H-pyran-4-yl)amino)-5H-pyrrolo[3,4-d]pyrimidine-6(7H)-carboxamide | 0.106 |
| 36 | 5,5-dimethyl-N-(1-phenylcyclopropyl)-2-((tetrahydro-2H-pyran-4-yl)amino)-5H-pyrrolo[3,4-d]pyrimidine-6(7H)-carboxamide | 0.017 |
| 37 | N-(cyclopropylmethyl)-5,5-dimethyl-2-((tetrahydro-2H-pyran-4-yl)amino)-5H-pyrrolo[3,4-d]pyrimidine-6(7H)-carboxamide | 0.541 |
| 38 | N-((1S,2R)-2-hydroxy-2,3-dihydro-1H-inden-1-yl)-5,5-dimethyl-2-((tetrahydro-2H-pyran-4-yl)amino)-5H-pyrrolo[3,4-d]pyrimidine-6(7H)-carboxamide | 0.516 |
| 39 | N-((1R,2S)-2-hydroxy-2,3-dihydro-1H-inden-1-yl)-5,5-dimethyl-2-((tetrahydro-2H-pyran-4-yl)amino)-5H-pyrrolo[3,4-d]pyrimidine-6(7H)-carboxamide | <25 |
| 40 | (S)-5,5-dimethyl-N-(1-phenylethyl)-2-((tetrahydro-2H-pyran-4-yl)amino)-5H-pyrrolo[3,4-d]pyrimidine-6(7H)-carboxamide | 0.799 |
| 41 | (R)-N-(1-((2-fluorophenyl)sulfonyl)piperidin-3-yl)-5,5-dimethyl-2-((tetrahydro-2H-pyran-4-yl)amino)-5H-pyrrolo[3,4-d]pyrimidine-6(7H)-carboxamide | 0.013 |
| 42 | (R)-5,5-dimethyl-N-(1-(phenylsulfonyl)piperidin-3-yl)-2-((tetrahydro-2H-pyran-4-yl)amino)-5H-pyrrolo[3,4-d]pyrimidine-6(7H)-carboxamide | 0.027 |

TABLE 2-continued

| Cmpd No. | Name | ERK2 IC$_{50}$ (µM) |
|---|---|---|
| 44 | 5,5-dimethyl-N-(4-phenyltetrahydro-2H-pyran-4-yl)-2-((tetrahydro-2H-pyran-4-yl)amino)-5H-pyrrolo[3,4-d]pyrimidine-6(7H)-carboxamide | 2.734 |
| 45 | (S)-N-(2-hydroxy-1-phenylethyl)-5,5-dimethyl-2-((2-methylpyridin-4-yl)amino)-5H-pyrrolo[3,4-d]pyrimidine-6(7H)-carboxamide | 0.625 |
| 46 | N-benzyl-5,5-dimethyl-2-((tetrahydro-2H-pyran-4-yl)amino)-5H-pyrrolo[3,4-d]pyrimidine-6(7H)-carboxamide | 0.031 |
| 47 | N-(cyclohexylmethyl)-5,5-dimethyl-2-((tetrahydro-2H-pyran-4-yl)amino)-5H-pyrrolo[3,4-d]pyrimidine-6(7H)-carboxamide | 0.031 |
| 49 | N,5,5-trimethyl-2-((tetrahydro-2H-pyran-4-yl)amino)-5H-pyrrolo[3,4-d]pyrimidine-6(7H)-carboxamide | 0.988 |
| 50 | N-ethyl-5,5-dimethyl-2-((tetrahydro-2H-pyran-4-yl)amino)-5H-pyrrolo[3,4-d]pyrimidine-6(7H)-carboxamide | 0.839 |
| 51 | N-isopropyl-5,5-dimethyl-2-((tetrahydro-2H-pyran-4-yl)amino)-5H-pyrrolo[3,4-d]pyrimidine-6(7H)-carboxamide | 0.938 |
| 52 | (S)-2-(4-fluorophenyl)amino)-N-(2-hydroxy-1-phenylethyl)-5,5-dimethyl-5H-pyrrolo[3,4-d]pyrimidine-6(7H)-carboxamide | 0.107 |
| 53 | (S)-2-((cyclopropylmethyl)amino)-N-(2-hydroxy-1-phenylethyl)-5,5-dimethyl-5H-pyrrolo[3,4-d]pyrimidine-6(7H)-carboxamide | 0.505 |
| 54 | (S)-2-((3,3-difluorocyclobutyl)amino)-N-(2-hydroxy-1-phenylethyl)-5,5-dimethyl-5H-pyrrolo[3,4-d]pyrimidine-6(7H)-carboxamide | 0.727 |
| 55 | N-(S)-2-hydroxy-1-phenylethyl)-2-(((1s,3R)-3-hydroxycyclobutyl)amino)-5,5-dimethyl-5H-pyrrolo[3,4-d]pyrimidine-6(7H)-carboxamide | 0.677 |
| 56 | (S)-2-((2-acetamidoethyl)amino)-N-(2-hydroxy-1-phenylethyl)-5,5-dimethyl-5H-pyrrolo[3,4-d]pyrimidine-6(7H)-carboxamide | 3.502 |
| 57 | (S)-N-(2-hydroxy-1-phenylethyl)-2-((2-methoxyethyl)amino)-5,5-dimethyl-5H-pyrrolo[3,4-d]pyrimidine-6(7H)-carboxamide | 3.476 |
| 58 | (S)-2-((2-cyanoethyl)amino)-N-(2-hydroxy-1-phenylethyl)-5,5-dimethyl-5H-pyrrolo[3,4-d]pyrimidine-6(7H)-carboxamide | 1.529 |
| 59 | N-((S)-2-hydroxy-1-phenylethyl)-2-(((1r,3S)-3-hydroxycyclobutyl)amino)-5,5-dimethyl-5H-pyrrolo[3,4-d]pyrimidine-6(7H)-carboxamide | 0.839 |
| 60 | N-((S)-2-hydroxy-1-phenylethyl)-2-(((1r,4S)-4-hydroxycyclohexyl)amino)-5,5-dimethyl-5H-pyrrolo[3,4-d]pyrimidine-6(7H)-carboxamide | 0.082 |
| 61 | (S)-N-(2-hydroxy-1-phenylethyl)-5,5-dimethyl-2-((1-methylpiperidin-4-yl)amino)-5H-pyrrolo[3,4-d]pyrimidine-6(7H)-carboxamide | 20.962 |
| 62 | N-((S)-2-hydroxy-1-phenylethyl)-2-(((1s,4R)-4-hydroxycyclohexyl)amino)-5,5-dimethyl-5H-pyrrolo[3,4-d]pyrimidine-6(7H)-carboxamide | 0.896 |
| 63 | 2-(((S)-1-acetylpyrrolidin-3-yl)amino)-N-((S)-2-hydroxy-1-phenylethyl)-5,5-dimethyl-5H-pyrrolo[3,4-d]pyrimidine-6(7H)-carboxamide | 3.559 |
| 64 | 2-(((R)-1-acetylpyrrolidin-3-yl)amino)-N-((S)-2-hydroxy-1-phenylethyl)-5,5-dimethyl-5H-pyrrolo[3,4-d]pyrimidine-6(7H)-carboxamide | 0.740 |
| 65 | (S)-methyl 3-((6-(((S)-2-hydroxy-1-phenylethyl)carbamoyl)-5,5-dimethyl-6,7-dihydro-5H-pyrrolo[3,4-d]pyrimidin-2-yl)amino)pyrrolidine-1-carboxylate | 8.827 |
| 66 | (R)-methyl 3-((6-(((S)-2-hydroxy-1-phenylethyl)carbamoyl)-5,5-dimethyl-6,7-dihydro-5H-pyrrolo[3,4-d]pyrimidin-2-yl)amino)pyrrolidine-1-carboxylate | 0.030 |
| 67 | N-((S)-2-hydroxy-1-phenylethyl)-2-(((1r,4S)-4-methoxycyclohexyl)amino)-5,5-dimethyl-5H-pyrrolo[3,4-d]pyrimidine-6(7H)-carboxamide | 0.068 |
| 68 | 2-((3-acetyl-3-azabicyclo[3.1.0]hexan-6-yl)amino)-N-((S)-2-hydroxy-1-phenylethyl)-5,5-dimethyl-5H-pyrrolo[3,4-d]pyrimidine-6(7H)-carboxamide | 0.450 |
| 69 | (S)-2-((1-acetylazetidin-3-yl)amino)-N-(2-hydroxy-1-phenylethyl)-5,5-dimethyl-5H-pyrrolo[3,4-d]pyrimidine-6(7H)-carboxamide | 5.575 |
| 70 | 2-((1,1-dioxidotetrahydrothiophen-3-yl)amino)-N-((S)-2-hydroxy-1-phenylethyl)-5,5-dimethyl-5H-pyrrolo[3,4-d]pyrimidine-6(7H)-carboxamide | 0.932 |
| 71 | (S)-N-(2-hydroxy-1-phenylethyl)-5,5-dimethyl-2-((1-methyl-1H-pyrazol-3-yl)amino)-5H-pyrrolo[3,4-d]pyrimidine-6(7H)-carboxamide | 2.547 |
| 72 | N-((S)-2-hydroxy-1-phenylethyl)-5,5-dimethyl-2-(((tetrahydro-2H-pyran-2-yl)methyl)amino)-5H-pyrrolo[3,4-d]pyrimidine-6(7H)-carboxamide | 5.311 |
| 73 | N-((S)-2-hydroxy-1-phenylethyl)-5,5-dimethyl-2-((1-(tetrahydrofuran-2-yl)ethyl)amino)-5H-pyrrolo[3,4-d]pyrimidine-6(7H)-carboxamide | 0.315 |
| 74 | (S)-N-(2-hydroxy-1-phenylethyl)-2-(isopropylamino)-5,5-dimethyl-5H-pyrrolo[3,4-d]pyrimidine-6(7H)-carboxamide | 0.122 |
| 75 | N-((S)-2-hydroxy-1-phenylethyl)-5,5-dimethyl-2-(((tetrahydrofuran-2-yl)methyl)amino)-5H-pyrrolo[3,4-d]pyrimidine-6(7H)-carboxamide | 2.638 |
| 76 | N-(4-chlorobenzyl)-2'-((tetrahydro-2H-pyran-4-yl)amino)spiro[cyclobutane-1,5'-pyrrolo[3,4-d]pyrimidine]-6'(7'H)-carboxamide | 0.031 |
| 77 | (S)-N-(2-hydroxy-1-phenylethyl)-2'-((tetrahydro-2H-pyran-4-yl)amino)spiro[cyclobutane-1,5'-pyrrolo[3,4-d]pyrimidine]-6'(7'H)-carboxamide | 0.013 |
| 78 | N-(4-chlorobenzyl)-5-ethyl-5-methyl-2-((tetrahydro-2H-pyran-4-yl)amino)-5H-pyrrolo[3,4-d]pyrimidine-6(7H)-carboxamide | 0.022 |
| 79 | (S)-5-ethyl-N-((S)-2-hydroxy-1-phenylethyl)-5-methyl-2-((tetrahydro-2H-pyran-4-yl)amino)-5H-pyrrolo[3,4-d]pyrimidine-6(7H)-carboxamide | 0.971 |
| 80 | (R)-5-ethyl-N-((S)-2-hydroxy-1-phenylethyl)-5-methyl-2-((tetrahydro-2H-pyran-4-yl)amino)-5H-pyrrolo[3,4-d]pyrimidine-6(7H)-carboxamide | 0.022 |
| 81 | 2-(((1r,4S)-4-cyanocyclohexyl)amino)-N-((S)-2-hydroxy-1-phenylethyl)-5,5-dimethyl-5H-pyrrolo[3,4-d]pyrimidine-6(7H)-carboxamide | 0.114 |
| 82 | N-((S)-2-hydroxy-1-phenylethyl)-5,5-dimethyl-2-((1-methyl-2-oxopiperidin-4-yl)amino)-5H-pyrrolo[3,4-d]pyrimidine-6(7H)-carboxamide | 0.208 |
| 83 | N-((S)-2-hydroxy-1-phenylethyl)-5,5-dimethyl-2-((1-methyl-2-oxopiperidin-4-yl)amino)-5H-pyrrolo[3,4-d]pyrimidine-6(7H)-carboxamide | 1.161 |
| 84 | N-((S)-2-hydroxy-1-phenylethyl)-5,5-dimethyl-2-((1-methyl-6-oxopiperidin-3-yl)amino)-5H-pyrrolo[3,4-d]pyrimidine-6(7H)-carboxamide | 0.164 |
| 85 | N-((S)-2-hydroxy-1-phenylethyl)-5,5-dimethyl-2-((6-oxopiperidin-3-yl)amino)-5H-pyrrolo[3,4-d]pyrimidine-6(7H)-carboxamide | 0.053 |
| 86 | (S)-2-(cyclohexylamino)-N-(2-hydroxy-1-phenylethyl)-5,5-dimethyl-5H-pyrrolo[3,4-d]pyrimidine-6(7H)-carboxamide | 0.022 |
| 87 | 5,5-dimethyl-N-(3-(1-methyl-1H-pyrazol-4-yl)benzyl)-2-((tetrahydro-2H-pyran-4-yl)amino)-5H-pyrrolo[3,4-d]pyrimidine-6(7H)-carboxamide | 0.091 |
| 88 | N-(3-carbamoylbenzyl)-5,5-dimethyl-2-((tetrahydro-2H-pyran-4-yl)amino)-5H-pyrrolo[3,4-d]pyrimidine-6(7H)-carboxamide | 0.011 |
| 89 | N-((4-(4-fluorophenyl)thiazol-2-yl)methyl)-5,5-dimethyl-2-((tetrahydro-2H-pyran-4-yl)amino)-5H-pyrrolo[3,4-d]pyrimidine-6(7H)-carboxamide | 0.131 |
| 90 | N-benzyl-5-(hydroxymethyl)-5-methyl-2-((tetrahydro-2H-pyran-4-yl)amino)-5H-pyrrolo[3,4-d]pyrimidine-6(7H)-carboxamide | 4.020 |
| 91 | 5-(hydroxymethyl)-5-methyl-N-((R)-1-phenylethyl)-2-((tetrahydro-2H-pyran-4-yl)amino)-5H-pyrrolo[3,4-d]pyrimidine-6(7H)-carboxamide | 0.657 |
| 92 | 5-(hydroxymethyl)-5-methyl-N-((R)-1-phenylethyl)-2-((tetrahydro-2H-pyran-4-yl)amino)-5H-pyrrolo[3,4-d]pyrimidine-6(7H)-carboxamide | 1.529 |
| 96 | N-phenethyl-2'-((tetrahydro-2H-pyran-4-yl)amino)spiro[cyclobutane-1,5'-pyrrolo[3,4-d]pyrimidine]-6'(7'H)-carboxamide | 0.090 |
| 99 | N-(1-(2-fluorobenzyl)-1H-pyrazol-4-yl)-2'-((tetrahydro-2H-pyran-4-yl)amino)spiro[cyclobutane-1,5'-pyrrolo[3,4-d]pyrimidine]-6'(7'H)-carboxamide | 0.012 |

TABLE 2-continued

| Cmpd No. | Name | ERK2 IC$_{50}$ (μM) |
|---|---|---|
| 100 | 5,5-dimethyl-N-(3-(methylcarbamoyl)benzyl)-2-((tetrahydro-2H-pyran-4-yl)amino)-5H-pyrrolo[3,4-d]pyrimidine-6(7H)-carboxamide | 0.045 |
| 101 | N-(3-(dimethylcarbamoyl)benzyl)-5,5-dimethyl-2-((tetrahydro-2H-pyran-4-yl)amino)-5H-pyrrolo[3,4-d]pyrimidine-6(7H)-carboxamide | 0.492 |
| 102 | N-(1-(2-fluorobenzyl)-5-(methylcarbamoyl)piperidin-3-yl)-5,5-dimethyl-2-((tetrahydro-2H-pyran-4-yl)amino)-5H-pyrrolo[3,4-d]pyrimidine-6(7H)-carboxamide | 2.305 |
| 103 | N-(1-(3-chlorobenzyl)-5-(methylcarbamoyl)piperidin-3-yl)-5,5-dimethyl-2-((tetrahydro-2H-pyran-4-yl)amino)-5H-pyrrolo[3,4-d]pyrimidine-6(7H)-carboxamide | 9.192 |
| 104 | N-(1-(3-chlorobenzyl)-5-(methylcarbamoyl)piperidin-3-yl)-5,5-dimethyl-2-((tetrahydro-2H-pyran-4-yl)amino)-5H-pyrrolo[3,4-d]pyrimidine-6(7H)-carboxamide | 0.037 |
| 105 | N-(1-(2-fluorobenzyl)-1H-pyrazol-4-yl)-5,5-dimethyl-2-((tetrahydro-2H-pyran-4-yl)amino)-5H-pyrrolo[3,4-d]pyrimidine-6(7H)-carboxamide | 0.039 |
| 106 | (R)-N-(1-(3-chlorobenzyl)piperidin-3-yl)-5,5-dimethyl-2-((tetrahydro-2H-pyran-4-yl)amino)-5H-pyrrolo[3,4-d]pyrimidine-6(7H)-carboxamide | — |
| 107 | N-(3-fluoro-5-(methylsulfonyl)benzyl)-5,5-dimethyl-2-((tetrahydro-2H-pyran-4-yl)amino)-5H-pyrrolo[3,4-d]pyrimidine-6(7H)-carboxamide | 0.044 |
| 108 | 5,5-dimethyl-N-(4-(methylsulfonyl)benzyl)-2-((tetrahydro-2H-pyran-4-yl)amino)-5H-pyrrolo[3,4-d]pyrimidine-6(7H)-carboxamide | 0.065 |
| 109 | N-(3-chloro-5-(methylsulfonyl)benzyl)-5,5-dimethyl-2-((tetrahydro-2H-pyran-4-yl)amino)-5H-pyrrolo[3,4-d]pyrimidine-6(7H)-carboxamide | 0.006 |
| 110 | 5,5-dimethyl-N-(3-(propylsulfonyl)benzyl)-2-((tetrahydro-2H-pyran-4-yl)amino)-5H-pyrrolo[3,4-d]pyrimidine-6(7H)-carboxamide | 0.039 |
| 111 | N-(3-(ethylsulfonyl)benzyl)-5,5-dimethyl-2-((tetrahydro-2H-pyran-4-yl)amino)-5H-pyrrolo[3,4-d]pyrimidine-6(7H)-carboxamide | 0.016 |
| 112 | 5,5-dimethyl-N-(2-(methylsulfonyl)benzyl)-2-((tetrahydro-2H-pyran-4-yl)amino)-5H-pyrrolo[3,4-d]pyrimidine-6(7H)-carboxamide | 0.806 |
| 113 | (R)-5,5-dimethyl-2-((tetrahydro-2H-pyran-4-yl)amino)-N-(1-(m-tolylsulfonyl)piperidin-3-yl)-5H-pyrrolo[3,4-d]pyrimidine-6(7H)-carboxamide | 0.045 |
| 114 | (R)-5,5-dimethyl-2-((tetrahydro-2H-pyran-4-yl)amino)-N-(1-tosylpiperidin-3-yl)-5H-pyrrolo[3,4-d]pyrimidine-6(7H)-carboxamide | 0.176 |
| 115 | (R)-N-(1-(3-fluoro-5-(methylsulfonyl)phenyl)ethyl)-5,5-dimethyl-2-((tetrahydro-2H-pyran-4-yl)amino)-5H-pyrrolo[3,4-d]pyrimidine-6(7H)-carboxamide | 0.002 |
| 116 | (S)-N-(1-(3-fluoro-5-(methylsulfonyl)phenyl)ethyl)-5,5-dimethyl-2-((tetrahydro-2H-pyran-4-yl)amino)-5H-pyrrolo[3,4-d]pyrimidine-6(7H)-carboxamide | 0.457 |
| 117 | (S)-N-(2-hydroxy-1-(3-(methylsulfonyl)phenyl)ethyl)-5,5-dimethyl-2-((tetrahydro-2H-pyran-4-yl)amino)-5H-pyrrolo[3,4-d]pyrimidine-6(7H)-carboxamide | 0.007 |
| 118 | (R)-N-(1-((3-chlorophenyl)sulfonyl)piperidin-3-yl)-5,5-dimethyl-2-((tetrahydro-2H-pyran-4-yl)amino)-5H-pyrrolo[3,4-d]pyrimidine-6(7H)-carboxamide | 0.023 |
| 119 | (R)-N-(1-((4-chlorophenyl)sulfonyl)piperidin-3-yl)-5,5-dimethyl-2-((tetrahydro-2H-pyran-4-yl)amino)-5H-pyrrolo[3,4-d]pyrimidine-6(7H)-carboxamide | 0.156 |
| 120 | N-(2-fluorobenzyl)-5,5-dimethyl-2-((tetrahydro-2H-pyran-4-yl)amino)-5H-pyrrolo[3,4-d]pyrimidine-6(7H)-carboxamide | 0.158 |
| 121 | 5,5-dimethyl-2-((tetrahydro-2H-pyran-4-yl)amino)-N-(4-(trifluoromethyl)benzyl)-5H-pyrrolo[3,4-d]pyrimidine-6(7H)-carboxamide | 0.010 |
| 122 | N-(4-cyanobenzyl)-5,5-dimethyl-2-((tetrahydro-2H-pyran-4-yl)amino)-5H-pyrrolo[3,4-d]pyrimidine-6(7H)-carboxamide | 0.038 |
| 123 | N-(4-bromobenzyl)-5,5-dimethyl-2-((tetrahydro-2H-pyran-4-yl)amino)-5H-pyrrolo[3,4-d]pyrimidine-6(7H)-carboxamide | 0.007 |
| 124 | N-(4-chloro-3-fluorobenzyl)-5,5-dimethyl-2-((tetrahydro-2H-pyran-4-yl)amino)-5H-pyrrolo[3,4-d]pyrimidine-6(7H)-carboxamide | 0.006 |
| 125 | N-(4-methoxybenzyl)-5,5-dimethyl-2-((tetrahydro-2H-pyran-4-yl)amino)-5H-pyrrolo[3,4-d]pyrimidine-6(7H)-carboxamide | 0.056 |
| 126 | N-(3,4-dichlorobenzyl)-5,5-dimethyl-2-((tetrahydro-2H-pyran-4-yl)amino)-5H-pyrrolo[3,4-d]pyrimidine-6(7H)-carboxamide | 0.001 |
| 127 | (S)-N-(2-hydroxy-1-(m-tolyl)ethyl)-5,5-dimethyl-2-((tetrahydro-2H-pyran-4-yl)amino)-5H-pyrrolo[3,4-d]pyrimidine-6(7H)-carboxamide | 0.016 |
| 128 | (S)-N-(1-(3-fluorophenyl)-2-hydroxyethyl)-5,5-dimethyl-2-((tetrahydro-2H-pyran-4-yl)amino)-5H-pyrrolo[3,4-d]pyrimidine-6(7H)-carboxamide | 0.009 |
| 129 | 5,5-dimethyl-N-(4-methylbenzyl)-2-((tetrahydro-2H-pyran-4-yl)amino)-5H-pyrrolo[3,4-d]pyrimidine-6(7H)-carboxamide | 0.021 |
| 130 | N-(3-(cyclopropylsulfonyl)benzyl)-5,5-dimethyl-2-((tetrahydro-2H-pyran-4-yl)amino)-5H-pyrrolo[3,4-d]pyrimidine-6(7H)-carboxamide | 0.071 |
| 131 | (R)-5,5-dimethyl-N-(1-(3-(methylsulfonyl)phenyl)ethyl)-2-((tetrahydro-2H-pyran-4-yl)amino)-5H-pyrrolo[3,4-d]pyrimidine-6(7H)-carboxamide | 0.009 |
| 132 | 5,5-dimethyl-2-((tetrahydro-2H-pyran-4-yl)amino)-N-(4-((trifluoromethyl)thio)benzyl)-5H-pyrrolo[3,4-d]pyrimidine-6(7H)-carboxamide | 0.011 |
| 133 | 5,5-dimethyl-N-(4-phenoxybenzyl)-2-((tetrahydro-2H-pyran-4-yl)amino)-5H-pyrrolo[3,4-d]pyrimidine-6(7H)-carboxamide | 0.011 |
| 134 | 5,5-dimethyl-2-((tetrahydro-2H-pyran-4-yl)amino)-N-(4-((trifluoromethyl)sulfinyl)benzyl)-5H-pyrrolo[3,4-d]pyrimidine-6(7H)-carboxamide | 0.039 |
| 135 | N-(3-cyanobenzyl)-5,5-dimethyl-2-((tetrahydro-2H-pyran-4-yl)amino)-5H-pyrrolo[3,4-d]pyrimidine-6(7H)-carboxamide | 0.038 |
| 136 | (R)-N-(1-(4-cyanophenyl)ethyl)-5,5-dimethyl-2-((tetrahydro-2H-pyran-4-yl)amino)-5H-pyrrolo[3,4-d]pyrimidine-6(7H)-carboxamide | 0.021 |
| 137 | 5,5-dimethyl-2-((tetrahydro-2H-pyran-4-yl)amino)-N-(4-((trifluoromethyl)sulfonyl)benzyl)-5H-pyrrolo[3,4-d]pyrimidine-6(7H)-carboxamide | 0.019 |
| 138 | (R)-N-(3-hydroxy-1-phenylpropyl)-5,5-dimethyl-2-((tetrahydro-2H-pyran-4-yl)amino)-5H-pyrrolo[3,4-d]pyrimidine-6(7H)-carboxamide | 0.073 |
| 139 | (R)-5,5-dimethyl-N-(1-(4-(methylsulfonyl)phenyl)ethyl)-2-((tetrahydro-2H-pyran-4-yl)amino)-5H-pyrrolo[3,4-d]pyrimidine-6(7H)-carboxamide | 0.032 |
| 146 | (R)-N-(1-(2-fluorobenzyl)pyrrolidin-3-yl)-5,5-dimethyl-2-((tetrahydro-2H-pyran-4-yl)amino)-5H-pyrrolo[3,4-d]pyrimidine-6(7H)-carboxamide | 0.014 |
| 147 | N-(1-(2-fluorobenzyl)-5-(hydroxymethyl)piperidin-3-yl)-5,5-dimethyl-2-((tetrahydro-2H-pyran-4-yl)amino)-5H-pyrrolo[3,4-d]pyrimidine-6(7H)-carboxamide | 0.214 |
| 148 | (S)-N-(2-(dimethylamino)-1-phenylethyl)-5,5-dimethyl-2-(phenylamino)-5H-pyrrolo[3,4-d]pyrimidine-6(7H)-carboxamide | 0.448 |
| 149 | (5,5-dimethyl-2-(phenylamino)-5H-pyrrolo[3,4-d]pyrimidin-6(7H)-yl)(3,3,4-trimethylpiperazin-1-yl)methanone | 37.7 |
| 150 | (R)-N-(1-(dimethylamino)propan-2-yl)-5,5-dimethyl-2-(phenylamino)-5H-pyrrolo[3,4-d]pyrimidine-6(7H)-carboxamide | 22.9 |
| 151 | (5,5-dimethyl-2-(phenylamino)-5H-pyrrolo[3,4-d]pyrimidin-6(7H)-yl)(4-methylpiperazin-1-yl)methanone | 5.57 |
| 152 | N-(1-(dimethylamino)propan-2-yl)-5,5-dimethyl-2-(phenylamino)-5H-pyrrolo[3,4-d]pyrimidine-6(7H)-carboxamide | 29.14 |
| 153 | 5,5-dimethyl-N-(1-methylazetidin-3-yl)-2-(phenylamino)-5H-pyrrolo[3,4-d]pyrimidine-6(7H)-carboxamide | 125 |

TABLE 2-continued

| Cmpd No. | Name | ERK2 IC$_{50}$ (μM) |
|---|---|---|
| 154 | (2-benzyl-4-methylpiperazin-1-yl)(5,5-dimethyl-2-(phenylamino)-5H-pyrrolo[3,4-d]pyrimidin-6(7H)-yl)methanone | 3.03 |
| 155 | N-(1-benzylpyrrolidin-3-yl)-5,5-dimethyl-2-(phenylamino)-5H-pyrrolo[3,4-d]pyrimidine-6(7H)-carboxamide | 0.969 |
| 156 | (R)-5,5-dimethyl-2-(phenylamino)-N-(1-phenylethyl)-5H-pyrrolo[3,4-d]pyrimidine-6(7H)-carboxamide | 0.117 |
| 157 | N-(2-(dimethylamino)ethyl)-5,5-dimethyl-2-(phenylamino)-5H-pyrrolo[3,4-d]pyrimidine-6(7H)-carboxamide | 25 |
| 158 | 5,5-dimethyl-N-(1-methylpyrrolidin-3-yl)-2-(phenylamino)-5H-pyrrolo[3,4-d]pyrimidine-6(7H)-carboxamide | 41.1 |
| 159 | N-((1-benzylpyrrolidin-3-yl)methyl)-5,5-dimethyl-2-(phenylamino)-5H-pyrrolo[3,4-d]pyrimidine-6(7H)-carboxamide | 19.6 |
| 160 | 5,5-dimethyl-N-((1-methyl-1H-imidazol-5-yl)methyl)-2-(phenylamino)-5H-pyrrolo[3,4-d]pyrimidine-6(7H)-carboxamide | 36.6 |
| 161 | N-((1R,2R)-2-(dimethylamino)cyclohexyl)-5,5-dimethyl-2-(phenylamino)-5H-pyrrolo[3,4-d]pyrimidine-6(7H)-carboxamide | 125 |
| 162 | 5,5-dimethyl-N-(oxazol-4-ylmethyl)-2-(phenylamino)-5H-pyrrolo[3,4-d]pyrimidine-6(7H)-carboxamide | 16.2 |
| 163 | 5,5-dimethyl-N-(1-methylpiperidin-4-yl)-2-(phenylamino)-5H-pyrrolo[3,4-d]pyrimidine-6(7H)-carboxamide | 83.5 |
| 164 | N-(2-hydroxyethyl)-5,5-dimethyl-2-(phenylamino)-5H-pyrrolo[3,4-d]pyrimidine-6(7H)-carboxamide | 18.4 |
| 165 | 5,5-dimethyl-2-(phenylamino)-N-(tetrahydro-2H-pyran-4-yl)-5H-pyrrolo[3,4-d]pyrimidine-6(7H)-carboxamide | 18.9 |
| 166 | N-(2-((dimethylamino)methyl)benzyl)-5,5-dimethyl-2-(phenylamino)-5H-pyrrolo[3,4-d]pyrimidine-6(7H)-carboxamide | 44.8 |
| 167 | (S)-N-(1-(dimethylamino)propan-2-yl)-5,5-dimethyl-2-(phenylamino)-5H-pyrrolo[3,4-d]pyrimidine-6(7H)-carboxamide | 125 |
| 168 | (R)-N-(2-(dimethylamino)-1-phenylethyl)-5,5-dimethyl-2-(phenylamino)-5H-pyrrolo[3,4-d]pyrimidine-6(7H)-carboxamide | 125 |
| 169 | (S)-5,5-dimethyl-2-(phenylamino)-N-(1-phenylethyl)-5H-pyrrolo[3,4-d]pyrimidine-6(7H)-carboxamide | 35.3 |
| 170 | N-((R)-1-(3-chlorophenyl)ethyl)-5-methyl-2-((tetrahydro-2H-pyran-4-yl)amino)-5H-pyrrolo[3,4-d]pyrimidine-6(7H)-carboxamide (72) | 0.00154 |
| 171 | N-((R)-1-(3-chlorophenyl)ethyl)-5-cyclopropyl-2-((tetrahydro-2H-pyran-4-yl)amino)-5H-pyrrolo[3,4-d]pyrimidine-6(7H)-carboxamide | 0.343 |
| 172 | N-((R)-1-(3-chlorophenyl)ethyl)-5-cyclopropyl-2-((tetrahydro-2H-pyran-4-yl)amino)-5H-pyrrolo[3,4-d]pyrimidine-6(7H)-carboxamide | 0.146 |

The following Table 3 lists compounds that were tested for inhibition of RSK; the IC50 values are in micromolar units, and refer to inhibition of RSK1 and RSK2, respectively. Where multiple measurements were made, each value is reported.

TABLE 3

In vitro activity on RSK1 and RSK2.

| Cmpd No. | Compound Name | RSK1 IC50 | RSK2 IC50 |
|---|---|---|---|
| 148 | (S)-N-(2-(dimethylamino)-1-phenylethyl)-5,5-dimethyl-2-(phenylamino)-5H-pyrrolo[3,4-d]pyrimidine-6(7H)-carboxamide | 0.094 | 0.096 |
|  |  |  | 0.086 |
|  |  |  | 0.461 |
|  |  |  | 0.112 |
| 149 | (5,5-dimethyl-2-(phenylamino)-5H-pyrrolo[3,4-d]pyrimidin-6(7H)-yl)(3,3,4-trimethylpiperazin-1-yl)methanone | — | 0.611 |
| 150 | (R)-N-(1-(dimethylamino)propan-2-yl)-5,5-dimethyl-2-(phenylamino)-5H-pyrrolo[3,4-d]pyrimidine-6(7H)-carboxamide | 0.903 | 0.906 |
| 151 | (5,5-dimethyl-2-(phenylamino)-5H-pyrrolo[3,4-d]pyrimidin-6(7H)-yl)(4-methylpiperazin-1-yl)methanone | 1.6125 | 1.17 |
| 152 | N-(1-(dimethylamino)propan-2-yl)-5,5-dimethyl-2-(phenylamino)-5H-pyrrolo[3,4-d]pyrimidine-6(7H)-carboxamide | 1.226 | 1.36 |
| 153 | 5,5-dimethyl-N-(1-methylazetidin-3-yl)-2-(phenylamino)-5H-pyrrolo[3,4-d]pyrimidine-6(7H)-carboxamide | — | 1.37 |
| 154 | (2-benzyl-4-methylpiperazin-1-yl)(5,5-dimethyl-2-(phenylamino)-5H-pyrrolo[3,4-d]pyrimidin-6(7H)-yl)methanone | — | 1.64 |
| 155 | N-(1-benzylpyrrolidin-3-yl)-5,5-dimethyl-2-(phenylamino)-5H-pyrrolo[3,4-d]pyrimidine-6(7H)-carboxamide | — | 1.91 |
| 156 | (R)-5,5-dimethyl-2-(phenylamino)-N-(1-phenylethyl)-5H-pyrrolo[3,4-d]pyrimidine-6(7H)-carboxamide | 3.60 | 2.57 |
| 157 | N-(2-(dimethylamino)ethyl)-5,5-dimethyl-2-(phenylamino)-5H-pyrrolo[3,4-d]pyrimidine-6(7H)-carboxamide | — | 3.85 |
| 158 | 5,5-dimethyl-N-(1-methylpyrrolidin-3-yl)-2-(phenylamino)-5H-pyrrolo[3,4-d]pyrimidine-6(7H)-carboxamide | — | 3.88 |
| 159 | N-((1-benzylpyrrolidin-3-yl)methyl)-5,5-dimethyl-2-(phenylamino)-5H-pyrrolo[3,4-d]pyrimidine-6(7H)-carboxamide | — | 5.65 |
| 160 | 5,5-dimethyl-N-((1-methyl-1H-imidazol-5-yl)methyl)-2-(phenylamino)-5H-pyrrolo[3,4-d]pyrimidine-6(7H)-carboxamide | — | 5.65 |
| 161 | N-((1R,2R)-2-(dimethylamino)cyclohexyl)-5,5-dimethyl-2-(phenylamino)-5H-pyrrolo[3,4-d]pyrimidine-6(7H)-carboxamide | — | 8.20 |
| 162 | 5,5-dimethyl-N-(oxazol-4-ylmethyl)-2-(phenylamino)-5H-pyrrolo[3,4-d]pyrimidine-6(7H)-carboxamide | — | 8.21 |
| 163 | 5,5-dimethyl-N-(1-methylpiperidin-4-yl)-2-(phenylamino)-5H-pyrrolo[3,4-d]pyrimidine-6(7H)-carboxamide | — | 13.96 |
| 164 | N-(2-hydroxyethyl)-5,5-dimethyl-2-(phenylamino)-5H-pyrrolo[3,4-d]pyrimidine-6(7H)-carboxamide | — | 13.97 |
| 165 | 5,5-dimethyl-2-(phenylamino)-N-(tetrahydro-2H-pyran-4-yl)-5H-pyrrolo[3,4-d]pyrimidine-6(7H)-carboxamide | — | 15.19 |
| 166 | N-(2-((dimethylamino)methyl)benzyl)-5,5-dimethyl-2-(phenylamino)-5H-pyrrolo[3,4-d]pyrimidine-6(7H)-carboxamide | — | 16.27 |
| 167 | (S)-N-(1-(dimethylamino)propan-2-yl)-5,5-dimethyl-2-(phenylamino)-5H-pyrrolo[3,4-d]pyrimidine-6(7H)-carboxamide | >25 | 17.52 |
| 168 | (R)-N-(2-(dimethylamino)-1-phenylethyl)-5,5-dimethyl-2-(phenylamino)-5H-pyrrolo[3,4-d]pyrimidine-6(7H)-carboxamide | 17.71 | 20.20 |
| 169 | (S)-5,5-dimethyl-2-(phenylamino)-N-(1-phenylethyl)-5H-pyrrolo[3,4-d]pyrimidine-6(7H)-carboxamide | — | >25 |

Comparative Example

Compounds wherein $R^1$ and $R^2$ are both H were found to be much less active as inhibitors of ERK than the compounds described herein having at least one non-hydrogen in those positions. For example, the following compound differs from Compound No. 23 only by the absence of the methyl groups at positions corresponding to $R^1$ and $R^2$.

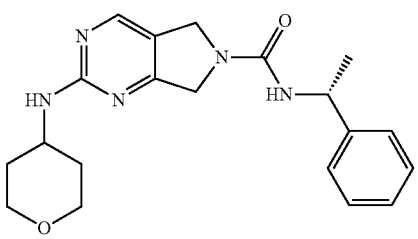 [SMILES: C[C@@H](NC(=O)N1Cc2cnc(NC3CCOCC3)nc2C1)c1ccccc1]

LCMS (M/Z) 0.59 min, 368.3

1H NMR (400 MHz, (CD3OD)) δ 8.14 (s, 1H), 7.29-7.34 (m, 2H), 7.24 (t, J=7.63 Hz, 2H), 7.09-7.17 (m, 1H), 4.92 (q, J=7.04 Hz, 1H), 4.35-4.59 (m, 4H), 3.82-4.07 (m, 3H), 3.45 (dt, J=1.96, 11.54 Hz, 2H), 1.89 (dd, J=1.96, 12.52 Hz, 2H), 1.45-1.61 (m, 2H), 1.44 (d, J=7.43 Hz, 3H).

This compound exhibited an IC50 of 0.36 uM on ERK2, while compound 23 has an IC50 of 0.014 uM on ERK2, and a very similar mono-methyl compound no. 170 (which has Cl on the phenyl ring) has an IC50 of 0.0015 on ERK2. Thus having at least one substituent other than H at $R^1$ or $R^2$ greatly enhances ERK activity.

sisting of $C_{1-4}$ alkyl, hydroxy, $C_{1-4}$ alkoxy, amino, $C_{1-4}$ alkylamino and di-($C_{1-4}$ alkyl)amino;

L is a bond, optionally substituted $C_{3-7}$ cycloalkyl, optionally substituted $C_{5-6}$ heteroaryl or optionally substituted $C_{4-7}$ heterocyclyl;

$L^2$ is a bond, —$(CR^3R^4)_{1-2}$—, —$S(O)_2$— or —$S(O)_2$—$(CR^3R^4)$—;

each $R^3$ and $R^4$ is independently H or optionally substituted $C_{1-4}$ alkyl, wherein $C_{1-4}$ alkyl is optionally substituted with 1, 2 or 3 substituents selected from the group consisting of methyl, ethyl, trifluoromethyl, fluoro, chloro, hydroxy, methoxy, oxo, amino, methylamino and dimethylamino; or $R^3$ and $R^4$, taken together with the carbon atom to which they are attached, form an optionally substituted $C_{3-5}$ cycloalkyl, wherein $C_{3-5}$ cycloalkyl is optionally substituted with 1, 2 or 3 substituents selected from the group consisting of methyl, ethyl, trifluoromethyl, fluoro, chloro, hydroxy, methoxy, oxo, amino, methylamino and dimethylamino;

Z is optionally substituted $C_{1-6}$ alkyl, optionally substituted 5-10 membered aryl, optionally substituted aryl-

The invention claimed is:

1. $R^1$ is H, COOR', optionally substituted $C_{1-4}$ alkyl, optionally substituted $C_{2-4}$ alkenyl, optionally substituted $C_{2-4}$ alkynyl or optionally substituted $C_{3-6}$ cycloalkyl, wherein R' is H or $C_{1-4}$ alkyl:

$R^2$ is H or optionally substituted $C_{1-4}$ alkyl, provided that $R^1$ and $R^2$ are not both H; or $R^1$ and $R^2$, taken together with the carbon to which they are attached, optionally form a cyclobutyl ring;

Y is $NR^6$, wherein $R^6$ is H or optionally substituted $C_{1-4}$ alkyl; or $R^6$ and L, taken together with the nitrogen atom to which they are attached, form a 5-7 membered heterocyclyl, which optionally contains an additional heteroatom selected from nitrogen, oxygen and sulfur as a ring member and which is substituted with -$L^2$-Z and 0, 1 or 2 additional substituents selected from the group con- ($C_{1-4}$ alkyl), optionally substituted heteroaryl, optionally substituted cycloalkyl or optionally substituted heterocyclyl; or when Y is $NR^6$, Z and $R^6$, taken together, optionally form a 5-6 membered heterocyclyl, wherein said heterocyclyl is optionally substituted with 1 or 2 substituents selected from the group consisting of methyl, ethyl, trifluoromethyl, fluoro, chloro, hydroxy, methoxy, oxo, amino, methylamino and dimethylamino;

X is a bond or $NR^5$;

$R^5$ is H, optionally substituted $C_{1-4}$ alkyl, optionally substituted 5-6 membered heterocyclyl or optionally substituted 5-6 membered heteroaryl;

W is optionally substituted $C_{1-6}$ alkyl, optionally substituted $C_{3-7}$ cycloalkyl, optionally substituted 4-7 membered heterocyclyl, optionally substituted aryl or optionally substituted 5-10 membered heteroaryl;

wherein the optional substituents for each optionally substituted alkyl, optionally substituted alkenyl, optionally substituted alkynyl, optionally substituted cycloalkyl and optionally substituted heterocyclyl are selected from the group consisting of halo, oxo, cyano, hydroxy, amino, $C_{1-4}$ alkyl, $C_{1-4}$ alkoxy, $C_{1-4}$ haloalkyl, $C_{1-4}$ haloalkoxy, ($C_{1-4}$ alkyl)amino, di-($C_{1-4}$ alkyl) amino, $C_{1-4}$ acylamino, $C_{3-6}$ cycloalkyl, 4-7 membered heterocyclyl, 5-6 membered heteroaryl, —S(O)$_q$— ($C_{1-4}$ alkyl), —S(O)$_q$—($C_{1-4}$ haloalkyl), —S(O)$_q$— ($C_{3-6}$ cycloalkyl), —S(O)$_q$—Ar, —OAr, COOR$^\#$ or CON(R$^\#$)$_2$, where each R$^\#$ is independently H or $C_{1-4}$ alkyl, and further wherein any two of the above optional substituents on the same atom or on adjacent atoms may cyclize to form a 3-6 membered cycloalkyl or a 5-6 membered heterocyclyl containing one nitrogen, oxygen or sulfur heteroatom, wherein the cycloalkyl or heterocyclyl is optionally substituted by 1, 2 or 3 substituents selected from the group consisting of halo, cyano, hydroxy, oxo, $C_{1-4}$ alkyl, $C_{1-4}$ haloalkyl, —OG, —COOG and —C(O)G, where each G is independently $C_{1-4}$ alkyl, and further wherein any two of the above optional substituents on the same atom or on adjacent atoms may cyclize to form a phenyl, wherein the phenyl is optionally substituted by 1, 2 or 3 substituents selected from the group consisting of halo, cyano, hydroxy, $C_{1-4}$ alkyl, $C_{1-4}$ haloalkyl, —OG, —COOG and —C(O)G, where each G is independently $C_{1-4}$ alkyl;

wherein the optional substituents for each optionally substituted aryl and optionally substituted heteroaryl are selected from the group consisting of $C_{1-4}$ alkyl and —(CH$_2$)$_m$—T, where each T is halo, cyano, hydroxy, amino, $C_{1-4}$ alkoxy, $C_{1-4}$ haloalkyl, $C_{1-4}$ haloalkoxy, ($C_{1-4}$ alkyl)amino, di-($C_{1-4}$ alkyl)amino, $C_{1-4}$ acylamino, $C_{3-6}$ cycloalkyl, 4-7 membered heterocyclyl, 5-6 membered heteroaryl, —S(O)$_p$—($C_{1-4}$ alkyl), —S(O)$_p$—($C_{1-4}$ haloalkyl), —S(O)$_p$—($C_{3-7}$ cycloalkyl), Ar, —S(O)$_p$—Ar, —OAr, COOR", CON (R")$_2$, —NR"C(O)R" and —NR"C(O)OR", where each R" is independently H or $C_{1-4}$ alkyl, and further where, at each occurrence, m is independently 0, 1 or 2, and further where the 4-7 membered heterocyclyl is optionally substituted with 1 or 2 substituents selected from the group consisting of $C_{1-4}$ alkyl and oxo, and further where the 5-6 membered heteroaryl is optionally substituted with 1 or 2 substituents selected from the group consisting of $C_{1-4}$ alkyl and halo, and further wherein any two of the above optional substituents on the same atom or on adjacent atoms may cyclize to form a 3-6 membered cycloalkyl or a 5-6 membered heterocyclyl containing one nitrogen, oxygen or sulfur heteroatom, wherein the cycloalkyl or heterocyclyl is optionally substituted by 1, 2 or 3 substituents selected from the group consisting of halo, cyano, hydroxy, oxo, $C_{1-4}$ alkyl, $C_{1-4}$ haloalkyl, —OG, —COOG and —C(O)G, where each G is independently $C_{1-4}$ alkyl, and further wherein any two of the above optional substituents on the same atom or on adjacent atoms may cyclize to form a phenyl, wherein the phenyl is optionally substituted by 1, 2 or 3 substituents selected from the group consisting of halo, cyano, hydroxy, $C_{1-4}$ alkyl, $C_{1-4}$ haloalkyl, —OG, —COOG and —C(O)G, where each G is independently $C_{1-4}$ alkyl;

each p is independently 0, 1 or 2;
each q is independently 0, 1 or 2; and each Ar is independently phenyl, which is optionally substituted with 1, 2 or 3 substituents selected from the group consisting of halo, cyano, $C_{1-4}$ alkyl, $C_{1-4}$ haloalkyl and $C_{1-4}$ alkoxy.

2. The compound of claim 1, or a pharmaceutically acceptable salt thereof, wherein $R^1$ and $R^2$ are each $CH_3$.

3. The compound of claim 2, or a pharmaceutically acceptable salt thereof, wherein X is NH and Y is NH.

4. The compound of claim 3, or a pharmaceutically acceptable salt thereof, wherein $L^2$ is —(CR$^3$R$^4$)—, wherein $R^4$ is H.

5. The compound of claim 3, or a pharmaceutically acceptable salt thereof, wherein Z is optionally substituted phenyl, optionally substituted pyridinyl, optionally substituted cyclohexyl, optionally substituted piperidinyl or optionally substituted tetrahydropyranyl;

wherein the optional substituents for cyclohexyl, piperidinyl and tetrahydropyranyl are selected from the group consisting of halo, oxo, cyano, —OR', —(CH$_2$)$_{0-2}$N(R')$_2$ and —S(O)$_2$—Ar, where each R' is independently H or $C_{1-4}$ alkyl, and where Ar is phenyl, which is optionally substituted with 1 or 2 substituents selected from the group consisting of halo, cyano, $C_{1-4}$ alkyl, $C_{1-4}$ haloalkyl and $C_{1-4}$ alkoxy;

wherein the optional substituents for phenyl and pyridinyl are selected from the group consisting of halo, cyano, —OR', —(CH$_2$)$_{0-2}$N(R')$_2$ and —S(O)$_2$—Ar, where each R' is independently H or $C_{1-4}$ alkyl, and where Ar is phenyl, which is optionally substituted with 1 or 2 substituents selected from the group consisting of halo, cyano, $C_{1-4}$ alkyl, $C_{1-4}$ haloalkyl and $C_{1-4}$ alkoxy; and further wherein two R', taken together with the nitrogen atom to which they are attached, may form a 5-6 membered heterocyclyl.

6. The compound of claim 3, or a pharmaceutically acceptable salt thereof, wherein L is optionally substituted $C_{3-7}$ cycloalkyl or optionally substituted $C_{4-7}$ heterocyclyl.

7. The compound of claim 6, or a pharmaceutically acceptable salt thereof, wherein L is cyclopropyl or piperidinyl.

8. The compound of claim 1, or a pharmaceutically acceptable salt thereof, wherein W is optionally substituted $C_{1-6}$ alkyl or optionally substituted 4-7 membered heterocyclyl.

9. The compound of claim 1, or a pharmaceutically acceptable salt thereof, wherein W is optionally substituted $C_{5-6}$ cycloalkyl or optionally substituted phenyl.

10. The compound of claim 1, or a pharmaceutically acceptable salt thereof, having the Formula (II):

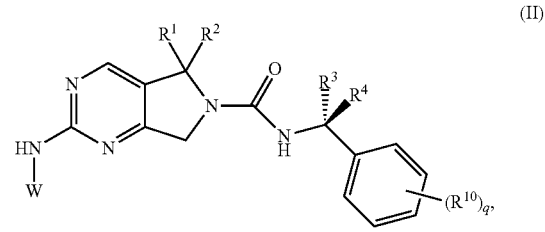

(II)

wherein:
$R^3$ is $CH_3$, $CH_2CH_3$, $CH_2OH$, $CH_2NH_2$, $CH_2NHCH_3$ or $CH_2N(CH_3)_2$;
R' is H or $CH_3$; or
$R^3$ and $R^4$, taken together with the carbon atom to which they are attached, form cyclopropyl;
q is 0, 1 or 2; and each $R^{10}$ is independently $C_{1-4}$ alkyl, halo, cyano, hydroxy, amino, $C_{1-4}$ alkoxy, $C_{1-4}$ haloalkyl, $C_{1-4}$acylamino, $S(O)_2$—($C_{1-4}$ alkyl), $CONH_2$ or $CONH(C_{1-4}$ alkyl).

11. The compound of claim 10, or a pharmaceutically acceptable salt thereof, wherein W is tetrahydropyranyl or pyridinyl.

12. The compound of claim 1, or a pharmaceutically acceptable salt thereof, having the formula:

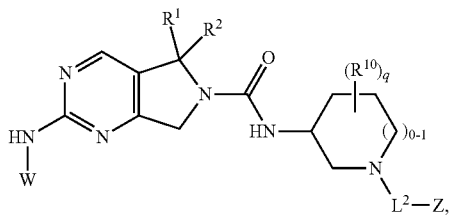

wherein:

each $R^{10}$ is halo, oxo, hydroxy, amino, $C_{1-4}$ alkyl, $C_{1-4}$ alkoxy, $C_{1-4}$ haloalkyl, —$S(O)_2$—($C_{1-4}$ alkyl), $COOR^\#$ or $CON(R^\#)_2$, where each $R^\#$ is independently H or $C_{1-4}$ alkyl;

$L^2$ is —$CH_2$— or —$S(O)_2$—; and q is 0, 1 or 2.

13. A pharmaceutical composition comprising a compound of claim 1 and at least one pharmaceutically acceptable excipient.

14. The pharmaceutical composition of claim 13, wherein the compound is selected from the group consisting of:

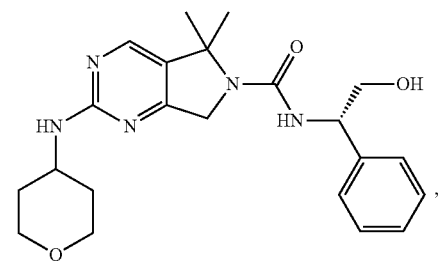

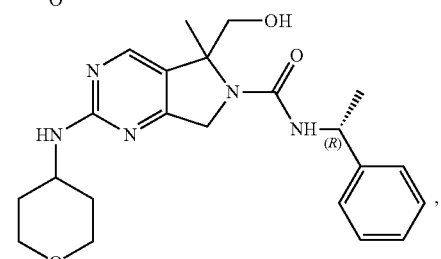

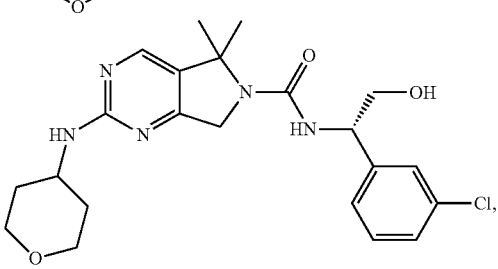

-continued

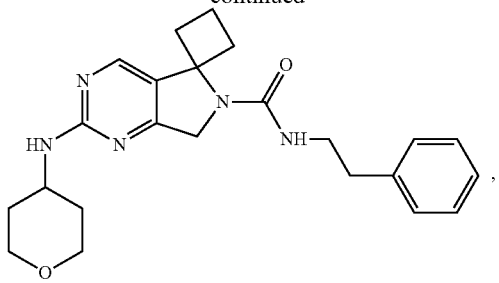

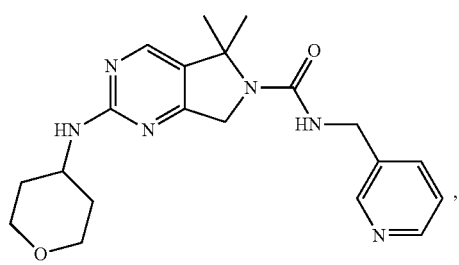

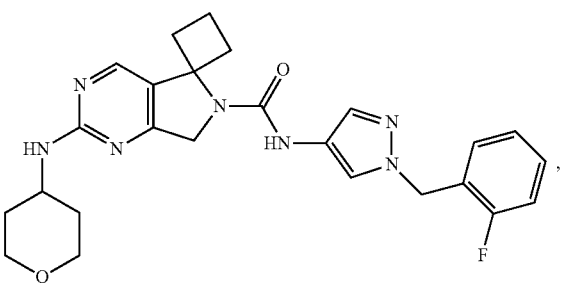

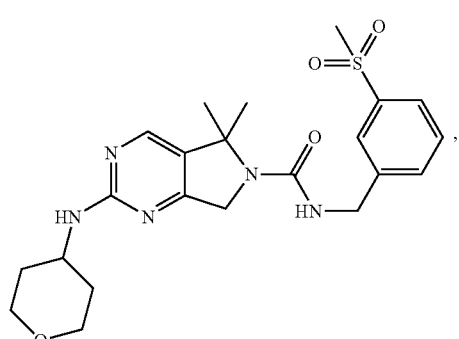

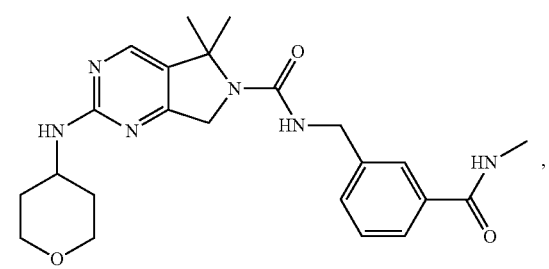

155
-continued
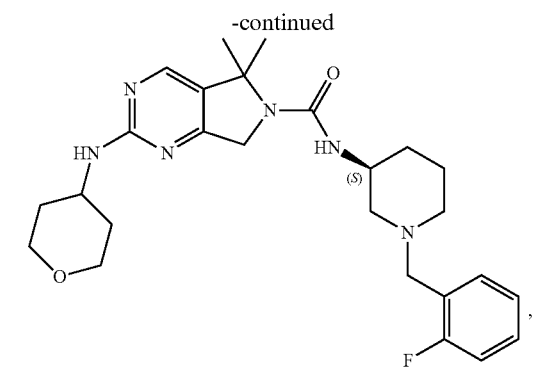
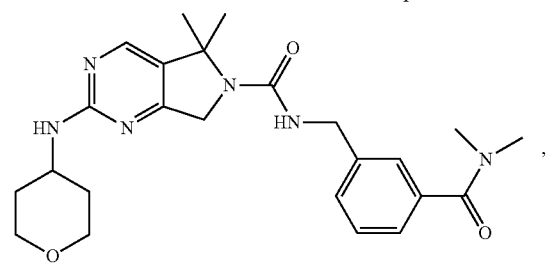
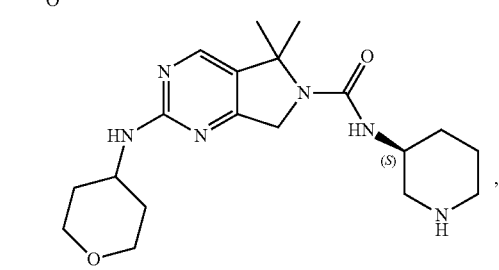
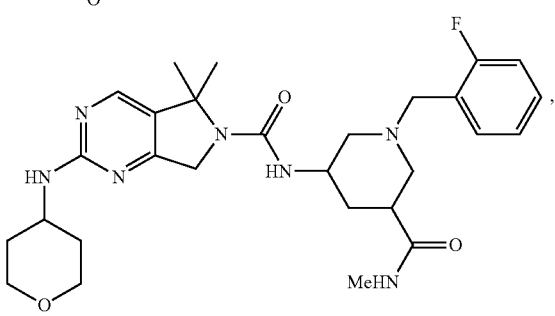
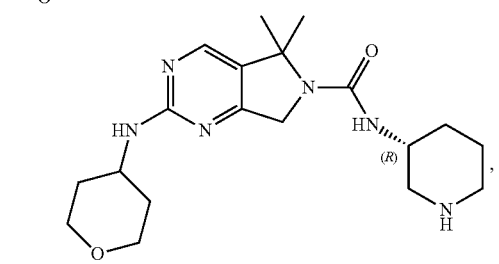
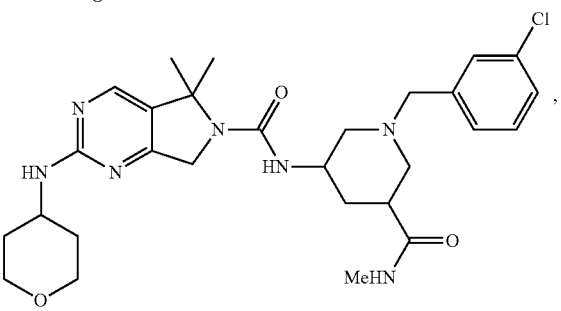
156
-continued
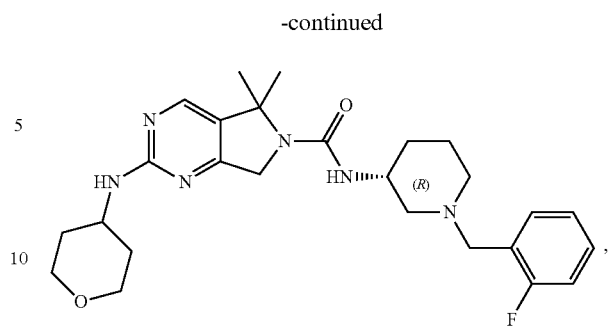
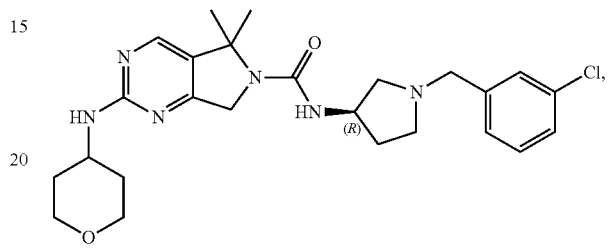
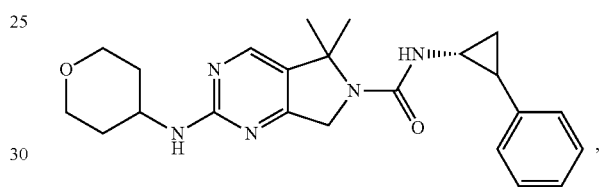
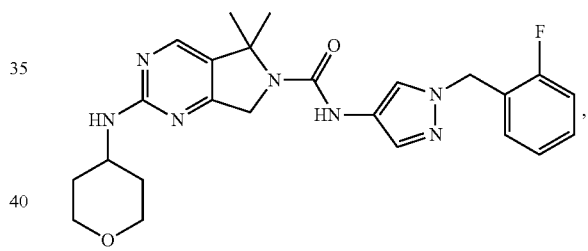
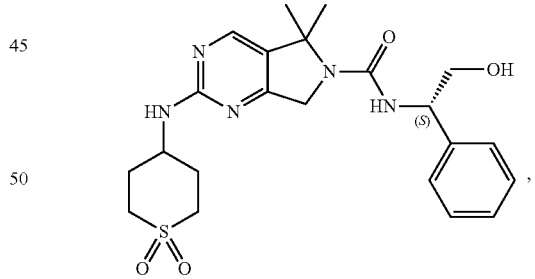
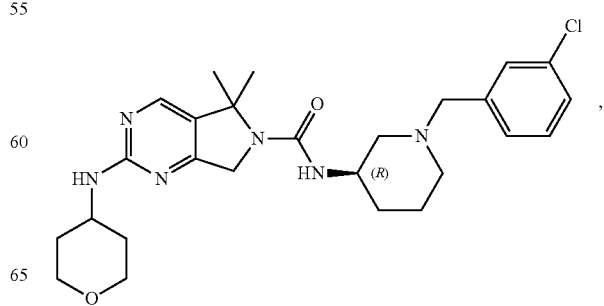

157
-continued
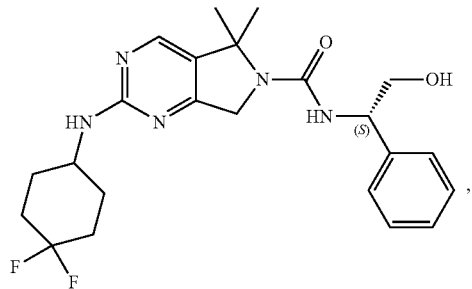
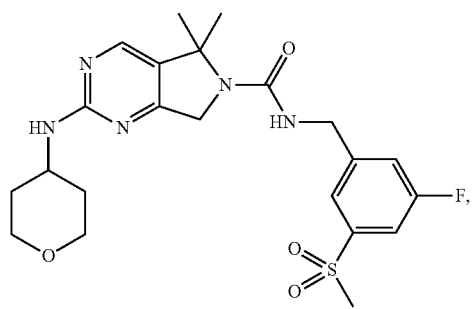
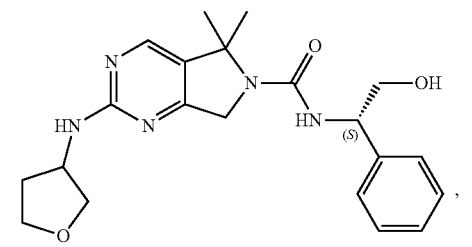
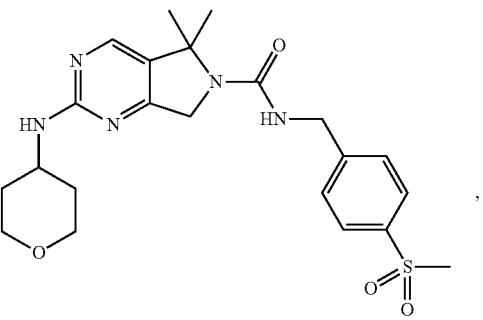
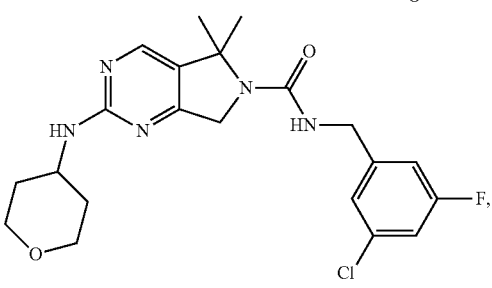
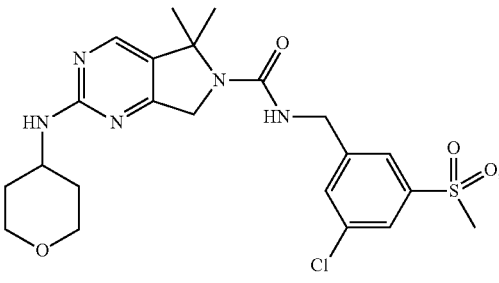
158
-continued
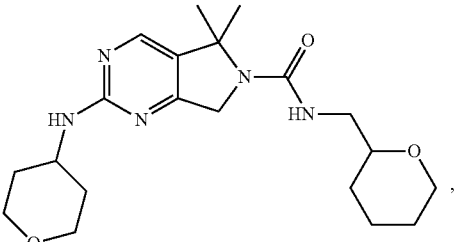
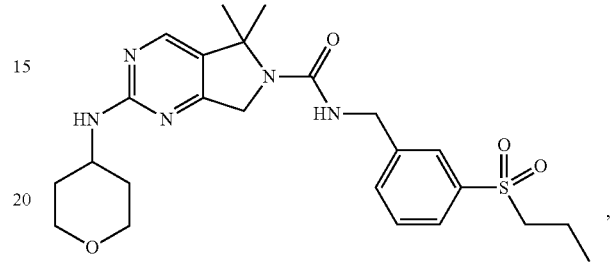
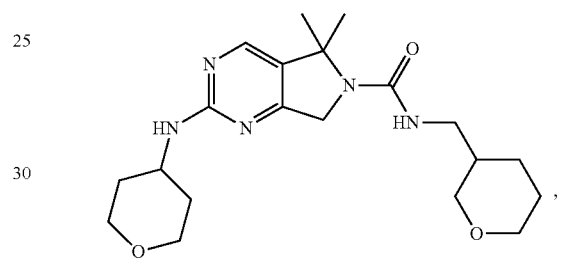
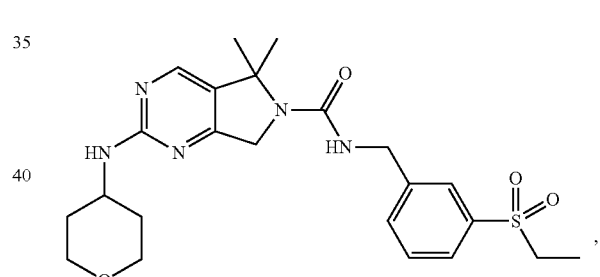
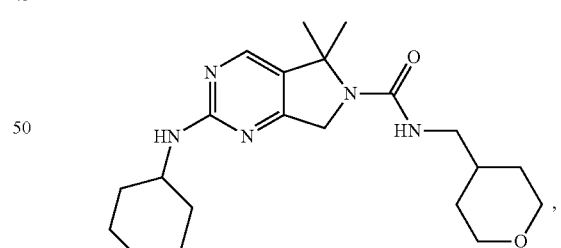
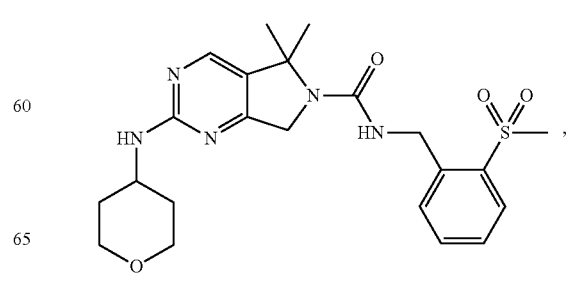

159
-continued
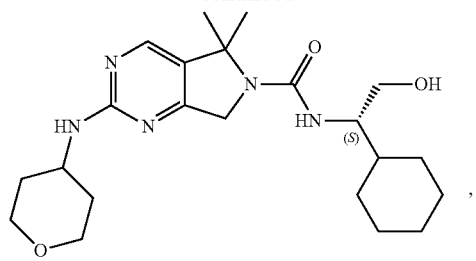
,
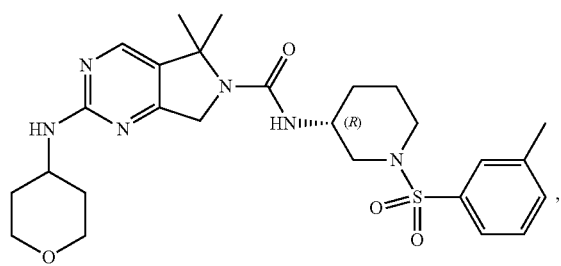
,
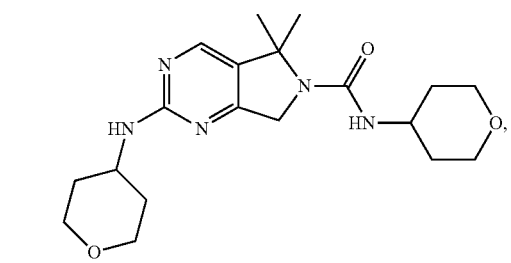
,
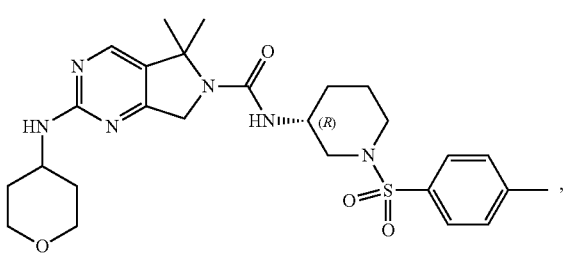
,
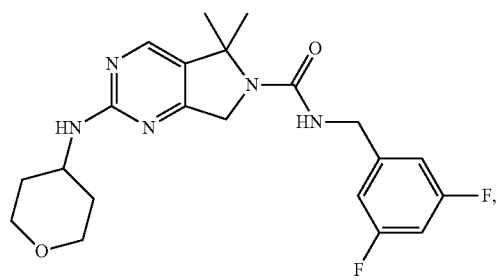
,
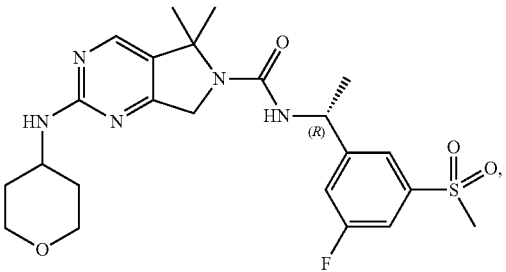
,
160
-continued
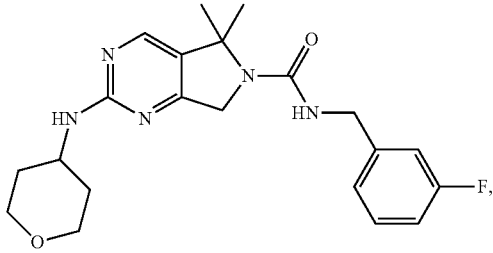
,
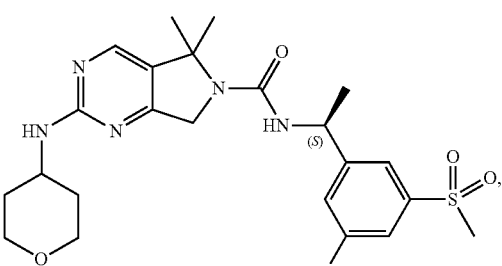
,
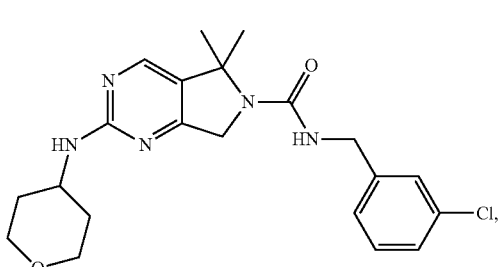
,
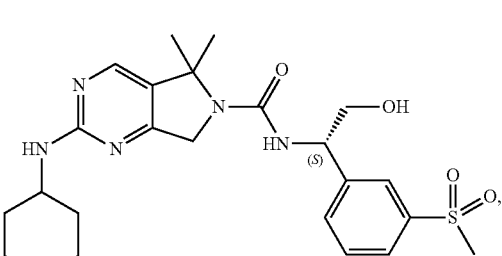
,
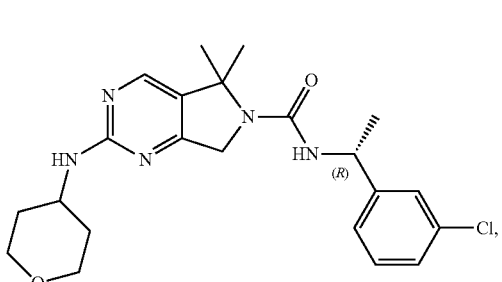
,
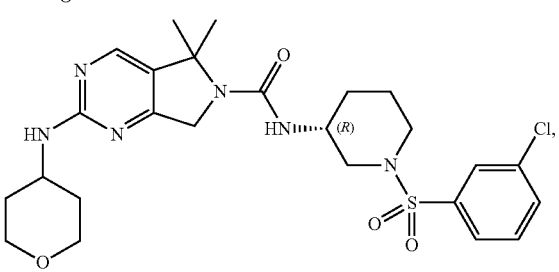
,

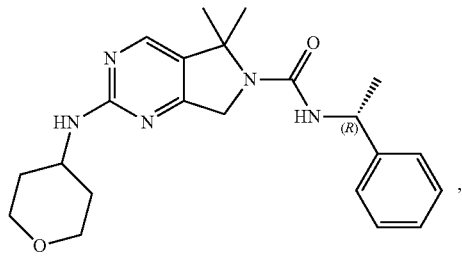
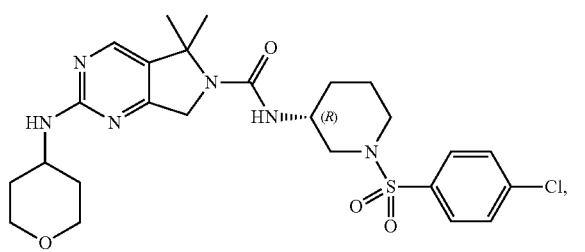
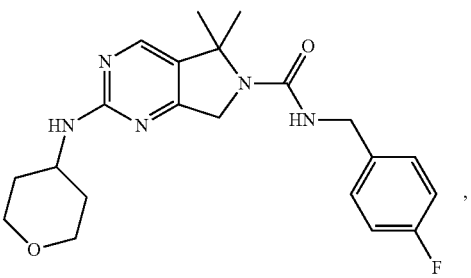
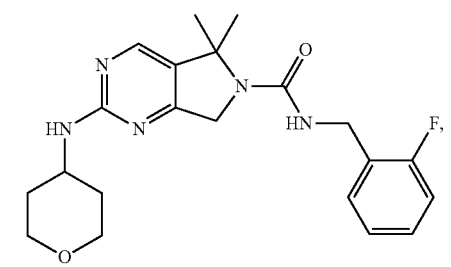
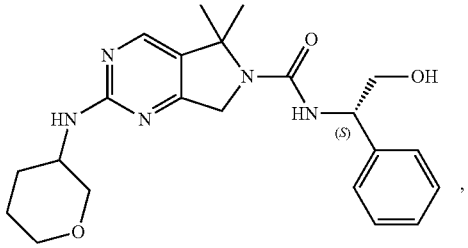
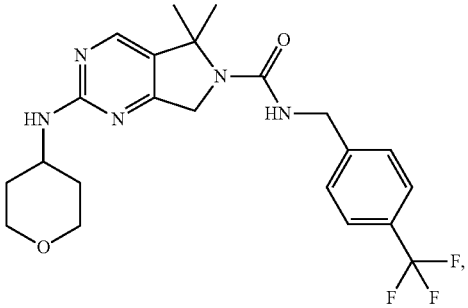
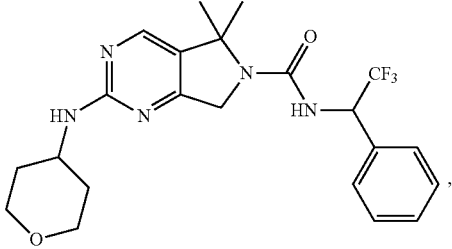
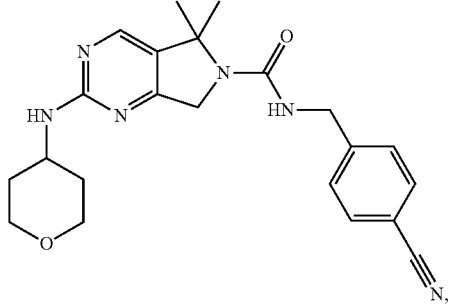
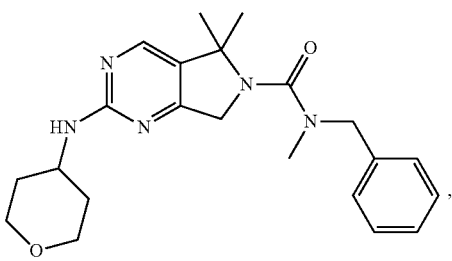
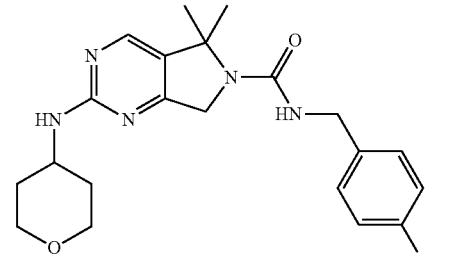
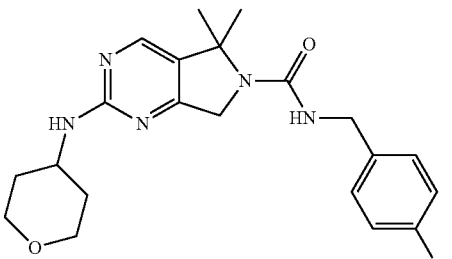
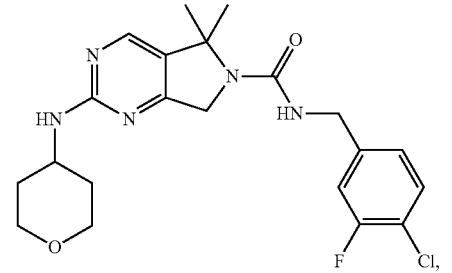

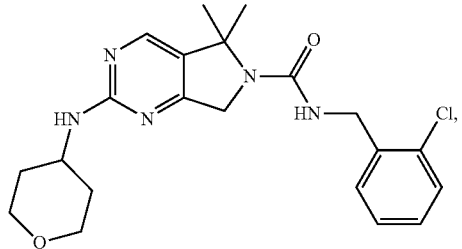
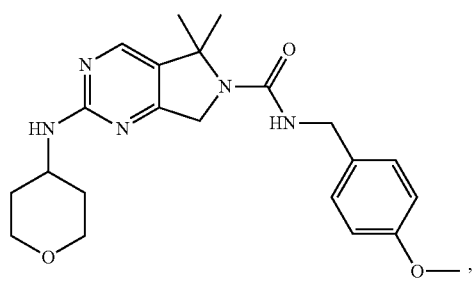
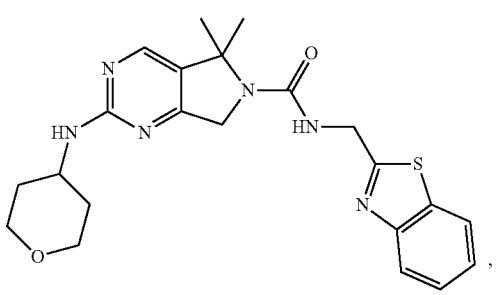
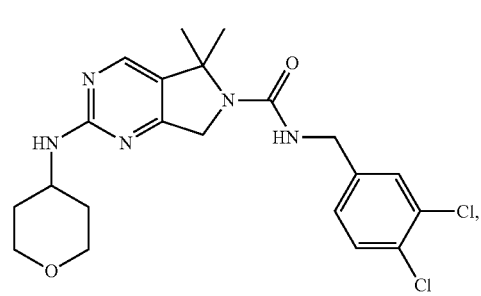
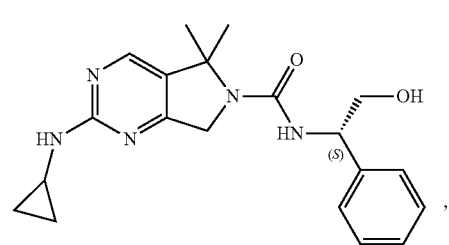
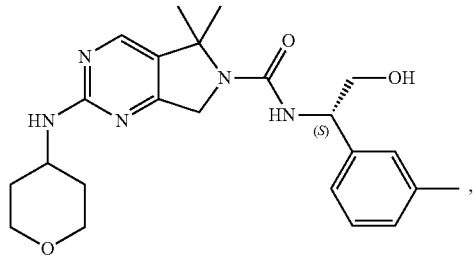
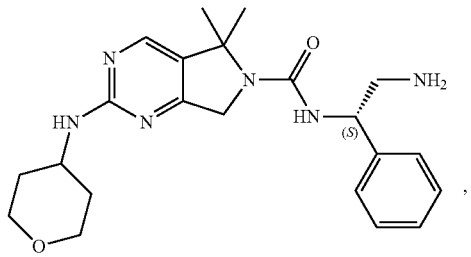
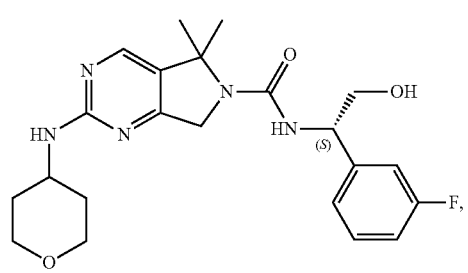
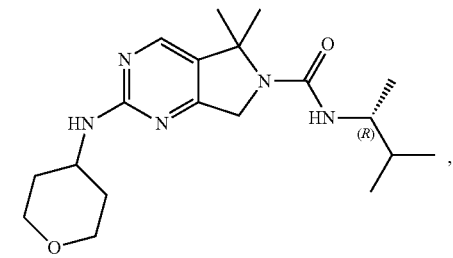
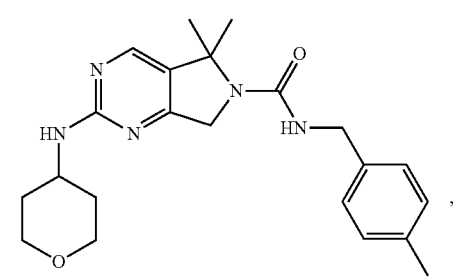
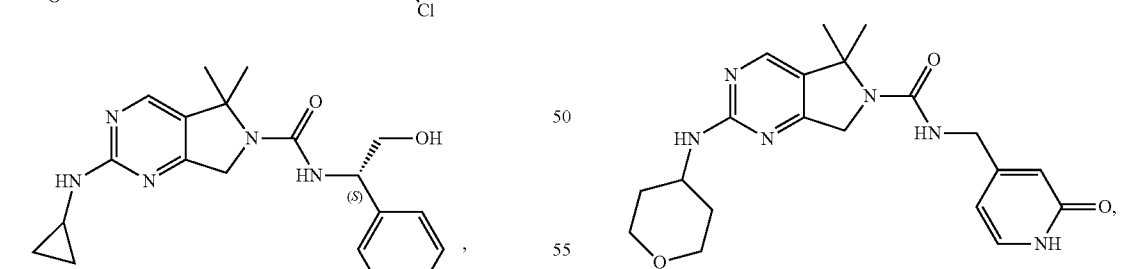
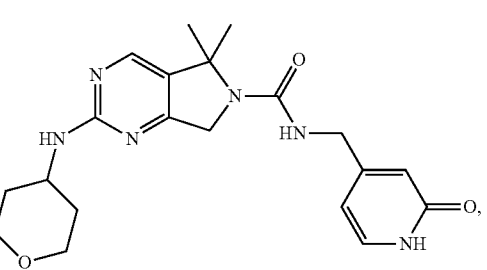
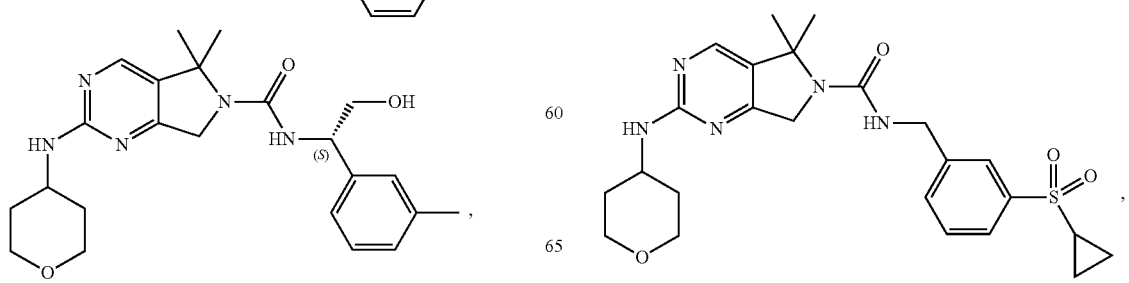
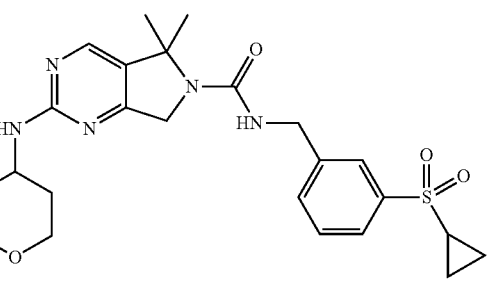

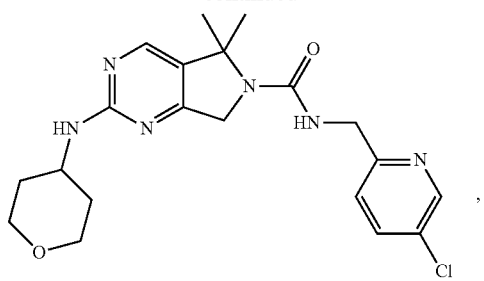,
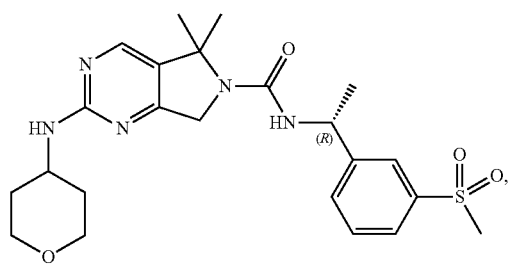,
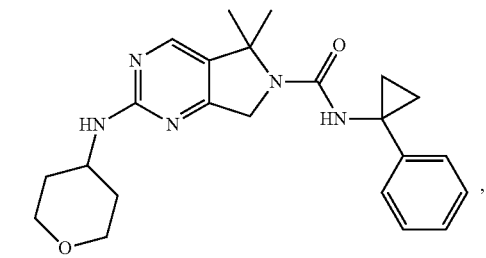,
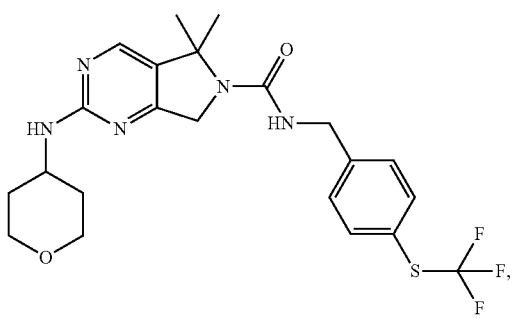,
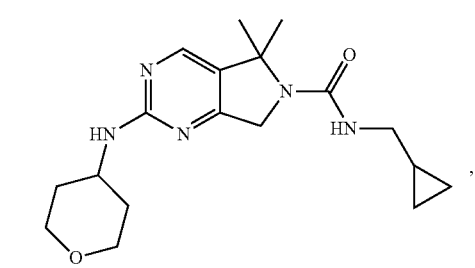,
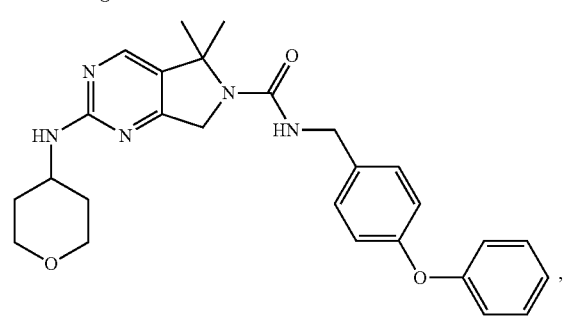,
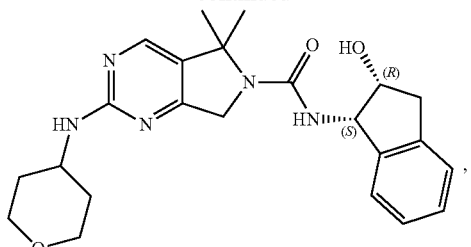,
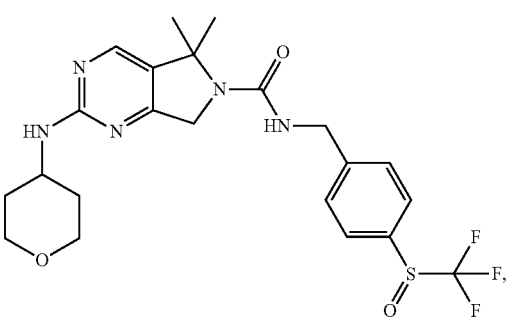,
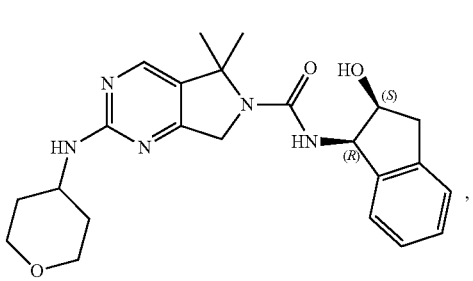,
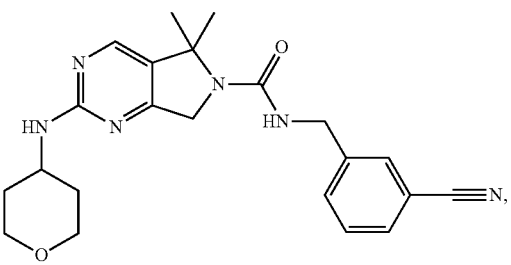,
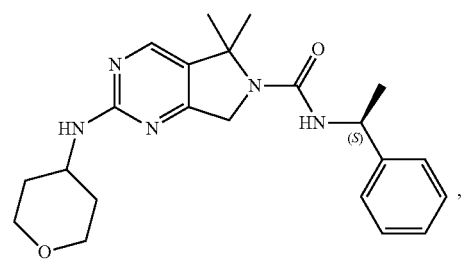,
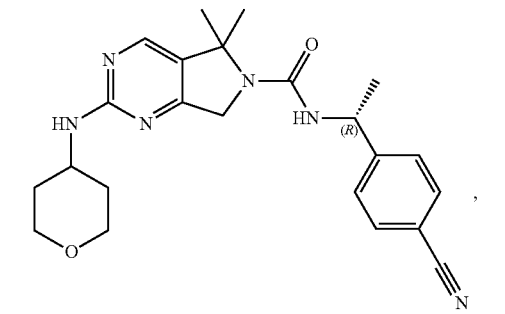, 167
-continued
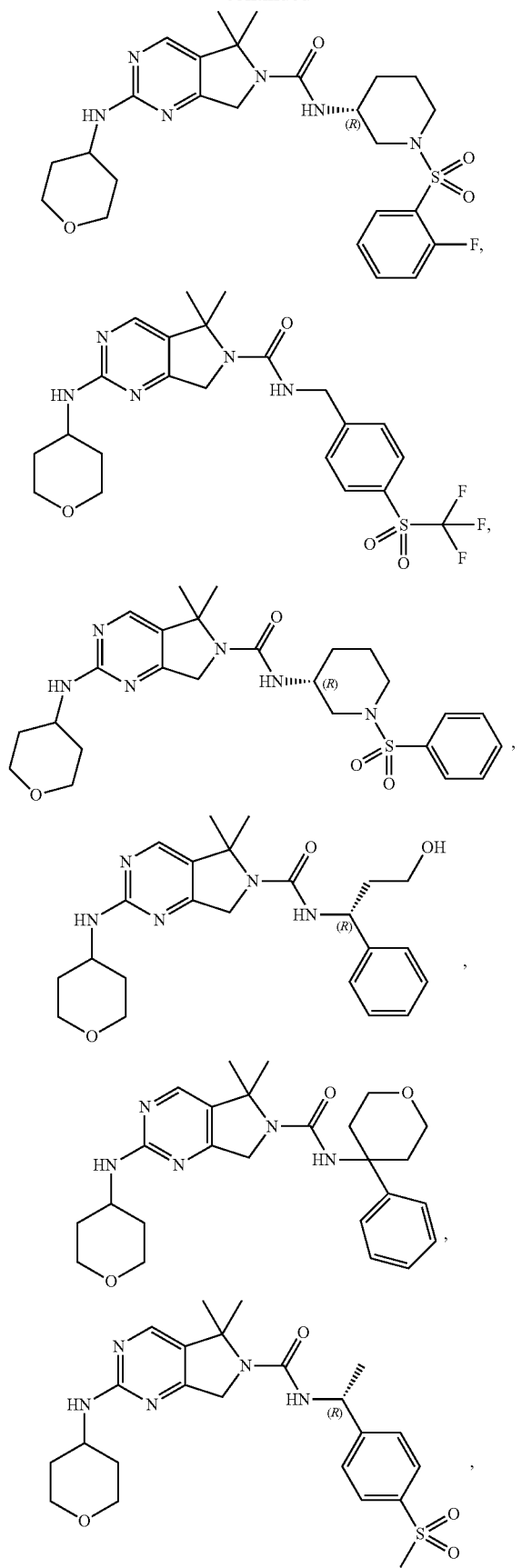
168
-continued
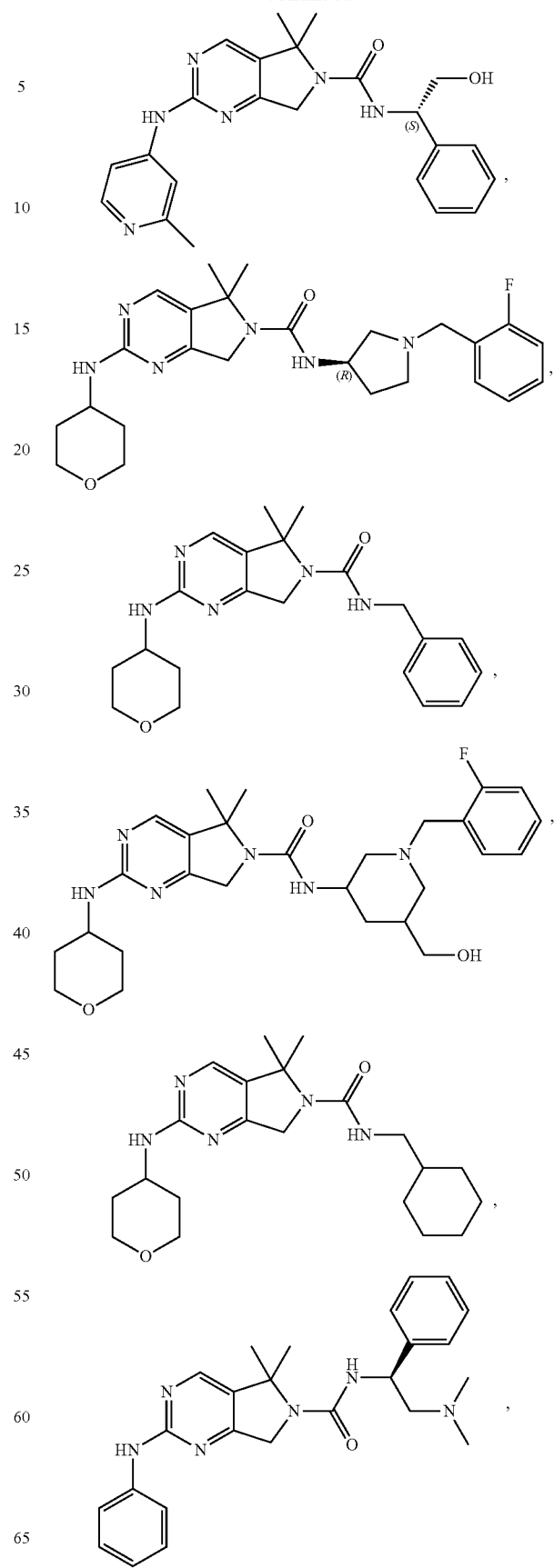

169
-continued
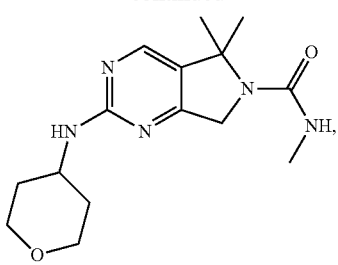,
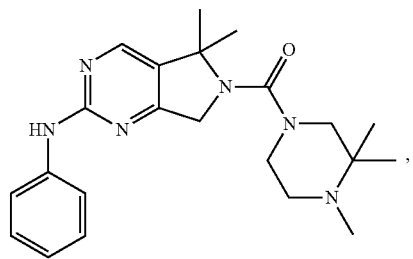,
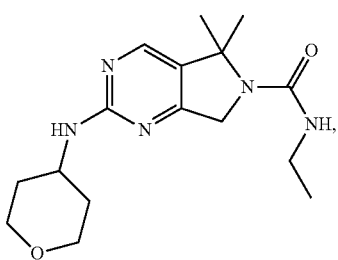,
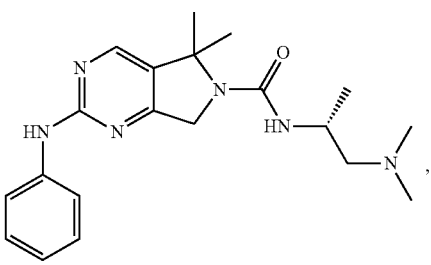,
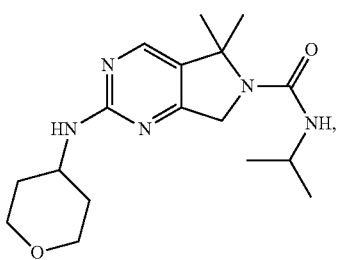,
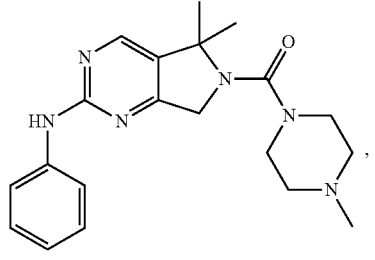,
170
-continued
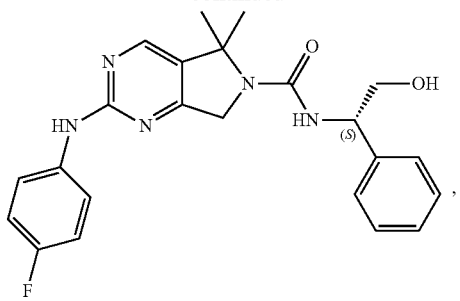,
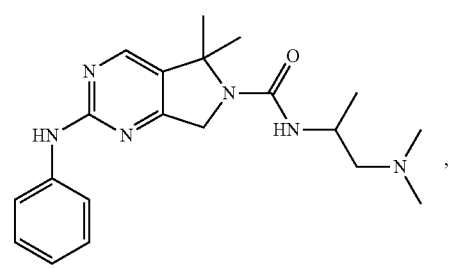,
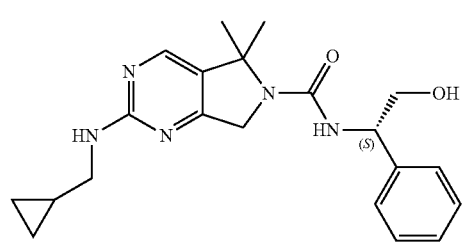,
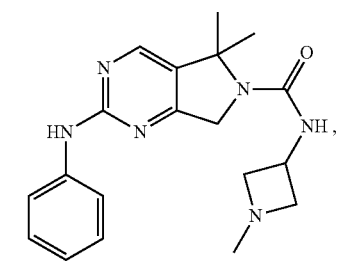,
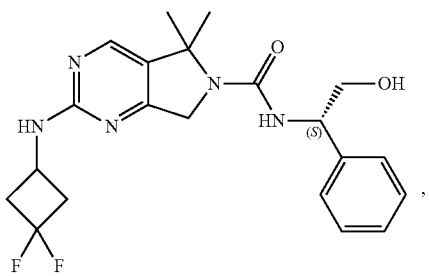,
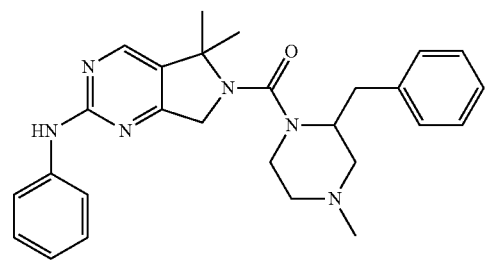, 171
-continued
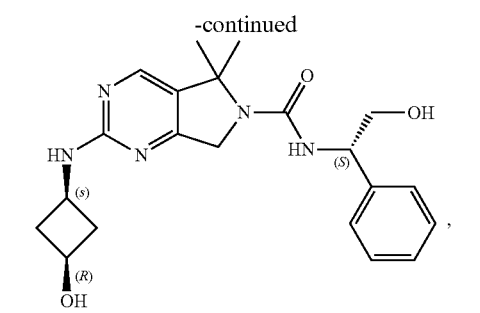
,
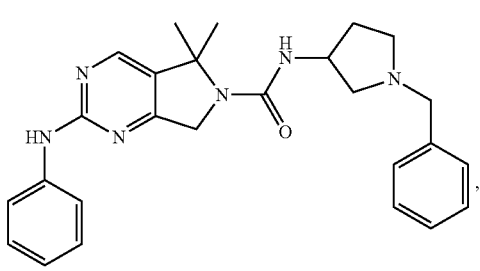
,
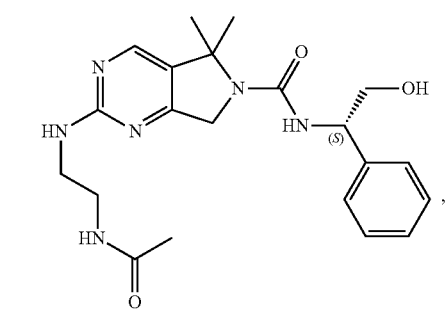
,
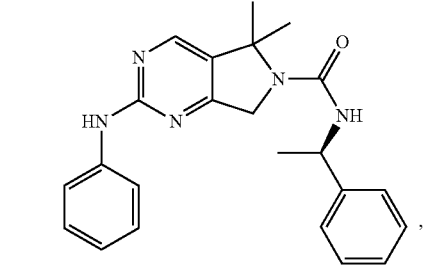
,
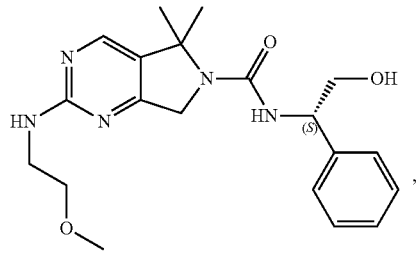
,
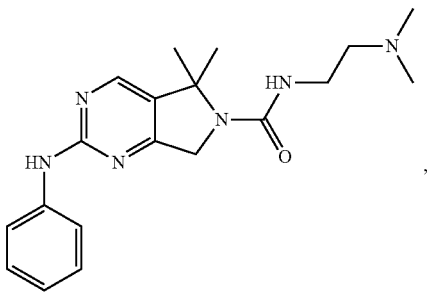
,
172
-continued
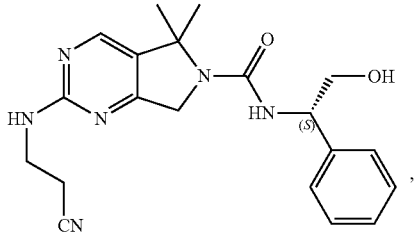
,
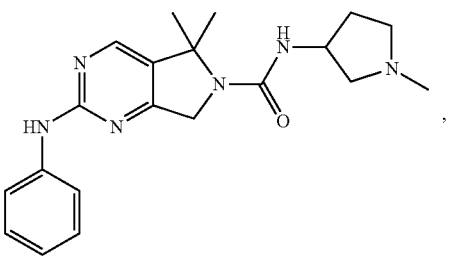
,
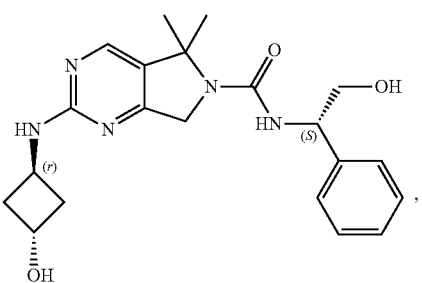
,
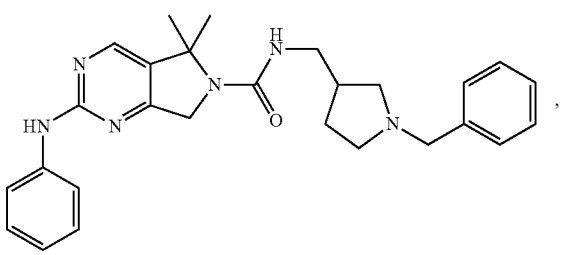
,
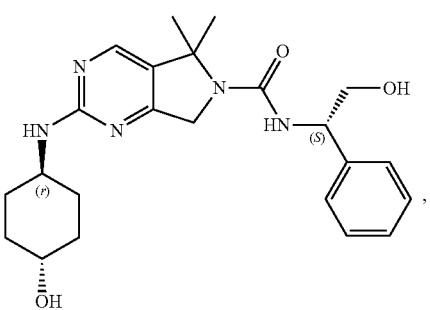
,
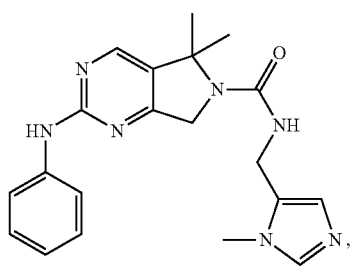
,

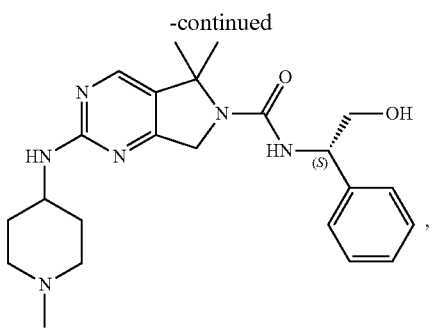
,
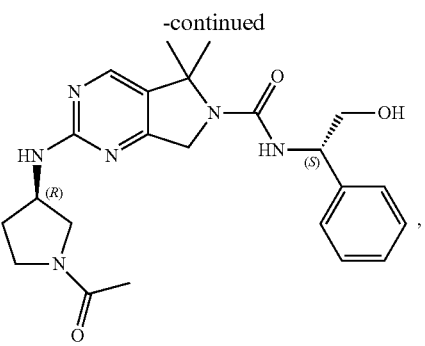
,
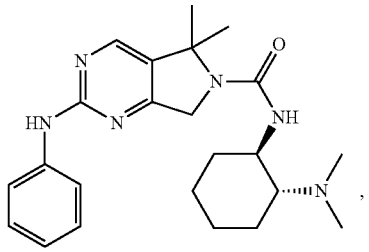
,
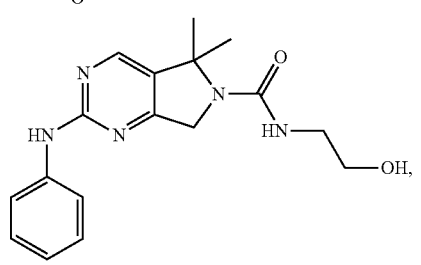
,
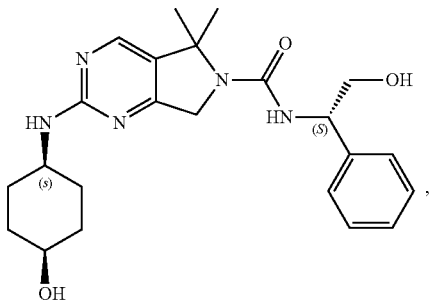
,
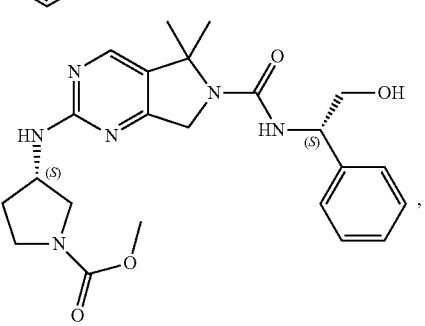
,
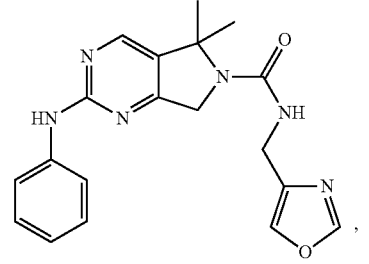
,
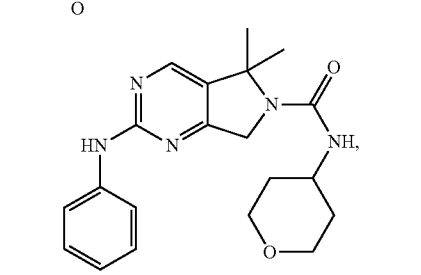
,
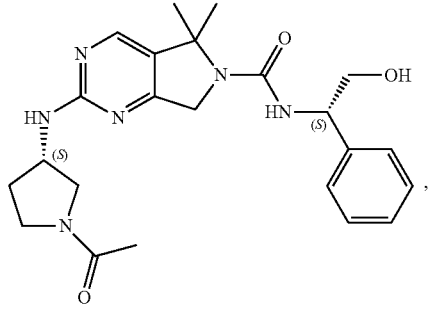
,
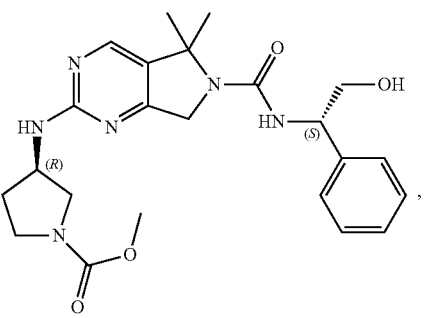
,
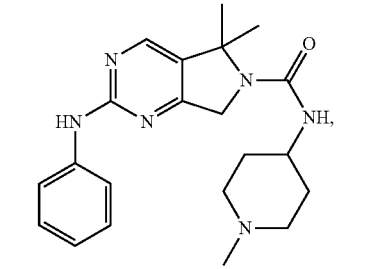
,
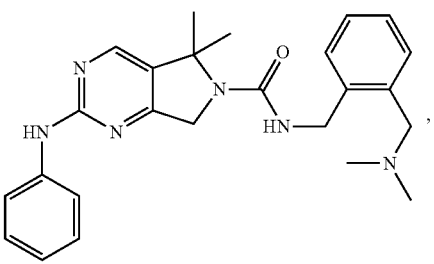
, -continued
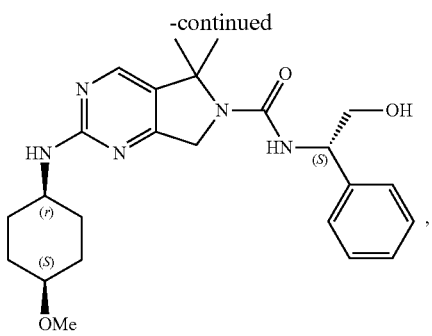
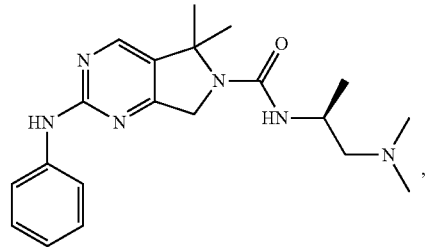
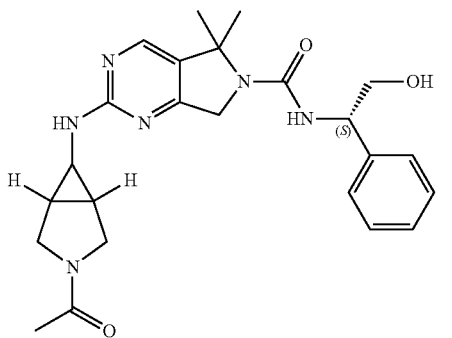
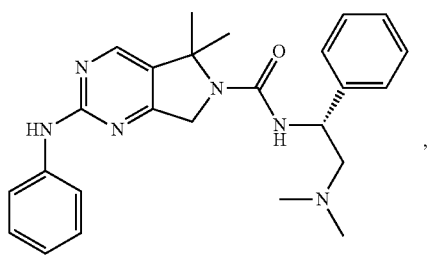
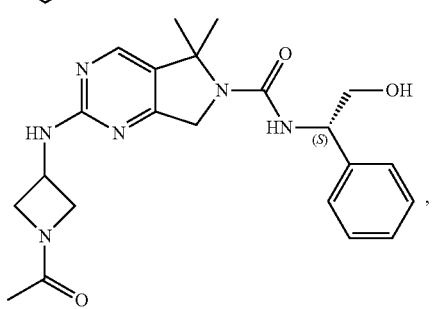
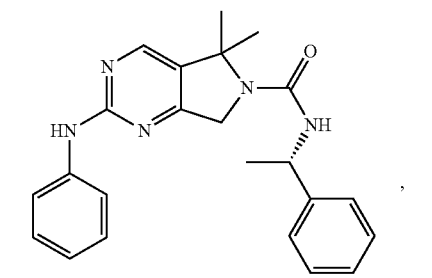
-continued
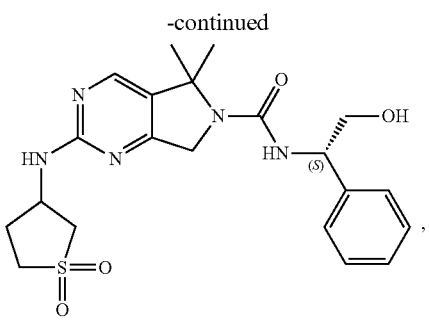
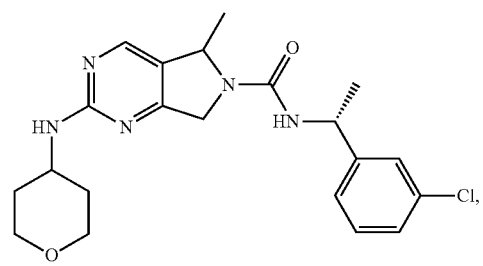
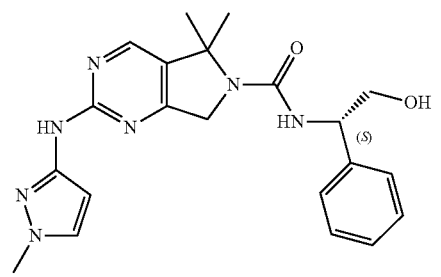
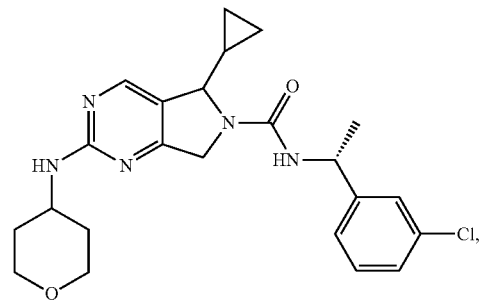
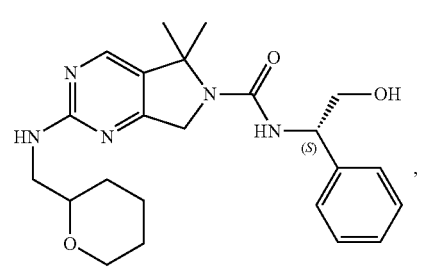
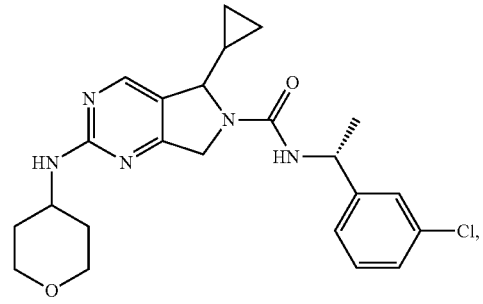

-continued
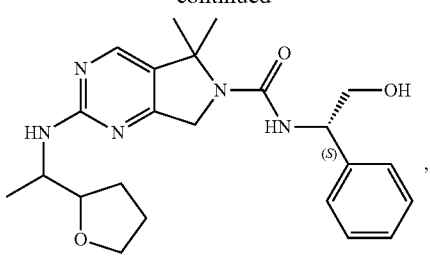
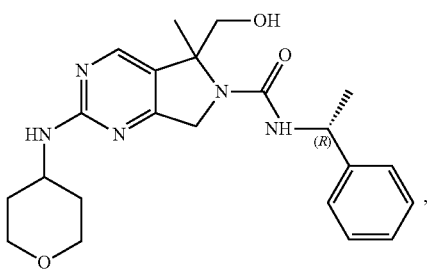
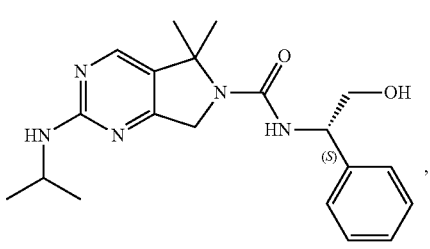
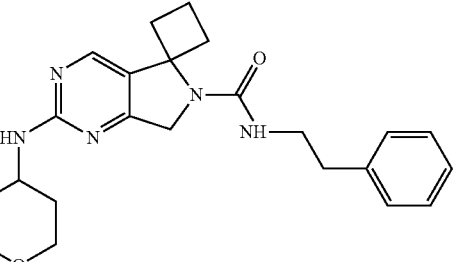
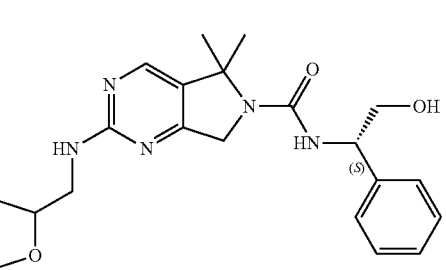
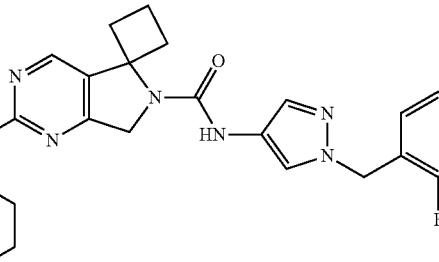
-continued
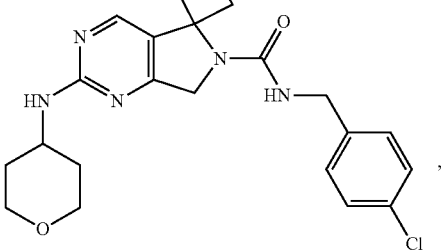
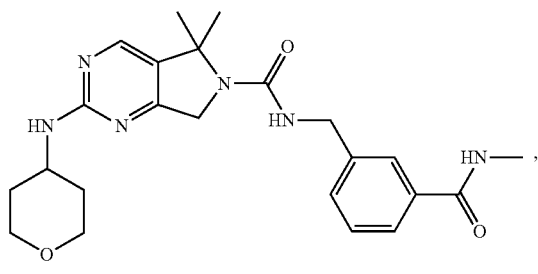
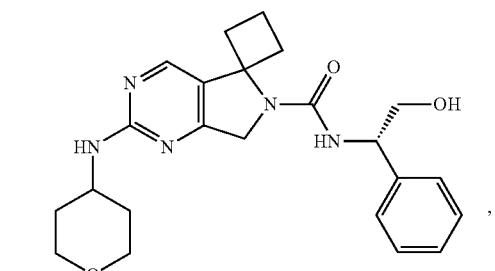
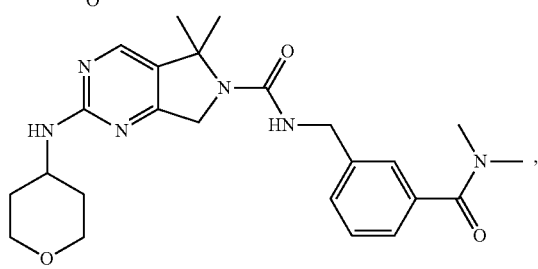
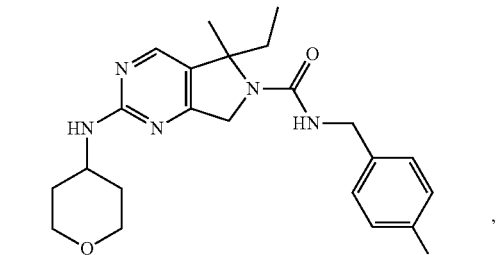
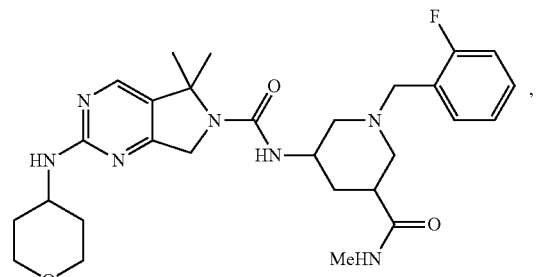

179
-continued
180
-continued
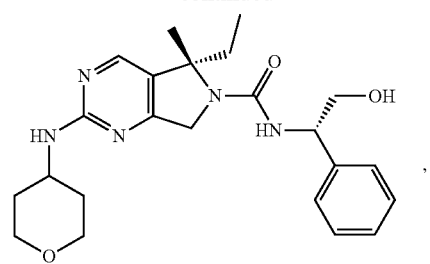
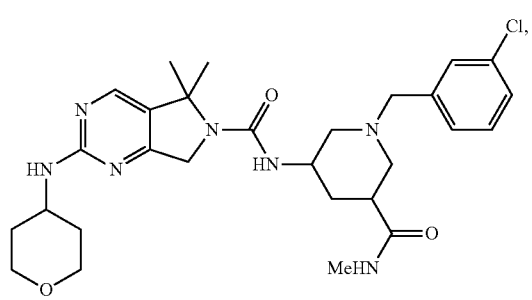
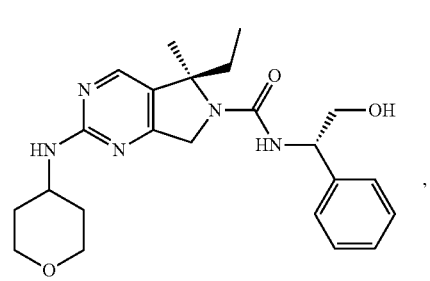
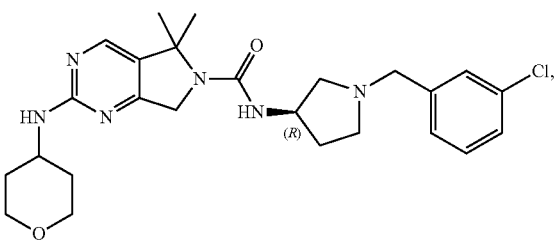
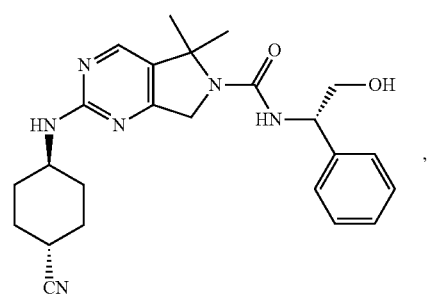
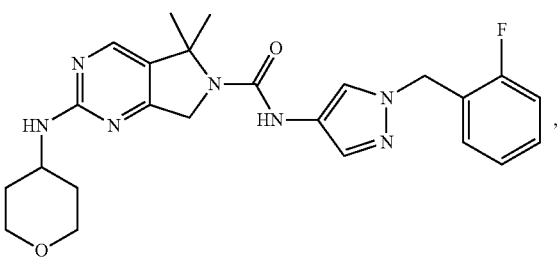

-continued

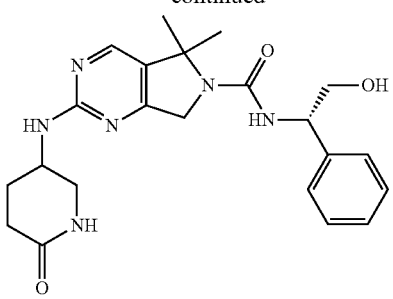

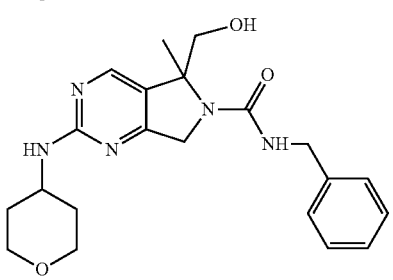

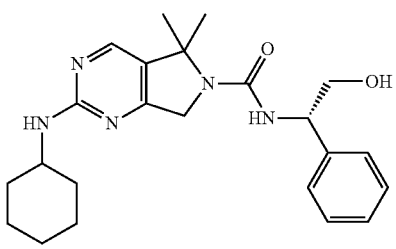

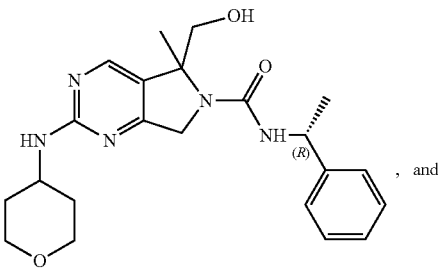

, and

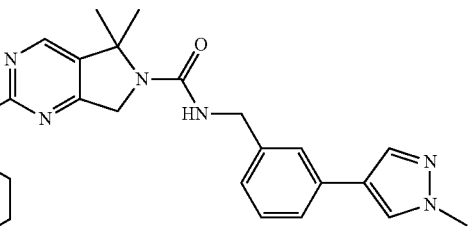

;

or a pharmaceutically acceptable salt thereof.

15. A method for modulating extracellular signal-regulated kinase activity in a subject, comprising administering to a subject in need thereof an effective amount of a compound of claim 1.

16. The method of claim 15, further comprising administering a second therapeutic agent to the subject, wherein the second therapeutic agent is selected from the group consisting of anticancer agents, analgesics, and anti-inflammatory agents.

17. A compound, or a pharmaceutically acceptable salt thereof, selected from the group consisting of:

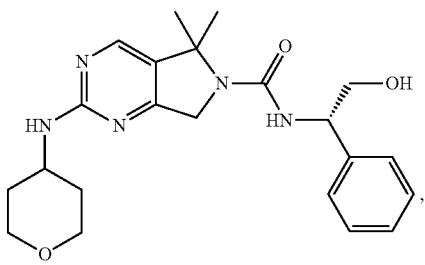

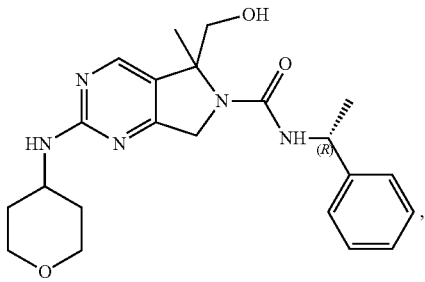

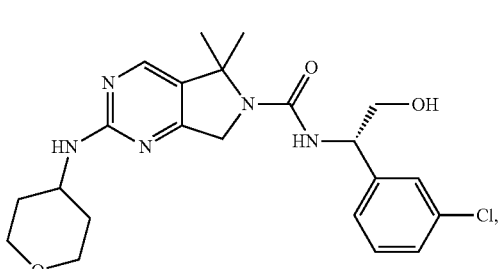

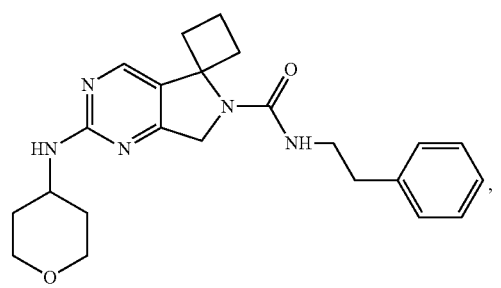

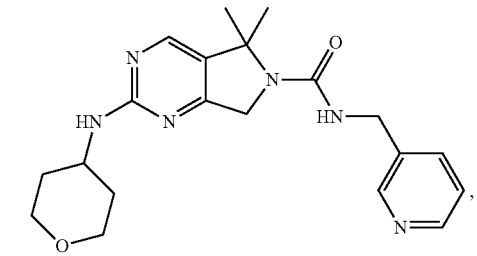

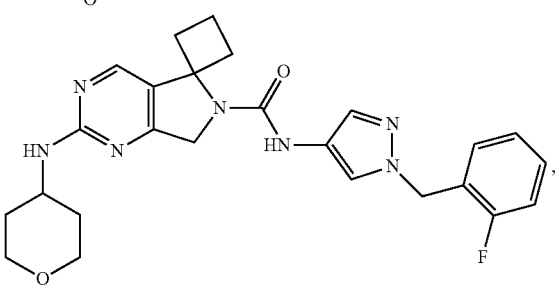

-continued
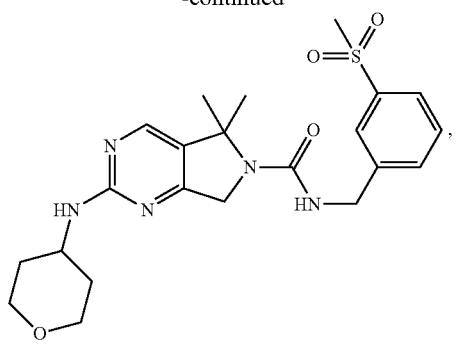
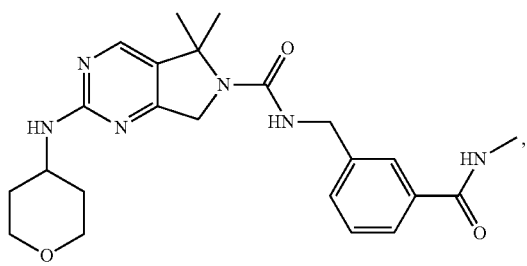
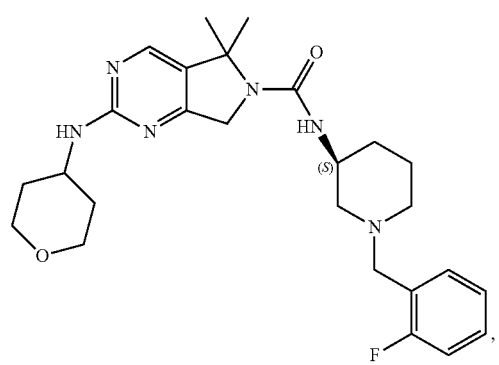
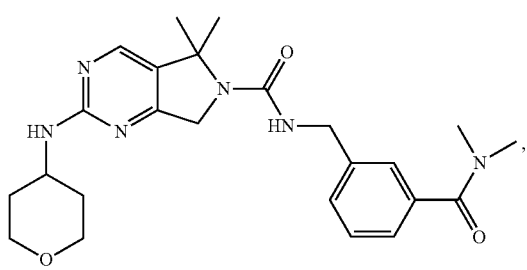
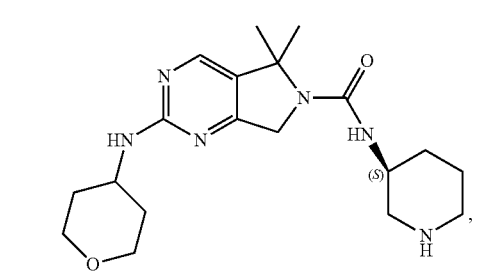
-continued
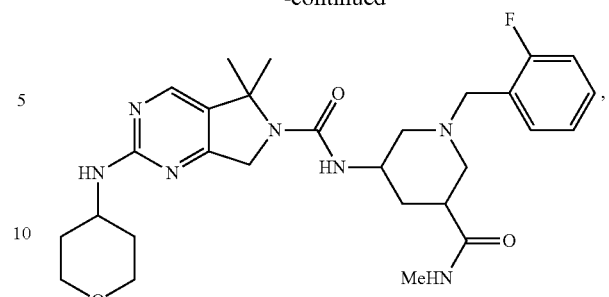
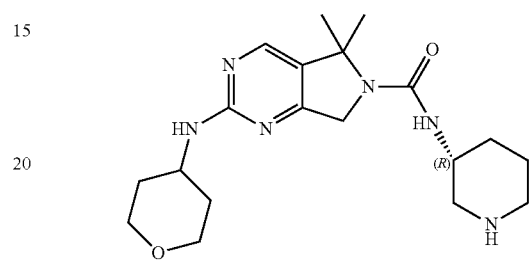
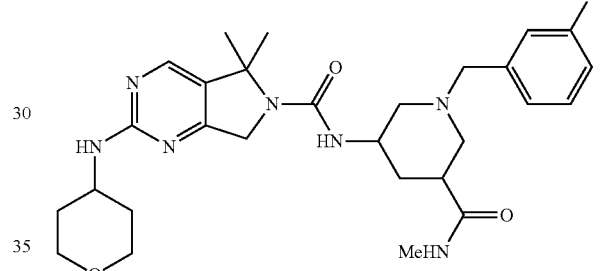
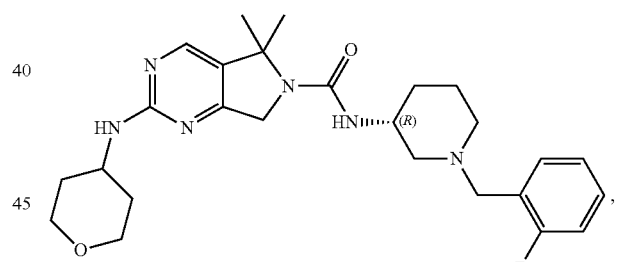
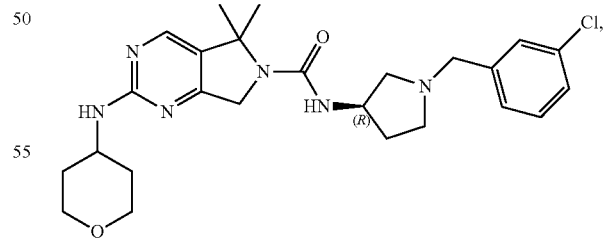

-continued
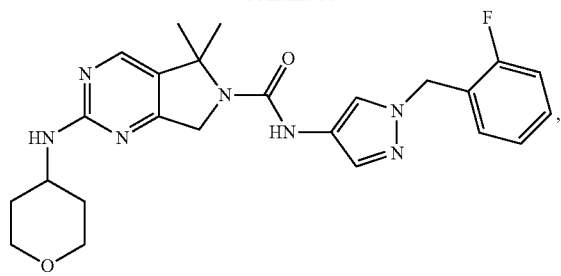
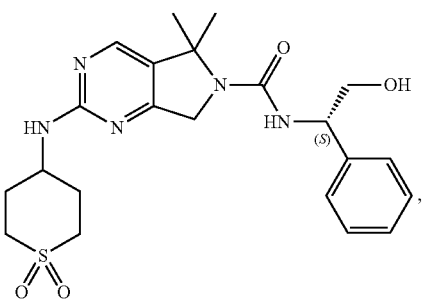
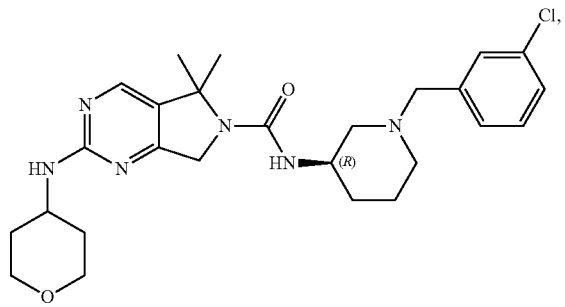
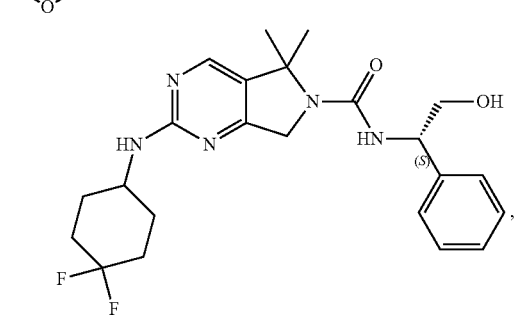
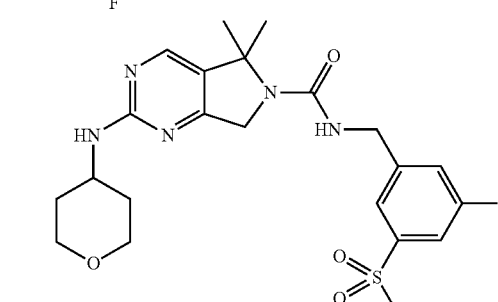
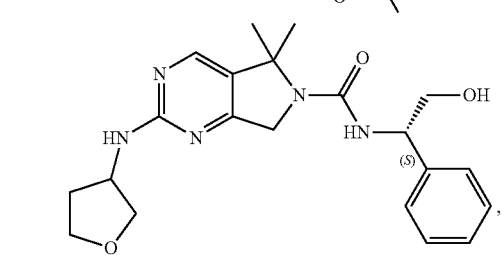
-continued
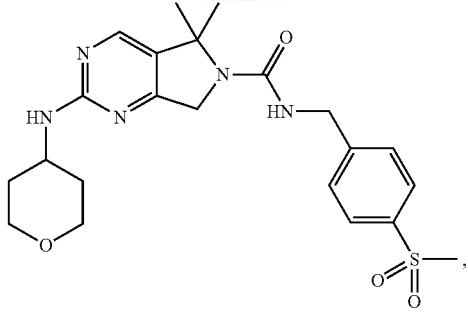
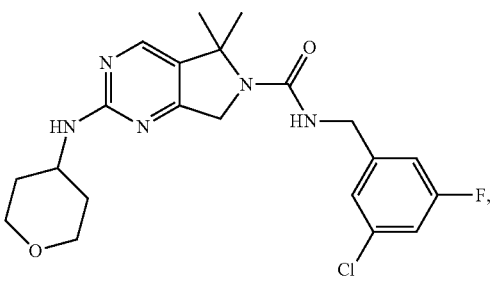
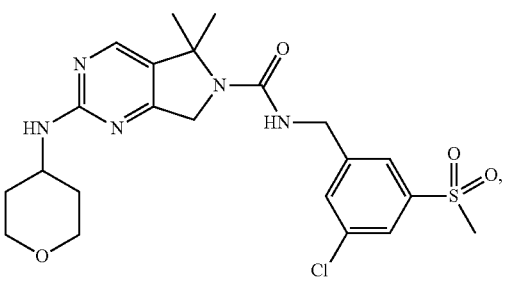
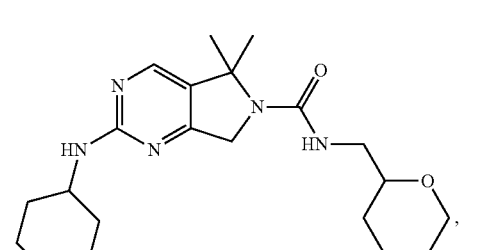
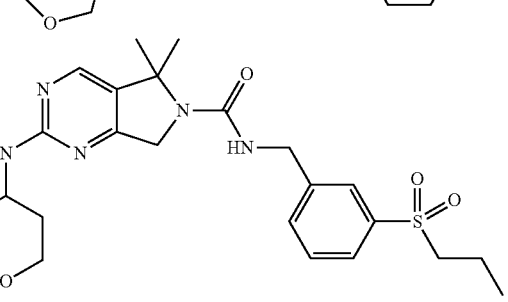
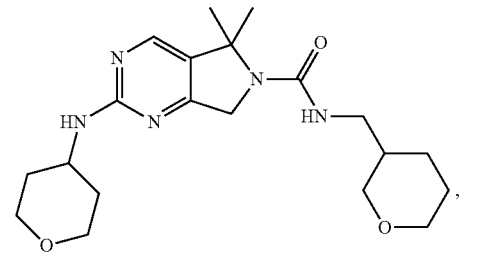

187
-continued
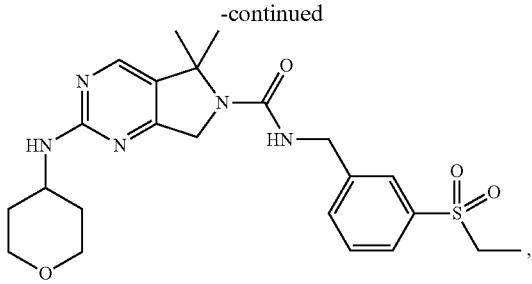
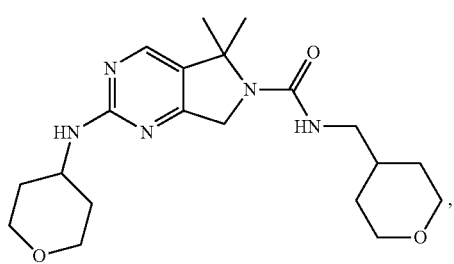
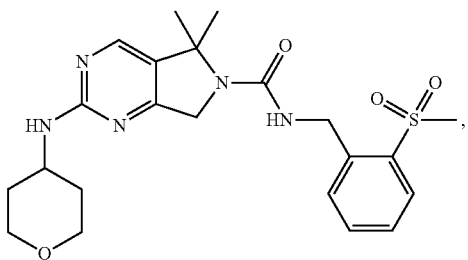
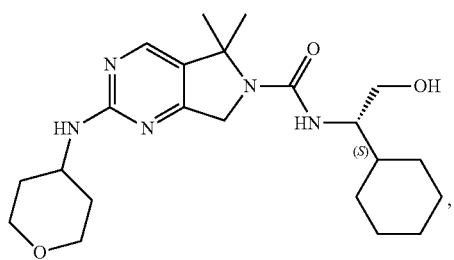
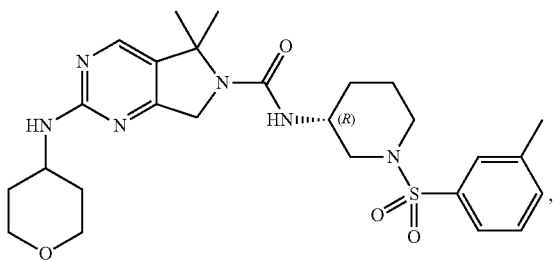
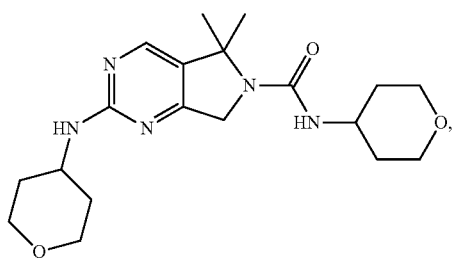
188
-continued
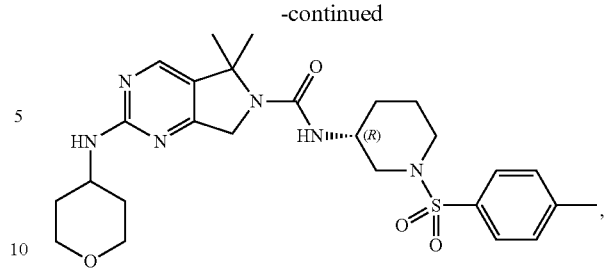
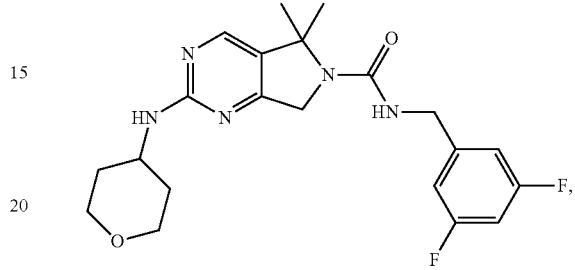
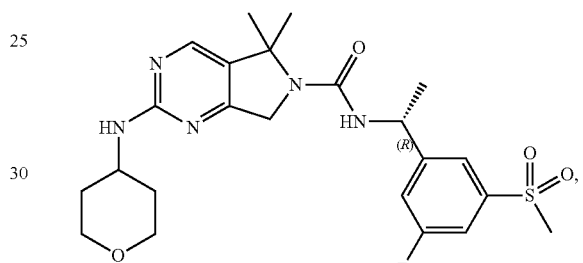
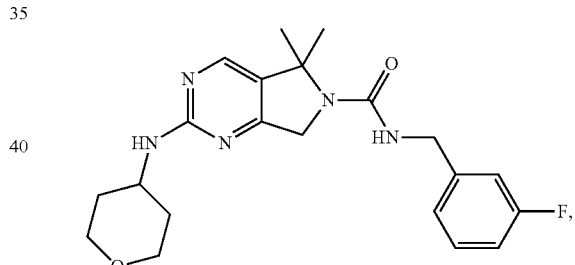
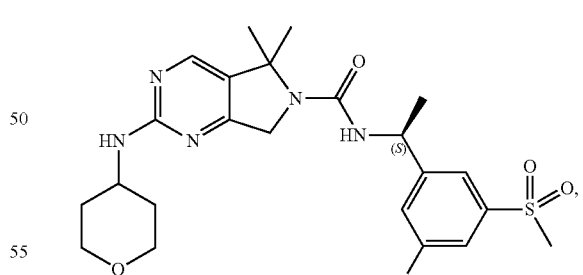
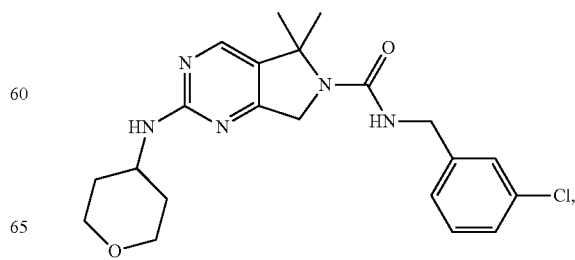

189
-continued
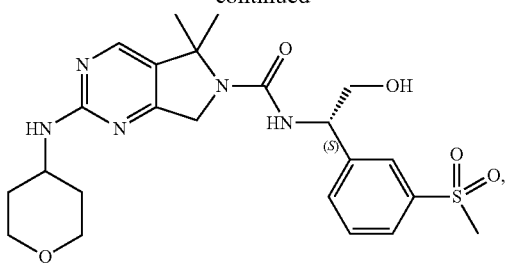
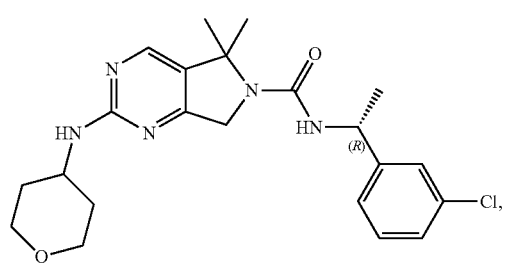
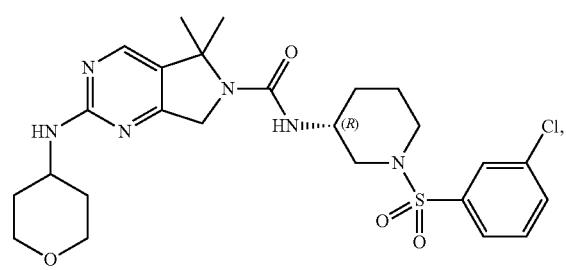
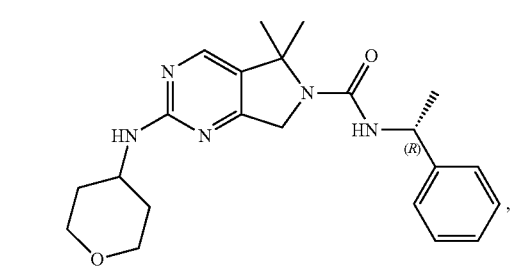
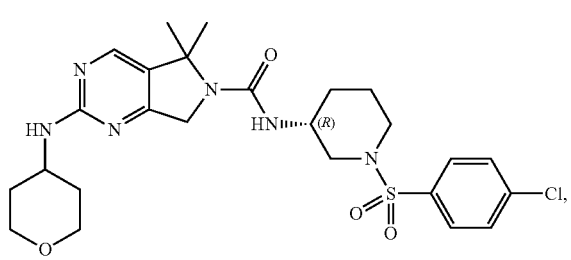
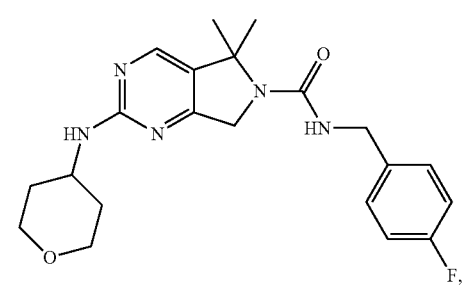
190
-continued
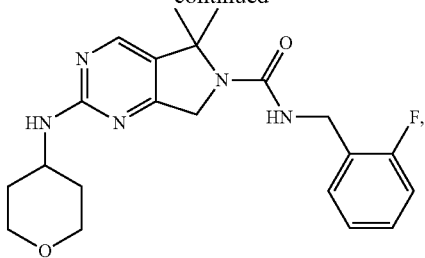
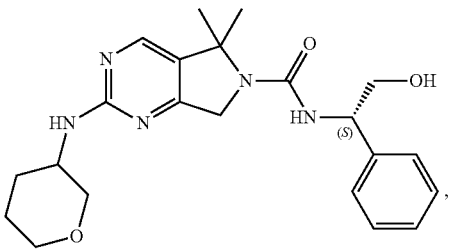
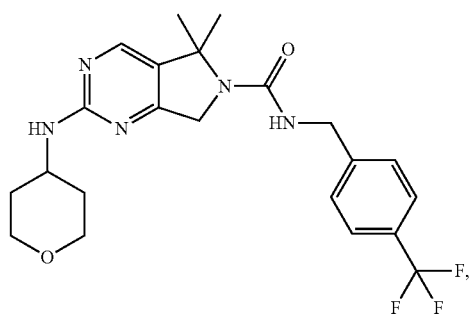
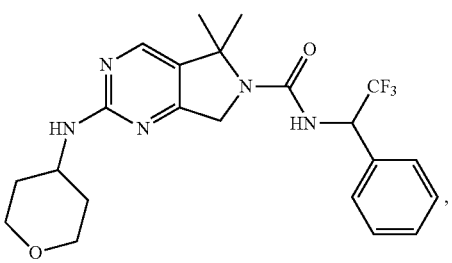
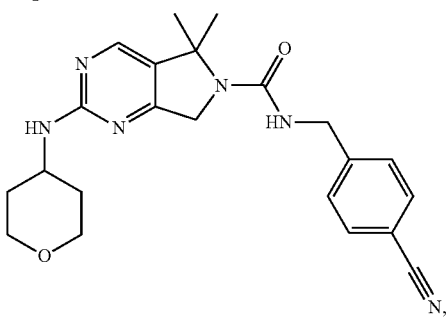
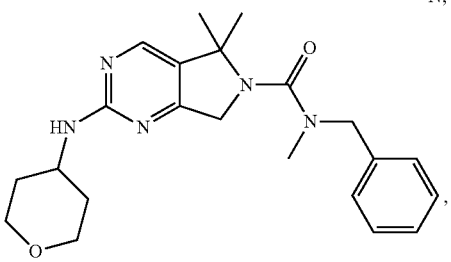

191
-continued
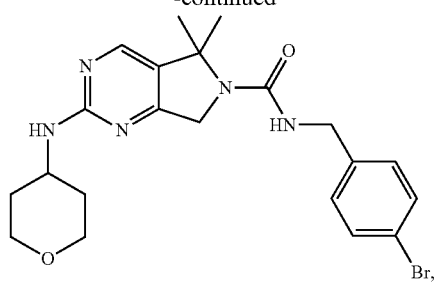
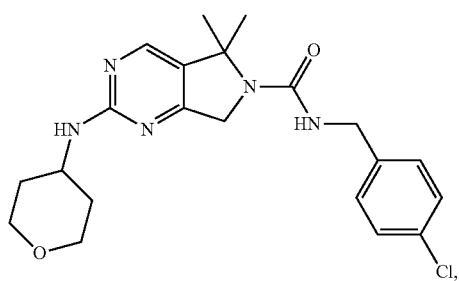
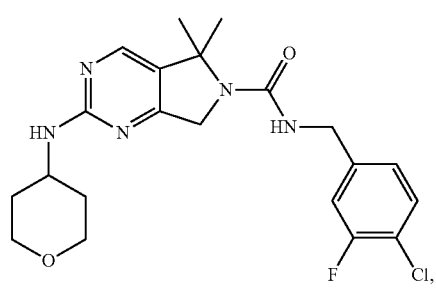
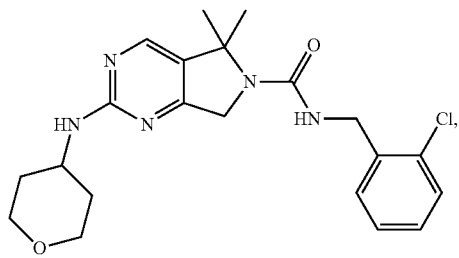
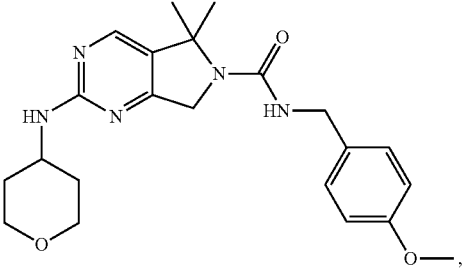
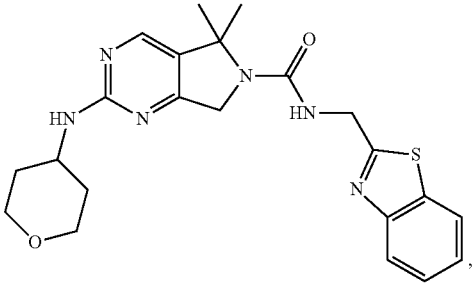
192
-continued
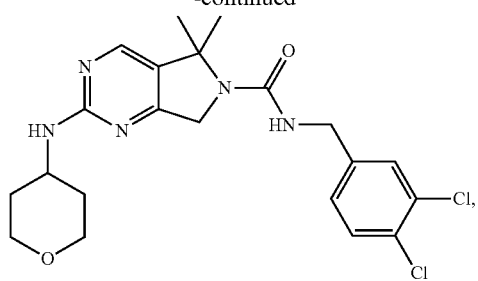
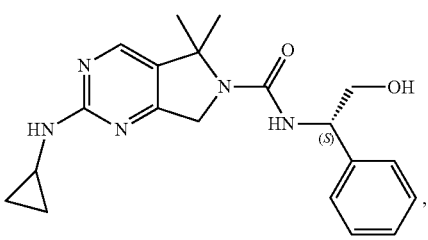
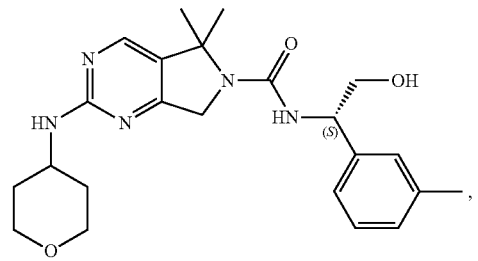
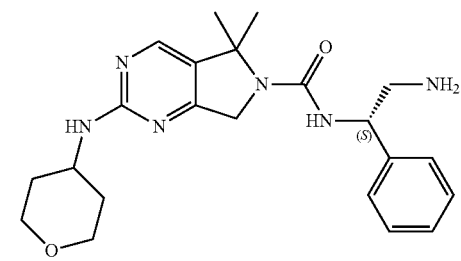
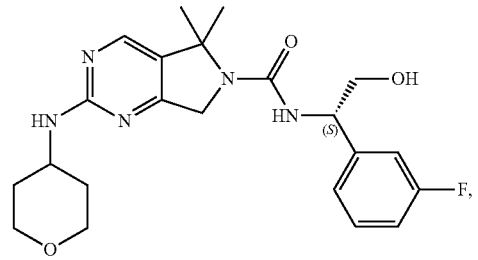
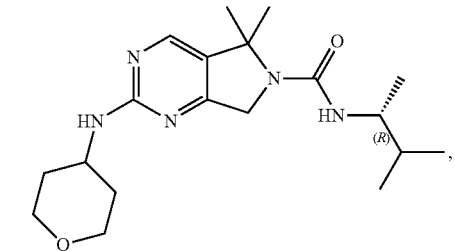

193
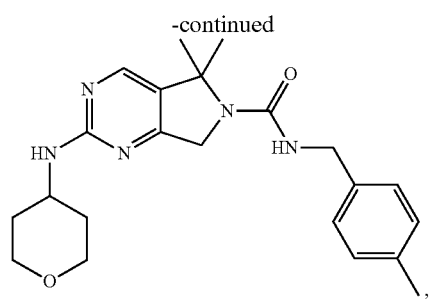
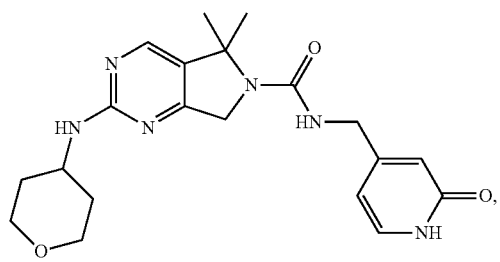
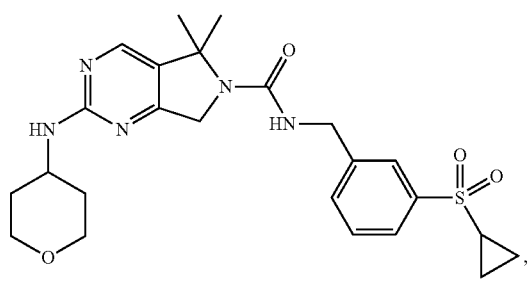
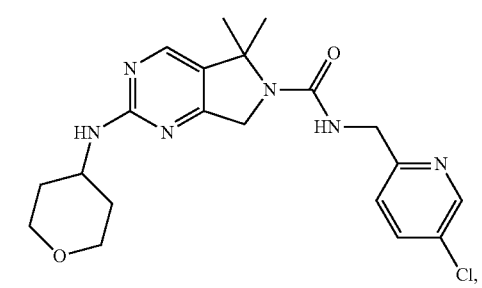
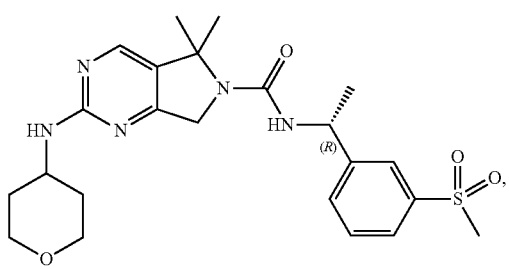
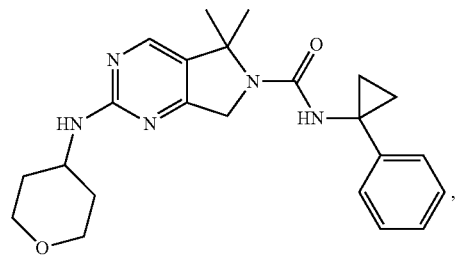
194
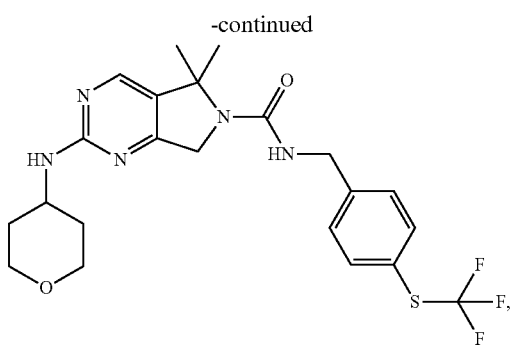
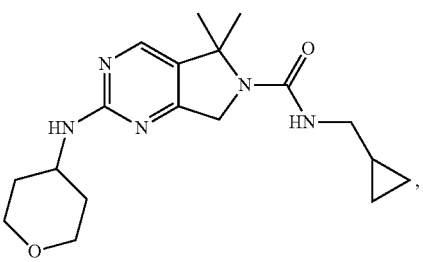
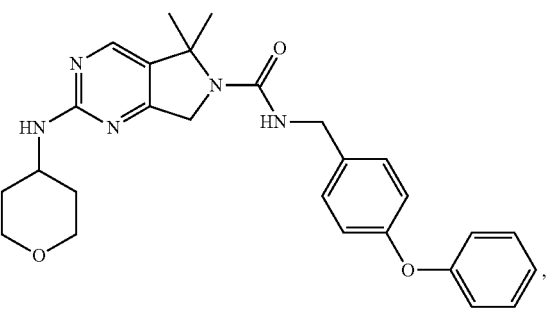
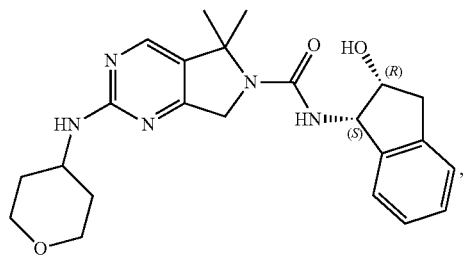
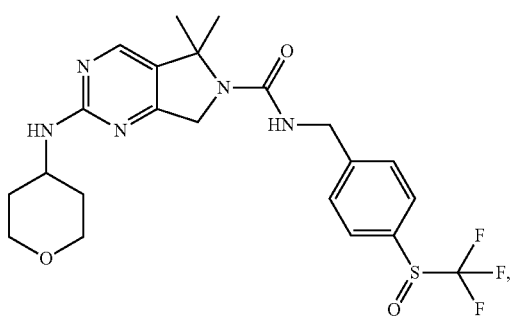
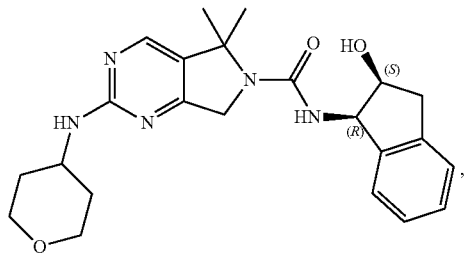

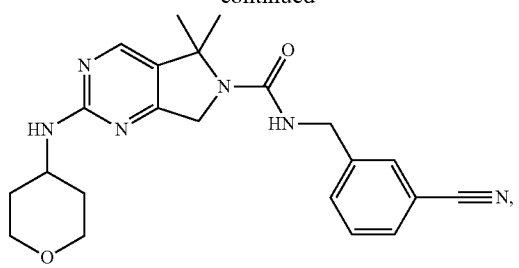
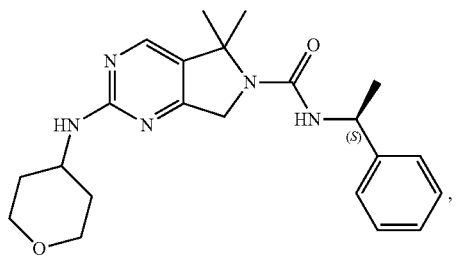
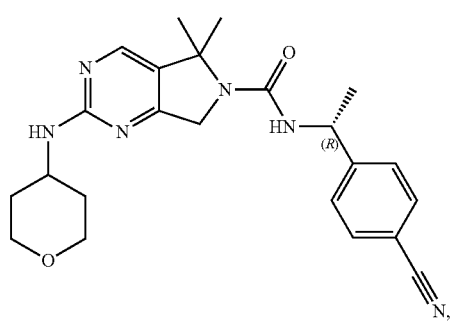
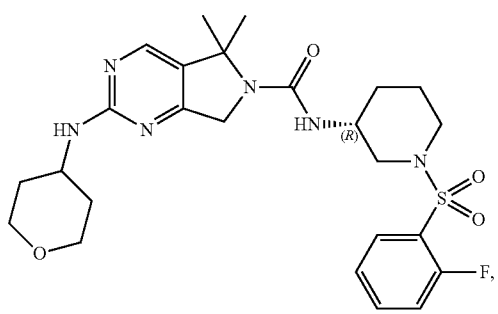
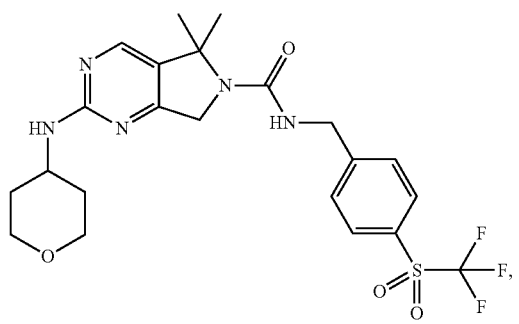
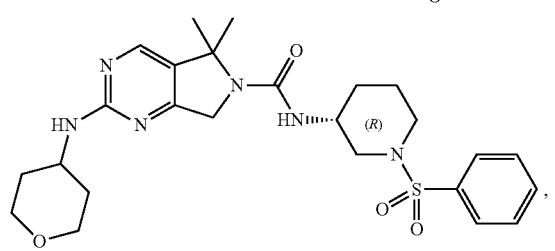
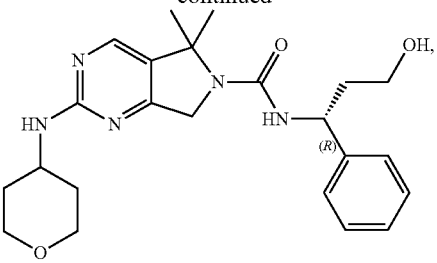
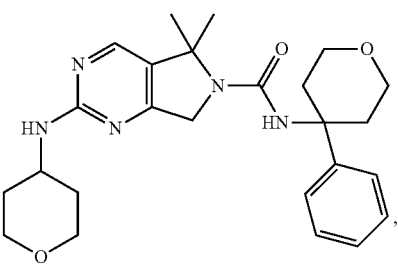
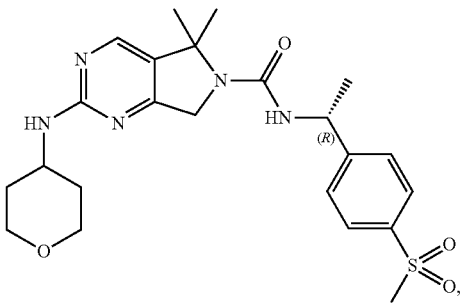
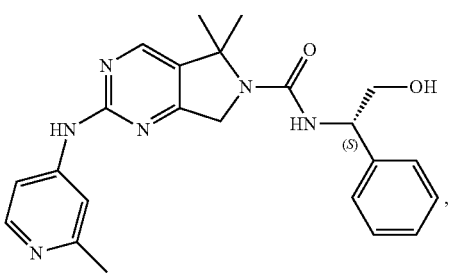
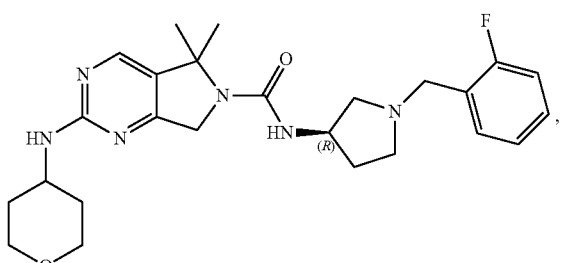
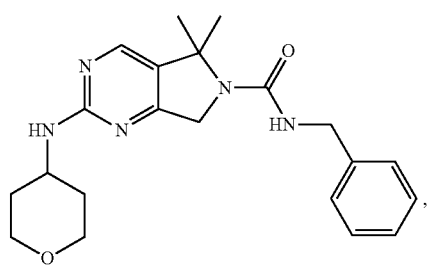

197
-continued
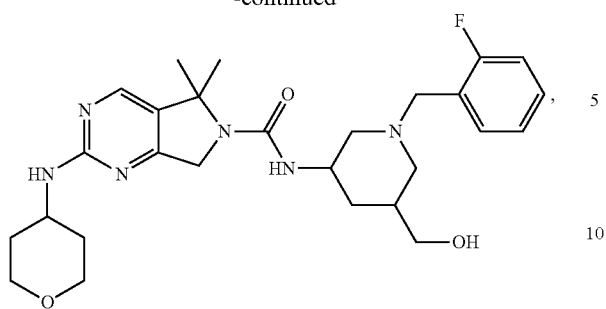
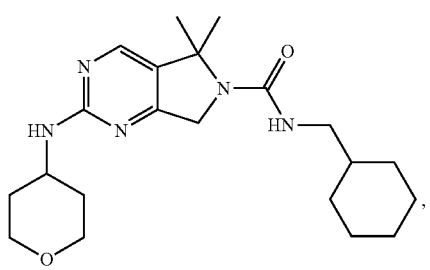
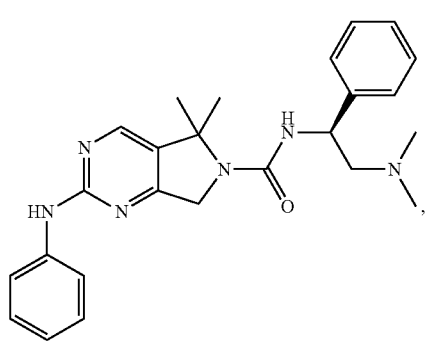
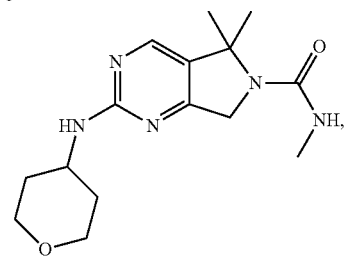
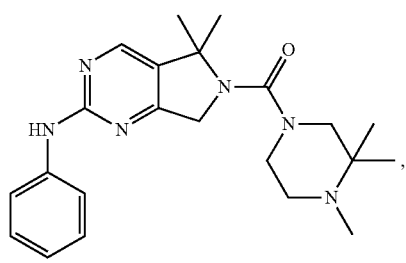
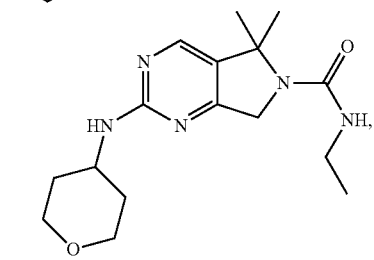
198
-continued
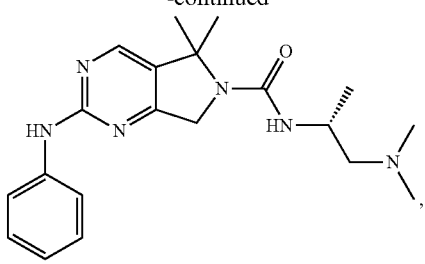
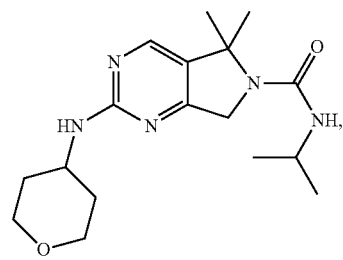
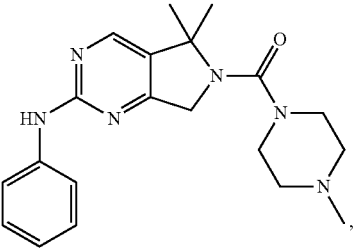
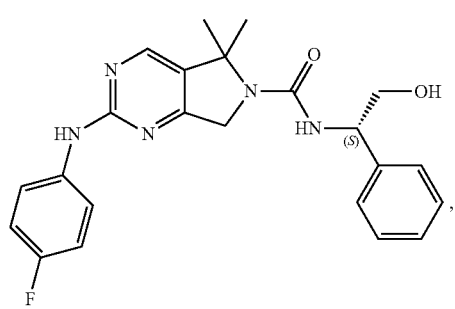
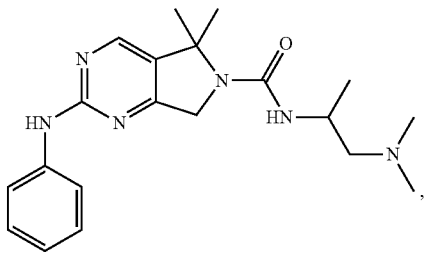
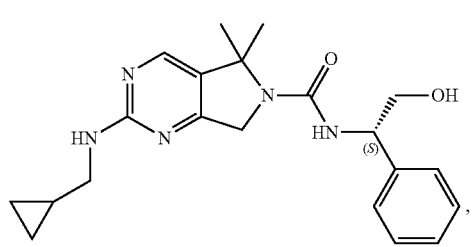

199
-continued
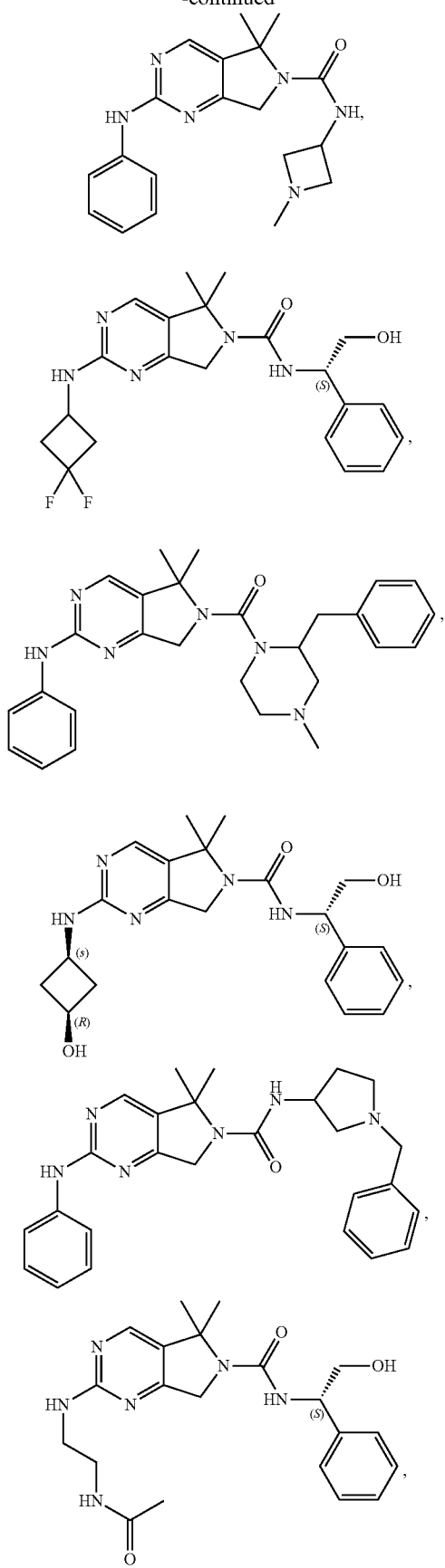
200
-continued
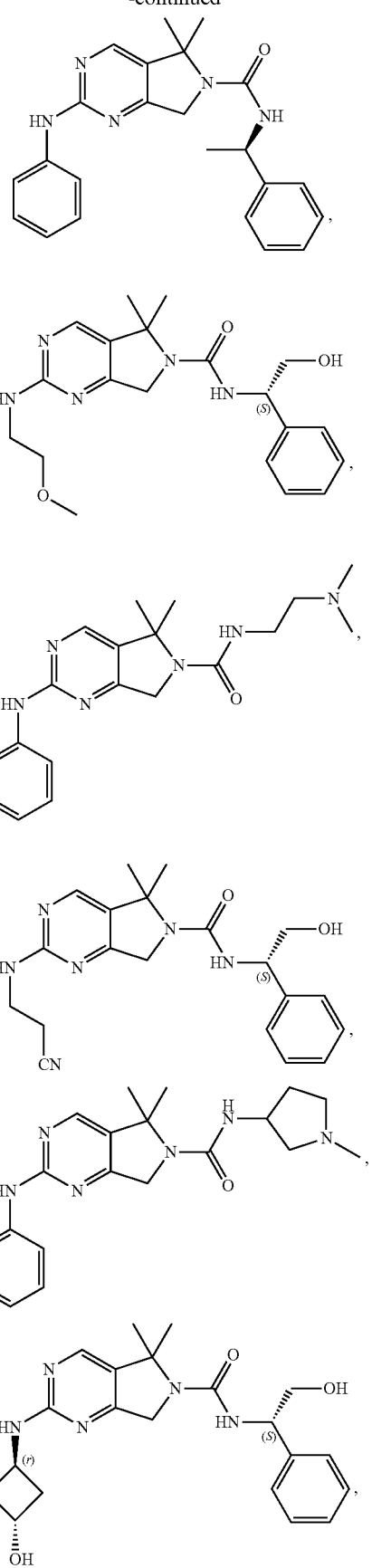

201
-continued
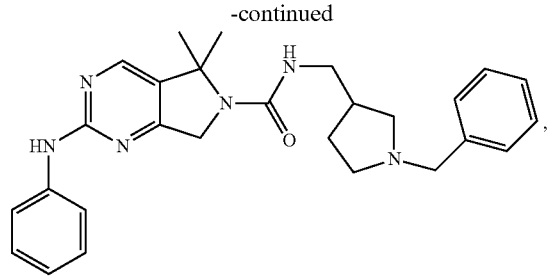,
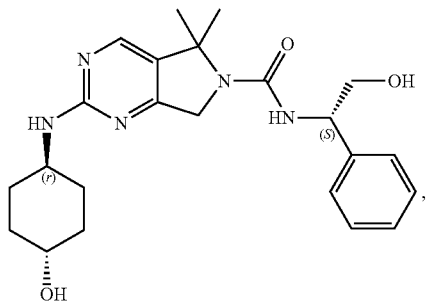,
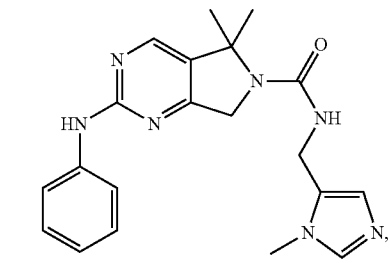,
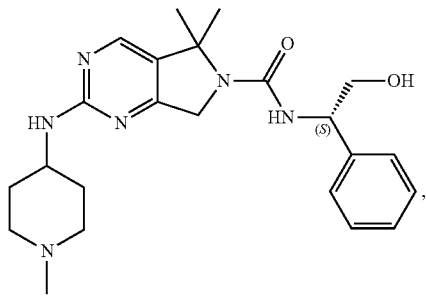,
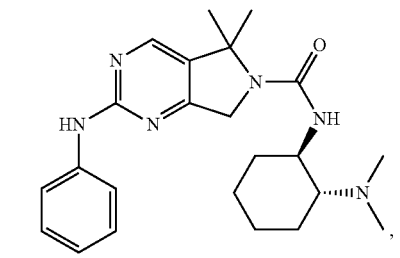,
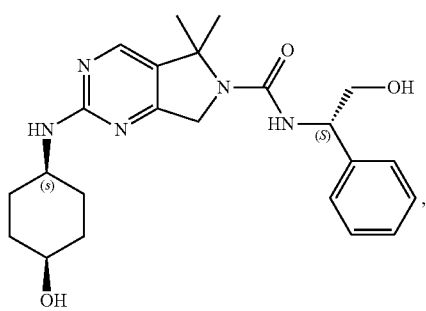,
202
-continued
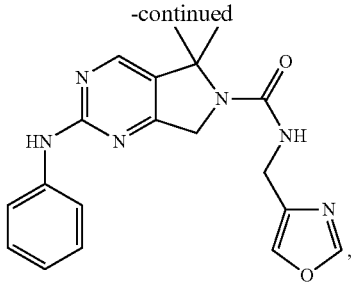,
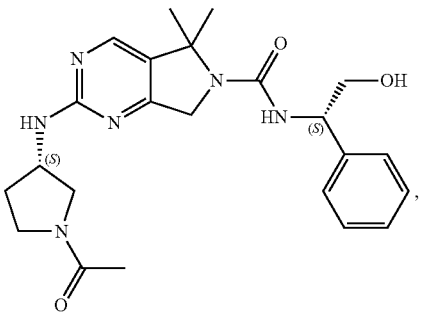,
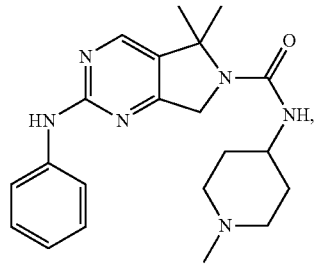,
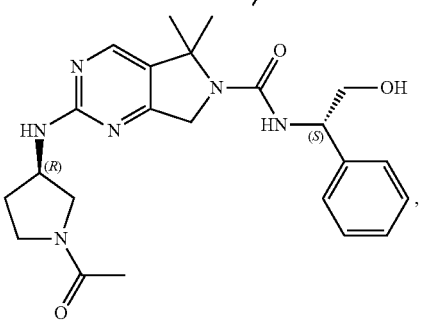,
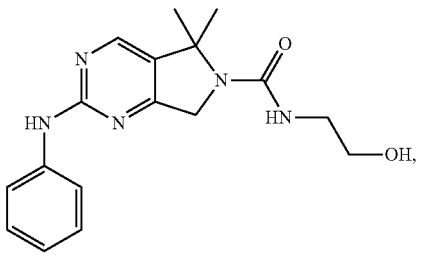,
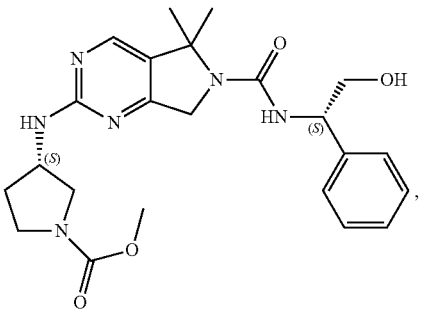, 203
-continued
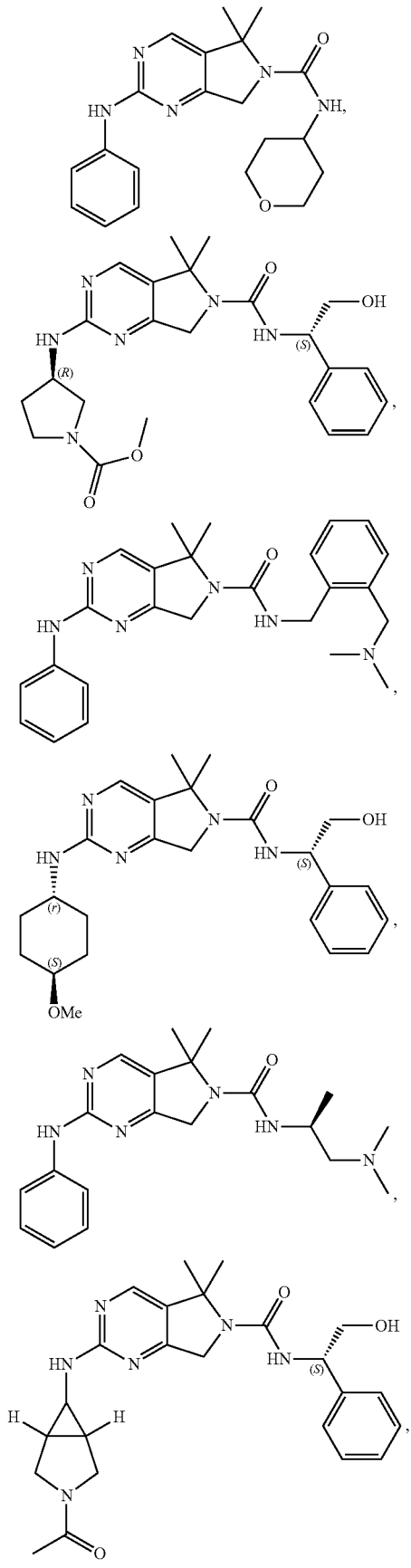
204
-continued
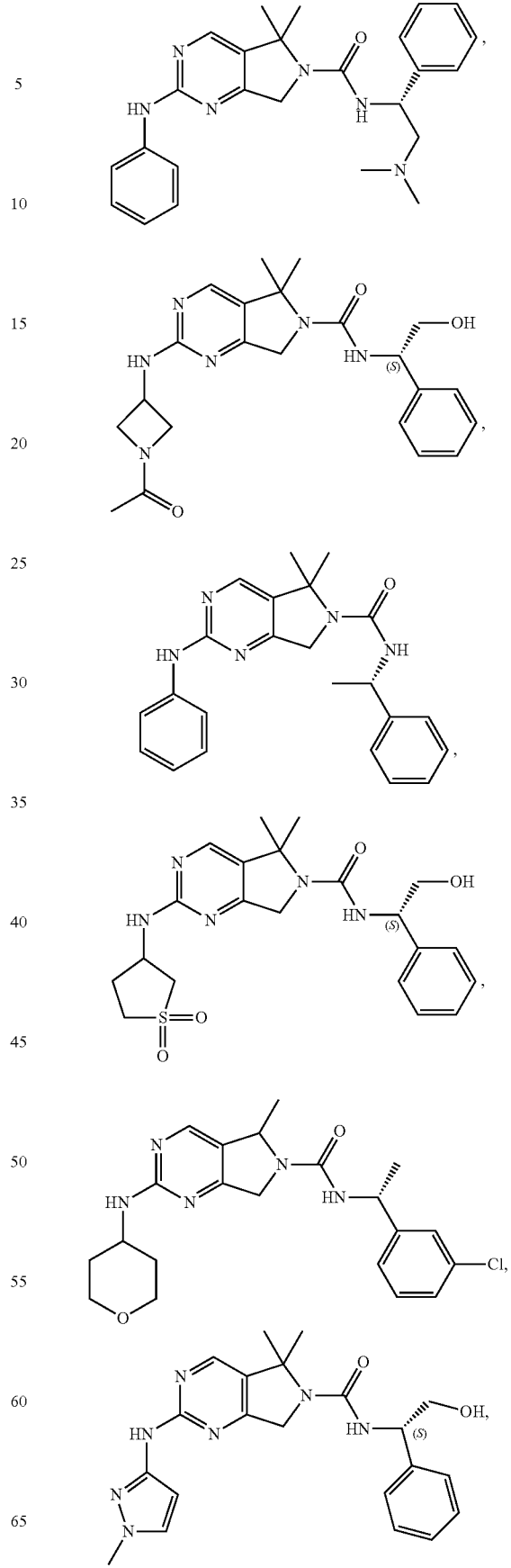

-continued
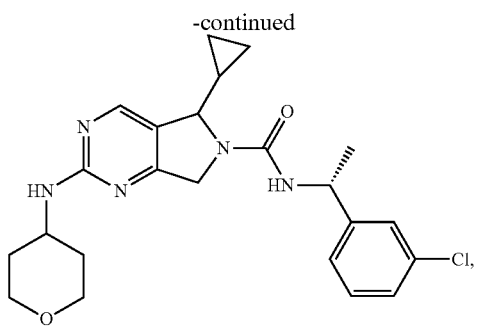
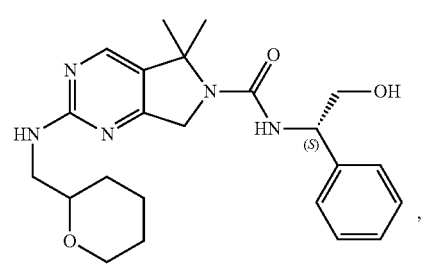
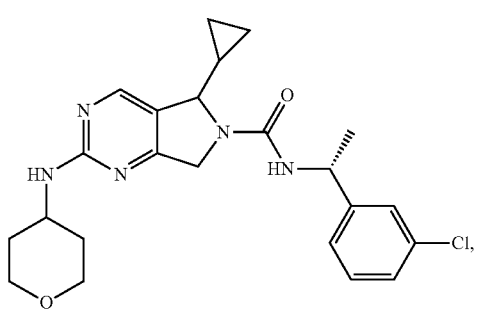
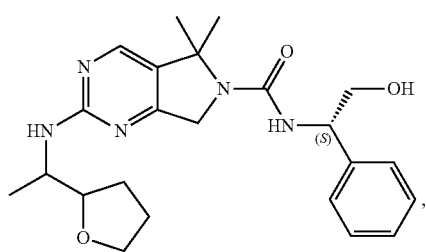
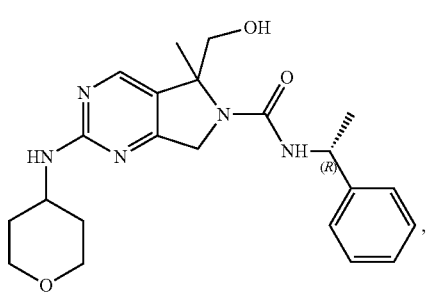
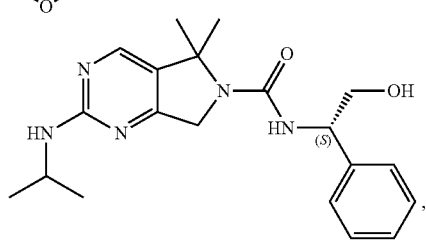
-continued
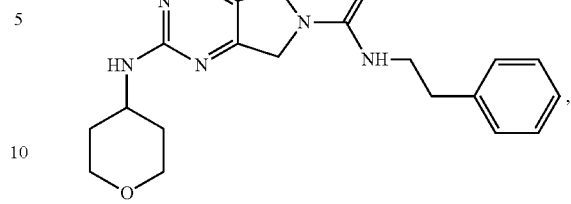
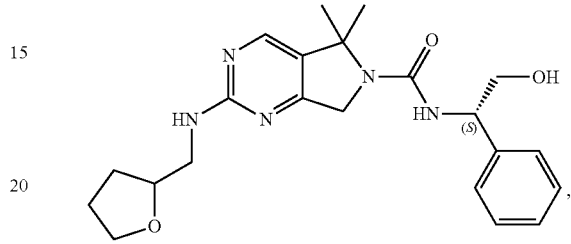
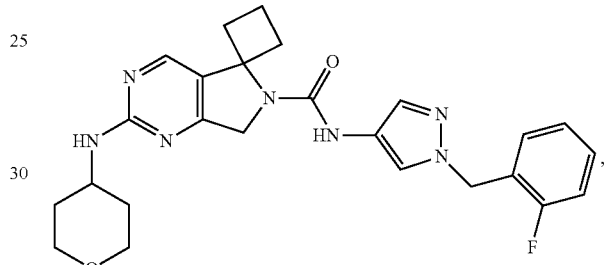

207
-continued
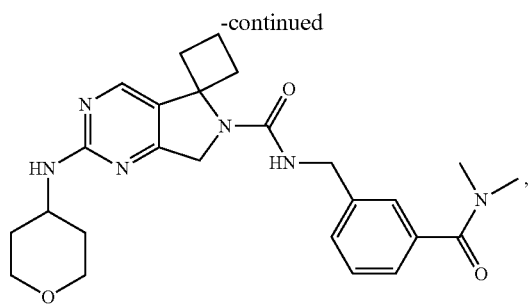
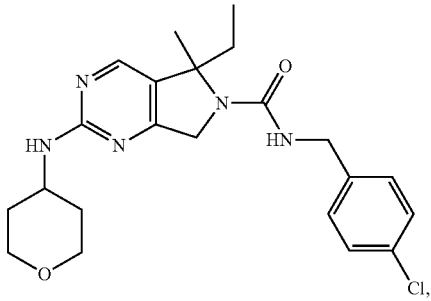
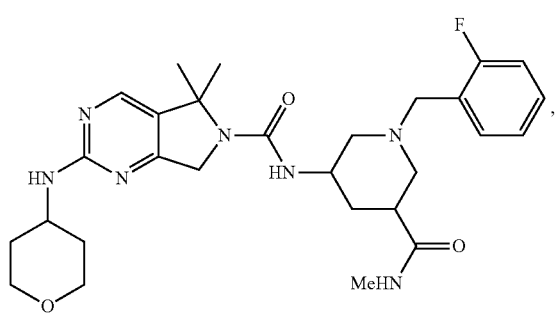
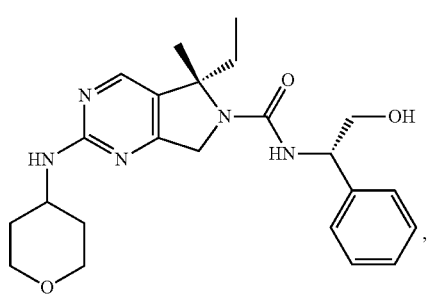
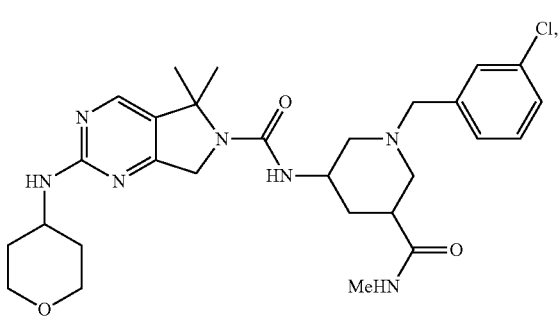
208
-continued
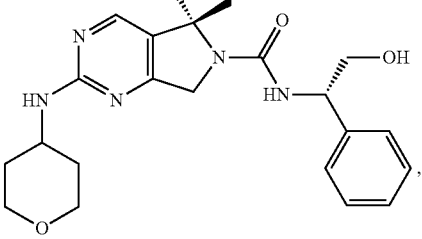
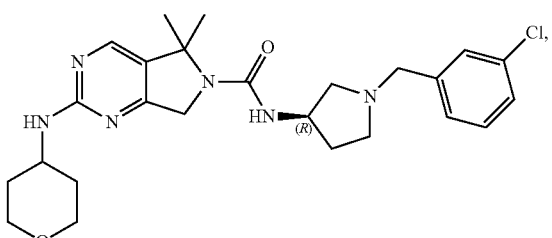
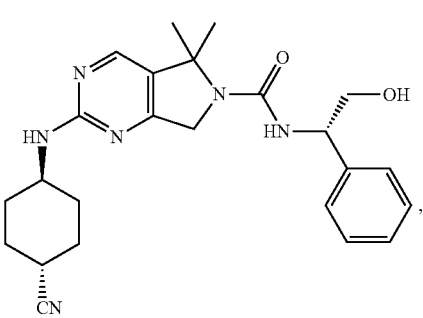
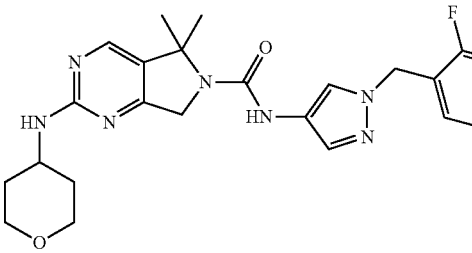
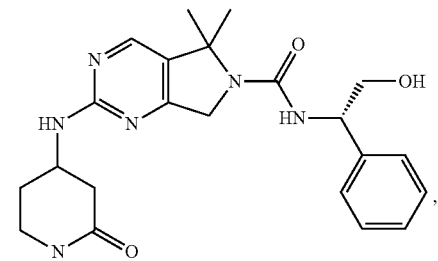
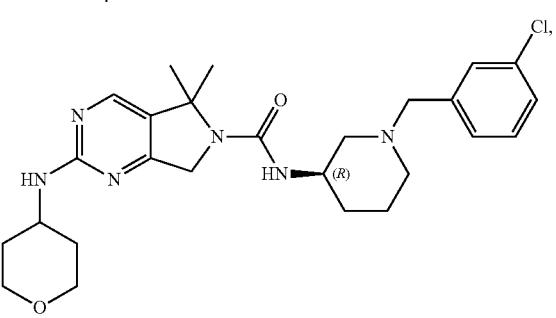

209
-continued
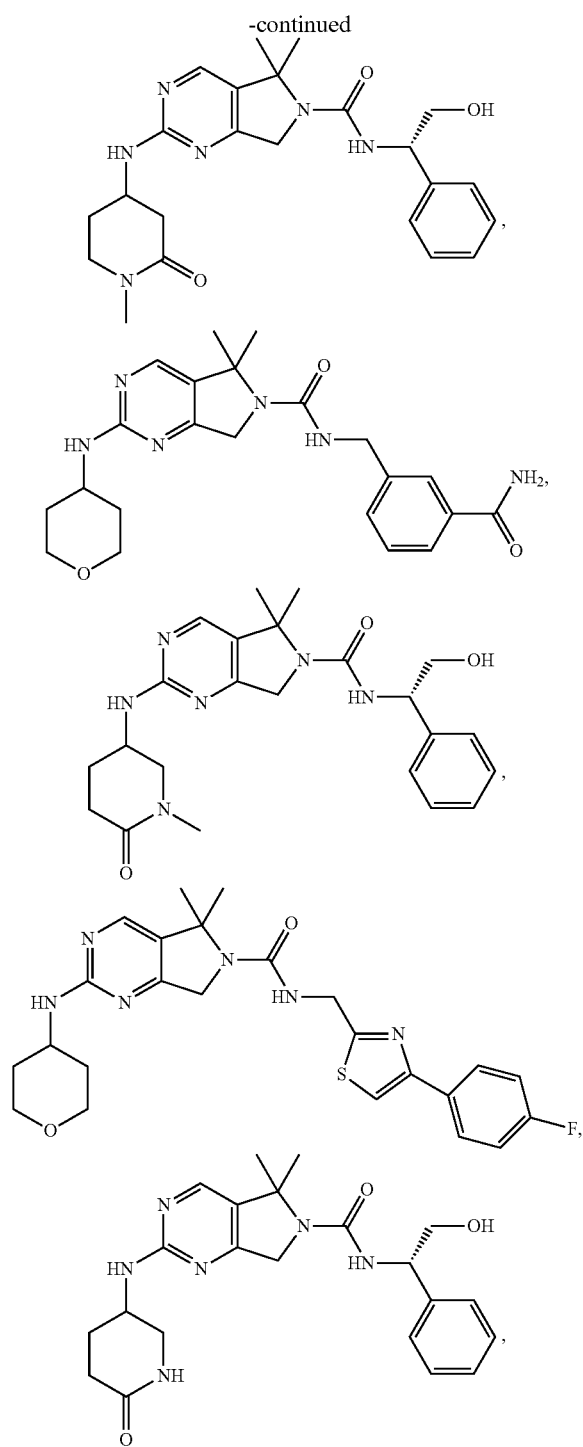
210
-continued
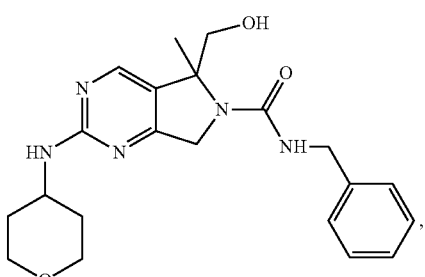
* * * * *

SEQUENCE LISTING

```
<160> NUMBER OF SEQ ID NOS: 1

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Biotin-Aminohexanoic acid
<220> FEATURE:
<221> NAME/KEY: MOD_RES
<222> LOCATION: (22)..(22)
<223> OTHER INFORMATION: Arg-NH2

<400> SEQUENCE: 1

Xaa Lys Arg Glu Leu Val Glu Pro Leu Thr Pro Ser Gly Glu Ala Pro
1               5                   10                  15

Asn Gln Ala Leu Leu Arg
            20
```